United States Patent
Frejd et al.

(10) Patent No.: US 10,669,314 B2
(45) Date of Patent: *Jun. 2, 2020

(54) POLYPEPTIDE

(71) Applicant: Affibody AB, Solna (SE)

(72) Inventors: Fredrik Frejd, Stockholm (SE); Elin Gunneriusson, Saltsjöbaden (SE); Ingmarie Höidén-Guthenberg, Kista (SE); Per-Ake Nygren, Ekerö (SE); Susanne Klint, Stockholm (SE); Feifan Yu, Sollentuna (SE)

(73) Assignee: AFFIBODY AB, Solina (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/317,188

(22) PCT Filed: Jun. 15, 2015

(86) PCT No.: PCT/EP2015/063362
§ 371 (c)(1),
(2) Date: Dec. 8, 2016

(87) PCT Pub. No.: WO2015/189430
PCT Pub. Date: Dec. 17, 2015

(65) Prior Publication Data
US 2017/0114099 A1    Apr. 27, 2017

(30) Foreign Application Priority Data
Jun. 13, 2014 (EP) ..................... 14172331

(51) Int. Cl.
| C07K 14/00 | (2006.01) |
| G01N 33/68 | (2006.01) |
| C07K 14/54 | (2006.01) |
| A61K 38/00 | (2006.01) |

(52) U.S. Cl.
CPC .......... *C07K 14/00* (2013.01); *C07K 14/5412* (2013.01); *G01N 33/6869* (2013.01); *A61K 38/00* (2013.01); *C07K 2319/70* (2013.01); *G01N 2333/5412* (2013.01)

(58) Field of Classification Search
CPC .... A61K 38/00; C07K 14/00; C07K 14/5412; C07K 2319/70; G01N 2333/5412; G01N 33/6869
See application file for complete search history.

(56) References Cited

U.S. PATENT DOCUMENTS 6,830,894 B1 * 12/2004 Blaschuk ............. C07K 14/705
435/7.21

2009/0305962 A1   12/2009 Bakker et al.

FOREIGN PATENT DOCUMENTS

| WO | 9713781       | 4/1997 |
| WO | 2007009018 A2 | 1/2007 |
| WO | 2009077175 A1 | 6/2009 |
| WO | 2011110515 A1 | 9/2011 |
| WO | 2013030362    | 3/2013 |
| WO | 2013083813 A2 | 6/2013 |
| WO | 2013126006 A1 | 8/2013 |
| WO | 2014064237 A1 | 5/2014 |
| WO | 2015189431 A1 | 12/2015 |

OTHER PUBLICATIONS

Stephanie Hennigan, Interleukin-6 inhibitors in the treatment of rheumatoid arthritis, Therapeutics and Clinical Risk Management 2008:4(4) 767-775.*
Mechanism of Carcinogenesis, Section 3, 2008, International agency for research on cancer, pp. 1-37.*
Grimm, S., et al., "Selection and Characterisation of affibody molecules inhibiting the interaction between Ras and Raf in vitro", New Biotechnology, Elsevier BV, NL, vol. 27, No. 6, Dec. 31, 2010, pp. 766-773.
International Search Report for International Application No. PCT/EP2015/063362; International Filing Date Jun. 15, 2015; dated Sep. 25, 2015; 6 pages.
Kobayashi, T. et al., "In Vitro Selection of a Peptide Inhibitor of Human IL-6 Using mRNA Display", Molecular Biotechnlogy, vol. 48, No. 2, published online Dec. 7, 2010, pp. 147-155.
Nygren, P., "Alternative binding proteins: Affibody binding proteins developed from a small three-helix bundle scaffold", FEBS Journal, Wiley-Blackwell Publishing Ltd, GB, vol. 275, No. 11, Jun. 1, 2008, pp. 2668-2676.
Wahlberg E. et al., "An affibody in complex with a target protein: Structure and coupled folding", Proceedings of the National Academy of Sciences, vol. 100, No. 6, Mar. 18, 2003, pp. 3185-3190.
Written Opinion of the International Searching Authority for International Application No. PCT/EP2015/063362; International Filing Date: Jun. 15, 2015; dated Sep. 25, 2009; 7 pages.
Dhillon S., "Intravenous Tocilizumab: A Review of Its Use in Adults with Rheumatoid Arthritis", BioDrugs, vol. 28, No. 1, Feb. 2014, published online Nov. 20, 2013, pp. 75-106.
U.S. Non Final Office Action in U.S. Appl. No. 15/317,633, filed Dec. 9, 2016; dated Aug. 8, 2018; 15 pages.
"AA Amyloidosis", Amyloidosis Foundation http://amloidosis.org/facts/al/ downloaded Jan. 29, 2019; 3 pages.

(Continued)

*Primary Examiner* — Rachael E Bredefeld
*Assistant Examiner* — Erinne R Dabkowski
(74) *Attorney, Agent, or Firm* — Cantor Colburn LLP

(57) ABSTRACT

The present disclosure relates to a class of engineered polypeptides having a binding affinity for interleukin-6, and provides an IL-6 binding polypeptide comprising the sequence $EEX_3X_4AWX_7EIH\ X_{11}\ LPNLX_{16}X_{17}X_{18}QX_{20}X_{21}AFIX_{25}X_{26}LX_{28}X_{29}$. The present disclosure also relates to the use of such an IL-6 binding polypeptide as a therapeutic, prognostic and/or diagnostic agent.

20 Claims, 54 Drawing Sheets

Specification includes a Sequence Listing.

(56) References Cited

OTHER PUBLICATIONS

"Data from Phase 2 Study of Alder Biopharmaceuticals' Anti-IL-6 Antibody Therapeutic, ALD518, Demonstrate Reversal of Anemia in Patients with Advanced Non-Small Cell Lung Cancer", PR Newswire, Dec. 7, 2010, downloaded Feb. 6, 2019 from https://www.prnewswire.com/news-releases/data-from-phase-2-study-of-alder-biopharmaceuticals-anti-il-6-antibody-therapeutic-ald518-demonstrate-reversal-of-anemia-in-patients-with-advanced-non-small-cell-lung-cancer-111450629.html.
Ataie-Kachoie, Parvin et al., "Inhibition of the IL-6 signaling pathway: A strategy to combat chronic inflammatory diseases and cancer" Cytokine & Growth Factor Reviews 24 (2013) 163-173.
Coward, Jermaine et al., "Interleukin-6 as a therapeutic target in human ovarian cancer", Clin Cancer Res. Sep. 15, 2011; 17(18): 6083-6096.
Danese, Silvio, et al, "Randomised trial and open-label extension study of an anti-interleukin-6 antibody in Crohn's disease (ANDANTE I and II)", Gut, 2019;68:40-48, first published as 10.1136/gutjnl-2017-314562 online Dec. 15, 2017.
Hagihara, K. et al., "IL-6 plays a critical role in the synergistic induction of human serum anmyloid A (SAA) gene when stimulated with proinflammatory cytokines as analyzed with an SAA iso form real-time quantitative RT-PCT assay system", BBRC, 314 (2004) 363-369.
Mease, Philip J., "The Efficacy and Safety of Clazakizumab, an Anti-Interleukin-6 Monoclonal Antibody, in a Phase IIb Study of Adults With Active Psoriatic Arthritis", Arthritis & Rheumatology, vol. 68, No. 9, Sep. 2016, pp. 2163-2173.
Takeuchi, Tsutomu et al., Efficacy and safety of olokizumab in Asian patients with moderate-to-sever rheumatoid arthritis, previously exposed to anti-TNF therapy: Results from a randomized phase II trial; Modern Rheumatology, 26:1, 15-23, DOI:10,3109/14397595,2015.1074648.
Tanaka et al., "IL-6 in Inflammation, Immunity, and Disease", Cold Spring Harb Perspect Biol 2014;6:a016295; 16 pages.
Weinblatt, Michael E., "The Efficacy and Safety of Subcutaneous Clazakizumab in Patients With Moderate-to-Sever Rheumatoid Arthritis and an Inadequate Response to Methotrexate", Arthritis & Rheumatology, vol. 67, No. 10, Oct. 2015; pp. 2591-2600.
Yao, Xin et al., "Targeting interleukin-6 in inflammatory autoimmune diseases and cancers", Pharmacology & Thereapeutics 141 (2014) 125-139.
Non Final Office Action for U.S. Appl. No. 15/317,633, filed Dec. 9, 2016; dated Apr. 4, 2019; 19 pages.
Gronwall Caroline, et al., "Selection and characterization of Affibody ligands binding to Alzheimer amyioid B peptides", Journal of Bioteohnology 128 (2007) pp. 162-183.

* cited by examiner

FIG. 1A

| Designation | Sequence | SEQ ID NO |
|---|---|---|
| Z14976 | VDAKYAKEERKAWYEIHLLPNLTVEQMAAFITKLFDDPSQSSELLSEAKKLNDSQAPK | 1 |
| Z15015 | VDAKYAKEERDAWWEIHALPNLTVEQMAAFITKLFDDPSQSSELLSEAKKLNDSQAPK | 2 |
| Z15122 | VDAKYAKEERHAWYEIHLLPNLTIDQMAAFISKLFDDPSQSSELLSEAKKLNDSQAPK | 3 |
| Z14861 | VDAKYAKEERKAWIEIHNLPNLTIDQMAAFITKLFDDPSQSSELLSEAKKLNDSQAPK | 4 |
| Z14984 | VDAKYAKEERKQAWREIHLLPNLTIDQMAAFITKLFDDPSQSSELLSEAKKLNDSQAPK | 5 |
| Z14630 | VDAKYAKEEKFAWWEIHKLPNLTVDQVAAFITKLFDDPSQSSELLSEAKKLNDSQAPK | 6 |
| Z11632 | VDAKYAKEEREAWFEIHTLPNLTVSQMAAFITKLFDDPSQSSELLSEAKKLNDSQAPK | 7 |
| Z14700 | VDAKYAKEERHAWFEIHKLPNLTVDQMAAFITKLFDDPSQSSELLSEAKKLNDSQAPK | 8 |
| Z14712 | VDAKYAKEEYLAWNEIHKLPNLTVDQMAAFITKLFDDPSQSSELLSEAKKLNDSQAPK | 9 |
| Z14862 | VDAKYAKEEAAAWREIHLLPNLTIDQMAAFITKLFDDPSQSSELLSEAKKLNDSQAPK | 10 |
| Z15036 | VDAKYAKEEYEAWFEIHALPNLTVEQMAAFITKLFDDPSQSSELLSEAKKLNDSQAPK | 11 |
| Z15110 | VDAKYAKEERRAWTEIHSLPNLTIDQMAAFISKLFDDPSQSSELLSEAKKLNDSQAPK | 12 |
| Z15126 | VDAKYAKEERNAWYEIHLLPNLTVEQMAAFITKLFDDPSQSSELLSEAKKLNDSQAPK | 13 |
| Z15142 | VDAKYAKEERMAWYEIHSLPNLTVDQMAAFISKLFDDPSQSSELLSEAKKLNDSQAPK | 14 |
| Z11213 | VDAKYAKEEREAWYEIHVLPNLTVSQIAAFISKLFDDPSQSSELLSEAKKLNDSQAPK | 15 |
| Z11214 | VDAKYAKEERTAWFEIHTLPNLTVEQMAAFISKLFDDPSQSSELLSEAKKLNDSQAPK | 16 |
| Z11215 | VDAKYAKEEAEAWWEIHLLPNLTVSQMAAFISKLFDDPSQSSELLSEAKKLNDSQAPK | 17 |
| Z11217 | VDAKYAKEEREAWYEIHLLPNLTVEQMAAFISKLFDDPSQSSELLSEAKKLNDSQAPK | 18 |
| Z11222 | VDAKYAKEERDAWYEIHLLPNLTIDQMAAFISKLFDDPSQSSELLSEAKKLNDSQAPK | 19 |
| Z11251 | VDAKYAKEERKAWFEIHALPNLTVDQMAAFISKLFDDPSQSSELLSEAKKLNDSQAPK | 20 |
| Z11277 | VDAKYAKEEAKAWFEIHALPNLTVEQMAAFISKLFDDPSQSSELLSEAKKLNDSQAPK | 21 |
| Z11278 | VDAKYAKEERTAWYEIHILPNLTVSQMAAFISKLFDDPSQSSELLSEAKKLNDSQAPK | 22 |
| Z11283 | VDAKYAKEEQQAWTEIHSLPNLTVDQMAAFISKLFDDPSQSSELLSEAKKLNDSQAPK | 23 |
| Z11300 | VDAKYAKEERDAWYEIHLLPNLTVEQIAAFISKLFDDPSQSSELLSEAKKLNDSQAPK | 24 |
| Z11321 | VDAKYAKEERVAWYEIHLLPNLTITQMAAFISKLFDDPSQSSELLSEAKKLNDSQAPK | 25 |
| Z11329 | VDAKYAKEERQAWYEIHLLPNLTVQQMAAFISKLFDDPSQSSELLSEAKKLNDSQAPK | 26 |
| Z11351 | VDAKYAKEEASAWFEIHTLPNLTVQQMAAFISKLFDDPSQSSELLSEAKKLNDSQAPK | 27 |
| Z11380 | VDAKYAKEEREAWYEIHVLPNLTVDQMAAFISKLFDDPSQSSELLSEAKKLNDSQAPK | 28 |
| Z11384 | VDAKYAKEERKAWYEIHLLPNLTVNQMAAFISKLFDDPSQSSELLSEAKKLNDSQAPK | 29 |
| Z11433 | VDAKYAKEERKAWYEIHLLPNLTVDQMAAFISKLFDDPSQSSELLSEAKKLNDSQAPK | 30 |
| Z11472 | VDAKYAKEEARAWHEIHILPNLTVSQIAAFISKLFDDPSQSSELLSEAKKLNDSQAPK | 31 |
| Z11552 | VDAKYAKEERAAWYEIHLLPNLTVDQMAAFISKLFDDPSQSSELLSEAKKLNDSQAPK | 32 |
| Z11642 | VDAKYAKEERQAWYEIHTLPNLTAEQMAAFISKLFDDPSQSSELLSEAKKLNDSQAPK | 33 |

FIG. 1B

| Designation | Sequence | SEQ ID NO |
|---|---|---|
| Z11644 | VDAKYAKEERQAWFEIHALPNLTVDQMAAFISKLFDDPSQSSELLSEAKKLNDSQAPK | 34 |
| Z11674 | VDAKYAKEEARAWREIHLLPNLTVQQMAAFISKLFDDPSQSSELLSEAKKLNDSQAPK | 35 |
| Z11698 | VDAKYAKEEAKAWREIHLLPNLTVTQMAAFISKLFDDPSQSSELLSEAKKLNDSQAPK | 36 |
| Z11711 | VDAKYAKEEAEAWREIHLLPNLTVNQMAAFISKLFDDPSQSSELLSEAKKLNDSQAPK | 37 |
| Z11723 | VDAKYAKEERDAWYEIHLLPNLTVQQMAAFISKLFDDPSQSSELLSEAKKLNDSQAPK | 38 |
| Z11781 | VDAKYAKEEREAWYEIHLLPNLTVRQMAAFISKLFDDPSQSSELLSEAKKLNDSQAPK | 39 |
| Z11784 | VDAKYAKEEREAWWEIHKLPNLTVNQMAAFISKLFDDPSQSSELLSEAKKLNDSQAPK | 40 |
| Z11788 | VDAKYAKEERRAWYEIHLLPNLTIQQMAAFISKLFDDPSQSSELLSEAKKLNDSQAPK | 41 |
| Z11789 | VDAKYAKEEAEAWREIHLLPNLTVHQMAAFISKLFDDPSQSSELLSEAKKLNDSQAPK | 42 |
| Z11791 | VDAKYAKEERDAWHEIHLLPNLTVSQMAAFISKLFDDPSQSSELLSEAKKLNDSQAPK | 43 |
| Z11794 | VDAKYAKEERRAWYEIHTLPNLTVEQMAAFISKLFDDPSQSSELLSEAKKLNDSQAPK | 44 |
| Z11802 | VDAKYAKEERKAWFEIHKLPNLTVTQMAAFISKLFDDPSQSSELLSEAKKLNDSQAPK | 45 |
| Z11803 | VDAKYAKEEHHAWFEIHLLPNLTVQQMAAFIQKLFDDPSQSSELLSEAKKLNDSQAPK | 46 |
| Z11805 | VDAKYAKEEARAWFEIHALPNLTVQQVAAFISKLFDDPSQSSELLSEAKKLNDSQAPK | 47 |
| Z11814 | VDAKYAKEEAKAWREIHILPNLTVQQMAAFISKLFDDPSQSSELLSEAKKLNDSQAPK | 48 |
| Z11815 | VDAKYAKEEATAWHEIHTLPNLTVHQMAAFISKLFDDPSQSSELLSEAKKLNDSQAPK | 49 |
| Z11817 | VDAKYAKEERSAWYEIHLLPNLTVTQMAAFISKLFDDPSQSSELLSEAKKLNDSQAPK | 50 |
| Z11818 | VDAKYAKEERAAWFEIHTLPNLTVQQMAAFISKLFDDPSQSSELLSEAKKLNDSQAPK | 51 |
| Z11819 | VDAKYAKEERTAWYEIHLLPNLTVQQMAAFIQKLFDDPSQSSELLSEAKKLNDSQAPK | 52 |
| Z11823 | VDAKYAKEERAAWFEIHLLPNLTVSQMAAFISKLFDDPSQSSELLSEAKKLNDSQAPK | 53 |
| Z11824 | VDAKYAKEEHRAWFEIHLLPNLTVEQMAAFISKLFDDPSQSSELLSEAKKLNDSQAPK | 54 |
| Z11833 | VDAKYAKEERAAWYEIHLLPNLTVQQMAAFIQKLFDDPSQSSELLSEAKKLNDSQAPK | 55 |
| Z11835 | VDAKYAKEERQAWYEIHLLPNLTVSQIAAFISKLFDDPSQSSELLSEAKKLNDSQAPK | 56 |
| Z11836 | VDAKYAKEEAAAWREIHLLPNLTISQIAAFISKLFDDPSQSSELLSEAKKLNDSQAPK | 57 |
| Z11860 | VDAKYAKEEREAWHEIHILPNLTIHQMAAFISKLFDDPSQSSELLSEAKKLNDSQAPK | 58 |
| Z11861 | VDAKYAKEEAQAWLEIHLLPNLTVDQIAAFISKLFDDPSQSSELLSEAKKLNDSQAPK | 59 |
| Z11862 | VDAKYAKEERKAWFEIHALPNLTVTQMAAFISKLFDDPSQSSELLSEAKKLNDSQAPK | 60 |
| Z11865 | VDAKYAKEERDAWYEIHLLPNLTVSQIAAFISKLFDDPSQSSELLSEAKKLNDSQAPK | 61 |
| Z11866 | VDAKYAKEEAAAWYEIHLLPNLTIISQIAAFISKLFDDPSQSSELLSEAKKLNDSQAPK | 62 |
| Z11871 | VDAKYAKEERVAWYEIHLLPNLTVRQMAAFIIKLFDDPSQSSELLSEAKKLNDSQAPK | 63 |
| Z11872 | VDAKYAKEEHHAWYEIHALPNLTVSQIAAFISKLFDDPSQSSELLSEAKKLNDSQAPK | 64 |
| Z11874 | VDAKYAKEERAAWFEIHALPNLTVEQVAAFISKLFDDPSQSSELLSEAKKLNDSQAPK | 65 |
| Z11875 | VDAKYAKEEQEAWYEIHVLPNLTVTQMAAFISKLFDDPSQSSELLSEAKKLNDSQAPK | 66 |

FIG. 1C

| Designation | Sequence | SEQ ID NO |
|---|---|---|
| Z11881 | VDAKYAKEEQQAWTEIHTLPNLTVDQMAAFISKLFDDPSQSSELLSEAKKLNDSQAPK | 67 |
| Z11882 | VDAKYAKEERDAWYEIHLLPNLTVTQMAAFISKLFDDPSQSSELLSEAKKLNDSQAPK | 68 |
| Z11883 | VDAKYAKEERDAWYEIHLLPNLTISQMAAFISKLFDDPSQSSELLSEAKKLNDSQAPK | 69 |
| Z11890 | VDAKYAKEEREAWHEIHILPNLTVEQIAAFISKLFDDPSQSSELLSEAKKLNDSQAPK | 70 |
| Z11892 | VDAKYAKEERDAWWEIHALPNLTVDQMAAFISKLFDDPSQSSELLSEAKKLNDSQAPK | 71 |
| Z11893 | VDAKYAKEEARAWHEIHVLPNLTVSQMAAFIQKLFDDPSQSSELLSEAKKLNDSQAPK | 72 |
| Z11895 | VDAKYAKEEAQAWYEIHTLPNLTVEQMAAFIAKLFDDPSQSSELLSEAKKLNDSQAPK | 73 |
| Z11896 | VDAKYAKEERSAWWEIHTLPNLTVTQMAAFISKLFDDPSQSSELLSEAKKLNDSQAPK | 74 |
| Z11897 | VDAKYAKEEADAWWEIHALPNLTIDQMAAFISKLFDDPSQSSELLSEAKKLNDSQAPK | 75 |
| Z11901 | VDAKYAKEEAEAWYEIHLLPNLTVDQMAAFITKLFDDPSQSSELLSEAKKLNDSQAPK | 76 |
| Z11903 | VDAKYAKEERAAWYEIHSLPNLTVDQMAAFISKLFDDPSQSSELLSEAKKLNDSQAPK | 77 |
| Z11904 | VDAKYAKEEQQAWLEIHLLPNLTIEQMAAFISKLFDDPSQSSELLSEAKKLNDSQAPK | 78 |
| Z11905 | VDAKYAKEERDAWYEIHLLPNLTVHQIAAFISKLFDDPSQSSELLSEAKKLNDSQAPK | 79 |
| Z11906 | VDAKYAKEERDAWYEIHTLPNLTVEQMAAFIWKLFDDPSQSSELLSEAKKLNDSQAPK | 80 |
| Z11907 | VDAKYAKEEQHAWLEIHKLPNLTVEQIAAFISKLFDDPSQSSELLSEAKKLNDSQAPK | 81 |
| Z11912 | VDAKYAKEEAAAWFEIHTLPNLTVDQMAAFISKLFDDPSQSSELLSEAKKLNDSQAPK | 82 |
| Z11918 | VDAKYAKEERDAWFEIHTLPNLTVTQMAAFIIKLFDDPSQSSELLSEAKKLNDSQAPK | 83 |
| Z11922 | VDAKYAKEERHAWHEIHILPNLTANQIAAFISKLFDDPSQSSELLSEAKKLNDSQAPK | 84 |
| Z11923 | VDAKYAKEEREAWFEIHLLPNLTISQMAAFISKLFDDPSQSSELLSEAKKLNDSQAPK | 85 |
| Z11929 | VDAKYAKEEAEAWWEIHLLPNLTVQQIAAFISKLFDDPSQSSELLSEAKKLNDSQAPK | 86 |
| Z11933 | VDAKYAKEEAHAWYEIHILPNLTVSQMAAFITKLFDDPSQSSELLSEAKKLNDSQAPK | 87 |
| Z11937 | VDAKYAKEERDAWYEIHLLPNLTIDQIAAFISKLFDDPSQSSELLSEAKKLNDSQAPK | 88 |
| Z11939 | VDAKYAKEEQRAWREIHLLPNLTIEQMSAFISKLFDDPSQSSELLSEAKKLNDSQAPK | 89 |
| Z14521 | VDAKYAKEEYDAWMEIHLLPNLTVDQMAAFITKLFDDPSQSSELLSEAKKLNDSQAPK | 90 |
| Z14524 | VDAKYAKEEKHAWREIHLLPNLTVEQMAAFITKLFDDPSQSSELLSEAKKLNDSQAPK | 91 |
| Z14525 | VDAKYAKEEKKAWTEIHLLPNLTIEQMAAFITKLFDDPSQSSELLSEAKKLNDSQAPK | 92 |
| Z14538 | VDAKYAKEERFAWTEIHLLPNLTVDQMAAFITKLFDDPSQSSELLSEAKKLNDSQAPK | 93 |
| Z14547 | VDAKYAKEERHAWTEIHLLPNLTVDQMAAFITKLFDDPSQSSELLSEAKKLNDSQAPK | 94 |
| Z14550 | VDAKYAKEERAAWFEIHALPNLTVEQVAAFITKLFDDPSQSSELLSEAKKLNDSQAPK | 95 |
| Z14551 | VDAKYAKEEKQAWYEIHNLPNLTVDQMAAFITKLFDDPSQSSELLSEAKKLNDSQAPK | 96 |
| Z14556 | VDAKYAKEEAQAWWEIHALPNLILPNLTVDQVAAFITKLFDDPSQSSELLSEAKKLNDSQAPK | 97 |
| Z14559 | VDAKYAKEEYEAWYEIHILPNLTVDQIAAFITKLFDDPSQSSELLSEAKKLNDSQAPK | 98 |
| Z14596 | VDAKYAKEEYEAWHEIHILPNLTVDQMAAFITKLFDDPSQSSELLSEAKKLNDSQAPK | 99 |

FIG. 1D

| Designation | Sequence | SEQ ID NO |
|---|---|---|
| Z14609 | VDAKYAKEERMAWMEIHLLPNLTVEQMAAFISKLFDDPSQSSELLSEAKKLNDSQAPK | 100 |
| Z14614 | VDAKYAKEEYDAWVEIHALPNLTVEQVAAFITKLFDDPSQSSELLSEAKKLNDSQAPK | 101 |
| Z14620 | VDAKYAKEEYEAWVEIHKLPNLTIDQMAAFITKLFDDPSQSSELLSEAKKLNDSQAPK | 102 |
| Z14634 | VDAKYAKEEYHAWYEIHLLPNLTIDQMAAFITKLFDDPSQSSELLSEAKKLNDSQAPK | 103 |
| Z14645 | VDAKYAKEEKDAWYEIHLLPNLTVEQIAAFITKLFDDPSQSSELLSEAKKLNDSQAPK | 104 |
| Z14651 | VDAKYAKEEKHAWHEIHLLPNLTVEQMAAFITKLFDDPSQSSELLSEAKKLNDSQAPK | 105 |
| Z14662 | VDAKYAKEEKAAWFEIHALPNLTVEQVAAFITKLFDDPSQSSELLSEAKKLNDSQAPK | 106 |
| Z14673 | VDAKYAKEEYHAWMEIHLLPNLTVSQMAAFITKLFDDPSQSSELLSEAKKLNDSQAPK | 107 |
| Z14706 | VDAKYAKEEAFAWKEIHLLPNLTIDQMAAFITKLFDDPSQSSELLSEAKKLNDSQAPK | 108 |
| Z14710 | VDAKYAKEEYEAWYEIHLLPNLTVSQIAAFITKLFDDPSQSSELLSEAKKLNDSQAPK | 109 |
| Z14720 | VDAKYAKEEYYAWWEIHKLPNLTVDQMAAFITKLFDDPSQSSELLSEAKKLNDSQAPK | 110 |
| Z14722 | VDAKYAKEEAVAWKEIHILPNLTVSQMAAFITKLFDDPSQSSELLSEAKKLNDSQAPK | 111 |
| Z14731 | VDAKYAKEEKAAWYEIHLLPNLTIEQMAAFISKLFDDPSQSSELLSEAKKLNDSQAPK | 112 |
| Z14746 | VDAKYAKEERAAWTEIHLLPNLTVEQMAAFITKLFDDPSQSSELLSEAKKLNDSQAPK | 113 |
| Z14765 | VDAKYAKEERMAWYEIHTLPNLTVDQMAAFITKLFDDPSQSSELLSEAKKLNDSQAPK | 114 |
| Z14767 | VDAKYAKEEHHAWREIHLLPNLTVDQMAAFITKLFDDPSQSSELLSEAKKLNDSQAPK | 115 |
| Z14782 | VDAKYAKEEAKAWMEIHLLPNLTIDQMAAFITKLFDDPSQSSELLSEAKKLNDSQAPK | 116 |
| Z14783 | VDAKYAKEEKAAWYEIHLLPNLTVDQIAAFITKLFDDPSQSSELLSEAKKLNDSQAPK | 117 |
| Z14784 | VDAKYAKEEKHAWMEIHKLPNLTVDQMAAFITKLFDDPSQSSELLSEAKKLNDSQAPK | 118 |
| Z14788 | VDAKYAKEEKAAWNEIHNLPNLTVDQMAAFITKLFDDPSQSSELLSEAKKLNDSQAPK | 119 |
| Z14829 | VDAKYAKEERKAWVEIHNLPNLTVDQIAAFITKLFDDPSQSSELLSEAKKLNDSQAPK | 120 |
| Z14867 | VDAKYAKEEATAWHEIHVLPNLTVDQIAAFITKLFDDPSQSSELLSEAKKLNDSQAPK | 121 |
| Z14868 | VDAKYAKEEYEAWYEIHLLPNLTIQQMAAFITKLFDDPSQSSELLSEAKKLNDSQAPK | 122 |
| Z14878 | VDAKYAKEEYHAWVEIHLLPNLTIDQMAAFITKLFDDPSQSSELLSEAKKLNDSQAPK | 123 |
| Z14888 | VDAKYAKEEAFAWREIHLLPNLTVEQIAAFITKLFDDPSQSSELLSEAKKLNDSQAPK | 124 |
| Z14929 | VDAKYAKEEKAAWYEIHLLPNLTVSQMAAFITKLFDDPSQSSELLSEAKKLNDSQAPK | 125 |
| Z14944 | VDAKYAKEEKAAWNEIHKLPNLTVDQMAAFITKLFDDPSQSSELLSEAKKLNDSQAPK | 126 |
| Z14990 | VDAKYAKEERKAWYEIHTLPNLTVEQIAAFITKLFDDPSQSSELLSEAKKLNDSQAPK | 127 |
| Z14992 | VDAKYAKEERNAWTEIHLLPNLTIEQMAAFITKLFDDPSQSSELLSEAKKLNDSQAPK | 128 |
| Z15003 | VDAKYAKEEYKAWLEIHNLPNLTVDQMAAFITKLFDDPSQSSELLSEAKKLNDSQAPK | 129 |
| Z15024 | VDAKYAKEEYEAWMEIHLLPNLTVEQIAAFITKLFDDPSQSSELLSEAKKLNDSQAPK | 130 |
| Z15025 | VDAKYAKEERDAWFEIHKLPNLTVDQMAAFITKLFDDPSQSSELLSEAKKLNDSQAPK | 131 |
| Z15031 | VDAKYAKEEAYAWKEIHLLPNLTVDQMAAFITKLFDDPSQSSELLSEAKKLNDSQAPK | 132 |

FIG. 1E

| Designation | Sequence | SEQ ID NO |
|---|---|---|
| Z15042 | VDAKYAKEEYFAWWEIHKLPNLTVNQMAAFITKLFDDPSQSSELLSEAKKLNDSQAPK | 133 |
| Z15053 | VDAKYAKEEKQAWVEIHNLPNLTITQMAAFITKLFDDPSQSSELLSEAKKLNDSQAPK | 134 |
| Z15057 | VDAKYAKEEQRAWYEIHILPNLTIDQMAAFITKLFDDPSQSSELLSEAKKLNDSQAPK | 135 |
| Z15067 | VDAKYAKEEARAWREIHALPNLTIDQMAAFITKLFDDPSQSSELLSEAKKLNDSQAPK | 136 |
| Z15079 | VDAKYAKEERYAWNEIHKLPNLTVDQMAAFITKLFDDPSQSSELLSEAKKLNDSQAPK | 137 |
| Z15082 | VDAKYAKEEAKAWYEIHILPNLTVDQIAAFITKLFDDPSQSSELLSEAKKLNDSQAPK | 138 |
| Z15097 | VDAKYAKEEARAWHEIHILPNLTIDQMAAFITKLFDDPSQSSELLSEAKKLNDSQAPK | 139 |
| Z15102 | VDAKYAKEEKKAWYEIHLLPNLTIEQMAAFITKLFDDPSQSSELLSEAKKLNDSQAPK | 140 |
| Z15111 | VDAKYAKEEARAWTEIHLLPNLTVDQMAAFITKLFDDPSQSSELLSEAKKLNDSQAPK | 141 |
| Z15117 | VDAKYAKEERSAWMEIHLLPNLTVDQMAAFITKLFDDPSQSSELLSEAKKLNDSQAPK | 142 |
| Z15129 | VDAKYAKEEREAWFEIHILPNLTIDQMAAFITKLFDDPSQSSELLSEAKKLNDSQAPK | 143 |
| Z15140 | VDAKYAKEEYEAWTEIHLLPNLTVDQIAAFITKLFDDPSQSSELLSEAKKLNDSQAPK | 144 |
| Z15141 | VDAKYAKEEYEAWNEIHNLPNLTITQMAAFITKLFDDPSQSSELLSEAKKLNDSQAPK | 145 |
| Z15145 | VDAKYAKEEYKAWHEIHILPNLTIDQMAAFITKLFDDPSQSSELLSEAKKLNDSQAPK | 146 |
| Z15151 | VDAKYAKEEREAWMEIHLLPNLTIEQMAAFITKLFDDPSQSSELLSEAKKLNDSQAPK | 147 |
| Z15159 | VDAKYAKEEYKAWVEIHLLPNLTVDQIAAFITKLFDDPSQSSELLSEAKKLNDSQAPK | 148 |
| Z15162 | VDAKYAKEEKIAWYEIHLLPNLTVNQIAAFITKLFDDPSQSSELLSEAKKLNDSQAPK | 149 |
| Z15164 | VDAKYAKEEAYAWKEIHLLPNLTIEQMAAFISKLFDDPSQSSELLSEAKKLNDSQAPK | 150 |
| Z11612 | VDAKYAKEEQVAWWEISHLPNLTITQVVAFIQKLFDDPSQSSELLSEAKKLNDSQAPK | 151 |
| Z11616 | VDAKYAKEEQVAWWEIHLLPNLTIEQVVAFIQKLFDDPSQSSELLSEAKKLNDSQAPK | 152 |
| Z11133 | VDAKYAKEEREAWYEIHTLPNLTAQQMAAFIVKLYDDPSQSSELLSEAKKLNDSQAPK | 153 |
| Z11134 | VDAKYAKEEAQAWLEIHLLPNLTVDQMAAFISKLFDDPSQSSELLSEAKKLNDSQAPK | 154 |
| Z11135 | VDAKYAKEERHAWFEIHSLPNLTVNQMSAFISKLFDDPSQSSELLSEAKKLNDSQAPK | 155 |
| Z11136 | VDAKYAKEEADAWWEIHALPNLTVDQMAAFISKLFDDPSQSSELLSEAKKLNDSQAPK | 156 |
| Z11137 | VDAKYAKEEARAWLEIHALPNLTVTQMAAFITKLFDDPSQSSELLSEAKKLNDSQAPK | 157 |
| Z11138 | VDAKYAKEERRAWNEIHLLPNLTIKLYDDPSQSSELLSEAKKLNDSQAPK | 158 |
| Z11139 | VDAKYAKEERHAWYEIHTLPNLTVTQMSAFIQKLFDDPSQSSELLSEAKKLNDSQAPK | 159 |
| Z11140 | VDAKYAKEEAQAWFEIHLLPNLTIDQMAAFISKLFDDPSQSSELLSEAKKLNDSQAPK | 160 |
| Z11141 | VDAKYAKEERAAWHEIHVLPNLTIVSQMAAFIIKLFDDPSQSSELLSEAKKLNDSQAPK | 161 |
| Z11142 | VDAKYAKEEREAWYEIHTLPNLTINQRTAFIQKLFDDPSQSSELLSEAKKLNDSQAPK | 162 |
| Z11143 | VDAKYAKEEAWYEIHVLPNLTVHQRAAFISKLFDDPSQSSELLSEAKKLNDSQAPK | 163 |
| Z11144 | VDAKYAKEERHAWFEIHTLPNLTVHVIAAFISKLFDDPSQSSELLSEAKKLNDSQAPK | 164 |
| Z11145 | VDAKYAKEERHAWYEIHVLPNLTVSQMAAFIMKLFDDPSQSSELLSEAKKLNDSQAPK | 165 |

FIG. 1F

| Designation | Sequence | SEQ ID NO |
|---|---|---|
| Z11146 | VDAKYAKEERDAWLEIHMLPNLTITQVAAFISKLFDDPSQSSELLSEAKKLNDSQAPK | 166 |
| Z11147 | VDAKYAKEEARAWHEIHVLPNLTAEQMAAFISKLFDDPSQSSELLSEAKKLNDSQAPK | 167 |
| Z11148 | VDAKYAKEEAEAWLEIHLLPNLTVEQITAFISKLFDDPSQSSELLSEAKKLNDSQAPK | 168 |
| Z11149 | VDAKYAKEERDAWHEIHLLPNLTVEQRAAFISKLFDDPSQSSELLSEAKKLNDSQAPK | 169 |
| Z11150 | VDAKYAKEERKAWTEIHSLPNLTVTQMAAFISKLFDDPSQSSELLSEAKKLNDSQAPK | 170 |
| Z11151 | VDAKYAKEERDAWHEIHILPNLTVEQMSAFISKLFDDPSQSSELLSEAKKLNDSQAPK | 171 |
| Z11152 | VDAKYAKEEAEAWFEIHALPNLTAEQMAAFISKLFDDPSQSSELLSEAKKLNDSQAPK | 172 |
| Z11153 | VDAKYAKEEHQAWWEIHLLPNLTVDQMSAFISKLFDDPSQSSELLSEAKKLNDSQAPK | 173 |
| Z11154 | VDAKYAKEERDAWHEIHKLPNLTVNQVAAFISKLFDDPSQSSELLSEAKKLNDSQAPK | 174 |
| Z11155 | VDAKYAKEEADAWFEIHLLPNLTVDQIAAFIQKLFDDPSQSSELLSEAKKLNDSQAPK | 175 |
| Z11156 | VDAKYAKEERAAWYEIHVLPNLTVEQMAAFIQKLFDDPSQSSELLSEAKKLNDSQAPK | 176 |
| Z11157 | VDAKYAKEEIHRAWHEIHLLPNLTVNQIAAFISKLFDDPSQSSELLSEAKKLNDSQAPK | 177 |
| Z11158 | VDAKYAKEEAVAWHEIHMLPNLTVEQMAAFISKLFDDPSQSSELLSEAKKLNDSQAPK | 178 |
| Z11159 | VDAKYAKEEREAWWEIHALPNLTVSQMAAFISKLFDDPSQSSELLSEAKKLNDSQAPK | 179 |
| Z11160 | VDAKYAKEERKAWFEIHSLPNLTVDQMSAFISKLFDDPSQSSELLSEAKKLNDSQAPK | 180 |
| Z11161 | VDAKYAKEEQRAWWEIHTLPNLTTDQMAAFISKLFDDPSQSSELLSEAKKLNDSQAPK | 181 |
| Z11162 | VDAKYAKEERQAWFEIHALPNLTVDQAAAFIIKLYDDPSQSSELLSEAKKLNDSQAPK | 182 |
| Z11163 | VDAKYAKEEARAWTEIHALPNLTVDWMAAFISKLFDDPSQSSELLSEAKKLNDSQAPK | 183 |
| Z11164 | VDAKYAKEERRAWHEIHMLPNLTVTQMSAFISKLFDDPSQSSELLSEAKKLNDSQAPK | 184 |
| Z11165 | VDAKYAKEEAKAWLEIHLLPNLTVNQMAAFISKLFDDPSQSSELLSEAKKLNDSQAPK | 185 |
| Z11166 | VDAKYAKEEREAWHEIHLLPNLTIISQIAAFISKLFDDPSQSSELLSEAKKLNDSQAPK | 186 |
| Z11167 | VDAKYAKEEQHAWYEIHLLPNLTVTQMAAFISKLFDDPSQSSELLSEAKKLNDSQAPK | 187 |
| Z11168 | VDAKYAKEEHKAWFEIHLLPNLTISQMAAFISKLFDDPSQSSELLSEAKKLNDSQAPK | 188 |
| Z11169 | VDAKYAKEERRAWYEIHLLPNLTVTQMTAFISKLFDDPSQSSELLSEAKKLNDSQAPK | 189 |
| Z11170 | VDAKYAKEERHAWTEIHILPNLTVRQMAAFISKLFDDPSQSSELLSEAKKLNDSQAPK | 190 |
| Z11171 | VDAKYAKEERHAWHEIHLLPNLTIQQMAAFISKLFDDPSQSSELLSEAKKLNDSQAPK | 191 |
| Z11172 | VDAKYAKEEQHAWTEIHKLPNLTIQQMAAFIQKLFDDPSQSSELLSEAKKLNDSQAPK | 192 |
| Z11173 | VDAKYAKEEHRAWTEIHLLPNLTVSQMVAFISKLFDDPSQSSELLSEAKKLNDSQAPK | 193 |
| Z11174 | VDAKYAKEEQDAWYEIHVLPNLTVEQLVAFISKLFDDPSQSSELLSEAKKLNDSQAPK | 194 |
| Z11175 | VDAKYAKEEREAWHEIHSLPNLTVDQMTAFIKLMDDPSQSSELLSEAKKLNDSQAPK | 195 |
| Z11176 | VDAKYAKEEAAAWFEIHLLPNLTTEQMAAFIMKLFDDPSQSSELLSEAKKLNDSQAPK | 196 |
| Z11177 | VDAKYAKEEARAWYEIHILPNLTVRQMAAFISKLFDDPSQSSELLSEAKKLNDSQAPK | 197 |
| Z11178 | VDAKYAKEEARAWTEIHALPNLTVDQVTAFIIKLYDDPSQSSELLSEAKKLNDSQAPK | 198 |

FIG. 1G

| Designation | Sequence | SEQ ID NO |
|---|---|---|
| Z11179 | VDAKYAKEEQRAWFEIHTLPNLTVDQIEAFISKLFDDPSQSSELLSEAKKLNDSQAPK | 199 |
| Z11180 | VDAKYAKEEAAAWHEIHILPNLTVSQMAAFISKLFDDPSQSSELLSEAKKLNDSQAPK | 200 |
| Z11181 | VDAKYAKEEAQAWWEIHSLPNLTVEQTSAFIQKLFDDPSQSSELLSEAKKLNDSQAPK | 201 |
| Z11182 | VDAKYAKEEREAWHEIHALPNLTIDQRVAFISKLFDDPSQSSELLSEAKKLNDSQAPK | 202 |
| Z11183 | VDAKYAKEEREAWYEIHLLPNLTINQMAAFISKLFDDPSQSSELLSEAKKLNDSQAPK | 203 |
| Z11184 | VDAKYAKEERDAWYEIHLLPNLTIRQMAAFISKLFDDPSQSSELLSEAKKLNDSQAPK | 204 |
| Z11185 | VDAKYAKEEQKAWTEIHLLPNLTVHQIAAFISKLFDDPSQSSELLSEAKKLNDSQAPK | 205 |
| Z11186 | VDAKYAKEERAAWREIHLLPNLTTEQRTAFISKLFDDPSQSSELLSEAKKLNDSQAPK | 206 |
| Z11187 | VDAKYAKEEQDAWREIHLLPNLTINQIVAFIQKLFDDPSQSSELLSEAKKLNDSQAPK | 207 |
| Z11188 | VDAKYAKEEREAWYEIHSLPNLTVTQIAAFISKLFDDPSQSSELLSEAKKLNDSQAPK | 208 |
| Z11189 | VDAKYAKEEATAWYEIHILPNLTVDQMAAFISKLFDDPSQSSELLSEAKKLNDSQAPK | 209 |
| Z11190 | VDAKYAKEERDAWYEIHKLPNLTANQMAAFISKLFDDPSQSSELLSEAKKLNDSQAPK | 210 |
| Z11191 | VDAKYAKEERDAWFEIHALPNLTVHQMTAFIIKLFDDPSQSSELLSEAKKLNDSQAPK | 211 |
| Z11192 | VDAKYAKEEREAWSEIHKLPNLTVDQMAAFISKLFDDPSQSSELLSEAKKLNDSQAPK | 212 |
| Z11193 | VDAKYAKEEREAWFEIHLLPNLTVDQMAAFISKLFDDPSQSSELLSEAKKLNDSQAPK | 213 |
| Z11194 | VDAKYAKEERKAWYEIHLLPNLTVQQMAAFISKLFDDPSQSSELLSEAKKLNDSQAPK | 214 |
| Z11195 | VDAKYAKEEREAWYEIHSLPNLTVNQVAAFISKLFDDPSQSSELLSEAKKLNDSQAPK | 215 |
| Z11196 | VDAKYAKEERHAWREIHLLPNLTTEQRVAFIQKLFDDPSQSSELLSEAKKLNDSQAPK | 216 |
| Z11197 | VDAKYAKEEREAWTEIHSLPNLTVDQVTAFISKLFDDPSQSSELLSEAKKLNDSQAPK | 217 |
| Z11198 | VDAKYAKEERDAWWEIHLLPNLTVNQISAFISKLFDDPSQSSELLSEAKKLNDSQAPK | 218 |
| Z11199 | VDAKYAKEEHHAWREIHLLPNLTVEQMAAFISKLFDDPSQSSELLSEAKKLNDSQAPK | 219 |
| Z11200 | VDAKYAKEEQQAWHEIHLLPNLTVDQMAAFISKLFDDPSQSSELLSEAKKLNDSQAPK | 220 |
| Z11201 | VDAKYAKEEAQAWHEIHTLPNLTIHQMSAFISKLFDDPSQSSELLSEAKKLNDSQAPK | 221 |
| Z11202 | VDAKYAKEEAKAWWEIHVLPNLTIDQIAAFISKLFDDPSQSSELLSEAKKLNDSQAPK | 222 |
| Z11203 | VDAKYAKEEAQAWHEIHTLPNLTTEQMAAFISKLFDDPSQSSELLSEAKKLNDSQAPK | 223 |
| Z11204 | VDAKYAKEERDAWSEIHSLPNLTISQMAAFISKLFDDPSQSSELLSEAKKLNDSQAPK | 224 |
| Z11205 | VDAKYAKEERKAWHEIHILPNLTAEQLAAFISKLFDDPSQSSELLSEAKKLNDSQAPK | 225 |
| Z11206 | VDAKYAKEEADAWREIHVLPNLTTQQITAFIQKLFDDPSQSSELLSEAKKLNDSQAPK | 226 |
| Z11207 | VDAKYAKEERSAWTEIHMLPNLTVQQRAAFISKLFDDPSQSSELLSEAKKLNDSQAPK | 227 |
| Z11208 | VDAKYAKEEREAWYEIHLLPNLTIDQMSAFISKLFDDPSQSSELLSEAKKLNDSQAPK | 228 |
| Z11209 | VDAKYAKEERKAWFEIHLLPNLTVEQIVAFIQKLFDDPSQSSELLSEAKKLNDSQAPK | 229 |
| Z11210 | VDAKYAKEEREAWYEIHLLPNLTVNQMAAFISKLFDDPSQSSELLSEAKKLNDSQAPK | 230 |
| Z11211 | VDAKYAKEEADAWFEIHLLPNLTIDQVSAFISKLFDDPSQSSELLSEAKKLNDSQAPK | 231 |

FIG. 1H

| Designation | Sequence | SEQ ID NO |
|---|---|---|
| Z11212 | VDAKYAKEERDAWFEIHLLPNLTIEQMAAFISKLFDDPSQSSELLSEAKKLNDSQAPK | 232 |
| Z11216 | VDAKYAKEEADAWREIHTLPNLTVDQMSAFISKLFDDPSQSSELLSEAKKLNDSQAPK | 233 |
| Z11219 | VDAKYAKEERVAWYEIHMLPNLTINQMAAFISKLFDDPSQSSELLSEAKKLNDSQAPK | 234 |
| Z11220 | VDAKYAKEERDAWYEIHLLPNLTVNQMAAFISKLFDDPSQSSELLSEAKKLNDSQAPK | 235 |
| Z11221 | VDAKYAKEERDAWWEIHSLPNLTTQQMAAFIIKLYDDPSQSSELLSEAKKLNDSQAPK | 236 |
| Z11223 | VDAKYAKEERARWHEIHTLPNLTIEQMAAFISKLFDDPSQSSELLSEAKKLNDSQAPK | 237 |
| Z11225 | VDAKYAKEERAAWYEIHLLPNLTVEQTAAFISKLFDDPSQSSELLSEAKKLNDSQAPK | 238 |
| Z11226 | VDAKYAKEEREAWYEIHLLPNLTVEQIAAFISKLFDDPSQSSELLSEAKKLNDSQAPK | 239 |
| Z11227 | VDAKYAKEEQHAWREIHLLPNLTTDQMAAFIQKLFDDPSQSSELLSEAKKLNDSQAPK | 240 |
| Z11228 | VDAKYAKEEASAWWEIHLLPNLTTTQRAAFISKLFDDPSQSSELLSEAKKLNDSQAPK | 241 |
| Z11230 | VDAKYAKEEATAWYEIHALPNLTVDQMVAFISKLFDDPSQSSELLSEAKKLNDSQAPK | 242 |
| Z11231 | VDAKYAKEEHKAWTEIHLLPNLTVSQISAFISKLFDDPSQSSELLSEAKKLNDSQAPK | 243 |
| Z11232 | VDAKYAKEEQAAWREIHTLPNLTIEQIAAFISKLFDDPSQSSELLSEAKKLNDSQAPK | 244 |
| Z11233 | VDAKYAKEERAAWFEIHTLPNLTVNQMAAFISKLFDDPSQSSELLSEAKKLNDSQAPK | 245 |
| Z11234 | VDAKYAKEEAAAWFEIHALPNLTVNQMAAFISKLFDDPSQSSELLSEAKKLNDSQAPK | 246 |
| Z11236 | VDAKYAKEEAKAWFEIHKLPNLTAEQISAFIIKLFDDPSQSSELLSEAKKLNDSQAPK | 247 |
| Z11238 | VDAKYAKEEREAWYEIHLLPNLTVQQIVAFIIKLFDDPSQSSELLSEAKKLNDSQAPK | 248 |
| Z11239 | VDAKYAKEEQQAWYEIHLLPNLTIEQMAAFISKLFDDPSQSSELLSEAKKLNDSQAPK | 249 |
| Z11240 | VDAKYAKEERDAWFEIHALPNLTVDQMVAFISKLFDDPSQSSELLSEAKKLNDSQAPK | 250 |
| Z11241 | VDAKYAKEERAAWFEIHTLPNLTVQQMAAFISKLFDDPSQSSELLSEAKKLNDSQAPK | 251 |
| Z11242 | VDAKYAKEEQKAWHEIHKLPNLTVDQTTAFISKLFDDPSQSSELLSEAKKLNDSQAPK | 252 |
| Z11243 | VDAKYAKEEREAWYEIHLLPNLTIEQMVAFISKLFDDPSQSSELLSEAKKLNDSQAPK | 253 |
| Z11244 | VDAKYAKEEAEAWFEIHTLPNLTVDQMAAFIVKLYDDPSQSSELLSEAKKLNDSQAPK | 254 |
| Z11245 | VDAKYAKEEAEAWFEIHLLPNLTVTQIAAFISKLFDDPSQSSELLSEAKKLNDSQAPK | 255 |
| Z11246 | VDAKYAKEERQAWYEIHALPNLTADQMAAFIQKLFDDPSQSSELLSEAKKLNDSQAPK | 256 |
| Z11247 | VDAKYAKEEQSAWYEIHALPNLTVQQMEAFISKLFDDPSQSSELLSEAKKLNDSQAPK | 257 |
| Z11248 | VDAKYAKEEADAWLEIHLLPNLTVEQMAAFISKLFDDPSQSSELLSEAKKLNDSQAPK | 258 |
| Z11249 | VDAKYAKEEQQAWWEIHTLPNLTVDQRSAFIVKLYDDPSQSSELLSEAKKLNDSQAPK | 259 |
| Z11250 | VDAKYAKEERKAWHEIHILPNLTVNQISAFIQKLFDDPSQSSELLSEAKKLNDSQAPK | 260 |
| Z11252 | VDAKYAKEEAHAWWEIHKLPNLTTDQTAAFISKLFDDPSQSSELLSEAKKLNDSQAPK | 261 |
| Z11253 | VDAKYAKEERDAWYEIHILPNLTVTQMAAFISKLFDDPSQSSELLSEAKKLNDSQAPK | 262 |
| Z11254 | VDAKYAKEEAQAWREIHTLPNLTAQQMAAFISKLFDDPSQSSELLSEAKKLNDSQAPK | 263 |
| Z11255 | VDAKYAKEERRAWHEIHVLPNLTVEQMAAFISKLFDDPSQSSELLSEAKKLNDSQAPK | 264 |

FIG. 11

| Designation | Sequence | SEQ ID NO |
|---|---|---|
| Z11256 | VDAKYAKEEREAWSEIHLLPNLTVTQMAAFISKLFDDPSQSSELLSEAKKLNDSQAPK | 265 |
| Z11257 | VDAKYAKEERKAWYEIHLLPNLTVSQMAAFISKLFDDPSQSSELLSEAKKLNDSQAPK | 266 |
| Z11258 | VDAKYAKEEARAWYEIHLLPNLTVTQMAAFISKLFDDPSQSSELLSEAKKLNDSQAPK | 267 |
| Z11259 | VDAKYAKEEHEAWTEIHKLPNLTTEQMAAFISKLFDDPSQSSELLSEAKKLNDSQAPK | 268 |
| Z11260 | VDAKYAKEERDAWFEIHSLPNLTVQQMAAFISKLFDDPSQSSELLSEAKKLNDSQAPK | 269 |
| Z11261 | VDAKYAKEEQSAWHEIHLLPNLTVDQIAAFISKLFDDPSQSSELLSEAKKLNDSQAPK | 270 |
| Z11262 | VDAKYAKEEQAAWYEIHALPNLTVDQMTAFISKLFDDPSQSSELLSEAKKLNDSQAPK | 271 |
| Z11263 | VDAKYAKEEAAAWREIHLLPNLTTQQMAAFISKLFDDPSQSSELLSEAKKLNDSQAPK | 272 |
| Z11264 | VDAKYAKEEREAWYEIHILPNLTVEQMAAFISKLFDDPSQSSELLSEAKKLNDSQAPK | 273 |
| Z11265 | VDAKYAKEERKAWYEIHTLPNLTVDQMAAFISKLFDDPSQSSELLSEAKKLNDSQAPK | 274 |
| Z11266 | VDAKYAKEEAKAWREIHLLPNLTVEQMAAFISKLFDDPSQSSELLSEAKKLNDSQAPK | 275 |
| Z11267 | VDAKYAKEEAQAWSEIHMLPNLTVTQIAAFISKLFDDPSQSSELLSEAKKLNDSQAPK | 276 |
| Z11268 | VDAKYAKEEAHAWHEIHILPNLTVDQMSAFISKLFDDPSQSSELLSEAKKLNDSQAPK | 277 |
| Z11269 | VDAKYAKEEREAWFEIHLLPNLTVEQIAAFISKLFDDPSQSSELLSEAKKLNDSQAPK | 278 |
| Z11270 | VDAKYAKEERKAWWEIHLLPNLTIEQMAAFISKLFDDPSQSSELLSEAKKLNDSQAPK | 279 |
| Z11271 | VDAKYAKEERDAWYEIHTLPNLTVEQMVAFISKLFDDPSQSSELLSEAKKLNDSQAPK | 280 |
| Z11272 | VDAKYAKEERKAWYEIHALPNLTVSQMAAFIKLYDDPSQSSELLSEAKKLNDSQAPK | 281 |
| Z11273 | VDAKYAKEEHKAWWEIHALPNLTISQITAFISKLFDDPSQSSELLSEAKKLNDSQAPK | 282 |
| Z11274 | VDAKYAKEEAQAWYEIHLLPNLTIEQMAAFISKLFDDPSQSSELLSEAKKLNDSQAPK | 283 |
| Z11275 | VDAKYAKEEAQAWYEIHALPNLTIDQMAAFISKLFDDPSQSSELLSEAKKLNDSQAPK | 284 |
| Z11276 | VDAKYAKEEHDAWWEIHILPNLTVEQIAAFISKLFDDPSQSSELLSEAKKLNDSQAPK | 285 |
| Z11279 | VDAKYAKEEARAWLEIHTLPNLTITQRAAFISKLFDDPSQSSELLSEAKKLNDSQAPK | 286 |
| Z11281 | VDAKYAKEERKAWHEIHILPNLTINQRAAFISKLFDDPSQSSELLSEAKKLNDSQAPK | 287 |
| Z11282 | VDAKYAKEEREAWYEIHMLPNLTVTQMAAFISKLFDDPSQSSELLSEAKKLNDSQAPK | 288 |
| Z11284 | VDAKYAKEERDAWFEIHILPNLTIHQMAAFISKLFDDPSQSSELLSEAKKLNDSQAPK | 289 |
| Z11285 | VDAKYAKEERDAWYEIHTLPNLTVDQMVAFISKLFDDPSQSSELLSEAKKLNDSQAPK | 290 |
| Z11286 | VDAKYAKEEAQAWYEIHTLPNLTVDQIAAFISKLFDDPSQSSELLSEAKKLNDSQAPK | 291 |
| Z11287 | VDAKYAKEERVAWWEIHSLPNLTIDQRSAFISKLFDDPSQSSELLSEAKKLNDSQAPK | 292 |
| Z11288 | VDAKYAKEEHEAWTEIHLLPNLTVSQIAAFISKLFDDPSQSSELLSEAKKLNDSQAPK | 293 |
| Z11289 | VDAKYAKEEAQAWREIHLLPNLTVDQIAAFISKLFDDPSQSSELLSEAKKLNDSQAPK | 294 |
| Z11290 | VDAKYAKEERDAWHEIHVLPNLTAEQMSAFISKLFDDPSQSSELLSEAKKLNDSQAPK | 295 |
| Z11291 | VDAKYAKEEATAWFEIHTLPNLTVDQMAAFISKLFDDPSQSSELLSEAKKLNDSQAPK | 296 |
| Z11293 | VDAKYAKEERHAWFEIHTLPNLTVTQMAAFISKLFDDPSQSSELLSEAKKLNDSQAPK | 297 |

FIG. 1J

| Designation | Sequence | SEQ ID NO |
|---|---|---|
| Z11294 | VDAKYAKEEREAWWEIHALPNLTTNQVAAFISKLFDDPSQSSELLSEAKKLNDSQAPK | 298 |
| Z11295 | VDAKYAKEERRAWWEIHLLPNLTIQQIAAFISKLFDDPSQSSELLSEAKKLNDSQAPK | 299 |
| Z11296 | VDAKYAKEEAHAWFEIHILPNLTIDQMAAFISKLFDDPSQSSELLSEAKKLNDSQAPK | 300 |
| Z11297 | VDAKYAKEEARAWREIHLLPNLTVEQMAAFISKLFDDPSQSSELLSEAKKLNDSQAPK | 301 |
| Z11298 | VDAKYAKEERRAWYEIHTLPNLTVEQLSAFISKLFDDPSQSSELLSEAKKLNDSQAPK | 302 |
| Z11299 | VDAKYAKEEAHAWHEIHVLPNLTVEQIAAFISKLFDDPSQSSELLSEAKKLNDSQAPK | 303 |
| Z11301 | VDAKYAKEEREAWFEIHTLPNLTVEQMAAFISKLFDDPSQSSELLSEAKKLNDSQAPK | 304 |
| Z11302 | VDAKYAKEERDAWWEIHSLPNLTIDQMAAFISKLFDDPSQSSELLSEAKKLNDSQAPK | 305 |
| Z11303 | VDAKYAKEEARAWHEIHILPNLTIQQITAFIQKLFDDPSQSSELLSEAKKLNDSQAPK | 306 |
| Z11304 | VDAKYAKEEQKAWHEIHLLPNLTINQIVAFISKLFDDPSQSSELLSEAKKLNDSQAPK | 307 |
| Z11305 | VDAKYAKEEREAWYEIHILPNLTVEQMAAFIVKLFDDPSQSSELLSEAKKLNDSQAPK | 308 |
| Z11306 | VDAKYAKEERVAWYEIHALPNLTVTQMAAFISKLFDDPSQSSELLSEAKKLNDSQAPK | 309 |
| Z11307 | VDAKYAKEERVAWLEIHALPNLTVDQMVAFIIKLFDDPSQSSELLSEAKKLNDSQAPK | 310 |
| Z11308 | VDAKYAKEERDAWFEIHMLPNLTVNQMAAFIKLFDDPSQSSELLSEAKKLNDSQAPK | 311 |
| Z11309 | VDAKYAKEEAVAWFEIHTLPNLTVEQMAAFIVKLFDDPSQSSELLSEAKKLNDSQAPK | 312 |
| Z11310 | VDAKYAKEEQDAWSEIHLLPNLTVNQMAAFISKLFDDPSQSSELLSEAKKLNDSQAPK | 313 |
| Z11311 | VDAKYAKEERDAWWEIHALPNLTVDQMVAFISKLFDDPSQSSELLSEAKKLNDSQAPK | 314 |
| Z11312 | VDAKYAKEEAHAWHEIHVLPNLTVHQVAAFISKLFDDPSQSSELLSEAKKLNDSQAPK | 315 |
| Z11313 | VDAKYAKEEREAWYEIHLLPNLTVDQITAFISKLFDDPSQSSELLSEAKKLNDSQAPK | 316 |
| Z11314 | VDAKYAKEEQEAWYEIHTLPNLTISQMAAFISKLFDDPSQSSELLSEAKKLNDSQAPK | 317 |
| Z11315 | VDAKYAKEERDAWYEIHTLPNLTVEQMAAFISKLFDDPSQSSELLSEAKKLNDSQAPK | 318 |
| Z11316 | VDAKYAKEERQAWTEIHLLPNLTVDQIAAFISKLFDDPSQSSELLSEAKKLNDSQAPK | 319 |
| Z11317 | VDAKYAKEERDAWLEIHLLPNLTVEQMAAFISKLFDDPSQSSELLSEAKKLNDSQAPK | 320 |
| Z11318 | VDAKYAKEEQRAWTEIHTLPNLTVDQMAAFISKLFDDPSQSSELLSEAKKLNDSQAPK | 321 |
| Z11319 | VDAKYAKEERKAWWEIHLLPNLTVDQITAFISKLFDDPSQSSELLSEAKKLNDSQAPK | 322 |
| Z11320 | VDAKYAKEEARAWHEIHILPNLTVDQIAAFISKLFDDPSQSSELLSEAKKLNDSQAPK | 323 |
| Z11322 | VDAKYAKEEREAWHEIHILPNLTVTQMAAFISKLFDDPSQSSELLSEAKKLNDSQAPK | 324 |
| Z11323 | VDAKYAKEEQDAWWEIHKLPNLTTHQVAAFISKLFDDPSQSSELLSEAKKLNDSQAPK | 325 |
| Z11324 | VDAKYAKEERRAWFEIHALPNLTTEQMAAFIWKLFDDPSQSSELLSEAKKLNDSQAPK | 326 |
| Z11325 | VDAKYAKEEAAAWFEIHTLPNLTIEQMSAFISKLFDDPSQSSELLSEAKKLNDSQAPK | 327 |
| Z11326 | VDAKYAKEEREAWFEIHLLPNLTIEQMVAFISKLFDDPSQSSELLSEAKKLNDSQAPK | 328 |
| Z11327 | VDAKYAKEERKAWYEIHTLPNLTVNQMAAFISKLFDDPSQSSELLSEAKKLNDSQAPK | 329 |
| Z11328 | VDAKYAKEERQAWLEIHLLPNLTIEQMAAFISKLFDDPSQSSELLSEAKKLNDSQAPK | 330 |

FIG. 1K

| Designation | Sequence | SEQ ID NO |
|---|---|---|
| Z11330 | VDAKYAKEEHHAWLEIHTLPNLTVDQMAAFISKLFDDPSQSSELLSEAKKLNDSQAPK | 331 |
| Z11331 | VDAKYAKEEQQAWWEIHKLPNLTVEQMTAFIIKLYDDPSQSSELLSEAKKLNDSQAPK | 332 |
| Z11332 | VDAKYAKEERKAWFEIHALPNLTVTQVAAFISKLFDDPSQSSELLSEAKKLNDSQAPK | 333 |
| Z11333 | VDAKYAKEEHRAWTEIHKLPNLTTQQMAAFISKLFDDPSQSSELLSEAKKLNDSQAPK | 334 |
| Z11334 | VDAKYAKEEAQAWHEIHILPNLTVDQMAAFISKLFDDPSQSSELLSEAKKLNDSQAPK | 335 |
| Z11335 | VDAKYAKEEQKAWFEIHLLPNLTVEQIAAFIQKLFDDPSQSSELLSEAKKLNDSQAPK | 336 |
| Z11336 | VDAKYAKEERHAWYEIHLLPNLTVRQMAAFISKLFDDPSQSSELLSEAKKLNDSQAPK | 337 |
| Z11337 | VDAKYAKEERDAWYEIHLLPNLTVNQIAAFISKLFDDPSQSSELLSEAKKLNDSQAPK | 338 |
| Z11338 | VDAKYAKEEAHAWWEIHALPNLTVDQMAAFISKLFDDPSQSSELLSEAKKLNDSQAPK | 339 |
| Z11339 | VDAKYAKEEADAWFEIHVLPNLTIQQIAAFISKLFDDPSQSSELLSEAKKLNDSQAPK | 340 |
| Z11340 | VDAKYAKEERRAWFEIHILPNLTVNQMAAFISKLFDDPSQSSELLSEAKKLNDSQAPK | 341 |
| Z11341 | VDAKYAKEERKAWYEIHVLPNLTVRQMAAFIQKLFDDPSQSSELLSEAKKLNDSQAPK | 342 |
| Z11342 | VDAKYAKEERHAWHEIHILPNLTVDQISAFISKLFDDPSQSSELLSEAKKLNDSQAPK | 343 |
| Z11343 | VDAKYAKEERKAWLEIHLLPNLTVEQMAAFISKLFDDPSQSSELLSEAKKLNDSQAPK | 344 |
| Z11344 | VDAKYAKEEREAWWEIHKLPNLTVTQMAAFISKLFDDPSQSSELLSEAKKLNDSQAPK | 345 |
| Z11345 | VDAKYAKEERHAWYEIHTLPNLTVNQMAAFISKLFDDPSQSSELLSEAKKLNDSQAPK | 346 |
| Z11346 | VDAKYAKEERHAWYEIHVLPNLTVQQMAAFIQKLFDDPSQSSELLSEAKKLNDSQAPK | 347 |
| Z11347 | VDAKYAKEERHAWWEIHALPNLTVEQIAAFIQKLFDDPSQSSELLSEAKKLNDSQAPK | 348 |
| Z11348 | VDAKYAKEEAAAWHEIHILPNLTVSQIAAFISKLFDDPSQSSELLSEAKKLNDSQAPK | 349 |
| Z11349 | VDAKYAKEEASAWTEIHLLPNLTIDQMAAFIQKLFDDPSQSSELLSEAKKLNDSQAPK | 350 |
| Z11350 | VDAKYAKEEQSAWYEIHILPNLTVDQIAAFISKLFDDPSQSSELLSEAKKLNDSQAPK | 351 |
| Z11352 | VDAKYAKEEADAWYEIHLLPNLTVNQMAAFISKLFDDPSQSSELLSEAKKLNDSQAPK | 352 |
| Z11353 | VDAKYAKEEQRAWFEIHTLPNLTVNQMAAFISKLFDDPSQSSELLSEAKKLNDSQAPK | 353 |
| Z11354 | VDAKYAKEEAHAWYEIHILPNLTVSQIAAFISKLFDDPSQSSELLSEAKKLNDSQAPK | 354 |
| Z11355 | VDAKYAKEEAAAWREIHSLPNLTTEQMAAFIMKLFDDPSQSSELLSEAKKLNDSQAPK | 355 |
| Z11356 | VDAKYAKEEHQAWTEIHLLPNLTVQQITAFISKLFDDPSQSSELLSEAKKLNDSQAPK | 356 |
| Z11357 | VDAKYAKEERKAWYEIHSLPNLTVSQMAAFISKLFDDPSQSSELLSEAKKLNDSQAPK | 357 |
| Z11358 | VDAKYAKEEAHAWREIHVLPNLTVDQMAAFISKLFDDPSQSSELLSEAKKLNDSQAPK | 358 |
| Z11359 | VDAKYAKEEAKAWTEIHLLPNLTVHQIAAFISKLFDDPSQSSELLSEAKKLNDSQAPK | 359 |
| Z11360 | VDAKYAKEEREAWFEIHKLPNLTVTQMAAFITKLFDDPSQSSELLSEAKKLNDSQAPK | 360 |
| Z11361 | VDAKYAKEEADAWYEIHILPNLTVSQMAAFISKLFDDPSQSSELLSEAKKLNDSQAPK | 361 |
| Z11362 | VDAKYAKEEARAWYEIHILPNLTVNQMAAFITKLFDDPSQSSELLSEAKKLNDSQAPK | 362 |
| Z11363 | VDAKYAKEEREAWFEIHLLPNLTITQMAAFISKLFDDPSQSSELLSEAKKLNDSQAPK | 363 |

FIG. 1L

| Designation | Sequence | SEQ ID NO |
|---|---|---|
| Z11364 | VDAKYAKEERDAWYEIHLLPNLTVTQMSAFISKLFDDPSQSSELLSEAKKLNDSQAPK | 364 |
| Z11365 | VDAKYAKEEHEAWLEIHALPNLTVEQMSAFIIKLYDDPSQSSELLSEAKKLNDSQAPK | 365 |
| Z11366 | VDAKYAKEEREAWFEIHLLPNLTVHQMAAFISKLFDDPSQSSELLSEAKKLNDSQAPK | 366 |
| Z11367 | VDAKYAKEEHQAWTEIHLLPNLTTEQMAAFIQKLFDDPSQSSELLSEAKKLNDSQAPK | 367 |
| Z11368 | VDAKYAKEEARAWYEIHVLPNLTTDQRSAFISKLFDDPSQSSELLSEAKKLNDSQAPK | 368 |
| Z11369 | VDAKYAKEERDAWFEIHTLPNLTVSQMAAFISKLFDDPSQSSELLSEAKKLNDSQAPK | 369 |
| Z11370 | VDAKYAKEERQAWFEIHSLPNLTVTQMAAFISKLFDDPSQSSELLSEAKKLNDSQAPK | 370 |
| Z11371 | VDAKYAKEERQAWWEIHALPNLTAEQVAAFISKLFDDPSQSSELLSEAKKLNDSQAPK | 371 |
| Z11372 | VDAKYAKEEAKAWYEIHTLPNLTVDQISAFIIKLFDDPSQSSELLSEAKKLNDSQAPK | 372 |
| Z11373 | VDAKYAKEEREAWWEIHLLPNLTVDQISAFISKLFDDPSQSSELLSEAKKLNDSQAPK | 373 |
| Z11374 | VDAKYAKEEADAWTEIHSLPNLTVEQMAAFIWKLLDDPSQSSELLSEAKKLNDSQAPK | 374 |
| Z11375 | VDAKYAKEEIRAAWWEIHTLPNLTTDQRSAFIIKLYDDPSQSSELLSEAKKLNDSQAPK | 375 |
| Z11376 | VDAKYAKEEHRAWTEIHLLPNLTTDQMAAFIIKLFDDPSQSSELLSEAKKLNDSQAPK | 376 |
| Z11377 | VDAKYAKEEADAWWEIHMLPNLTTEQRSAFISKLFDDPSQSSELLSEAKKLNDSQAPK | 377 |
| Z11378 | VDAKYAKEEREAWWEIHKLPNLTVEQVAAFISKLFDDPSQSSELLSEAKKLNDSQAPK | 378 |
| Z11379 | VDAKYAKEEAHAWWEIHALPNLTVHQMAAFISKLFDDPSQSSELLSEAKKLNDSQAPK | 379 |
| Z11381 | VDAKYAKEEAQAWREIHVLPNLTVQQIAAFISKLFDDPSQSSELLSEAKKLNDSQAPK | 380 |
| Z11382 | VDAKYAKEERHAWWEIHKLPNLTVEQVAAFISKLFDDPSQSSELLSEAKKLNDSQAPK | 381 |
| Z11383 | VDAKYAKEEAQAWWEIHKLPNLTVEQLAAFISKLFDDPSQSSELLSEAKKLNDSQAPK | 382 |
| Z11385 | VDAKYAKEERKAWYEIHTLPNLTTDQVAAFISKLFDDPSQSSELLSEAKKLNDSQAPK | 383 |
| Z11386 | VDAKYAKEEREAWHEIHLLPNLTIEQMAAFISKLFDDPSQSSELLSEAKKLNDSQAPK | 384 |
| Z11387 | VDAKYAKEEQKAWWEIHLLPNLTVHQMAAFISKLFDDPSQSSELLSEAKKLNDSQAPK | 385 |
| Z11388 | VDAKYAKEEQAAWLEIHLLPNLTVEQMAAFISKLFDDPSQSSELLSEAKKLNDSQAPK | 386 |
| Z11389 | VDAKYAKEEREAWWEIHALPNLTTNQMAAFISKLFDDPSQSSELLSEAKKLNDSQAPK | 387 |
| Z11390 | VDAKYAKEEAEAWYEIHILPNLTITTQMAAFISKLFDDPSQSSELLSEAKKLNDSQAPK | 388 |
| Z11391 | VDAKYAKEERQAWYEIHLLPNLTVDQMAAFISKLFDDPSQSSELLSEAKKLNDSQAPK | 389 |
| Z11392 | VDAKYAKEEAKAWFEIHTLPNLTVTQMAAFISKLFDDPSQSSELLSEAKKLNDSQAPK | 390 |
| Z11393 | VDAKYAKEEADAWWEIHSLPNLTVDQTAAFISKLFDDPSQSSELLSEAKKLNDSQAPK | 391 |
| Z11394 | VDAKYAKEERVAWYEIHILPNLTVEQTAAFISKLFDDPSQSSELLSEAKKLNDSQAPK | 392 |
| Z11395 | VDAKYAKEERKAWYEIHTLPNLTVDQMSAFISKLFDDPSQSSELLSEAKKLNDSQAPK | 393 |
| Z11396 | VDAKYAKEEAQAWFEIHTLPNLTIEQMAAFIIKLYDDPSQSSELLSEAKKLNDSQAPK | 394 |
| Z11397 | VDAKYAKEERQAWYEIHALPNLTVDQMAAFISKLFDDPSQSSELLSEAKKLNDSQAPK | 395 |
| Z11398 | VDAKYAKEEADAWFEIHVLPNLTTEQMTAFISKLFDDPSQSSELLSEAKKLNDSQAPK | 396 |

FIG. 1M

| Designation | Sequence | SEQ ID NO |
|---|---|---|
| Z11399 | VDAKYAKEERRAWFEIHALPNLTVEQMAAFISKLFDDPSQSSELLSEAKKLNDSQAPK | 397 |
| Z11400 | VDAKYAKEEAKAWYEIHSLPNLTVNQMAAFISKLFDDPSQSSELLSEAKKLNDSQAPK | 398 |
| Z11401 | VDAKYAKEEARAWHEIHTLPNLTVHQMAAFIQKLFDDPSQSSELLSEAKKLNDSQAPK | 399 |
| Z11402 | VDAKYAKEERRAWREIHTLPNLTVSQMAAFISKLFDDPSQSSELLSEAKKLNDSQAPK | 400 |
| Z11403 | VDAKYAKEERAAWYEIHLLPNLTISQMAAFISKLFDDPSQSSELLSEAKKLNDSQAPK | 401 |
| Z11404 | VDAKYAKEERKAWWEIHTLPNLTVSQMAAFISKLFDDPSQSSELLSEAKKLNDSQAPK | 402 |
| Z11405 | VDAKYAKEERHAWYEIHMLPNLTIEQITAFISKLFDDPSQSSELLSEAKKLNDSQAPK | 403 |
| Z11406 | VDAKYAKEEAQAWHEIHLLPNLTVEQMAAFIQKLFDDPSQSSELLSEAKKLNDSQAPK | 404 |
| Z11407 | VDAKYAKEERKAWYEIHMLPNLTVDQIAAFISKLFDDPSQSSELLSEAKKLNDSQAPK | 405 |
| Z11408 | VDAKYAKEEAHAWWEIHKLPNLTVEQVAAFISKLFDDPSQSSELLSEAKKLNDSQAPK | 406 |
| Z11409 | VDAKYAKEERKAWWEIHLLPNLTVNQMAAFISKLFDDPSQSSELLSEAKKLNDSQAPK | 407 |
| Z11410 | VDAKYAKEEREAWYEIHLLPNLTVSQMAAFISKLFDDPSQSSELLSEAKKLNDSQAPK | 408 |
| Z11411 | VDAKYAKEEAKAWHEIHILPNLTVDQMAAFIIKLFDDPSQSSELLSEAKKLNDSQAPK | 409 |
| Z11412 | VDAKYAKEERHAWYEIHTLPNLTVEQMAAFISKLFDDPSQSSELLSEAKKLNDSQAPK | 410 |
| Z11413 | VDAKYAKEERHAWTEIHTLPNLTVQQMAAFISKLFDDPSQSSELLSEAKKLNDSQAPK | 411 |
| Z11414 | VDAKYAKEERDAWHEIHTLPNLTVNQMAAFISKLFDDPSQSSELLSEAKKLNDSQAPK | 412 |
| Z11415 | VDAKYAKEEREAWYEIHLLPNLTTNQRSAFISKLFDDPSQSSELLSEAKKLNDSQAPK | 413 |
| Z11416 | VDAKYAKEEAVAWREIHLLPNLTVDQLAAFISKLFDDPSQSSELLSEAKKLNDSQAPK | 414 |
| Z11417 | VDAKYAKEERAAWTEIHLLPNLTVDQIAAFISKLFDDPSQSSELLSEAKKLNDSQAPK | 415 |
| Z11418 | VDAKYAKEEQAAWFEIHVLPNLTIEQRAAFISKLFDDPSQSSELLSEAKKLNDSQAPK | 416 |
| Z11419 | VDAKYAKEERTAWWEIHALPNLTVEQIAAFISKLFDDPSQSSELLSEAKKLNDSQAPK | 417 |
| Z11420 | VDAKYAKEEAEAWFEIHTLPNLTVDQRVAFIIKLFDDPSQSSELLSEAKKLNDSQAPK | 418 |
| Z11421 | VDAKYAKEEREAWFEIHTLPNLTINQMAAFISKLFDDPSQSSELLSEAKKLNDSQAPK | 419 |
| Z11422 | VDAKYAKEERQAWFEIHALPNLTVQQRAAFISKLFDDPSQSSELLSEAKKLNDSQAPK | 420 |
| Z11423 | VDAKYAKEEREAWHEIHLLPNLTIDQLAAFISKLFDDPSQSSELLSEAKKLNDSQAPK | 421 |
| Z11424 | VDAKYAKEEHHAWWEIHALPNLTVDQVAAFIIKLYDDPSQSSELLSEAKKLNDSQAPK | 422 |
| Z11425 | VDAKYAKEEAKAWYEIHILPNLTVTQITAFISKLFDDPSQSSELLSEAKKLNDSQAPK | 423 |
| Z11426 | VDAKYAKEEQQAWFEIHTLPNLTVQQVTAFISKLFDDPSQSSELLSEAKKLNDSQAPK | 424 |
| Z11427 | VDAKYAKEERTAWWEIHTLPNLTVTQMAAFISKLFDDPSQSSELLSEAKKLNDSQAPK | 425 |
| Z11428 | VDAKYAKEERAAWYEIHLLPNLTVDQMSAFIIKLFDDPSQSSELLSEAKKLNDSQAPK | 426 |
| Z11429 | VDAKYAKEEQQAWWEIHALPNLTVDQITAFISKLFDDPSQSSELLSEAKKLNDSQAPK | 427 |
| Z11430 | VDAKYAKEERRAWYEIHTLPNLTVSQMAAFIIKLFDDPSQSSELLSEAKKLNDSQAPK | 428 |
| Z11431 | VDAKYAKEEQRAWTEIHMLPNLTANQMAAFISKLFDDPSQSSELLSEAKKLNDSQAPK | 429 |

FIG. 1N

| Designation | Sequence | SEQ ID NO |
|---|---|---|
| Z11432 | VDAKYAKEEHEAWYEIHVLPNLTVNQISAFISKLFDDPSQSSELLSEAKKLNDSQAPK | 430 |
| Z11434 | VDAKYAKEEADAWHEIHLLPNLTVEQMAAFIQKLFDDPSQSSELLSEAKKLNDSQAPK | 431 |
| Z11435 | VDAKYAKEERAWFEIHALPNLTVTQMAAFISKLFDDPSQSSELLSEAKKLNDSQAPK | 432 |
| Z11436 | VDAKYAKEERDAWYEIHLLPNLTVEQMAAFIQKLFDDPSQSSELLSEAKKLNDSQAPK | 433 |
| Z11437 | VDAKYAKEERKAWFEIHLLPNLTVTQMAAFISKLFDDPSQSSELLSEAKKLNDSQAPK | 434 |
| Z11438 | VDAKYAKEEAEAWSEIHLLPNLTVEQMAAFISKLFDDPSQSSELLSEAKKLNDSQAPK | 435 |
| Z11439 | VDAKYAKEERKAWYEIHSLPNLTVNQMAAFIKLFDDPSQSSELLSEAKKLNDSQAPK | 436 |
| Z11440 | VDAKYAKEEAAAWHEIHVLPNLTVDQMAAFIIKLYDDPSQSSELLSEAKKLNDSQAPK | 437 |
| Z11441 | VDAKYAKEERHAWTEIHKLPNLTIQQITAFISKLFDDPSQSSELLSEAKKLNDSQAPK | 438 |
| Z11442 | VDAKYAKEERRAWFEIHALPNLTVQQMVAFISKLFDDPSQSSELLSEAKKLNDSQAPK | 439 |
| Z11443 | VDAKYAKEERDAWYEIHILPNLTVNQIAAFISKLFDDPSQSSELLSEAKKLNDSQAPK | 440 |
| Z11444 | VDAKYAKEEAEAWHEIHVLPNLTVDQMAAFISKLFDDPSQSSELLSEAKKLNDSQAPK | 441 |
| Z11445 | VDAKYAKEEARAWHEIHLLPNLTIQQMAAFISKLFDDPSQSSELLSEAKKLNDSQAPK | 442 |
| Z11446 | VDAKYAKEEAQAWWEIHALPNLTVDQTAAFIKLFDDPSQSSELLSEAKKLNDSQAPK | 443 |
| Z11447 | VDAKYAKEEADAWFEIHTLPNLTVEQIAAFISKLFDDPSQSSELLSEAKKLNDSQAPK | 444 |
| Z11448 | VDAKYAKEEAAAWYEIHILPNLTVQQMAAFISKLFDDPSQSSELLSEAKKLNDSQAPK | 445 |
| Z11449 | VDAKYAKEEAEAWFEIHVLPNLTVSQIAAFISKLFDDPSQSSELLSEAKKLNDSQAPK | 446 |
| Z11450 | VDAKYAKEEQSAWYEIHLLPNLTTNQLTAFISKLFDDPSQSSELLSEAKKLNDSQAPK | 447 |
| Z11451 | VDAKYAKEEARAWYEIHTLPNLTATQMAAFISKLFDDPSQSSELLSEAKKLNDSQAPK | 448 |
| Z11452 | VDAKYAKEEADAWWEIHALPNLTVDQVTAFITKLFDDPSQSSELLSEAKKLNDSQAPK | 449 |
| Z11453 | VDAKYAKEEAHAWREIHILPNLTVNQMAAFISKLFDDPSQSSELLSEAKKLNDSQAPK | 450 |
| Z11454 | VDAKYAKEEAQAWHEIHLLPNLTVHQMAAFISKLFDDPSQSSELLSEAKKLNDSQAPK | 451 |
| Z11455 | VDAKYAKEEARAWHEIHILPNLTTDQMAAFISKLFDDPSQSSELLSEAKKLNDSQAPK | 452 |
| Z11456 | VDAKYAKEERHAWHEIHILPNLTVDQMAAFISKLFDDPSQSSELLSEAKKLNDSQAPK | 453 |
| Z11457 | VDAKYAKEERHAWREIHALPNLTVNQMAAFISKLFDDPSQSSELLSEAKKLNDSQAPK | 454 |
| Z11458 | VDAKYAKEERTAWWEIHALPNLTVSQVAAFISKLFDDPSQSSELLSEAKKLNDSQAPK | 455 |
| Z11459 | VDAKYAKEERHAWYEIHIHLPNLTVDQMAAFITKLFDDPSQSSELLSEAKKLNDSQAPK | 456 |
| Z11460 | VDAKYAKEEQRAWREIHLLPNLTVDQMAAFISKLFDDPSQSSELLSEAKKLNDSQAPK | 457 |
| Z11461 | VDAKYAKEERQAWYEIHVLPNLTVHQMAAFISKLFDDPSQSSELLSEAKKLNDSQAPK | 458 |
| Z11462 | VDAKYAKEEAQAWHEIHTLPNLTVSQMAAFISKLFDDPSQSSELLSEAKKLNDSQAPK | 459 |
| Z11463 | VDAKYAKEEREAWLEIHLLPNLTIDQMSAFISKLFDDPSQSSELLSEAKKLNDSQAPK | 460 |
| Z11464 | VDAKYAKEEHRAWFEIHLLPNLTTEQMAAFISKLFDDPSQSSELLSEAKKLNDSQAPK | 461 |
| Z11465 | VDAKYAKEERRAWYEIHLLPNLTTDQMAAFISKLFDDPSQSSELLSEAKKLNDSQAPK | 462 |

FIG. 10

| Designation | Sequence | SEQ ID NO |
|---|---|---|
| Z11466 | VDAKYAKEEREAWYEIHILPNLTVSQIAAFISKLFDDPSQSSELLSEAKKLNDSQAPK | 463 |
| Z11467 | VDAKYAKEERDAWYEIHILPNLTVSQMAAFISKLFDDPSQSSELLSEAKKLNDSQAPK | 464 |
| Z11468 | VDAKYAKEERDAWYEIHLLPNLTVSQMAAFISKLFDDPSQSSELLSEAKKLNDSQAPK | 465 |
| Z11469 | VDAKYAKEERTAWFEIHSLPNLTAEQMAAFIIKLYDDPSQSSELLSEAKKLNDSQAPK | 466 |
| Z11470 | VDAKYAKEEHRAWLEIHTLPNLTVDQMAAFISKLFDDPSQSSELLSEAKKLNDSQAPK | 467 |
| Z11471 | VDAKYAKEEHAAWYEIHLLPNLTVSQISAFIQKLFDDPSQSSELLSEAKKLNDSQAPK | 468 |
| Z11473 | VDAKYAKEEADAWYEIHALPNLTVDQMAAFISKLFDDPSQSSELLSEAKKLNDSQAPK | 469 |
| Z11474 | VDAKYAKEEAEAWWEIHTLPNLTVDQMAAFISKLFDDPSQSSELLSEAKKLNDSQAPK | 470 |
| Z11475 | VDAKYAKEEAEAWWEIHKLPNLTVEQMTAFIIKLYDDPSQSSELLSEAKKLNDSQAPK | 471 |
| Z11476 | VDAKYAKEEHHAWREIHILPNLTVEQMAAFIIKLFDDPSQSSELLSEAKKLNDSQAPK | 472 |
| Z11477 | VDAKYAKEEREAWYEIHILPNLTIQQMAAFISKLFDDPSQSSELLSEAKKLNDSQAPK | 473 |
| Z11478 | VDAKYAKEEHAAWLEIHLLPNLTIDQMAAFISKLFDDPSQSSELLSEAKKLNDSQAPK | 474 |
| Z11479 | VDAKYAKEERAAWYEIHLLPNLTIHQMAAFISKLFDDPSQSSELLSEAKKLNDSQAPK | 475 |
| Z11480 | VDAKYAKEERTAWYEIHLLPNLTVHQMAAFISKLFDDPSQSSELLSEAKKLNDSQAPK | 476 |
| Z11481 | VDAKYAKEERHAWHEIHSLPNLTIDQLTAFISKLFDDPSQSSELLSEAKKLNDSQAPK | 477 |
| Z11482 | VDAKYAKEEREAWYEIHSLPNLTVDQVAAFISKLFDDPSQSSELLSEAKKLNDSQAPK | 478 |
| Z11483 | VDAKYAKEEHHAWHEIHTLPNLTVHQMAAFISKLFDDPSQSSELLSEAKKLNDSQAPK | 479 |
| Z11484 | VDAKYAKEEAHAWHEIHLLPNLTVEQAAAFISKLFDDPSQSSELLSEAKKLNDSQAPK | 480 |
| Z11485 | VDAKYAKEEAHAWWEIHLLPNLTVNQVAAFISKLFDDPSQSSELLSEAKKLNDSQAPK | 481 |
| Z11486 | VDAKYAKEEARAWYEIHILPNLTVTQMAAFISKLFDDPSQSSELLSEAKKLNDSQAPK | 482 |
| Z11487 | VDAKYAKEEARAWWEIHLLPNLTVDQISAFISKLFDDPSQSSELLSEAKKLNDSQAPK | 483 |
| Z11488 | VDAKYAKEEHDAWFEIHLLPNLTVEQIAAFISKLFDDPSQSSELLSEAKKLNDSQAPK | 484 |
| Z11489 | VDAKYAKEEHTAWYEIHLLPNLTVDQMAAFISKLFDDPSQSSELLSEAKKLNDSQAPK | 485 |
| Z11490 | VDAKYAKEEREAWWEIHALPNLTVNQMAAFIIKLFDDPSQSSELLSEAKKLNDSQAPK | 486 |
| Z11491 | VDAKYAKEERDAWYEISTLPNLTVEQAAAFISKLFDDPSQSSELLSEAKKLNDSQAPK | 487 |
| Z11492 | VDAKYAKEEREAWYEIHLLPNLTITQMAAFISKLFDDPSQSSELLSEAKKLNDSQAPK | 488 |
| Z11493 | VDAKYAKEEAKAWFEIHTLPNLTVDQVAAFISKLFDDPSQSSELLSEAKKLNDSQAPK | 489 |
| Z11494 | VDAKYAKEERQAWWEIHTLPNLTVEQMSAFISKLYDDPSQSSELLSEAKKLNDSQAPK | 490 |
| Z11495 | VDAKYAKEEHEAWHEIHILPNLTVEQMAAFISKLFDDPSQSSELLSEAKKLNDSQAPK | 491 |
| Z11496 | VDAKYAKEERDAWFEIHLLPNLTVDQMAAFISKLFDDPSQSSELLSEAKKLNDSQAPK | 492 |
| Z11497 | VDAKYAKEEAKAWWEIHLLPNLTVNQMAAFISKLFDDPSQSSELLSEAKKLNDSQAPK | 493 |
| Z11498 | VDAKYAKEEARAWWEIHLLPNLTIDQMAAFISKLFDDPSQSSELLSEAKKLNDSQAPK | 494 |
| Z11499 | VDAKYAKEEQKAWWEIHSLPNLTVDQITAFISKLFDDPSQSSELLSEAKKLNDSQAPK | 495 |

FIG. 1P

| Designation | Sequence | SEQ ID NO |
|---|---|---|
| Z11500 | VDAKYAKEEREAWYEIHLLPNLTVSQIAAFISKLFDDPSQSSELLSEAKKLNDSQAPK | 496 |
| Z11501 | VDAKYAKEERRAWHEIQTLPNLTVRQMAAFISKLFDDPSQSSELLSEAKKLNDSQAPK | 497 |
| Z11502 | VDAKYAKEERQAWYEIHTLPNLTATQMAAFIQKLFDDPSQSSELLSEAKKLNDSQAPK | 498 |
| Z11503 | VDAKYAKEERHAWTEIHLLPNLTVNQMAAFIIKLFDDPSQSSELLSEAKKLNDSQAPK | 499 |
| Z11504 | VDAKYAKEEARAWHEIHVLPNLTVNQMTAFISKLFDDPSQSSELLSEAKKLNDSQAPK | 500 |
| Z11505 | VDAKYAKEEAEAWYEIHLLPNLTVNQIAAFISKLFDDPSQSSELLSEAKKLNDSQAPK | 501 |
| Z11506 | VDAKYAKEEAEAWREIHLLPNLTVDQMAAFISKLFDDPSQSSELLSEAKKLNDSQAPK | 502 |
| Z11507 | VDAKYAKEERSAWFEIHTLPNLTVDQMAAFISKLFDDPSQSSELLSEAKKLNDSQAPK | 503 |
| Z11508 | VDAKYAKEEAQAWYEIHALPNLTVEQMAAFISKLFDDPSQSSELLSEAKKLNDSQAPK | 504 |
| Z11509 | VDAKYAKEERTAWWEIHALPNLTVNQVTAFISKLFDDPSQSSELLSEAKKLNDSQAPK | 505 |
| Z11510 | VDAKYAKEEAEAWFEIHVLPNLTTDQRVAFITKLFDDPSQSSELLSEAKKLNDSQAPK | 506 |
| Z11511 | VDAKYAKEEAEAWYEIHVLPNLTVDQMAAFIQKLFDDPSQSSELLSEAKKLNDSQAPK | 507 |
| Z11512 | VDAKYAKEEREAWLEIHLLPNLTVEQMAAFISKLFDDPSQSSELLSEAKKLNDSQAPK | 508 |
| Z11513 | VDAKYAKEERAAWWEIHSLPNLTVSQMAAFISKLFDDPSQSSELLSEAKKLNDSQAPK | 509 |
| Z11514 | VDAKYAKEEAKAWREIHLLPNLTTDQIAAFIMKLFDDPSQSSELLSEAKKLNDSQAPK | 510 |
| Z11515 | VDAKYAKEERQAWHEIHALPNLTVTQMAAFISKLFDDPSQSSELLSEAKKLNDSQAPK | 511 |
| Z11516 | VDAKYAKEERDAWFEIHTLPNLTVDQMAAFIQKLFDDPSQSSELLSEAKKLNDSQAPK | 512 |
| Z11517 | VDAKYAKEERRAWYEIHSLPNLTVNQMAAFIIKLFDDPSQSSELLSEAKKLNDSQAPK | 513 |
| Z11518 | VDAKYAKEEHQAWHEIHLLPNLTVSQMAAFIQKLFDDPSQSSELLSEAKKLNDSQAPK | 514 |
| Z11519 | VDAKYAKEEAEAWLEIHLLPNLTTDQIAAFISKLFDDPSQSSELLSEAKKLNDSQAPK | 515 |
| Z11520 | VDAKYAKEEAHAWHEIHLLPNLTIDQMAAFIMKLFDDPSQSSELLSEAKKLNDSQAPK | 516 |
| Z11521 | VDAKYAKEERAAWYEIHLLPNLTIEQMSAFISKLFDDPSQSSELLSEAKKLNDSQAPK | 517 |
| Z11522 | VDAKYAKEEAKAWFEIHALPNLTTTQMAAFISKLFDDPSQSSELLSEAKKLNDSQAPK | 518 |
| Z11523 | VDAKYAKEERHAWTEIHILPNLTVDQMAAFISKLFDDPSQSSELLSEAKKLNDSQAPK | 519 |
| Z11524 | VDAKYAKEERQAWHEIHILPNLTITQRTAFISKLFDDPSQSSELLSEAKKLNDSQAPK | 520 |
| Z11525 | VDAKYAKEERRAWYEIHTLPNLTITQMAAFIQKLFDDPSQSSELLSEAKKLNDSQAPK | 521 |
| Z11526 | VDAKYAKEEAEAWLEIHLLPNLTVSQMAAFIWKLFDDPSQSSELLSEAKKLNDSQAPK | 522 |
| Z11527 | VDAKYAKEEAHAWWEIHALPNLTTNQMAAFISKLFDDPSQSSELLSEAKKLNDSQAPK | 523 |
| Z11528 | VDAKYAKEERHAWTEIHKLPNLTVRQMAAFISKLFDDPSQSSELLSEAKKLNDSQAPK | 524 |
| Z11529 | VDAKYAKEERQAWTEIHLLPNLTINQMVAFIIKLFDDPSQSSELLSEAKKLNDSQAPK | 525 |
| Z11530 | VDAKYAKEEAHAWHEIHILPNLTVDQMAAFISKLFDDPSQSSELLSEAKKLNDSQAPK | 526 |
| Z11531 | VDAKYAKEERQAWHEIHTLPNLTVNQMAAFISKLFDDPSQSSELLSEAKKLNDSQAPK | 527 |
| Z11532 | VDAKYAKEERHAWWEIHKLPNLTVNQMAAFISKLFDDPSQSSELLSEAKKLNDSQAPK | 528 |

FIG. 1Q

| Designation | Sequence | SEQ ID NO |
|---|---|---|
| Z11533 | VDAKYAKEEAKAWFEIHKLPNLTANQMAAFIIKLYDDPSQSSELLSEAKKLNDSQAPK | 529 |
| Z11534 | VDAKYAKEEREAWYEIHILPNLTVQQRVAFISKLFDDPSQSSELLSEAKKLNDSQAPK | 530 |
| Z11535 | VDAKYAKEEQEAWHEIHILPNLTVTQMTAFISKLFDDPSQSSELLSEAKKLNDSQAPK | 531 |
| Z11536 | VDAKYAKEERQAWFEIHVLPNLTIEQMAAFISKLFDDPSQSSELLSEAKKLNDSQAPK | 532 |
| Z11537 | VDAKYAKEERQAWYEIHKLPNLTVSQMTAFISKLFDDPSQSSELLSEAKKLNDSQAPK | 533 |
| Z11538 | VDAKYAKEEREAWWEIHLLPNLTIDQMAAFIQKLFDDPSQSSELLSEAKKLNDSQAPK | 534 |
| Z11539 | VDAKYAKEEERDAWYEIHTLPNLTVHQMAAFISKLFDDPSQSSELLSEAKKLNDSQAPK | 535 |
| Z11540 | VDAKYAKEEQAAWFEIHALPNLTVSQMAAFISKLFDDPSQSSELLSEAKKLNDSQAPK | 536 |
| Z11541 | VDAKYAKEEAHAWYEIHILPNLTVRQIAAFIQKLFDDPSQSSELLSEAKKLNDSQAPK | 537 |
| Z11542 | VDAKYAKEEAKAWWEIHSLPNLTAEQVSAFIQKLFDDPSQSSELLSEAKKLNDSQAPK | 538 |
| Z11543 | VDAKYAKEEQKAWHEIHILPNLTTHQRVAFISKLFDDPSQSSELLSEAKKLNDSQAPK | 539 |
| Z11544 | VDAKYAKEERQAWYEIHALPNLTVTQMAAFISKLFDDPSQSSELLSEAKKLNDSQAPK | 540 |
| Z11545 | VDAKYAKEEERDAWYEIHILPNLTVSQMSAFIQKLFDDPSQSSELLSEAKKLNDSQAPK | 541 |
| Z11546 | VDAKYAKEEHDAWYEIHLLPNLTVQQMAAFISKLFDDPSQSSELLSEAKKLNDSQAPK | 542 |
| Z11547 | VDAKYAKEEAHAWREIHLLPNLTVHQRTAFISKLFDDPSQSSELLSEAKKLNDSQAPK | 543 |
| Z11548 | VDAKYAKEERHAWREIHLLPNLTHTQMAAFISKLFDDPSQSSELLSEAKKLNDSQAPK | 544 |
| Z11549 | VDAKYAKEERHAWYEIHVLPNLTIQQMAAFIQKLFDDPSQSSELLSEAKKLNDSQAPK | 545 |
| Z11550 | VDAKYAKEERKAWYEIHILPNLTTNQMAAFISKLFDDPSQSSELLSEAKKLNDSQAPK | 546 |
| Z11551 | VDAKYAKEEERDAWREIHLLPNLTVRQLSAFISKLFDDPSQSSELLSEAKKLNDSQAPK | 547 |
| Z11553 | VDAKYAKEERQAWYEIHLLPNLTTQQMAAFIQKLFDDPSQSSELLSEAKKLNDSQAPK | 548 |
| Z11554 | VDAKYAKEERKAWREIHTLPNLTVQQMAAFISKLFDDPSQSSELLSEAKKLNDSQAPK | 549 |
| Z11555 | VDAKYAKEERHAWLEIHKLPNLTITATQMAAFISKLFDDPSQSSELLSEAKKLNDSQAPK | 550 |
| Z11556 | VDAKYAKEEREAWYEIHVLPNLTVEQMVAFISKLFDDPSQSSELLSEAKKLNDSQAPK | 551 |
| Z11557 | VDAKYAKEERQAWFEIHTLPNLTVDQMVAFISKLFDDPSQSSELLSEAKKLNDSQAPK | 552 |
| Z11558 | VDAKYAKEEARAWYEIHSLPNLTVDQMSAFIIKLYDDPSQSSELLSEAKKLNDSQAPK | 553 |
| Z11559 | VDAKYAKEEAHAWWEIHLLPNLTVHQIAAFISKLFDDPSQSSELLSEAKKLNDSQAPK | 554 |
| Z11560 | VDAKYAKEEAQAWHEIHILPNLTIQQIAAFIQKLFDDPSQSSELLSEAKKLNDSQAPK | 555 |
| Z11561 | VDAKYAKEEQDAWWEIHKLPNLTVNQMAAFISKLYDDPSQSSELLSEAKKLNDSQAPK | 556 |
| Z11562 | VDAKYAKEEERAAWHEIHLLPNLTISQMAAFISKLFDDPSQSSELLSEAKKLNDSQAPK | 557 |
| Z11563 | VDAKYAKEERQAWFEIHVLPNLTIHQIAAFISKLFDDPSQSSELLSEAKKLNDSQAPK | 558 |
| Z11564 | VDAKYAKEEREAWWEIHALPNLTANQMAAFITTQMAAFISKLFDDPSQSSELLSEAKKLNDSQAPK | 559 |
| Z11565 | VDAKYAKEEATAWHEIHLLPNLTITTQMAAFISKLFDDPSQSSELLSEAKKLNDSQAPK | 560 |
| Z11566 | VDAKYAKEERKAWFEIHLLPNLTISQMTAFISKLFDDPSQSSELLSEAKKLNDSQAPK | 561 |

FIG. 1R

| Designation | Sequence | SEQ ID NO |
|---|---|---|
| Z11567 | VDAKYAKEEAKAWFEIHALPNLTIQQMAAFISKLFDDPSQSSELLSEAKKLNDSQAPK | 562 |
| Z11568 | VDAKYAKEEARAWHEIHILPNLTTQQMAAFISKLFDDPSQSSELLSEAKKLNDSQAPK | 563 |
| Z11569 | VDAKYAKEEAQAWYEIHLLPNLTVSQIAAFIVKLYDDPSQSSELLSEAKKLNDSQAPK | 564 |
| Z11570 | VDAKYAKEERHAWFEIHKLPNLTVDQVSAFIIKLYDDPSQSSELLSEAKKLNDSQAPK | 565 |
| Z11571 | VDAKYAKEERQAWYEIHVLPNLTVSQMTAFISKLFDDPSQSSELLSEAKKLNDSQAPK | 566 |
| Z11572 | VDAKYAKEEADAWHEIHLLPNLTIDQMAAFISKLFDDPSQSSELLSEAKKLNDSQAPK | 567 |
| Z11573 | VDAKYAKEEASAWREIHILPNLTVNQMAAFISKLFDDPSQSSELLSEAKKLNDSQAPK | 568 |
| Z11574 | VDAKYAKEEAQAWYEIHILPNLTVDQMAAFISKLFDDPSQSSELLSEAKKLNDSQAPK | 569 |
| Z11575 | VDAKYAKEERSAWYEIHILPNLTVHQMTAFISKLFDDPSQSSELLSEAKKLNDSQAPK | 570 |
| Z11576 | VDAKYAKEEATAWREIHLLPNLTVEQMAAFISKLFDDPSQSSELLSEAKKLNDSQAPK | 571 |
| Z11577 | VDAKYAKEERTAWYEIHILPNLTVEQMTAFIQKLFDDPSQSSELLSEAKKLNDSQAPK | 572 |
| Z11578 | VDAKYAKEEAHAWHEIHIIPNLTVDQVVAFISKLFDDPSQSSELLSEAKKLNDSQAPK | 573 |
| Z11579 | VDAKYAKEERRAWYEIHLLPNLTVEQMAAFISKLFDDPSQSSELLSEAKKLNDSQAPK | 574 |
| Z11580 | VDAKYAKEERKAWYEIHLLPNLTVSQMTAFISKLFDDPSQSSELLSEAKKLNDSQAPK | 575 |
| Z11581 | VDAKYAKEERRAWFEIHSLPNLTVRQIAAFIIKLFDDPSQSSELLSEAKKLNDSQAPK | 576 |
| Z11582 | VDAKYAKEERQAWTEIHVLPNLTVNQMAAFISKLFDDPSQSSELLSEAKKLNDSQAPK | 577 |
| Z11583 | VDAKYAKEEAHAWYEIHILPNLTIQQMAAFISKLFDDPSQSSELLSEAKKLNDSQAPK | 578 |
| Z11584 | VDAKYAKEERSAWYEIHLLPNLTVDQMTAFIQKLFDDPSQSSELLSEAKKLNDSQAPK | 579 |
| Z11585 | VDAKYAKEERRAWWEIHTLPNLTVDQMVAFISKLFDDPSQSSELLSEAKKLNDSQAPK | 580 |
| Z11586 | VDAKYAKEERAAWFEIHMLPNLTVEQMAAFISKLFDDPSQSSELLSEAKKLNDSQAPK | 581 |
| Z11587 | VDAKYAKEERTAWYEIHALPNLTVDQMVAFISKLFDDPSQSSELLSEAKKLNDSQAPK | 582 |
| Z11588 | VDAKYAKEERQAWWEIHALPNLTVSQMAAFISKLFDDPSQSSELLSEAKKLNDSQAPK | 583 |
| Z11589 | VDAKYAKEERAAWYEIHLLPNLTVEQMAAFISKLFDDPSQSSELLSEAKKLNDSQAPK | 584 |
| Z11590 | VDAKYAKEEAAAWWEIHMLPNLTIDQMTAFISKLFDDPSQSSELLSEAKKLNDSQAPK | 585 |
| Z11591 | VDAKYAKEERRAWFEIHSLPNLTVRQMAAFISKLFDDPSQSSELLSEAKKLNDSQAPK | 586 |
| Z11592 | VDAKYAKEERHAWWEIHLLPNLTVDQMVAFISKLFDDPSQSSELLSEAKKLNDSQAPK | 587 |
| Z11593 | VDAKYAKEERKAWWEIHLLPNLTVTQIAAFISKLFDDPSQSSELLSEAKKLNDSQAPK | 588 |
| Z11594 | VDAKYAKEERRAWFEIHSLPNLTVHQMTAFISKLFDDPSQSSELLSEAKKLNDSQAPK | 589 |
| Z11595 | VDAKYAKEEAAAWWEIHMLPNLTVSQMAAFISKLFDDPSQSSELLSEAKKLNDSQAPK | 590 |
| Z11596 | VDAKYAKEEAKAWHEIHLLPNLTVHQMAAFISKLFDDPSQSSELLSEAKKLNDSQAPK | 591 |
| Z11597 | VDAKYAKEERKAWTEIHLLPNLTVEQMAAFIIKLFDDPSQSSELLSEAKKLNDSQAPK | 592 |
| Z11598 | VDAKYAKEEREAWFEIHVLPNLTIRQMAAFISKLFDDPSQSSELLSEAKKLNDSQAPK | 593 |
| Z11599 | VDAKYAKEEREAWYEIHALPNLTVQQMSAFISKLFDDPSQSSELLSEAKKLNDSQAPK | 594 |

FIG. 1S

| Designation | Sequence | SEQ ID NO |
|---|---|---|
| Z11600 | VDAKYAKEERQAWFEIHTLPNLTANQMAAFIIKLYDDPSQSSELLSEAKKLNDSQAPK | 595 |
| Z11601 | VDAKYAKEERHAWYEIHTLPNLTVQQMAAFISKLFDDPSQSSELLSEAKKLNDSQAPK | 596 |
| Z11602 | VDAKYAKEERRAWYEIHLLPNLTVNQMVAFISKLFDDPSQSSELLSEAKKLNDSQAPK | 597 |
| Z11603 | VDAKYAKEERHAWYEIHLLPNLTVEQMAAFISKLFDDPSQSSELLSEAKKLNDSQAPK | 598 |
| Z11604 | VDAKYAKEERKAWYEIHLLPNLTVHQMAAFISKLFDDPSQSSELLSEAKKLNDSQAPK | 599 |
| Z11605 | VDAKYAKEERSAWWEIHTLPNLTVDQMVAFISKLFDDPSQSSELLSEAKKLNDSQAPK | 600 |
| Z11606 | VDAKYAKEEARAWFEIHTLPNLTVDQMAAFISKLFDDPSQSSELLSEAKKLNDSQAPK | 601 |
| Z11607 | VDAKYAKEERRAWYEIHSLPNLTVTQMVAFISKLFDDPSQSSELLSEAKKLNDSQAPK | 602 |
| Z11608 | VDAKYAKEEARAWHEIHVLPNLTVEQMTAFIIKLFDDPSQSSELLSEAKKLNDSQAPK | 603 |
| Z11609 | VDAKYAKEERDAWYEIHLLPNLTIDQMAAFIQKLFDDPSQSSELLSEAKKLNDSQAPK | 604 |
| Z11610 | VDAKYAKEEREAWWEIHLLPNLTIRQMAAFISKLFDDPSQSSELLSEAKKLNDSQAPK | 605 |
| Z11618 | VDAKYAKEEQQAWYEIHLLPNLTVQQRSAFISKLFDDPSQSSELLSEAKKLNDSQAPK | 606 |
| Z11619 | VDAKYAKEERDAWWEIHALPNLTVNQMAAFISKLFDDPSQSSELLSEAKKLNDSQAPK | 607 |
| Z11620 | VDAKYAKEEARAWYEIHILPNLTVTQMAAFIQKLFDDPSQSSELLSEAKKLNDSQAPK | 608 |
| Z11621 | VDAKYAKEERVAWYEIHMLPNLTVSQMAAFISKLFDDPSQSSELLSEAKKLNDSQAPK | 609 |
| Z11622 | VDAKYAKEERTAWWEIHALPNLTVQQRSAFISKLFDDPSQSSELLSEAKKLNDSQAPK | 610 |
| Z11623 | VDAKYAKEEAKAWYEIHLLPNLTVRQMAAFISKLFDDPSQSSELLSEAKKLNDSQAPK | 611 |
| Z11624 | VDAKYAKEEAKAWYEIHLLPNLTVRQMAAFIWKLLDDPSQSSELLSEAKKLNDSQAPK | 612 |
| Z11625 | VDAKYAKEERQAWYEIHTLPNLTIDQMSAFISKLFDDPSQSSELLSEAKKLNDSQAPK | 613 |
| Z11626 | VDAKYAKEERKAWWEIHKLPNLTVTQMAAFISKLFDDPSQSSELLSEAKKLNDSQAPK | 614 |
| Z11627 | VDAKYAKEEAHAWYEIHALPNLTVEQMAAFIQKLFDDPSQSSELLSEAKKLNDSQAPK | 615 |
| Z11628 | VDAKYAKEEAHAWREIHLLPNLTVQQIAAFISKLFDDPSQSSELLSEAKKLNDSQAPK | 616 |
| Z11629 | VDAKYAKEERHAWHEIHILPNLTVQQMAAFISKLFDDPSQSSELLSEAKKLNDSQAPK | 617 |
| Z11630 | VDAKYAKEERDAWFEIHALPNLTANQMAAFISKLFDDPSQSSELLSEAKKLNDSQAPK | 618 |
| Z11631 | VDAKYAKEEAKAWYEIHLLPNLTVNQMAAFISKLFDDPSQSSELLSEAKKLNDSQAPK | 619 |
| Z11633 | VDAKYAKEERDAWFEIHSLPNLTVSQMAAFISKLFDDPSQSSELLSEAKKLNDSQAPK | 620 |
| Z11634 | VDAKYAKEERKAWWEIHVLPNLTVDQMAAFISKLFDDPSQSSELLSEAKKLNDSQAPK | 621 |
| Z11635 | VDAKYAKEEAHAWYEIHTLPNLTVRQMAAFISKLFDDPSQSSELLSEAKKLNDSQAPK | 622 |
| Z11636 | VDAKYAKEEARAWREIHTLPNLTVNQMAAFISKLFDDPSQSSELLSEAKKLNDSQAPK | 623 |
| Z11637 | VDAKYAKEERRAWTEIHLLPNLTVEQMAAFISKLFDDPSQSSELLSEAKKLNDSQAPK | 624 |
| Z11638 | VDAKYAKEEAHAWHEIHTLPNLTIDQMVAFISKLFDDPSQSSELLSEAKKLNDSQAPK | 625 |
| Z11639 | VDAKYAKEERQAWYEIHLLPNLTVHQMAAFISKLFDDPSQSSELLSEAKKLNDSQAPK | 626 |
| Z11640 | VDAKYAKEERRAWWEIHLLPNLTVRQMAAFISKLFDDPSQSSELLSEAKKLNDSQAPK | 627 |

FIG. 1T

| Designation | Sequence | SEQ ID NO |
|---|---|---|
| Z11641 | VDAKYAKEEAHAWTEIHKLPNLTVDQMTAFIIKLYDDPSQSSELLSEAKKLNDSQAPK | 628 |
| Z11643 | VDAKYAKEEARAWREIHLLPNLTVTQMAAFISKLFDDPSQSSELLSEAKKLNDSQAPK | 629 |
| Z11645 | VDAKYAKEERQAWWEIHSLPNLTIEQMVAFISKLFDDPSQSSELLSEAKKLNDSQAPK | 630 |
| Z11646 | VDAKYAKEERDAWYEIHLLPNLTIQQMAAFIQKLFDDPSQSSELLSEAKKLNDSQAPK | 631 |
| Z11647 | VDAKYAKEERTAWWEIHLLPNLTVTQMAAFISKLFDDPSQSSELLSEAKKLNDSQAPK | 632 |
| Z11648 | VDAKYAKEERDAWYEIHILPNLTIEQMAAFISKLFDDPSQSSELLSEAKKLNDSQAPK | 633 |
| Z11649 | VDAKYAKEEREAWWEIHSLPNLTAHQMAAFIIKLFDDPSQSSELLSEAKKLNDSQAPK | 634 |
| Z11650 | VDAKYAKEERKAWYEIHSLPNLTVSQMSAFISKLFDDPSQSSELLSEAKKLNDSQAPK | 635 |
| Z11651 | VDAKYAKEERHAWFEIHALPNLTVSQMVAFISKLFDDPSQSSELLSEAKKLNDSQAPK | 636 |
| Z11652 | VDAKYAKEERHAWREIHLLPNLTTEQMSAFIQKLFDDPSQSSELLSEAKKLNDSQAPK | 637 |
| Z11653 | VDAKYAKEEHRAWTEIHLLPNLTVDQMAAFIISKLFDDPSQSSELLSEAKKLNDSQAPK | 638 |
| Z11654 | VDAKYAKEERDAWYEIHLLPNLTTQQRAAFIVKLFDDPSQSSELLSEAKKLNDSQAPK | 639 |
| Z11655 | VDAKYAKEEAQAWWEIHALPNLTVSQMVAFIMKLFDDPSQSSELLSEAKKLNDSQAPK | 640 |
| Z11656 | VDAKYAKEEREAWWEIHALPNLTVNQVVAFISKLFDDPSQSSELLSEAKKLNDSQAPK | 641 |
| Z11657 | VDAKYAKEERQAWYEIHVLPNLTVNQMAAFISKLFDDPSQSSELLSEAKKLNDSQAPK | 642 |
| Z11658 | VDAKYAKEERSAWYEIHLLPNLTVHQMTAFISKLFDDPSQSSELLSEAKKLNDSQAPK | 643 |
| Z11659 | VDAKYAKEEAKAWYEIHILPNLTVHQIAAFISKLFDDPSQSSELLSEAKKLNDSQAPK | 644 |
| Z11660 | VDAKYAKEEQQAWLEIHTLPNLTVSQMQMAAFISKLFDDPSQSSELLSEAKKLNDSQAPK | 645 |
| Z11661 | VDAKYAKEERAAWFEIHLLPNLTVEQMTAFIHKLYDDPSQSSELLSEAKKLNDSQAPK | 646 |
| Z11662 | VDAKYAKEEAHAWREIHLLPNLTVTQMAAFISKLFDDPSQSSELLSEAKKLNDSQAPK | 647 |
| Z11663 | VDAKYAKEEQQAWYEIHLLPNLTITQMAAFIQKLFDDPSQSSELLSEAKKLNDSQAPK | 648 |
| Z11664 | VDAKYAKEERDAWYEIHTLPNLTIHLLPNLTVTQVVAFISKLFDDPSQSSELLSEAKKLNDSQAPK | 649 |
| Z11665 | VDAKYAKEEAHAWYEIHVLPNLTVSQIAAFISKLFDDPSQSSELLSEAKKLNDSQAPK | 650 |
| Z11666 | VDAKYAKEERRAWWEIHALPNLTVSQMVAFISKLFDDPSQSSELLSEAKKLNDSQAPK | 651 |
| Z11667 | VDAKYAKEEAQAWYEIHTLPNLTVHQMAAFISKLFDDPSQSSELLSEAKKLNDSQAPK | 652 |
| Z11668 | VDAKYAKEERAAWFEIHLLPNLTVEQMTAFIHKLYDDPSQSSELLSEAKKLNDSQAPK | 653 |
| Z11669 | VDAKYAKEEAHAWREIHLLPNLTITQMAAFIQKLFDDPSQSSELLSEAKKLNDSQAPK | 654 |
| Z11670 | VDAKYAKEEARAWHEIHVLPNLTVSQIAAFISKLFDDPSQSSELLSEAKKLNDSQAPK | 655 |
| Z11671 | VDAKYAKEEAKAWHEIHVLPNLTVSQIAAFISKLFDDPSQSSELLSEAKKLNDSQAPK | 656 |
| Z11672 | VDAKYAKEEHRAWYEIHLLPNLTINQMAAFIVKLFDDPSQSSELLSEAKKLNDSQAPK | 657 |
| Z11673 | VDAKYAKEEAHAWTEIHKLPNLTVRQMVAFISKLFDDPSQSSELLSEAKKLNDSQAPK | 658 |
| Z11675 | VDAKYAKEERTAWYEIHLLPNLTIQQMAAFISKLFDDPSQSSELLSEAKKLNDSQAPK | 659 |
| Z11676 | VDAKYAKEERKAWYEIHLLPNLTIQQIAAFISKLFDDPSQSSELLSEAKKLNDSQAPK | 660 |

FIG. 1U

| Designation | Sequence | SEQ ID NO |
|---|---|---|
| Z11677 | VDAKYAKEEREAWHEIHLLPNLTVTQMAAFIIKLFDDPSQSSELLSEAKKLNDSQAPK | 661 |
| Z11678 | VDAKYAKEEARAWWEIHLLPNLTVEQMAAFISKLFDDPSQSSELLSEAKKLNDSQAPK | 662 |
| Z11679 | VDAKYAKEERQAWWEIHLLPNLTVTQMAAFISKLFDDPSQSSELLSEAKKLNDSQAPK | 663 |
| Z11680 | VDAKYAKEEAQAWREIHTLPNLTANQMAAFIIKLYDDPSQSSELLSEAKKLNDSQAPK | 664 |
| Z11681 | VDAKYAKEERHAWTEIHLLPNLTISQMAAFISKLFDDPSQSSELLSEAKKLNDSQAPK | 665 |
| Z11682 | VDAKYAKEEARAWWEIHMLPNLTVTQMAAFISKLFDDPSQSSELLSEAKKLNDSQAPK | 666 |
| Z11683 | VDAKYAKEEREAWWEIHLLPNLTAEQMAAFISKLFDDPSQSSELLSEAKKLNDSQAPK | 667 |
| Z11684 | VDAKYAKEEATAWWEIHLLPNLTVTQMAAFIQKLFDDPSQSSELLSEAKKLNDSQAPK | 668 |
| Z11685 | VDAKYAKEEAKAWHEIHLLPNLTVNQMAAFISKLFDDPSQSSELLSEAKKLNDSQAPK | 669 |
| Z11686 | VDAKYAKEERRAWYEIHLLPNLTITQMTAFISKLFDDPSQSSELLSEAKKLNDSQAPK | 670 |
| Z11687 | VDAKYAKEERRAWYEIHLLPNLTVHQIAAFISKLFDDPSQSSELLSEAKKLNDSQAPK | 671 |
| Z11688 | VDAKYAKEIHEAWWEIHLLPNLTVTQMAAFISKLFDDPSQSSELLSEAKKLNDSQAPK | 672 |
| Z11689 | VDAKYAKEERKAWTEIHSLPNLTVDQMSAFIIKLFDDPSQSSELLSEAKKLNDSQAPK | 673 |
| Z11690 | VDAKYAKEEAKAWFEIHLLPNLTINQMAAFISKLFDDPSQSSELLSEAKKLNDSQAPK | 674 |
| Z11691 | VDAKYAKEERDAWYEIHVLPNLTVPNLTIEQMSAFISKLFDDPSQSSELLSEAKKLNDSQAPK | 675 |
| Z11692 | VDAKYAKEEAHAWWEIHALPNLTVTQMAAFISKLFDDPSQSSELLSEAKKLNDSQAPK | 676 |
| Z11693 | VDAKYAKEEAKAWYEIHLLPNLTVTQMAAFIKLFDDPSQSSELLSEAKKLNDSQAPK | 677 |
| Z11694 | VDAKYAKEERDAWWEIHKLPNLTVSQMAAFIQKLFDDPSQSSELLSEAKKLNDSQAPK | 678 |
| Z11695 | VDAKYAKEERDAWYEIHLLPNLTVRQMAAFISKLFDDPSQSSELLSEAKKLNDSQAPK | 679 |
| Z11696 | VDAKYAKEEERAAWWEIHLLPNLTVQQMAAFISKLFDDPSQSSELLSEAKKLNDSQAPK | 680 |
| Z11697 | VDAKYAKEEQQAWYEIHLLPNLTVTQMAAFIIKLFDDPSQSSELLSEAKKLNDSQAPK | 681 |
| Z11699 | VDAKYAKEEADAWFEIHILPNLTIDQMAAFIQKLFDDPSQSSELLSEAKKLNDSQAPK | 682 |
| Z11700 | VDAKYAKEEREAWHEIHTLPNLTVSQMAAFIWKLFDDPSQSSELLSEAKKLNDSQAPK | 683 |
| Z11701 | VDAKYAKEEATAWFEIHTLPNLTVSQMAAFISKLFDDPSQSSELLSEAKKLNDSQAPK | 684 |
| Z11702 | VDAKYAKEEAAAWHEIHILPNLTHHQMAAFIQKLFDDPSQSSELLSEAKKLNDSQAPK | 685 |
| Z11703 | VDAKYAKEEDAWFEIHALPNLTVNQMAAFIIKLYDDPSQSSELLSEAKKLNDSQAPK | 686 |
| Z11704 | VDAKYAKEERKAWYEIHLLPNLTTSQHAAFISKLFDDPSQSSELLSEAKKLNDSQAPK | 687 |
| Z11705 | VDAKYAKEERDAWYEIHLLPNLTVRQMAAFIIKLFDDPSQSSELLSEAKKLNDSQAPK | 688 |
| Z11706 | VDAKYAKEEAVAWHEIHALPNLTVDQMAAFISKLFDDPSQSSELLSEAKKLNDSQAPK | 689 |
| Z11707 | VDAKYAKEEAAAWWEIHALPNLTIEQMVAAFISKLFDDPSQSSELLSEAKKLNDSQAPK | 690 |
| Z11708 | VDAKYAKEEAKAWFEIHALPNLTVQQMAAFIQKLFDDPSQSSELLSEAKKLNDSQAPK | 691 |
| Z11709 | VDAKYAKEEAAAWWEIHSLPNLTVSQMAAFIWKLFDDPSQSSELLSEAKKLNDSQAPK | 692 |
| Z11710 | VDAKYAKEEAKAWHEIHTLPNLTVDQMAAFISKLFDDPSQSSELLSEAKKLNDSQAPK | 693 |

FIG. 1V

| Designation | Sequence | SEQ ID NO |
|---|---|---|
| Z11712 | VDAKYAKEEAQAWWEIHTLPNLTVNQIAAFISKLFDDPSQSSELLSEAKKLNDSQAPK | 694 |
| Z11713 | VDAKYAKEERSAWFEIHVLPNLTIRQMSAFISKLFDDPSQSSELLSEAKKLNDSQAPK | 695 |
| Z11714 | VDAKYAKEERRAWLEIHLLPNLTVTQMTAFISKLFDDPSQSSELLSEAKKLNDSQAPK | 696 |
| Z11715 | VDAKYAKEERAAWFEIHLLPNLTATQIAAFISKLFDDPSQSSELLSEAKKLNDSQAPK | 697 |
| Z11716 | VDAKYAKEERAAWHEIHVLPNLTIHQMAAFISKLFDDPSQSSELLSEAKKLNDSQAPK | 698 |
| Z11717 | VDAKYAKEEARAWYEIHTLPNLTIHQMAAFIQKLFDDPSQSSELLSEAKKLNDSQAPK | 699 |
| Z11718 | VDAKYAKEEAEAWFEIHALPNLTVHQMAAFISKLFDDPSQSSELLSEAKKLNDSQAPK | 700 |
| Z11719 | VDAKYAKEERAAWYEIHSLPNLTTNQMAAFISKLFDDPSQSSELLSEAKKLNDSQAPK | 701 |
| Z11720 | VDAKYAKEEAKAWHEIHVLPNLTIEQRAAFISKLFDDPSQSSELLSEAKKLNDSQAPK | 702 |
| Z11721 | VDAKYAKEERTAWYEIHVLPNLTATQMAAFISKLFDDPSQSSELLSEAKKLNDSQAPK | 703 |
| Z11722 | VDAKYAKEERRAWWEIHLLPNLTVDQMSAFISKLFDDPSQSSELLSEAKKLNDSQAPK | 704 |
| Z11724 | VDAKYAKEEADAWREIHLLPNLTVTQIAAFISKLFDDPSQSSELLSEAKKLNDSQAPK | 705 |
| Z11725 | VDAKYAKEERDAWFEIHVLPNLTTEQMVAFISKLFDDPSQSSELLSEAKKLNDSQAPK | 706 |
| Z11726 | VDAKYAKEEQQAWYEIHVLPNLTVSQMAAFISKLFDDPSQSSELLSEAKKLNDSQAPK | 707 |
| Z11727 | VDAKYAKEERRAWFEIHALPNLTVNQMVAFISKLFDDPSQSSELLSEAKKLNDSQAPK | 708 |
| Z11728 | VDAKYAKEERKAWFEIHSLPNLTATQMHAFISKLFDDPSQSSELLSEAKKLNDSQAPK | 709 |
| Z11729 | VDAKYAKEEQQAWLEIHLLPNLTVEQMTAFIHKLYDDPSQSSELLSEAKKLNDSQAPK | 710 |
| Z11730 | VDAKYAKEEAEAWLEIHLLPNLTVHQMAAFISKLFDDPSQSSELLSEAKKLNDSQAPK | 711 |
| Z11731 | VDAKYAKEERDAWHEIHLLPNLTINQMTAFISKLFDDPSQSSELLSEAKKLNDSQAPK | 712 |
| Z11732 | VDAKYAKEERRAWYEIHTLPNLTVHQMTAFIQKLLDDPSQSSELLSEAKKLNDSQAPK | 713 |
| Z11733 | VDAKYAKEEARAWHEIHLLPNLTVDQTTAFISKLFDDPSQSSELLSEAKKLNDSQAPK | 714 |
| Z11734 | VDAKYAKEERQAWREIHTLPNLTVHQMAAFISKLFDDPSQSSELLSEAKKLNDSQAPK | 715 |
| Z11735 | VDAKYAKEEHDAWREIHTLPNLTVSQMAAFISKLFDDPSQSSELLSEAKKLNDSQAPK | 716 |
| Z11736 | VDAKYAKEERAAWWEIHLLPNLTVHQMSQAFISKLFDDPSQSSELLSEAKKLNDSQAPK | 717 |
| Z11737 | VDAKYAKEEAKAWHEIHALPNLTVSQMAAFISKLFDDPSQSSELLSEAKKLNDSQAPK | 718 |
| Z11738 | VDAKYAKEEAAWWEIHTLPNLTVDQMAAFISKLFDDPSQSSELLSEAKKLNDSQAPK | 719 |
| Z11739 | VDAKYAKEERQAWFEIHKLPNLTVNQMAAFISKLFDDPSQSSELLSEAKKLNDSQAPK | 720 |
| Z11740 | VDAKYAKEERSAWFEIHVLPNLTVNQRAAFISKLFDDPSQSSELLSEAKKLNDSQAPK | 721 |
| Z11741 | VDAKYAKEEAAAWHEIHLLPNLTVTQIAAFISKLFDDPSQSSELLSEAKKLNDSQAPK | 722 |
| Z11742 | VDAKYAKEEREAWAEIHKLPNLTATQMHAFISKLFDDPSQSSELLSEAKKLNDSQAPK | 723 |
| Z11743 | VDAKYAKEEQRAWSEIHSLPNLTVNQMAAFIMKLYDDPSQSSELLSEAKKLNDSQAPK | 724 |
| Z11744 | VDAKYAKEEAKAWWEIHVLPNLTIDQITAFIHKLYDDPSQSSELLSEAKKLNDSQAPK | 725 |
| Z11745 | VDAKYAKEEAQAWWEIHTLPNLTVDQMAAFISKLFDDPSQSSELLSEAKKLNDSQAPK | 726 |

FIG. 1W

| Designation | Sequence | SEQ ID NO |
|---|---|---|
| Z11746 | VDAKYAKEERRAWHEIHILPNLTTSQMAAFIQKLFDDPSQSSELLSEAKKLNDSQAPK | 727 |
| Z11747 | VDAKYAKEERSAWYEIHTLPNLTTNQRTAFISKLFDDPSQSSELLSEAKKLNDSQAPK | 728 |
| Z11748 | VDAKYAKEERRAWFEIHMLPNLTIDQMAAFISKLFDDPSQSSELLSEAKKLNDSQAPK | 729 |
| Z11749 | VDAKYAKEEAKAWYEIHALPNLTVDQMVAFITKLFDDPSQSSELLSEAKKLNDSQAPK | 730 |
| Z11750 | VDAKYAKEEHVAWLEIHLLPNLTAEQMAAFISKLYDDPSQSSELLSEAKKLNDSQAPK | 731 |
| Z11751 | VDAKYAKEERDAWFEIHALPNLTVQQMAAFISKLFDDPSQSSELLSEAKKLNDSQAPK | 732 |
| Z11752 | VDAKYAKEEARAWREIHLLPNLTVDQMAAFISKLFDDPSQSSELLSEAKKLNDSQAPK | 733 |
| Z11753 | VDAKYAKEEARAWWEIHMLPNLTINQMAAFISKLFDDPSQSSELLSEAKKLNDSQAPK | 734 |
| Z11754 | VDAKYAKEEAAAWLEIHKLPNLTVHQMAAFISKLFDDPSQSSELLSEAKKLNDSQAPK | 735 |
| Z11755 | VDAKYAKEERQAWFEIHVLPNLTTDQMAAFIHKLYDDPSQSSELLSEAKKLNDSQAPK | 736 |
| Z11756 | VDAKYAKEEQRAWTEIHLLPNLTVNQMAAFISKLFDDPSQSSELLSEAKKLNDSQAPK | 737 |
| Z11757 | VDAKYAKEEQQAWYEIHTLPNLTVQQMAAFIQKLFDDPSQSSELLSEAKKLNDSQAPK | 738 |
| Z11758 | VDAKYAKEEQHAWREIHILPNLTVTQIAAFISKLFDDPSQSSELLSEAKKLNDSQAPK | 739 |
| Z11759 | VDAKYAKEEQRAWYEIHLLPNLTVTQMAAFISKLFDDPSQSSELLSEAKKLNDSQAPK | 740 |
| Z11760 | VDAKYAKEERAAWFEIHSLPNLTVSQMAAFISKLFDDPSQSSELLSEAKKLNDSQAPK | 741 |
| Z11761 | VDAKYAKEERQAWYEIHILPNLTAEQMAAFISKLFDDPSQSSELLSEAKKLNDSQAPK | 742 |
| Z11762 | VDAKYAKEEAQAWWEIHVLPNLTVRQIVAFISKLFDDPSQSSELLSEAKKLNDSQAPK | 743 |
| Z11763 | VDAKYAKEERRAWFEIHTLPNLTVHQMTAFIQKLFDDPSQSSELLSEAKKLNDSQAPK | 744 |
| Z11764 | VDAKYAKEEQRAWHEIHLLPNLTTRQMAAFISKLFDDPSQSSELLSEAKKLNDSQAPK | 745 |
| Z11765 | VDAKYAKEERHAWHEIHILPNLTIEQMVAFISKLFDDPSQSSELLSEAKKLNDSQAPK | 746 |
| Z11766 | VDAKYAKEERQAWFEIHALPNLTVQQVEAFISKLFDDPSQSSELLSEAKKLNDSQAPK | 747 |
| Z11767 | VDAKYAKEEQRAWREIHLLPNLTVTQMAAFISKLFDDPSQSSELLSEAKKLNDSQAPK | 748 |
| Z11768 | VDAKYAKEERHAWWEIHSLPNLTISQMAAFISKLFDDPSQSSELLSEAKKLNDSQAPK | 749 |
| Z11769 | VDAKYAKEEARAMLEIHALPNLTVDQMAAFISKLFDDPSQSSELLSEAKKLNDSQAPK | 750 |
| Z11770 | VDAKYAKEEQRAWHEIHTLPNLTVRQMAAFIIKLFDDPSQSSELLSEAKKLNDSQAPK | 751 |
| Z11771 | VDAKYAKEERHAWFEIHKLPNLTVEQMAAFIWKLFDDPSQSSELLSEAKKLNDSQAPK | 752 |
| Z11772 | VDAKYAKEERDAWYEIHLLPNLTINQIAAFISKLFDDPSQSSELLSEAKKLNDSQAPK | 753 |
| Z11773 | VDAKYAKEERQAWHEIHILPNLTVTQMTAFISKLFDDPSQSSELLSEAKKLNDSQAPK | 754 |
| Z11774 | VDAKYAKEEQAWTEIHSLPNLTATQVAAFIQKLFDDPSQSSELLSEAKKLNDSQAPK | 755 |
| Z11775 | VDAKYAKEEREAWWEIHHLPNLTVHQRAAFISKLFDDPSQSSELLSEAKKLNDSQAPK | 756 |
| Z11776 | VDAKYAKEERRAAWYEIHTLPNLTVSQMTAFISKLFDDPSQSSELLSEAKKLNDSQAPK | 757 |
| Z11777 | VDAKYAKEEHQAWWEIHLLPNLTARQMEAFIQKLFDDPSQSSELLSEAKKLNDSQAPK | 758 |
| Z11778 | VDAKYAKEEAHAWTEIHLLPNLTVDQMVAFISKLFDDPSQSSELLSEAKKLNDSQAPK | 759 |

FIG. 1X

| Designation | Sequence | SEQ ID NO |
|---|---|---|
| Z11779 | VDAKYAKEERRAWHEIHLLPNLTIQQIAAFISKLFDDPSQSSELLSEAKKLNDSQAPK | 760 |
| Z11780 | VDAKYAKEEHDAWFEIHTLPNLTVEQMAAFIMKLFDDPSQSSELLSEAKKLNDSQAPK | 761 |
| Z11782 | VDAKYAKEEHRAWLEIHLLPNLTVRQMAAFISKLFDDPSQSSELLSEAKKLNDSQAPK | 762 |
| Z11783 | VDAKYAKEEAKAWWEIHLLPNLTVDQMAAFISKLFDDPSQSSELLSEAKKLNDSQAPK | 763 |
| Z11785 | VDAKYAKEERKAWHEIHVLPNLTTNQRVAFIMKLMDDPSQSSELLSEAKKLNDSQAPK | 764 |
| Z11786 | VDAKYAKEERRAWWEIHLLPNLTVEQAAAFISKLFDDPSQSSELLSEAKKLNDSQAPK | 765 |
| Z11787 | VDAKYAKEEAAAWYEIHTLPNLTIDQMAAFISKLFDDPSQSSELLSEAKKLNDSQAPK | 766 |
| Z11790 | VDAKYAKEERAAWFEIHKLPNLTVSQMAAFIQKLFDDPSQSSELLSEAKKLNDSQAPK | 767 |
| Z11792 | VDAKYAKEEAEAWTEIHKLPNLTVHQMTAFIIKLFDDPSQSSELLSEAKKLNDSQAPK | 768 |
| Z11793 | VDAKYAKEERHAWWEIHKLPNLTISQMAAFISKLFDDPSQSSELLSEAKKLNDSQAPK | 769 |
| Z11795 | VDAKYAKEERKAWYEIHLLPNLTTSQRVAFISKLFDDPSQSSELLSEAKKLNDSQAPK | 770 |
| Z11796 | VDAKYAKEEASAWWEIHVLPNLTVNQIAAFISKLFDDPSQSSELLSEAKKLNDSQAPK | 771 |
| Z11797 | VDAKYAKEERDAWYEIHLLPNLTTDQMAAFISKLFDDPSQSSELLSEAKKLNDSQAPK | 772 |
| Z11798 | VDAKYAKEEAEAWLEIHLLPNLTVQQMAAFISKLFDDPSQSSELLSEAKKLNDSQAPK | 773 |
| Z11799 | VDAKYAKEEAKAWHEIHVLPNLTVRQIAAFISKLFDDPSQSSELLSEAKKLNDSQAPK | 774 |
| Z11800 | VDAKYAKEEASAWFEIHTLPNLTVDQMSAFIIKLFDDPSQSSELLSEAKKLNDSQAPK | 775 |
| Z11801 | VDAKYAKEERKAWYEIHVLPNLTVEQIAAFISKLFDDPSQSSELLSEAKKLNDSQAPK | 776 |
| Z11804 | VDAKYAKEERAAWHEIHVLPNLTTEQRVAFIKLYDDPSQSSELLSEAKKLNDSQAPK | 777 |
| Z11806 | VDAKYAKEEAQAWYEIHVLPNLTVRQMVAFISKLFDDPSQSSELLSEAKKLNDSQAPK | 778 |
| Z11807 | VDAKYAKEEAQAWWEIHLLPNLTVRQIAAFISKLFDDPSQSSELLSEAKKLNDSQAPK | 779 |
| Z11808 | VDAKYAKEEAAAWTEIHALPNLTVHQMAAFISKLFDDPSQSSELLSEAKKLNDSQAPK | 780 |
| Z11809 | VDAKYAKEERTAWWEIHALPNLTIDDPSQSSELLSEAKKLNDSQAPK | 781 |
| Z11810 | VDAKYAKEEHKAWREIHLLPNLTTEQMTAFISKLFDDPSQSSELLSEAKKLNDSQAPK | 782 |
| Z11811 | VDAKYAKEEQRAWFEIHLLPNLTVNQMAAFITKLFDDPSQSSELLSEAKKLNDSQAPK | 783 |
| Z11812 | VDAKYAKEERHAWWEIHKLPNLTIRQMAAFISKLFDDPSQSSELLSEAKKLNDSQAPK | 784 |
| Z11813 | VDAKYAKEEARAWHEIHILPNLTVRQISAFISKLFDDPSQSSELLSEAKKLNDSQAPK | 785 |
| Z11816 | VDAKYAKEERQAWFEIHALPNLTVNQMAAFIKLYDDPSQSSELLSEAKKLNDSQAPK | 786 |
| Z11820 | VDAKYAKEEAQAWSEIHLLPNLTIDQRVAFISKLFDDPSQSSELLSEAKKLNDSQAPK | 787 |
| Z11821 | VDAKYAKEERHAWHEIHILPNLTIINQMAAFISKLFDDPSQSSELLSEAKKLNDSQAPK | 788 |
| Z11822 | VDAKYAKEEAKAWAEIHALPNLTVTQMSAFIQKLFDDPSQSSELLSEAKKLNDSQAPK | 789 |
| Z11825 | VDAKYAKEERQAWFEIHILPNLTATQMAAFISKLFDDPSQSSELLSEAKKLNDSQAPK | 790 |
| Z11826 | VDAKYAKEERRAWWEIHVLPNLTVRQMAAFISKLFDDPSQSSELLSEAKKLNDSQAPK | 791 |
| Z11827 | VDAKYAKEEAHAWFEIHIDQRSAFISKLFDDPSQSSELLSEAKKLNDSQAPK | 792 |

FIG. 1Y

| Designation | Sequence | SEQ ID NO |
|---|---|---|
| Z11828 | VDAKYAKEEARARAWWEIHLLPNLTIRQMTAFISKLFDDPSQSSELLSEAKKLNDSQAPK | 793 |
| Z11829 | VDAKYAKEEAEAWHEIHVLPNLTVSQMAAFISKLFDDPSQSSELLSEAKKLNDSQAPK | 794 |
| Z11830 | VDAKYAKEERQAWREIHLLPNLTTDQMSAFISKLFDDPSQSSELLSEAKKLNDSQAPK | 795 |
| Z11831 | VDAKYAKEEATAWREIHLLPNLTVDQMAAFISKLFDDPSQSSELLSEAKKLNDSQAPK | 796 |
| Z11832 | VDAKYAKEERQAWWEIHKLPNLTVTQMAAFISKLFDDPSQSSELLSEAKKLNDSQAPK | 797 |
| Z11834 | VDAKYAKEEARAWREIHLLPNLTISQMAAFISKLFDDPSQSSELLSEAKKLNDSQAPK | 798 |
| Z11837 | VDAKYAKEEAEAWHEIHVLPNLTVEQMAAFISKLFDDPSQSSELLSEAKKLNDSQAPK | 799 |
| Z11838 | VDAKYAKEEAAAWLEIHLLPNLTIDQMAAFISKLFDDPSQSSELLSEAKKLNDSQAPK | 800 |
| Z11839 | VDAKYAKEERDAWYEIHLLPNLTVQQMSAFISKLFDDPSQSSELLSEAKKLNDSQAPK | 801 |
| Z11840 | VDAKYAKEERAAWFEIHTLPNLTVHQMAAFISKLFDDPSQSSELLSEAKKLNDSQAPK | 802 |
| Z11841 | VDAKYAKEEQSAWHEIHTLPNLTVNQMAAFIIKLFDDPSQSSELLSEAKKLNDSQAPK | 803 |
| Z11842 | VDAKYAKEERSAWFEIHIPNLTVRQMAAFIQKLFDDPSQSSELLSEAKKLNDSQAPK | 804 |
| Z11843 | VDAKYAKEEAQAWHEIHVLPNLTVNQMAAFISKLFDDPSQSSELLSEAKKLNDSQAPK | 805 |
| Z11844 | VDAKYAKEEAHAWREIHLLPNLTIKLFDDPSQSSELLSEAKKLNDSQAPK | 806 |
| Z11845 | VDAKYAKEEARAWREIHLLPNLTVQQMAAFIQKLFDDPSQSSELLSEAKKLNDSQAPK | 807 |
| Z11846 | VDAKYAKEERQAWYEIHMLPNLTITQLEAFISKLFDDPSQSSELLSEAKKLNDSQAPK | 808 |
| Z11847 | VDAKYAKEEREAWYEIHVLPNLTHHQMEAFIQKLFDDPSQSSELLSEAKKLNDSQAPK | 809 |
| Z11848 | VDAKYAKEERRAWFEIHLLPNLTVTQISAFISKLFDDPSQSSELLSEAKKLNDSQAPK | 810 |
| Z11849 | VDAKYAKEEREAWFEIHALPNLTVDQMSAFIIKLYDDPSQSSELLSEAKKLNDSQAPK | 811 |
| Z11850 | VDAKYAKEEREAWWEIHLLPNLTVEQMAAFIHKLYDDPSQSSELLSEAKKLNDSQAPK | 812 |
| Z11851 | VDAKYAKEEREAWHEIHTLPNLTVHQRAAFISKLFDDPSQSSELLSEAKKLNDSQAPK | 813 |
| Z11852 | VDAKYAKEEAQAWHEIHTLPNLTVDQMAAFISKLFDDPSQSSELLSEAKKLNDSQAPK | 814 |
| Z11853 | VDAKYAKEEQHAWYEIHIPNLTVTQMAAFISKLFDDPSQSSELLSEAKKLNDSQAPK | 815 |
| Z11854 | VDAKYAKEEHHAWYEIHTLPNLTIQQMAAFISKLFDDPSQSSELLSEAKKLNDSQAPK | 816 |
| Z11855 | VDAKYAKEEAHAWYEIHLLPNLTVNQMAAFIQMAAFISKLFDDPSQSSELLSEAKKLNDSQAPK | 817 |
| Z11856 | VDAKYAKEEAAWREIHTLPNLTAEQMAAFISKLFDDPSQSSELLSEAKKLNDSQAPK | 818 |
| Z11857 | VDAKYAKEEASAWYEIHTLPNLTVEQMAAFISKLFDDPSQSSELLSEAKKLNDSQAPK | 819 |
| Z11858 | VDAKYAKEERKAWYEIHVLPNLTVDQMAAFIQKLFDDPSQSSELLSEAKKLNDSQAPK | 820 |
| Z11859 | VDAKYAKEEAHAWHEIHILPNLTVNQIAAFISKLFDDPSQSSELLSEAKKLNDSQAPK | 821 |
| Z11863 | VDAKYAKEERRAWAEIHKLPNLTISQIAAFISKLFDDPSQSSELLSEAKKLNDSQAPK | 822 |
| Z11864 | VDAKYAKEEAHAWLEIHALPNLTIEQISAFIIKLYDDPSQSSELLSEAKKLNDSQAPK | 823 |
| Z11867 | VDAKYAKEERTAWYEIHILPNLTIQQMAAFISKLFDDPSQSSELLSEAKKLNDSQAPK | 824 |
| Z11868 | VDAKYAKEERHAWYEIHVLPNLTVTQMAAFISKLFDDPSQSSELLSEAKKLNDSQAPK | 825 |

FIG. 1Z

| Designation | Sequence | SEQ ID NO |
|---|---|---|
| Z11869 | VDAKYAKEERRAWYEIHLLPNLTVEQIAAFISKLFDDPSQSSELLSEAKKLNDSQAPK | 826 |
| Z11870 | VDAKYAKEERDAWFEIHALPNLTVTQVAAFISKLFDDPSQSSELLSEAKKLNDSQAPK | 827 |
| Z11873 | VDAKYAKEEQEAWTEIHTLPNLTIDQMTAFIIKLFDDPSQSSELLSEAKKLNDSQAPK | 828 |
| Z11876 | VDAKYAKEEREAWWEIHALPNLTTNQIAAFISKLFDDPSQSSELLSEAKKLNDSQAPK | 829 |
| Z11877 | VDAKYAKEERAAWYEIHLLPNLTVNQMAAFISKLFDDPSQSSELLSEAKKLNDSQAPK | 830 |
| Z11878 | VDAKYAKEEAKAWYEIHILPNLTVTQIAAFISKLFDDPSQSSELLSEAKKLNDSQAPK | 831 |
| Z11879 | VDAKYAKEEREAWHEIHILPNLTVNQMAAFISKLFDDPSQSSELLSEAKKLNDSQAPK | 832 |
| Z11880 | VDAKYAKEERAAWREIHLLPNLTVSQMEAFISKLFDDPSQSSELLSEAKKLNDSQAPK | 833 |
| Z11884 | VDAKYAKEERTAWFEIHTLPNLTVQQMAAFIIKLFDDPSQSSELLSEAKKLNDSQAPK | 834 |
| Z11885 | VDAKYAKEEREAWHEIHILPNLTIEQMAAFIQKLFDDPSQSSELLSEAKKLNDSQAPK | 835 |
| Z11886 | VDAKYAKEERQAWYEIHILPNLTVRQISAFISKLFDDPSQSSELLSEAKKLNDSQAPK | 836 |
| Z11887 | VDAKYAKEEAQAWTEIHIPNLTVSQMAAFIQKLFDDPSQSSELLSEAKKLNDSQAPK | 837 |
| Z11888 | VDAKYAKEEHDAWYEIHTLPNLTVDQVSAFISKLFDDPSQSSELLSEAKKLNDSQAPK | 838 |
| Z11889 | VDAKYAKEEAEAWREIHLLPNLTINQIAAFISKLFDDPSQSSELLSEAKKLNDSQAPK | 839 |
| Z11891 | VDAKYAKEEQSAWTEIHTLPNLTVDQRVAFISKLFDDPSQSSELLSEAKKLNDSQAPK | 840 |
| Z11894 | VDAKYAKEERDAWHEIHILPNLTIEQRAAFISKLFDDPSQSSELLSEAKKLNDSQAPK | 841 |
| Z11898 | VDAKYAKEEARAWHEIHVLPNLTTDQRVAFISKLFDDPSQSSELLSEAKKLNDSQAPK | 842 |
| Z11899 | VDAKYAKEEADAWFEIHMLPNLTIDQMTAFIMKLFDDPSQSSELLSEAKKLNDSQAPK | 843 |
| Z11900 | VDAKYAKEEAEAWWEIHALPNLTVSQTAAFISKLFDDPSQSSELLSEAKKLNDSQAPK | 844 |
| Z11902 | VDAKYAKEEARAWHEIHLLPNLTISQMTAFIIKLFDDPSQSSELLSEAKKLNDSQAPK | 845 |
| Z11908 | VDAKYAKEERRAWYEIHTLPNLTVSQMAAFISKLFDDPSQSSELLSEAKKLNDSQAPK | 846 |
| Z11909 | VDAKYAKEEREAWYEIHLLPNLTVTRQMAAFIIKLFDDPSQSSELLSEAKKLNDSQAPK | 847 |
| Z11910 | VDAKYAKEEHDAWYEIHVLPNLTVNQIAAFISKLFDDPSQSSELLSEAKKLNDSQAPK | 848 |
| Z11911 | VDAKYAKEEAHAWAEIHSLPNLTVDQMVAFIQKLFDDPSQSSELLSEAKKLNDSQAPK | 849 |
| Z11913 | VDAKYAKEEREAWWEIHKLPNLTVTQMAAFIQKLFDDPSQSSELLSEAKKLNDSQAPK | 850 |
| Z11914 | VDAKYAKEERVAWYEIHLLPNLTIDQMAAFISKLFDDPSQSSELLSEAKKLNDSQAPK | 851 |
| Z11915 | VDAKYAKEEARAWHEIHILPNLTVSQITAFISKLFDDPSQSSELLSEAKKLNDSQAPK | 852 |
| Z11916 | VDAKYAKEEADAWREIHLLPNLTASQMAAFIIKLYDDPSQSSELLSEAKKLNDSQAPK | 853 |
| Z11917 | VDAKYAKEEREAWTEIHSLPNLTVDQMAAFIIKLYDDPSQSSELLSEAKKLNDSQAPK | 854 |
| Z11919 | VDAKYAKEEARAWHEIHLLPNLTIEQMAAFISKLFDDPSQSSELLSEAKKLNDSQAPK | 855 |
| Z11920 | VDAKYAKEERRAWYEIHILPNLTVSQMAAFISKLFDDPSQSSELLSEAKKLNDSQAPK | 856 |
| Z11921 | VDAKYAKEEARAWYEIHLLPNLTIDQMAAFISKLFDDPSQSSELLSEAKKLNDSQAPK | 857 |
| Z11924 | VDAKYAKEERQAWHEIHTLPNLTTDQMAAFISKLFDDPSQSSELLSEAKKLNDSQAPK | 858 |

FIG. 1AA

| Designation | Sequence | SEQ ID NO |
|---|---|---|
| Z11925 | VDAKYAKEEHDAWWEIHKLPNLTVNQTAAFISKLFDDPSQSSELLSEAKKLNDSQAPK | 859 |
| Z11926 | VDAKYAKEERTAWHEIHSLPNLTIDQMAAFIIKLFDDPSQSSELLSEAKKLNDSQAPK | 860 |
| Z11927 | VDAKYAKEERAAWWEIHLLPNLTTTQMAAFISKLFDDPSQSSELLSEAKKLNDSQAPK | 861 |
| Z11928 | VDAKYAKEERDAWREIHLLPNLTIDQMAAFISKLFDDPSQSSELLSEAKKLNDSQAPK | 862 |
| Z11930 | VDAKYAKEEQVAWHEIHLLPNLTIDQMTAFISKLFDDPSQSSELLSEAKKLNDSQAPK | 863 |
| Z11931 | VDAKYAKEEAQAWREIHLLPNLTVDQMAAFISKLFDDPSQSSELLSEAKKLNDSQAPK | 864 |
| Z11932 | VDAKYAKEEAKAWFEIHILPNLTVQQVAAFISKLFDDPSQSSELLSEAKKLNDSQAPK | 865 |
| Z11934 | VDAKYAKEEHAAWREITLLPNLTINQRAAFISKLFDDPSQSSELLSEAKKLNDSQAPK | 866 |
| Z11935 | VDAKYAKEEAEAWSEIHKLPNLTVTQMAAFISKLFDDPSQSSELLSEAKKLNDSQAPK | 867 |
| Z11936 | VDAKYAKEEQQAWYEIHLLPNLTVTQMSAFISKLFDDPSQSSELLSEAKKLNDSQAPK | 868 |
| Z11938 | VDAKYAKEEARAWYEIHLLPNLTIEQMAAFISKLFDDPSQSSELLSEAKKLNDSQAPK | 869 |
| Z11940 | VDAKYAKEEAEAWTEIHLLPNLTVEQRVAFISKLFDDPSQSSELLSEAKKLNDSQAPK | 870 |
| Z11941 | VDAKYAKEERQAWTEIHLLPNLTVEQMAAFIQKLFDDPSQSSELLSEAKKLNDSQAPK | 871 |
| Z14455 | VDAKYAKEEYYAWTEIHKLPNLTIDQMAAFITKLFDDPSQSSELLSEAKKLNDSQAPK | 872 |
| Z14456 | VDAKYAKEEQAAWMEIHLLPNLTIDQMAAFITKLFDDPSQSSELLSEAKKLNDSQAPK | 873 |
| Z14457 | VDAKYAKEEYAAWTEIHLLPNLTIDQMAAFITKLFDDPSQSSELLSEAKKLNDSQAPK | 874 |
| Z14458 | VDAKYAKEEKEAWYEIHLLPNLTISQMAAFITKLFDDPSQSSELLSEAKKLNDSQAPK | 875 |
| Z14459 | VDAKYAKEEREAWYEIHLLPNLTIVQMAAFITKLFDDPSQSSELLSEAKKLNDSQAPK | 876 |
| Z14460 | VDAKYAKEEAAWVEIHKLPNLTVDQMAAFITKLFDDPSQSSELLSEAKKLNDSQAPK | 877 |
| Z14461 | VDAKYAKEEYAWKEIHLLPNLTIEQMAAFITKLFDDPSQSSELLSEAKKLNDSQAPK | 878 |
| Z14462 | VDAKYAKEEKAAWTEIHLLPNLTIFQMAAFITKLFDDPSQSSELLSEAKKLNDSQAPK | 879 |
| Z14463 | VDAKYAKEEKEAWYEIHLLPNLTITTQMAAFITKLFDDPSQSSELLSEAKKLNDSQAPK | 880 |
| Z14464 | VDAKYAKEERKAWYEIHLLPNLTVTQMAAFITKLFDDPSQSSELLSEAKKLNDSQAPK | 881 |
| Z14465 | VDAKYAKEEAMAWREIHLLPNLTVNQIAAFITKLFDDPSQSSELLSEAKKLNDSQAPK | 882 |
| Z14466 | VDAKYAKEEKHAWNEIHKLPNLTIVEQMAAFITKLFDDPSQSSELLSEAKKLNDSQAPK | 883 |
| Z14467 | VDAKYAKEEYEAWTEIHLLPNLTIDQMAAFITKLFDDPSQSSELLSEAKKLNDSQAPK | 884 |
| Z14468 | VDAKYAKEEWNAWTEIHNLPNLTIDQMAAFITKLFDDPSQSSELLSEAKKLNDSQAPK | 885 |
| Z14469 | VDAKYAKEERAAWTEIHGLPNLTVEQMAAFITKLFDDPSQSSELLSEAKKLNDSQAPK | 886 |
| Z14470 | VDAKYAKEEADAWLEIHNLPNLTISQMAAFITKLFDDPSQSSELLSEAKKLNDSQAPK | 887 |
| Z14471 | VDAKYAKEEKAAWHEIHILPNLTVYQIAAFITKLFDDPSQSSELLSEAKKLNDSQAPK | 888 |
| Z14472 | VDAKYAKEEKAWWEIHILPNLTIEQMAAFITKLFDDPSQSSELLSEAKKLNDSQAPK | 889 |
| Z14473 | VDAKYAKEEKSAWMEIHLLPNLTIEQMAAFITKLFDDPSQSSELLSEAKKLNDSQAPK | 890 |
| Z14474 | VDAKYAKEEYAAWMEIHRLPNLTIEQIAAFITKLFDDPSQSSELLSEAKKLNDSQAPK | 891 |

FIG. 1BB

| Designation | Sequence | SEQ ID NO |
|---|---|---|
| Z14475 | VDAKYAKEEFRAWIEIHTLPNLTVDQMAAFITKLFDDPSQSSELLSEAKKLNDSQAPK | 892 |
| Z14476 | VDAKYAKEEKDAWNEIHKLPNLTIEQIAAFITKLFDDPSQSSELLSEAKKLNDSQAPK | 893 |
| Z14477 | VDAKYAKEEKHAWYEIHLLPNLTVEQMAAFITKLFDDPSQSSELLSEAKKLNDSQAPK | 894 |
| Z14478 | VDAKYAKEEYEAWLEIHLLPNLTVDQMAAFISKLFDDPSQSSELLSEAKKLNDSQAPK | 895 |
| Z14479 | VDAKYAKEEKNAWHEIHRLPNLTVNQMAAFITKLFDDPSQSSELLSEAKKLNDSQAPK | 896 |
| Z14480 | VDAKYAKEEKNAWTEIHNLPNLTISQMAAFITKLFDDPSQSSELLSEAKKLNDSQAPK | 897 |
| Z14481 | VDAKYAKEEAAAWYEIHALPNLTVEQMAAFITKLFDDPSQSSELLSEAKKLNDSQAPK | 898 |
| Z14482 | VDAKYAKEEWNAWMEIHLLPNLTVTQMAAFITKLFDDPSQSSELLSEAKKLNDSQAPK | 899 |
| Z14483 | VDAKYAKEEAKAWHEIHILPNLTVHQIAAFITKLFDDPSQSSELLSEAKKLNDSQAPK | 900 |
| Z14484 | VDAKYAKEERKAWHEIHILPNLTVHQIAAFITKLFDDPSQSSELLSEAKKLNDSQAPK | 901 |
| Z14485 | VDAKYAKEESKAWFEIHALPNLTVEQIAAFITKLFDDPSQSSELLSEAKKLNDSQAPK | 902 |
| Z14486 | VDAKYAKEEKRAWYEIHILPNLTISQIAAFISKLFDDPSQSSELLSEAKKLNDSQAPK | 903 |
| Z14487 | VDAKYAKEEKKAWTEIHVLPNLTISQIAAFISKLFDDPSQSSELLSEAKKLNDSQAPK | 904 |
| Z14488 | VDAKYAKEERDAWFEIHALPNLTIDQMAAFITKLFDDPSQSSELLSEAKKLNDSQAPK | 905 |
| Z14489 | VDAKYAKEEYEAWEIHRLPNLTIDQMAAFITKLFDDPSQSSELLSEAKKLNDSQAPK | 906 |
| Z14490 | VDAKYAKEERNAWFEIHLLPNLTINQMAAFISKLFDDPSQSSELLSEAKKLNDSQAPK | 907 |
| Z14491 | VDAKYAKEEHHAWNEIHILPNLTVDQIAAFITKLFDDPSQSSELLSEAKKLNDSQAPK | 908 |
| Z14492 | VDAKYAKEEHYAWKEIHLLPNLTIDQMAAFISKLFDDPSQSSELLSEAKKLNDSQAPK | 909 |
| Z14493 | VDAKYAKEESDAWYEIHLLPNLTIEQMAAFITKLFDDPSQSSELLSEAKKLNDSQAPK | 910 |
| Z14494 | VDAKYAKEEYEAWMEIHLLPNLTIGQMAAFITKLFDDPSQSSELLSEAKKLNDSQAPK | 911 |
| Z14495 | VDAKYAKEEKEAWYEIHLLPNLTVEQMAAFITKLFDDPSQSSELLSEAKKLNDSQAPK | 912 |
| Z14496 | VDAKYAKEERAAWKEIHILPNLTVEQIAAFITKLFDDPSQSSELLSEAKKLNDSQAPK | 913 |
| Z14497 | VDAKYAKEEKEAWYEIHLLPNLTVHQMAAFITKLFDDPSQSSELLSEAKKLNDSQAPK | 914 |
| Z14498 | VDAKYAKEEYDAWIEIHALPNLTVDQMAAFISKLFDDPSQSSELLSEAKKLNDSQAPK | 915 |
| Z14499 | VDAKYAKEERKAWTEIHLLPNLTIDQMAAFITKLFDDPSQSSELLSEAKKLNDSQAPK | 916 |
| Z14500 | VDAKYAKEEYHAWVEIHNLPNLTIDQIAAFITKLFDDPSQSSELLSEAKKLNDSQAPK | 917 |
| Z14501 | VDAKYAKEEREAWTEIHKLPNLTIDQMAAFITKLFDDPSQSSELLSEAKKLNDSQAPK | 918 |
| Z14502 | VDAKYAKEEQWAWYEIHLLPNLTVDQIAAFITKLFDDPSQSSELLSEAKKLNDSQAPK | 919 |
| Z14503 | VDAKYAKEEKQAWMEIHKLPNLTVHQVAAFISKLFDDPSQSSELLSEAKKLNDSQAPK | 920 |
| Z14504 | VDAKYAKEESDAWTEIHKLPNLTIDQMAAFITKLFDDPSQSSELLSEAKKLNDSQAPK | 921 |
| Z14505 | VDAKYAKEEAQAWWEIHSLPNLTVDQIAAFITKLFDDPSQSSELLSEAKKLNDSQAPK | 922 |
| Z14506 | VDAKYAKEEKMAWYEIHNLPNLTVNQMAAFITKLFDDPSQSSELLSEAKKLNDSQAPK | 923 |
| Z14507 | VDAKYAKEEWMAWMEIHNLPNLTVNQMAAFITKLFDDPSQSSELLSEAKKLNDSQAPK | 924 |

FIG. 1CC

| Designation | Sequence | SEQ ID NO |
|---|---|---|
| Z14508 | VDAKYAKEEARAWYEIHILPNLTVKQMAAFITKLFDDPSQSSELLSEAKKLNDSQAPK | 925 |
| Z14509 | VDAKYAKEEAKAWHEIHILPNLTVSQVAAFITKLFDDPSQSSELLSEAKKLNDSQAPK | 926 |
| Z14510 | VDAKYAKEERAAWHEIHILPNLTVDQMAAFISKLFDDPSQSSELLSEAKKLNDSQAPK | 927 |
| Z14511 | VDAKYAKEEWQAWTEIHLLPNLTLDQVAAFITKLFDDPSQSSELLSEAKKLNDSQAPK | 928 |
| Z14512 | VDAKYAKEEAFAWEEIHRLPNLTIEQMAAFISKLFDDPSQSSELLSEAKKLNDSQAPK | 929 |
| Z14513 | VDAKYAKEERKAWYEIHKLPNLTVDQMAAFITKLFDDPSQSSELLSEAKKLNDSQAPK | 930 |
| Z14514 | VDAKYAKEEKQAWYEIHLLPNLTVEQMAAFITKLFDDPSQSSELLSEAKKLNDSQAPK | 931 |
| Z14515 | VDAKYAKEEYDAWWEIHLLPNLTVDQMAAFITKLFDDPSQSSELLSEAKKLNDSQAPK | 932 |
| Z14516 | VDAKYAKEEHDAWNEIHLLPNLTIDQMAAFITKLFDDPSQSSELLSEAKKLNDSQAPK | 933 |
| Z14517 | VDAKYAKEEYTAWTEIHQLPNLTVQQMAAFITKLFDDPSQSSELLSEAKKLNDSQAPK | 934 |
| Z14518 | VDAKYAKEEARAWHEIHILPNLTVRQIAAFITKLFDDPSQSSELLSEAKKLNDSQAPK | 935 |
| Z14519 | VDAKYAKEERNAWFEIHQLPNLTVHQVAAFITKLFDDPSQSSELLSEAKKLNDSQAPK | 936 |
| Z14520 | VDAKYAKEEADAWYEIHLLPNLTVEQMAAFITKLFDDPSQSSELLSEAKKLNDSQAPK | 937 |
| Z14522 | VDAKYAKEEFEAWKEIHILPNLTVHQMAAFITKLFDDPSQSSELLSEAKKLNDSQAPK | 938 |
| Z14523 | VDAKYAKEEAYAWWEIHKLPNLTVHQMAAFITKLFDDPSQSSELLSEAKKLNDSQAPK | 939 |
| Z14526 | VDAKYAKEEKTAWHEIHNLPNLTIDQMAAFITKLFDDPSQSSELLSEAKKLNDSQAPK | 940 |
| Z14527 | VDAKYAKEEAKAWNEIHKLPNLTIDQIAAFISKLFDDPSQSSELLSEAKKLNDSQAPK | 941 |
| Z14528 | VDAKYAKEEKDAWIEIHNLPNLTVEQMAAFITKLFDDPSQSSELLSEAKKLNDSQAPK | 942 |
| Z14529 | VDAKYAKEEFFAWKEIHLLPNLTVEQIAAFITKLFDDPSQSSELLSEAKKLNDSQAPK | 943 |
| Z14530 | VDAKYAKEEQAAWLEIHLLPNLTVSQIAAFITKLFDDPSQSSELLSEAKKLNDSQAPK | 944 |
| Z14531 | VDAKYAKEEYFAWREIHVLPNLTVDQMAAFISKLFDDPSQSSELLSEAKKLNDSQAPK | 945 |
| Z14532 | VDAKYAKEEYYAWREIHLLPNLTITQMAAFITKLFDDPSQSSELLSEAKKLNDSQAPK | 946 |
| Z14533 | VDAKYAKEEKMAWTEIHLLPNLTISQMAAFITKLFDDPSQSSELLSEAKKLNDSQAPK | 947 |
| Z14534 | VDAKYAKEERNAWFEIHVLPNLTVKQMAAFITKLFDDPSQSSELLSEAKKLNDSQAPK | 948 |
| Z14535 | VDAKYAKEEKRAWTEIHILPNLTVEQMAAFISKLFDDPSQSSELLSEAKKLNDSQAPK | 949 |
| Z14536 | VDAKYAKEEAAAWKEIHLLPNLTIDQMAAFITKLFDDPSQSSELLSEAKKLNDSQAPK | 950 |
| Z14537 | VDAKYAKEEAWMEIHALPNLTVDQVAAFITKLFDDPSQSSELLSEAKKLNDSQAPK | 951 |
| Z14539 | VDAKYAKEEKEAWYEIHNLPNLTIIQMAAFITKLFDDPSQSSELLSEAKKLNDSQAPK | 952 |
| Z14540 | VDAKYAKEEYDAWFEIHILPNLTVHQIAAFITKLFDDPSQSSELLSEAKKLNDSQAPK | 953 |
| Z14541 | VDAKYAKEEYGAWNEIHKLPNLTIDQMAAFITKLFDDPSQSSELLSEAKKLNDSQAPK | 954 |
| Z14542 | VDAKYAKEEWQAWMEIHSLPNLTVDQMAAFITKLFDDPSQSSELLSEAKKLNDSQAPK | 955 |
| Z14543 | VDAKYAKEEWNAWFEIHLLPNLTVEQMAAFITKLFDDPSQSSELLSEAKKLNDSQAPK | 956 |
| Z14544 | VDAKYAKEEANAWKEIHLLPNLTVDQMAAFITKLFDDPSQSSELLSEAKKLNDSQAPK | 957 |

FIG. 1DD

| Designation | Sequence | SEQ ID NO |
|---|---|---|
| Z14545 | VDAKYAKEEYEAWTEIHLLPNLTVHQMAAFITKLFDDPSQSSELLSEAKKLNDSQAPK | 958 |
| Z14546 | VDAKYAKEERIAWWEIHSLPNLTVNQVAAFISKLFDDPSQSSELLSEAKKLNDSQAPK | 959 |
| Z14548 | VDAKYAKEEYNAWVEIHTLPNLTVNQMAAFITKLFDDPSQSSELLSEAKKLNDSQAPK | 960 |
| Z14549 | VDAKYAKEEAFAWSEIHILPNLTIDQIAAFITKLFDDPSQSSELLSEAKKLNDSQAPK | 961 |
| Z14552 | VDAKYAKEEAHAWHEIHILPNLTIDQMAAFITKLFDDPSQSSELLSEAKKLNDSQAPK | 962 |
| Z14553 | VDAKYAKEEAAAWNEIHRLPNLTVDQIAAFISKLFDDPSQSSELLSEAKKLNDSQAPK | 963 |
| Z14554 | VDAKYAKEEKAAWTEIHLLPNLTVDQMAAFITKLFDDPSQSSELLSEAKKLNDSQAPK | 964 |
| Z14555 | VDAKYAKEEKGAWNEIHLLPNLTIQQMAAFISKLFDDPSQSSELLSEAKKLNDSQAPK | 965 |
| Z14557 | VDAKYAKEEYAAWMEIHSLPNLTVDQMAAFITKLFDDPSQSSELLSEAKKLNDSQAPK | 966 |
| Z14558 | VDAKYAKEEAAAWKEIHILPNLTIEQIAAFISKLFDDPSQSSELLSEAKKLNDSQAPK | 967 |
| Z14560 | VDAKYAKEEKFAWNEIHILPNLTVHQIAAFITKLFDDPSQSSELLSEAKKLNDSQAPK | 968 |
| Z14561 | VDAKYAKEEYNAWLEIHILPNLTINQMAAFITKLFDDPSQSSELLSEAKKLNDSQAPK | 969 |
| Z14562 | VDAKYAKEEHTAWLEIHSLPNLTIEQVAAFITKLFDDPSQSSELLSEAKKLNDSQAPK | 970 |
| Z14563 | VDAKYAKEEKDAWMEIHILPNLTVDQMAAFITKLFDDPSQSSELLSEAKKLNDSQAPK | 971 |
| Z14564 | VDAKYAKEEATAWIEIHSLPNLTVDQMAAFITKLFDDPSQSSELLSEAKKLNDSQAPK | 972 |
| Z14565 | VDAKYAKEEKEAWWEIHILPNLTVDQMAAFITKLFDDPSQSSELLSEAKKLNDSQAPK | 973 |
| Z14566 | VDAKYAKEEQHAWIEIHKLPNLTVDQMAAFITKLFDDPSQSSELLSEAKKLNDSQAPK | 974 |
| Z14567 | VDAKYAKEEKHAWHEIHILPNLTIEQMAAFISKLFDDPSQSSELLSEAKKLNDSQAPK | 975 |
| Z14568 | VDAKYAKEEAKAWHEIHIHLPNLTIEQMAAFITKLFDDPSQSSELLSEAKKLNDSQAPK | 976 |
| Z14569 | VDAKYAKEEKKAWTEIHILPNLTVEQIAAFITKLFDDPSQSSELLSEAKKLNDSQAPK | 977 |
| Z14570 | VDAKYAKEERAAWYEIHVLPNLTVSQMAAFISKLFDDPSQSSELLSEAKKLNDSQAPK | 978 |
| Z14571 | VDAKYAKEERFAWAEIHKLPNLTIDQMAAFITKLFDDPSQSSELLSEAKKLNDSQAPK | 979 |
| Z14572 | VDAKYAKEEYAAWFEIHLLPNLTIDQMAAFISKLFDDPSQSSELLSEAKKLNDSQAPK | 980 |
| Z14573 | VDAKYAKEEYDAWFEIHLLPNLTIDQMAAFITKLFDDPSQSSELLSEAKKLNDSQAPK | 981 |
| Z14574 | VDAKYAKEEWEAWMEIHALPNLTVDQMAAFITKLFDDPSQSSELLSEAKKLNDSQAPK | 982 |
| Z14575 | VDAKYAKEEKDAWWEIHALPNLTIEQMAAFITKLFDDPSQSSELLSEAKKLNDSQAPK | 983 |
| Z14576 | VDAKYAKEERDAWFEIHSLPNLTVDQMAAFITKLFDDPSQSSELLSEAKKLNDSQAPK | 984 |
| Z14577 | VDAKYAKEEFYAWLEIHKLPNLTVSQMAAFITKLFDDPSQSSELLSEAKKLNDSQAPK | 985 |
| Z14578 | VDAKYAKEEYEAWYEIHILPNLTIEQMAAFISKLFDDPSQSSELLSEAKKLNDSQAPK | 986 |
| Z14579 | VDAKYAKEERDAWFEIHLLPNLTVNQMAAFITKLFDDPSQSSELLSEAKKLNDSQAPK | 987 |
| Z14580 | VDAKYAKEEYRAWTEIHILPNLTITQIAAFITKLFDDPSQSSELLSEAKKLNDSQAPK | 988 |
| Z14581 | VDAKYAKEEYEAWLEIHILLPNLTIEQMAAFITKLFDDPSQSSELLSEAKKLNDSQAPK | 989 |
| Z14582 | VDAKYAKEEYDAWLEIHILPNLTVEQIAAFISKLFDDPSQSSELLSEAKKLNDSQAPK | 990 |

FIG. 1EE

| Designation | Sequence | SEQ ID NO |
|---|---|---|
| Z14583 | VDAKYAKEERKAWYEIHSLPNLTVDQMAAFITKLFDDPSQSSELLSEAKKLNDSQAPK | 991 |
| Z14584 | VDAKYAKEEHTAWTEIHRLPNLTIEQMAAFITKLFDDPSQSSELLSEAKKLNDSQAPK | 992 |
| Z14585 | VDAKYAKEEYQAWTEIHLLPNLTVEQMAAFITKLFDDPSQSSELLSEAKKLNDSQAPK | 993 |
| Z14586 | VDAKYAKEERRMAWFEIHSLPNLTVDQMAAFITKLFDDPSQSSELLSEAKKLNDSQAPK | 994 |
| Z14587 | VDAKYAKEEYDAWYEIHILPNLTVEQIAAFITKLFDDPSQSSELLSEAKKLNDSQAPK | 995 |
| Z14588 | VDAKYAKEEKEAWMEIHLLPNLTIDQMAAFITKLFDDPSQSSELLSEAKKLNDSQAPK | 996 |
| Z14589 | VDAKYAKEEYDAWFEIHSLPNLTVNQMAAFITKLFDDPSQSSELLSEAKKLNDSQAPK | 997 |
| Z14590 | VDAKYAKEEAFAWREIHILPNLTIDQMAAFITKLFDDPSQSSELLSEAKKLNDSQAPK | 998 |
| Z14591 | VDAKYAKEERKAWMEIHLLPNLTIEQMAAFITKLFDDPSQSSELLSEAKKLNDSQAPK | 999 |
| Z14592 | VDAKYAKEEKAAWIEIHNLPNLTVDQMAAFITKLFDDPSQSSELLSEAKKLNDSQAPK | 1000 |
| Z14593 | VDAKYAKEERNAWIEIHNLPNLTIEQMAAFITKLFDDPSQSSELLSEAKKLNDSQAPK | 1001 |
| Z14594 | VDAKYAKEEKNAWTEIHLLPNLTVGQIAAFITKLFDDPSQSSELLSEAKKLNDSQAPK | 1002 |
| Z14595 | VDAKYAKEEAEAAWWEIHILPNLTIDQMAAFITKLFDDPSQSSELLSEAKKLNDSQAPK | 1003 |
| Z14597 | VDAKYAKEEKLAWWEIHKLPNLTVDQMAAFITHQMAAFITKLFDDPSQSSELLSEAKKLNDSQAPK | 1004 |
| Z14598 | VDAKYAKEEYEAWYEIHILPNLTIHQMAAFITKLFDDPSQSSELLSEAKKLNDSQAPK | 1005 |
| Z14599 | VDAKYAKEEARAWKEIHLLPNLTVGQIAAFITKLFDDPSQSSELLSEAKKLNDSQAPK | 1006 |
| Z14600 | VDAKYAKEEKQAWMEIHLLPNLTVDQMAAFITKLFDDPSQSSELLSEAKKLNDSQAPK | 1007 |
| Z14601 | VDAKYAKEEAAAWHEIHILPNLTVHQIAAFITKLFDDPSQSSELLSEAKKLNDSQAPK | 1008 |
| Z14602 | VDAKYAKEEKEAWFEIHILPNLTVSQMAAFITKLFDDPSQSSELLSEAKKLNDSQAPK | 1009 |
| Z14603 | VDAKYAKEEKEAWFEIHTLPNLTVDQMAAFISKLFDDPSQSSELLSEAKKLNDSQAPK | 1010 |
| Z14604 | VDAKYAKEEYLAWVEIHNLPNLTIDQMAAFITKLFDDPSQSSELLSEAKKLNDSQAPK | 1011 |
| Z14605 | VDAKYAKEERDANYEIHNLPNLTVGQMAAFITKLFDDPSQSSELLSEAKKLNDSQAPK | 1012 |
| Z14606 | VDAKYAKEESAAWFEIHLLPNLTINQMAAFITKLFDDPSQSSELLSEAKKLNDSQAPK | 1013 |
| Z14607 | VDAKYAKEEQYAWTEIHILPNLTVNQIAAFITKLFDDPSQSSELLSEAKKLNDSQAPK | 1014 |
| Z14608 | VDAKYAKEEKRAWMEIHLLPNLTVSQMAAFITKLFDDPSQSSELLSEAKKLNDSQAPK | 1015 |
| Z14610 | VDAKYAKEEKKAWFEIHLLPNLTIHQVAAFISKLFDDPSQSSELLSEAKKLNDSQAPK | 1016 |
| Z14611 | VDAKYAKEEKEAWYEIHSLPNLTVDQVAAFITKLFDDPSQSSELLSEAKKLNDSQAPK | 1017 |
| Z14612 | VDAKYAKEEKEWLAWNEIHLLPNLTISQIAAFISKLFDDPSQSSELLSEAKKLNDSQAPK | 1018 |
| Z14613 | VDAKYAKEEYNAWLEIHILPNLTVHQIAAFISKLFDDPSQSSELLSEAKKLNDSQAPK | 1019 |
| Z14615 | VDAKYAKEEHTAWMEIHRLPNLTIDQIAAFISKLFDDPSQSSELLSEAKKLNDSQAPK | 1020 |
| Z14616 | VDAKYAKEEKFAWTEIHLLPNLTVHVMAAFITKLFDDPSQSSELLSEAKKLNDSQAPK | 1021 |
| Z14617 | VDAKYAKEEKYAWTEIHILPNLTVNQMAAFITKLFDDPSQSSELLSEAKKLNDSQAPK | 1022 |
| Z14618 | VDAKYAKEEKFAWHEIHKLPNLTVDQIAAFITKLFDDPSQSSELLSEAKKLNDSQAPK | 1023 |

FIG. 1FF

| Designation | Sequence | SEQ ID NO |
|---|---|---|
| Z14619 | VDAKYAKEERKAWYEIHGLPNLTVEQMAAFITKLFDDPSQSSELLSEAKKLNDSQAPK | 1024 |
| Z14621 | VDAKYAKEEYQAWLEIHLLPNLTVDQIAAFITKLFDDPSQSSELLSEAKKLNDSQAPK | 1025 |
| Z14622 | VDAKYAKEEKHAWMEIHLLPNLTVEQMAAFITKLFDDPSQSSELLSEAKKLNDSQAPK | 1026 |
| Z14623 | VDAKYAKEEKQAWREIHLLPNLTVDQIAAFISKLFDDPSQSSELLSEAKKLNDSQAPK | 1027 |
| Z14624 | VDAKYAKEEAMAWTEIHLLPNLTVSQMAAFITKLFDDPSQSSELLSEAKKLNDSQAPK | 1028 |
| Z14625 | VDAKYAKEEKHAWREIHLLPNLTLNQMAAFITKLFDDPSQSSELLSEAKKLNDSQAPK | 1029 |
| Z14626 | VDAKYAKEERYAWNEIHALPNLTVEQVAAFITKLFDDPSQSSELLSEAKKLNDSQAPK | 1030 |
| Z14627 | VDAKYAKEEREAWWEIHKLPNLTVDQMAAFISKLFDDPSQSSELLSEAKKLNDSQAPK | 1031 |
| Z14628 | VDAKYAKEEHRAWTEIHLLPNLTVDQMAAFISKLFDDPSQSSELLSEAKKLNDSQAPK | 1032 |
| Z14629 | VDAKYAKEEAYAWAEIHKLPNLTVQMAAFITKLFDDPSQSSELLSEAKKLNDSQAPK | 1033 |
| Z14631 | VDAKYAKEEYFAWTEIHKLPNLTIDQIAAFITKLFDDPSQSSELLSEAKKLNDSQAPK | 1034 |
| Z14632 | VDAKYAKEEAHAWQEIHKLPNLTINQIAAFISKLFDDPSQSSELLSEAKKLNDSQAPK | 1035 |
| Z14633 | VDAKYAKEEKHAWTEIHLLPNLTIDQMAAFITKLFDDPSQSSELLSEAKKLNDSQAPK | 1036 |
| Z14635 | VDAKYAKEEYRAWYEIHILPNLTVKQMAAFITKLFDDPSQSSELLSEAKKLNDSQAPK | 1037 |
| Z14636 | VDAKYAKEEANAWIEIHKLPNLTVDQMAAFITKLFDDPSQSSELLSEAKKLNDSQAPK | 1038 |
| Z14637 | VDAKYAKEEKDAWTEIHKLPNLTIDQMAAFITKLFDDPSQSSELLSEAKKLNDSQAPK | 1039 |
| Z14638 | VDAKYAKEEREAWYEIHNLPNLTITIQMAAFITKLFDDPSQSSELLSEAKKLNDSQAPK | 1040 |
| Z14639 | VDAKYAKEEYYAWNEIHLLPNLTIEQMAAFITKLFDDPSQSSELLSEAKKLNDSQAPK | 1041 |
| Z14640 | VDAKYAKEEKTAWREIHLLPNLTIDQIAAFITKLFDDPSQSSELLSEAKKLNDSQAPK | 1042 |
| Z14641 | VDAKYAKEEAHAWREIHIILPNLTIDQMAAFITKLFDDPSQSSELLSEAKKLNDSQAPK | 1043 |
| Z14642 | VDAKYAKEEAAAWLEIHQLPNLTVDQMAAFITKLFDDPSQSSELLSEAKKLNDSQAPK | 1044 |
| Z14643 | VDAKYAKEEAEAWLEIHILPNLTIDQMAAFITKLFDDPSQSSELLSEAKKLNDSQAPK | 1045 |
| Z14644 | VDAKYAKEEANAWFEIHILPNLTVEQMAAFITKLFDDPSQSSELLSEAKKLNDSQAPK | 1046 |
| Z14646 | VDAKYAKEERYAWMEIHLLPNLTVQQMAAFITKLFDDPSQSSELLSEAKKLNDSQAPK | 1047 |
| Z14647 | VDAKYAKEERFAWNEIHKLPNLTIDQMAAFITKLFDDPSQSSELLSEAKKLNDSQAPK | 1048 |
| Z14648 | VDAKYAKEEAKAWFEIHLLPNLTIDQIAAFITKLFDDPSQSSELLSEAKKLNDSQAPK | 1049 |
| Z14649 | VDAKYAKEEREAWTEIHILPNLTIQQIAAFITKLFDDPSQSSELLSEAKKLNDSQAPK | 1050 |
| Z14650 | VDAKYAKEEFEAWNEIHKLPNLTIEQMAAFITKLFDDPSQSSELLSEAKKLNDSQAPK | 1051 |
| Z14652 | VDAKYAKEEKEAWYEIHILPNLTVHQIAAFISKLFDDPSQSSELLSEAKKLNDSQAPK | 1052 |
| Z14653 | VDAKYAKEEYQAWVEIHNLPNLTVDQMAAFISKLFDDPSQSSELLSEAKKLNDSQAPK | 1053 |
| Z14654 | VDAKYAKEEKKAWREIHILPNLTINQIAAFITKLFDDPSQSSELLSEAKKLNDSQAPK | 1054 |
| Z14655 | VDAKYAKEEQDAWIEIHLLPNLTIDQMAAFISKLFDDPSQSSELLSEAKKLNDSQAPK | 1055 |
| Z14656 | VDAKYAKEEHDAWWEIHALPNLTINQMAAFISKLFDDPSQSSELLSEAKKLNDSQAPK | 1056 |

FIG. 1GG

| Designation | Sequence | SEQ ID NO |
|---|---|---|
| Z14657 | VDAKYAKEEYDAWYEIHLLPNLTIQQMAAFISKLFDDPSQSSELLSEAKKLNDSQAPK | 1057 |
| Z14658 | VDAKYAKEEYQAWVEIHILPNLTIQQIAAFITKLFDDPSQSSELLSEAKKLNDSQAPK | 1058 |
| Z14659 | VDAKYAKEESKAWNEIHKLPNLTITQMAAFITKLFDDPSQSSELLSEAKKLNDSQAPK | 1059 |
| Z14660 | VDAKYAKEEYQAWYEIHLLPNLTVEQMAAFITKLFDDPSQSSELLSEAKKLNDSQAPK | 1060 |
| Z14661 | VDAKYAKEEKRAWMEIHLLPNLTVGQMAAFITKLFDDPSQSSELLSEAKKLNDSQAPK | 1061 |
| Z14663 | VDAKYAKEERVAWLEIHILPNLTIGQIAAFITKLFDDPSQSSELLSEAKKLNDSQAPK | 1062 |
| Z14664 | VDAKYAKEEQAAWYEIHLLPNLTIEQMAAFITKLFDDPSQSSELLSEAKKLNDSQAPK | 1063 |
| Z14665 | VDAKYAKEEKDAWYEIHILPNLTVSQIAAFITKLFDDPSQSSELLSEAKKLNDSQAPK | 1064 |
| Z14666 | VDAKYAKEEKKAWYEIHLLPNLTISQMAAFITKLFDDPSQSSELLSEAKKLNDSQAPK | 1065 |
| Z14667 | VDAKYAKEEKKAWYEIHLLPNLTINQMAAFITKLFDDPSQSSELLSEAKKLNDSQAPK | 1066 |
| Z14668 | VDAKYAKEEHKAWTEIHLLPNLTVDQIAAFITKLFDDPSQSSELLSEAKKLNDSQAPK | 1067 |
| Z14669 | VDAKYAKEEAAAWHEIHLLPNLTIDQMAAFITKLFDDPSQSSELLSEAKKLNDSQAPK | 1068 |
| Z14670 | VDAKYAKEERSAWTEIHLLPNLTITQIAAFITKLFDDPSQSSELLSEAKKLNDSQAPK | 1069 |
| Z14671 | VDAKYAKEERLAWQEIHRLPNLTVDQMAAFITKLFDDPSQSSELLSEAKKLNDSQAPK | 1070 |
| Z14672 | VDAKYAKEEKDAWTEIHLLPNLTVEQMAAFISKLFDDPSQSSELLSEAKKLNDSQAPK | 1071 |
| Z14674 | VDAKYAKEEKAAWMEIHNLPNLTIDQMAAFITKLFDDPSQSSELLSEAKKLNDSQAPK | 1072 |
| Z14675 | VDAKYAKEEYEAWVEIHLLPNLTIDQMAAFITKLFDDPSQSSELLSEAKKLNDSQAPK | 1073 |
| Z14676 | VDAKYAKEEAKAWTEIHLLPNLTVNQIAAFITKLFDDPSQSSELLSEAKKLNDSQAPK | 1074 |
| Z14677 | VDAKYAKEEKKAWYEIHITLPNLTHQIAAFITKLFDDPSQSSELLSEAKKLNDSQAPK | 1075 |
| Z14678 | VDAKYAKEEKKAWFEIHLLPNLTVDQMAAFISKLFDDPSQSSELLSEAKKLNDSQAPK | 1076 |
| Z14679 | VDAKYAKEERKAWFEIHSLPNLTIDQMAAFITKLFDDPSQSSELLSEAKKLNDSQAPK | 1077 |
| Z14680 | VDAKYAKEERNAWYEIHLLPNLTVDQMAAFITKLFDDPSQSSELLSEAKKLNDSQAPK | 1078 |
| Z14681 | VDAKYAKEEASAWKEIHLLPNLTIDQVAAFITKLFDDPSQSSELLSEAKKLNDSQAPK | 1079 |
| Z14682 | VDAKYAKEEAAAWKEIHILPNLTIDQMAAFITKLFDDPSQSSELLSEAKKLNDSQAPK | 1080 |
| Z14683 | VDAKYAKEEAWAWHEIHILPNLTIEQMAAFITKLFDDPSQSSELLSEAKKLNDSQAPK | 1081 |
| Z14684 | VDAKYAKEEKYAWLEIHLLPNLTVDQVAAFITKLFDDPSQSSELLSEAKKLNDSQAPK | 1082 |
| Z14685 | VDAKYAKEERSAWMEIHLLPNLTINQMAAFISKLFDDPSQSSELLSEAKKLNDSQAPK | 1083 |
| Z14686 | VDAKYAKEERMAWNEIHGLPNLTVDQMAAFITKLFDDPSQSSELLSEAKKLNDSQAPK | 1084 |
| Z14687 | VDAKYAKEEAKAWYEIHILPNLTIIQMAAFITKLFDDPSQSSELLSEAKKLNDSQAPK | 1085 |
| Z14688 | VDAKYAKEEKWAWTEIHKLPNLTISQMAAFITKLFDDPSQSSELLSEAKKLNDSQAPK | 1086 |
| Z14689 | VDAKYAKEERMAWTEIHNLPNLTVEQVAAFITKLFDDPSQSSELLSEAKKLNDSQAPK | 1087 |
| Z14690 | VDAKYAKEEWAWKEIHLLPNLTVEQVAAFITKLFDDPSQSSELLSEAKKLNDSQAPK | 1088 |
| Z14691 | VDAKYAKEEKFAWTEIHKLPNLTVDQMAAFITKLFDDPSQSSELLSEAKKLNDSQAPK | 1089 |

FIG. 1HH

| Designation | Sequence | SEQ ID NO |
|---|---|---|
| Z14692 | VDAKYAKEEHYAWQEIHKLPNLTIDQMAAFITKLFDDPSQSSELLSEAKKLNDSQAPK | 1090 |
| Z14693 | VDAKYAKEERKAWYEIHILPNLTITQIAAFITKLFDDPSQSSELLSEAKKLNDSQAPK | 1091 |
| Z14694 | VDAKYAKEERYAWTEIHKLPNLTVDQVAAFISKLFDDPSQSSELLSEAKKLNDSQAPK | 1092 |
| Z14695 | VDAKYAKEEKEAWYEIHILPNLTVSQIAAFITKLFDDPSQSSELLSEAKKLNDSQAPK | 1093 |
| Z14696 | VDAKYAKEEYSAWFEIHILPNLTVEQMAAFISKLFDDPSQSSELLSEAKKLNDSQAPK | 1094 |
| Z14697 | VDAKYAKEERMAWNEIHKLPNLTIDQMAAFISKLFDDPSQSSELLSEAKKLNDSQAPK | 1095 |
| Z14698 | VDAKYAKEEAKAWTEIHLLPNLTVNQVAAFITKLFDDPSQSSELLSEAKKLNDSQAPK | 1096 |
| Z14699 | VDAKYAKEEKFAWREIHLLPNLTIEQMAAFISKLFDDPSQSSELLSEAKKLNDSQAPK | 1097 |
| Z14701 | VDAKYAKEEANAWHEIHLLPNLTIDQMAAFITKLFDDPSQSSELLSEAKKLNDSQAPK | 1098 |
| Z14702 | VDAKYAKEEKHAWNEIHRLPNLTVEQMAAFITKLFDDPSQSSELLSEAKKLNDSQAPK | 1099 |
| Z14703 | VDAKYAKEEHMAWTEIHALPNLTVDQMAAFISKLFDDPSQSSELLSEAKKLNDSQAPK | 1100 |
| Z14704 | VDAKYAKEEAWMEIHNLPNLTIEQMAAFITKLFDDPSQSSELLSEAKKLNDSQAPK | 1101 |
| Z14705 | VDAKYAKEERAAWYEIHILPNLTVEQMAAFITKLFDDPSQSSELLSEAKKLNDSQAPK | 1102 |
| Z14707 | VDAKYAKEEKNAWYEIHLLPNLTVVQMAAFITKLFDDPSQSSELLSEAKKLNDSQAPK | 1103 |
| Z14708 | VDAKYAKEEQIAWYEIHILPNLTVDQVAAFISKLFDDPSQSSELLSEAKKLNDSQAPK | 1104 |
| Z14709 | VDAKYAKEEYYAWTEIHRLPNLTVDQMAAFITKLFDDPSQSSELLSEAKKLNDSQAPK | 1105 |
| Z14711 | VDAKYAKEEADAWFEIHILPNLTVDQIAAFITKLFDDPSQSSELLSEAKKLNDSQAPK | 1106 |
| Z14713 | VDAKYAKEEAWMEIHKLPNLTVDQMAAFITKLFDDPSQSSELLSEAKKLNDSQAPK | 1107 |
| Z14714 | VDAKYAKEEYLAWIEIHALPNLTVSQMAAFITKLFDDPSQSSELLSEAKKLNDSQAPK | 1108 |
| Z14715 | VDAKYAKEEAFAWWEIHILPNLTINQMAAFITKLFDDPSQSSELLSEAKKLNDSQAPK | 1109 |
| Z14716 | VDAKYAKEEYNAWFEIHILPNLTISQMAAFITKLFDDPSQSSELLSEAKKLNDSQAPK | 1110 |
| Z14717 | VDAKYAKEEKEAWREIHILPNLTVDQMAAFISKLFDDPSQSSELLSEAKKLNDSQAPK | 1111 |
| Z14718 | VDAKYAKEEKKAWHEIHILPNLTITQIAAFISKLFDDPSQSSELLSEAKKLNDSQAPK | 1112 |
| Z14719 | VDAKYAKEEYHAWTEIHILPNLTINQMAAFISKLFDDPSQSSELLSEAKKLNDSQAPK | 1113 |
| Z14721 | VDAKYAKEEFSAWYEIHLLPNLTVDQMAAFITKLFDDPSQSSELLSEAKKLNDSQAPK | 1114 |
| Z14723 | VDAKYAKEERAAWWEIHILPNLTVSQMAAFISKLFDDPSQSSELLSEAKKLNDSQAPK | 1115 |
| Z14724 | VDAKYAKEEYEAWVEIHLLPNLTIDQMAAFITKLFDDPSQSSELLSEAKKLNDSQAPK | 1116 |
| Z14725 | VDAKYAKEEAEAWVEIHLLPNLTVNQMAAFITKLFDDPSQSSELLSEAKKLNDSQAPK | 1117 |
| Z14726 | VDAKYAKEEAKAWHEIHILPNLTITQIAAFISKLFDDPSQSSELLSEAKKLNDSQAPK | 1118 |
| Z14727 | VDAKYAKEEFYAWNEIHILPNLTVNQMAAFITKLFDDPSQSSELLSEAKKLNDSQAPK | 1119 |
| Z14728 | VDAKYAKEEYLAWTEIHLLPNLTIEQMAAFITKLFDDPSQSSELLSEAKKLNDSQAPK | 1120 |
| Z14729 | VDAKYAKEEHAAWREIHALPNLTVDQMAAFISKLFDDPSQSSELLSEAKKLNDSQAPK | 1121 |
| Z14730 | VDAKYAKEEQRAWMEIHLLPNLTIEQIAAFISKLFDDPSQSSELLSEAKKLNDSQAPK | 1122 |

FIG. 1II

| Designation | Sequence | SEQ ID NO |
|---|---|---|
| Z14732 | VDAKYAKEERDAWTEIHKLPNLTVDQMAAFITKLFDDPSQSSELLSEAKKLNDSQAPK | 1123 |
| Z14733 | VDAKYAKEERDAWFEIHRLPNLTVDQMAAFITKLFDDPSQSSELLSEAKKLNDSQAPK | 1124 |
| Z14734 | VDAKYAKEESYAWTEIHKLPNLTIDQMAAFITKLFDDPSQSSELLSEAKKLNDSQAPK | 1125 |
| Z14735 | VDAKYAKEEKFAWKEIHILPNLTIDQIAAFITKLFDDPSQSSELLSEAKKLNDSQAPK | 1126 |
| Z14736 | VDAKYAKEEHRAWMEIHQLPNLTVDQMAAFITKLFDDPSQSSELLSEAKKLNDSQAPK | 1127 |
| Z14737 | VDAKYAKEERTAWFEIHKLPNLTVDQMAAFITKLFDDPSQSSELLSEAKKLNDSQAPK | 1128 |
| Z14738 | VDAKYAKEERYAWWEIHKLPNLTVEQVAAFITKLFDDPSQSSELLSEAKKLNDSQAPK | 1129 |
| Z14739 | VDAKYAKEEEAWNEIHRLPNLTVVQMAAFISKLFDDPSQSSELLSEAKKLNDSQAPK | 1130 |
| Z14740 | VDAKYAKEEYEAWVEIHILPNLTVEQMAAFITKLFDDPSQSSELLSEAKKLNDSQAPK | 1131 |
| Z14741 | VDAKYAKEEYHAWTEIHLLPNLTIEQMAAFITKLFDDPSQSSELLSEAKKLNDSQAPK | 1132 |
| Z14742 | VDAKYAKEEYNAWYEIHVLPNLTIDQIAAFITKLFDDPSQSSELLSEAKKLNDSQAPK | 1133 |
| Z14743 | VDAKYAKEERKAWYEIHILPNLTVHQIAAFITKLFDDPSQSSELLSEAKKLNDSQAPK | 1134 |
| Z14744 | VDAKYAKEEWAAWIEIHSLPNLTVDQMAAFITKLFDDPSQSSELLSEAKKLNDSQAPK | 1135 |
| Z14745 | VDAKYAKEEAIAWSEIHSLPNLTVGQMAAFITKLFDDPSQSSELLSEAKKLNDSQAPK | 1136 |
| Z14747 | VDAKYAKEEKYAWTEIHILPNLTIDQMAAFITKLFDDPSQSSELLSEAKKLNDSQAPK | 1137 |
| Z14748 | VDAKYAKEEHTAWREIHLLPNLTISQMAAFITKLFDDPSQSSELLSEAKKLNDSQAPK | 1138 |
| Z14749 | VDAKYAKEEYTAWYEIHLLPNLTIEQMAAFITKLFDDPSQSSELLSEAKKLNDSQAPK | 1139 |
| Z14750 | VDAKYAKEEYEAWYEIHILPNLTIDQMAAFITKLFDDPSQSSELLSEAKKLNDSQAPK | 1140 |
| Z14751 | VDAKYAKEEKHAWTEIHLLPNLTISQMAAFITKLFDDPSQSSELLSEAKKLNDSQAPK | 1141 |
| Z14752 | VDAKYAKEEYTAWYEIHVLPNLTIRQMAAFITKLFDDPSQSSELLSEAKKLNDSQAPK | 1142 |
| Z14753 | VDAKYAKEEQRAWYEIHTLPNLTIDQMAAFITKLFDDPSQSSELLSEAKKLNDSQAPK | 1143 |
| Z14754 | VDAKYAKEEAVAWKEIHLLPNLTIDQIAAFISKLFDDPSQSSELLSEAKKLNDSQAPK | 1144 |
| Z14755 | VDAKYAKEEYRAWMEIHALPNLTIVQIAAFITKLFDDPSQSSELLSEAKKLNDSQAPK | 1145 |
| Z14756 | VDAKYAKEERSAWNEIHILPNLTIDQMAAFITKLFDDPSQSSELLSEAKKLNDSQAPK | 1146 |
| Z14757 | VDAKYAKEEAEAWFEIHILPNLTVGQIAAFITKLFDDPSQSSELLSEAKKLNDSQAPK | 1147 |
| Z14758 | VDAKYAKEEKMAWNEIHILPNLTVEQIAAFISKLFDDPSQSSELLSEAKKLNDSQAPK | 1148 |
| Z14759 | VDAKYAKEERTAWMEIHKLPNLTIDQMAAFISKLFDDPSQSSELLSEAKKLNDSQAPK | 1149 |
| Z14760 | VDAKYAKEEYEAWYEIHALPNLTLHQMAAFISKLFDDPSQSSELLSEAKKLNDSQAPK | 1150 |
| Z14761 | VDAKYAKEEYDAWFEIHVLPNLTVNQMAAFITKLFDDPSQSSELLSEAKKLNDSQAPK | 1151 |
| Z14762 | VDAKYAKEESLAWMEIHKLPNLTVDQVAAFITKLFDDPSQSSELLSEAKKLNDSQAPK | 1152 |
| Z14763 | VDAKYAKEERNAWWEIHALPNLTVNQMAAFITKLFDDPSQSSELLSEAKKLNDSQAPK | 1153 |
| Z14764 | VDAKYAKEEKKAWKEIHLLPNLTVNQMAAFISKLFDDPSQSSELLSEAKKLNDSQAPK | 1154 |
| Z14766 | VDAKYAKEEKYAWTEIHNLPNLTILQMAAFITKLFDDPSQSSELLSEAKKLNDSQAPK | 1155 |

FIG. 1JJ

| Designation | Sequence | SEQ ID NO |
|---|---|---|
| Z14768 | VDAKYAKEEYKAWVEIHLLPNLTVDQMAAFISKLFDDPSQSSELLSEAKKLNDSQAPK | 1156 |
| Z14769 | VDAKYAKEEHAAWLEIHLLPNLTVSQIAAFITKLFDDPSQSSELLSEAKKLNDSQAPK | 1157 |
| Z14770 | VDAKYAKEEYHAWWEIHALPNLTVEQMAAFITKLFDDPSQSSELLSEAKKLNDSQAPK | 1158 |
| Z14771 | VDAKYAKEERYAWNEIHRLPNLTVDQMAAFITKLFDDPSQSSELLSEAKKLNDSQAPK | 1159 |
| Z14772 | VDAKYAKEEAQAWMEIHLLPNLTIAQMAAFITKLFDDPSQSSELLSEAKKLNDSQAPK | 1160 |
| Z14773 | VDAKYAKEEREAWYEIHLLPNLTVNQMAAFITKLFDDPSQSSELLSEAKKLNDSQAPK | 1161 |
| Z14774 | VDAKYAKEEAYAWNEIHKLPNLTVEQMAAFISKLFDDPSQSSELLSEAKKLNDSQAPK | 1162 |
| Z14775 | VDAKYAKEEYDAWAEIHRLPNLTISQMAAFITKLFDDPSQSSELLSEAKKLNDSQAPK | 1163 |
| Z14776 | VDAKYAKEEYHAWTEIHILPNLTINQIAAFITKLFDDPSQSSELLSEAKKLNDSQAPK | 1164 |
| Z14777 | VDAKYAKEERQAWFEIHILPNLTVGQMAAFISKLFDDPSQSSELLSEAKKLNDSQAPK | 1165 |
| Z14778 | VDAKYAKEEAEAWFEIHILPNLTVDQIAAFITKLFDDPSQSSELLSEAKKLNDSQAPK | 1166 |
| Z14779 | VDAKYAKEEKKAWYEIHILPNLTVYQMAAFITKLFDDPSQSSELLSEAKKLNDSQAPK | 1167 |
| Z14780 | VDAKYAKEEKAAWNEIHILPNLTVHQMAAFITKLFDDPSQSSELLSEAKKLNDSQAPK | 1168 |
| Z14781 | VDAKYAKEEAQAWNEIHILPNLTVEQMAAFISKLFDDPSQSSELLSEAKKLNDSQAPK | 1169 |
| Z14785 | VDAKYAKEEYEAWYEIHILPNLTVHQIAAFITKLFDDPSQSSELLSEAKKLNDSQAPK | 1170 |
| Z14786 | VDAKYAKEEYEAWMEIHLLPNLTVHQMAAFITKLFDDPSQSSELLSEAKKLNDSQAPK | 1171 |
| Z14787 | VDAKYAKEEYDAWFEIHVLPNLTINQMAAFITKLFDDPSQSSELLSEAKKLNDSQAPK | 1172 |
| Z14789 | VDAKYAKEEKRAWNEIHQLPNLTIEQIAAFITKLFDDPSQSSELLSEAKKLNDSQAPK | 1173 |
| Z14790 | VDAKYAKEEARAWWEIHLLPNLTVDQIAAFITKLFDDPSQSSELLSEAKKLNDSQAPK | 1174 |
| Z14791 | VDAKYAKEEKHAWREIHLLPNLTVDQIAAFITKLFDDPSQSSELLSEAKKLNDSQAPK | 1175 |
| Z14792 | VDAKYAKEESRAWTEIHLLPNLTVDQMAAFITKLFDDPSQSSELLSEAKKLNDSQAPK | 1176 |
| Z14793 | VDAKYAKEEAEAWKEIHLLPNLTIGQIAAFITKLFDDPSQSSELLSEAKKLNDSQAPK | 1177 |
| Z14794 | VDAKYAKEEADAWKEIHLLPNLTIEQMAAFITKLFDDPSQSSELLSEAKKLNDSQAPK | 1178 |
| Z14795 | VDAKYAKEEYQAWMEIHILPNLTIEQMAAFITKLFDDPSQSSELLSEAKKLNDSQAPK | 1179 |
| Z14796 | VDAKYAKEEAHAWWEIHKLPNLTVNQMAAFITKLFDDPSQSSELLSEAKKLNDSQAPK | 1180 |
| Z14797 | VDAKYAKEEWYAWNEIHNLPNLTVDQMAAFITKLFDDPSQSSELLSEAKKLNDSQAPK | 1181 |
| Z14798 | VDAKYAKEEKKAWNEIHGLPNLTVDQVAAFISKLFDDPSQSSELLSEAKKLNDSQAPK | 1182 |
| Z14799 | VDAKYAKEEAAAWMEIHLLPNLTVEQMAAFITKLFDDPSQSSELLSEAKKLNDSQAPK | 1183 |
| Z14800 | VDAKYAKEEKFAWREIHILPNLTIEQMAAFITKLFDDPSQSSELLSEAKKLNDSQAPK | 1184 |
| Z14801 | VDAKYAKEEYHAWTEIHQLPNLTIDQMAAFISKLFDDPSQSSELLSEAKKLNDSQAPK | 1185 |
| Z14802 | VDAKYAKEEAMAWNEIHRLPNLTVNQMAAFISKLFDDPSQSSELLSEAKKLNDSQAPK | 1186 |
| Z14803 | VDAKYAKEEQKAWREIHILPNLTVNQMAAFISKLFDDPSQSSELLSEAKKLNDSQAPK | 1187 |
| Z14804 | VDAKYAKEEFAAWLEIHKLPNLTIDQMAAFITKLFDDPSQSSELLSEAKKLNDSQAPK | 1188 |

FIG. 1KK

| Designation | Sequence | SEQ ID NO |
|---|---|---|
| Z14805 | VDAKYAKEEAYAWAEIHKLPNLTVNQMAAFITKLFDDPSQSSELLSEAKKLNDSQAPK | 1189 |
| Z14806 | VDAKYAKEEKDAWYEIHILPNLTVRQMAAFISKLFDDPSQSSELLSEAKKLNDSQAPK | 1190 |
| Z14807 | VDAKYAKEEKDAWMEIHLLPNLTVSQIAAFITKLFDDPSQSSELLSEAKKLNDSQAPK | 1191 |
| Z14808 | VDAKYAKEEKEAWTEIHKLPNLTINQMAAFISKLFDDPSQSSELLSEAKKLNDSQAPK | 1192 |
| Z14809 | VDAKYAKEEKDAWREIHILPNLTIEQMAAFISKLFDDPSQSSELLSEAKKLNDSQAPK | 1193 |
| Z14810 | VDAKYAKEEYRAWTEIHLLPNLTIEHMAAFITKLFDDPSQSSELLSEAKKLNDSQAPK | 1194 |
| Z14811 | VDAKYAKEEKFAWHEIHILPNLTVHQMAAFITKLFDDPSQSSELLSEAKKLNDSQAPK | 1195 |
| Z14812 | VDAKYAKEEWEAWLEIHALPNLTVEQMAAFITKLFDDPSQSSELLSEAKKLNDSQAPK | 1196 |
| Z14813 | VDAKYAKEEAAAWQEIHLLPNLTVGQIAAFITKLFDDPSQSSELLSEAKKLNDSQAPK | 1197 |
| Z14814 | VDAKYAKEEKVAWKEIHILPNLTVNQIAAFISKLFDDPSQSSELLSEAKKLNDSQAPK | 1198 |
| Z14815 | VDAKYAKEERVAWQEIHLLPNLTIEQMAAFITKLFDDPSQSSELLSEAKKLNDSQAPK | 1199 |
| Z14816 | VDAKYAKEEYEAWLEIHLLPNLTIDQMAAFITKLFDDPSQSSELLSEAKKLNDSQAPK | 1200 |
| Z14817 | VDAKYAKEEAEAWFEIHNLPNLTIDQMAAFITKLFDDPSQSSELLSEAKKLNDSQAPK | 1201 |
| Z14818 | VDAKYAKEEKYAWWEIHKLPNLTVRQMAAFITKLFDDPSQSSELLSEAKKLNDSQAPK | 1202 |
| Z14819 | VDAKYAKEEYDAWHEIHVLPNLTVSQIAAFISKLFDDPSQSSELLSEAKKLNDSQAPK | 1203 |
| Z14820 | VDAKYAKEEAAAWREIHLLPNLTVDQMAAFITKLFDDPSQSSELLSEAKKLNDSQAPK | 1204 |
| Z14821 | VDAKYAKEEKHAWNEIHKLPNLTVKQVAAFITKLFDDPSQSSELLSEAKKLNDSQAPK | 1205 |
| Z14822 | VDAKYAKEEYDAWTEIHLLPNLTIAQIAAFITKLFDDPSQSSELLSEAKKLNDSQAPK | 1206 |
| Z14823 | VDAKYAKEERKAWHEIHILPNLTIDQMAAFITKLFDDPSQSSELLSEAKKLNDSQAPK | 1207 |
| Z14824 | VDAKYAKEEHDAWHEIHLLPNLTVDQIAAFITKLFDDPSQSSELLSEAKKLNDSQAPK | 1208 |
| Z14825 | VDAKYAKEEYAAWNEIHKLPNLTIIQMAAFITKLFDDPSQSSELLSEAKKLNDSQAPK | 1209 |
| Z14826 | VDAKYAKEEYEAWMEIHLLPNLTIEQMAAFITKLFDDPSQSSELLSEAKKLNDSQAPK | 1210 |
| Z14827 | VDAKYAKEEKHAWIEIHALPNLTIDQMAAFITKLFDDPSQSSELLSEAKKLNDSQAPK | 1211 |
| Z14828 | VDAKYAKEEKYAWHEIHILPNLTVDQVAAFISKLFDDPSQSSELLSEAKKLNDSQAPK | 1212 |
| Z14830 | VDAKYAKEEKDAWHEIHILPNLTVDQMAAFITKLFDDPSQSSELLSEAKKLNDSQAPK | 1213 |
| Z14831 | VDAKYAKEEYHAWMEIHILPNLTIEQIAAFITKLFDDPSQSSELLSEAKKLNDSQAPK | 1214 |
| Z14832 | VDAKYAKEEYRAWHEIHLLPNLTIIQMAAFITKLFDDPSQSSELLSEAKKLNDSQAPK | 1215 |
| Z14833 | VDAKYAKEEKFAWHEIHILPNLTVDQMAAFITKLFDDPSQSSELLSEAKKLNDSQAPK | 1216 |
| Z14834 | VDAKYAKEEKHAWTEIHILPNLTVNQMAAFITKLFDDPSQSSELLSEAKKLNDSQAPK | 1217 |
| Z14835 | VDAKYAKEEEFAWREIHILPNLTISQIAAFITKLFDDPSQSSELLSEAKKLNDSQAPK | 1218 |
| Z14836 | VDAKYAKEEKMAWKEIHVLPNLTVDQMAAFITKLFDDPSQSSELLSEAKKLNDSQAPK | 1219 |
| Z14837 | VDAKYAKEEYAAWHEIHVLPNLTIGQMAAFITKLFDDPSQSSELLSEAKKLNDSQAPK | 1220 |
| Z14838 | VDAKYAKEEQYAWQEIHKLPNLTVEQMAAFITKLFDDPSQSSELLSEAKKLNDSQAPK | 1221 |

FIG. 1LL

| Designation | Sequence | SEQ ID NO |
|---|---|---|
| Z14839 | VDAKYAKEEWEAWNEIHSLPNLTIDQIAAFITKLFDDPSQSSELLSEAKKLNDSQAPK | 1222 |
| Z14840 | VDAKYAKEEKMAWKEIHLLPNLTVEQMAAFITKLFDDPSQSSELLSEAKKLNDSQAPK | 1223 |
| Z14841 | VDAKYAKEEAHAWREIHNLPNLTIEQMAAFISKLFDDPSQSSELLSEAKKLNDSQAPK | 1224 |
| Z14842 | VDAKYAKEERRAWTEIHILPNLTVDQIAAFISKLFDDPSQSSELLSEAKKLNDSQAPK | 1225 |
| Z14843 | VDAKYAKEEYEAWMEIHLLPNLTINQIAAFITKLFDDPSQSSELLSEAKKLNDSQAPK | 1226 |
| Z14844 | VDAKYAKEEKHAWMEIHALPNLTIDQMAAFITKLFDDPSQSSELLSEAKKLNDSQAPK | 1227 |
| Z14845 | VDAKYAKEEHQAWHEIHILPNLTIQQMAAFITKLFDDPSQSSELLSEAKKLNDSQAPK | 1228 |
| Z14846 | VDAKYAKEEYYAWREIHLLPNLTVDQMAAFITKLFDDPSQSSELLSEAKKLNDSQAPK | 1229 |
| Z14847 | VDAKYAKEEQEAWMEIHKLPNLTIDQVAAFITKLFDDPSQSSELLSEAKKLNDSQAPK | 1230 |
| Z14848 | VDAKYAKEEAHAWTEIHSLPNLTVDQMAAFITKLFDDPSQSSELLSEAKKLNDSQAPK | 1231 |
| Z14849 | VDAKYAKEEKLAWKEIHLLPNLTISQMAAFITKLFDDPSQSSELLSEAKKLNDSQAPK | 1232 |
| Z14850 | VDAKYAKEEYDAWTEIHKLPNLTVDQMAAFISKLFDDPSQSSELLSEAKKLNDSQAPK | 1233 |
| Z14851 | VDAKYAKEEARAWMEIHNLPNLTVDQMAAFITKLFDDPSQSSELLSEAKKLNDSQAPK | 1234 |
| Z14852 | VDAKYAKEEYRAWTEIHLLPNLTVHQMAAFITKLFDDPSQSSELLSEAKKLNDSQAPK | 1235 |
| Z14853 | VDAKYAKEEYHAWYEIHILPNLTVEQIAAFITKLFDDPSQSSELLSEAKKLNDSQAPK | 1236 |
| Z14854 | VDAKYAKEESDAWKEIHLLPNLTIEQMAAFISKLFDDPSQSSELLSEAKKLNDSQAPK | 1237 |
| Z14855 | VDAKYAKEEAYAWREIHILPNLTVDQMAAFISKLFDDPSQSSELLSEAKKLNDSQAPK | 1238 |
| Z14856 | VDAKYAKEEAAAWNEIHRLPNLTIDQMAAFITKLFDDPSQSSELLSEAKKLNDSQAPK | 1239 |
| Z14858 | VDAKYAKEEYHAWWEIHKLPNLTVNQMAAFITKLFDDPSQSSELLSEAKKLNDSQAPK | 1240 |
| Z14859 | VDAKYAKEEKAAWYEIHKLPNLTIDQMAAFITKLFDDPSQSSELLSEAKKLNDSQAPK | 1241 |
| Z14860 | VDAKYAKEEKEAWTEIHLLPNLTVDQIAAFITKLFDDPSQSSELLSEAKKLNDSQAPK | 1242 |
| Z14863 | VDAKYAKEEKRAWYEIHGLPNLTISQMAAFISKLFDDPSQSSELLSEAKKLNDSQAPK | 1243 |
| Z14864 | VDAKYAKEEARAWYEIHILPNLTVHQMAAFITKLFDDPSQSSELLSEAKKLNDSQAPK | 1244 |
| Z14865 | VDAKYAKEEKTAWVEIHKLPNLTINQMAAFITKLFDDPSQSSELLSEAKKLNDSQAPK | 1245 |
| Z14866 | VDAKYAKEERDAWFEIHILPNLTIEQMAAFISKLFDDPSQSSELLSEAKKLNDSQAPK | 1246 |
| Z14869 | VDAKYAKEEAMAWKEIHGLPNLTIEQMAAFITKLFDDPSQSSELLSEAKKLNDSQAPK | 1247 |
| Z14870 | VDAKYAKEEQYAWREIHILPNLTVHQVAAFITKLFDDPSQSSELLSEAKKLNDSQAPK | 1248 |
| Z14871 | VDAKYAKEEWEAWIEIHNLPNLTVEQMAAFITKLFDDPSQSSELLSEAKKLNDSQAPK | 1249 |
| Z14872 | VDAKYAKEEYAAWTEIHTLPNLTVDQVAAFITKLFDDPSQSSELLSEAKKLNDSQAPK | 1250 |
| Z14873 | VDAKYAKEEDAWHEIHLLPNLTIEQMAAFITKLFDDPSQSSELLSEAKKLNDSQAPK | 1251 |
| Z14874 | VDAKYAKEERNAWYEIHALPNLTVEQMAAFITKLFDDPSQSSELLSEAKKLNDSQAPK | 1252 |
| Z14875 | VDAKYAKEEKRAWYEIHILPNLTVEQIAAFITKLFDDPSQSSELLSEAKKLNDSQAPK | 1253 |
| Z14876 | VDAKYAKEEYQAWIEIHILPNLTISQMAAFITKLFDDPSQSSELLSEAKKLNDSQAPK | 1254 |

FIG. 1MM

| Designation | Sequence | SEQ ID NO |
|---|---|---|
| Z14877 | VDAKYAKEEKRAWYEIHLLPNLTIGQMAAFITKLFDDPSQSSELLSEAKKLNDSQAPK | 1255 |
| Z14879 | VDAKYAKEEYLAWLEIHNLPNLTVDQMAAFITKLFDDPSQSSELLSEAKKLNDSQAPK | 1256 |
| Z14880 | VDAKYAKEEYFAWYEIHNLPNLTVDQMAAFITKLFDDPSQSSELLSEAKKLNDSQAPK | 1257 |
| Z14881 | VDAKYAKEEAFAWWEIHKLPNLTVEQMAAFITKLFDDPSQSSELLSEAKKLNDSQAPK | 1258 |
| Z14882 | VDAKYAKEESIAWQEIHLLPNLTIEQMAAFITKLFDDPSQSSELLSEAKKLNDSQAPK | 1259 |
| Z14883 | VDAKYAKEEWDAWNEIHLLPNLTINQMAAFITKLFDDPSQSSELLSEAKKLNDSQAPK | 1260 |
| Z14884 | VDAKYAKEEAYAWNEIHRLPNLTVEQMAAFITKLFDDPSQSSELLSEAKKLNDSQAPK | 1261 |
| Z14885 | VDAKYAKEEAEAWFEIHKLPNLTVGQMAAFITKLFDDPSQSSELLSEAKKLNDSQAPK | 1262 |
| Z14886 | VDAKYAKEEREAWHEIHILPNLTVEQVAAFITKLFDDPSQSSELLSEAKKLNDSQAPK | 1263 |
| Z14887 | VDAKYAKEEHDAWMEIHLLPNLTIEQMAAFITKLFDDPSQSSELLSEAKKLNDSQAPK | 1264 |
| Z14889 | VDAKYAKEEYSAWIEIHLLPNLTVSQMAAFITKLFDDPSQSSELLSEAKKLNDSQAPK | 1265 |
| Z14890 | VDAKYAKEEYDAWYEIHTLPNLTVDQVAAFITKLFDDPSQSSELLSEAKKLNDSQAPK | 1266 |
| Z14891 | VDAKYAKEEKMAWTEIHNLPNLTIDQMAAFITKLFDDPSQSSELLSEAKKLNDSQAPK | 1267 |
| Z14892 | VDAKYAKEEYAAWFEIHSLPNLTVEQMAAFITKLFDDPSQSSELLSEAKKLNDSQAPK | 1268 |
| Z14893 | VDAKYAKEERRAWDEIHRLPNLTIEQMAAFITKLFDDPSQSSELLSEAKKLNDSQAPK | 1269 |
| Z14894 | VDAKYAKEEYDAWLEIHLLPNLTIEQMAAFITKLFDDPSQSSELLSEAKKLNDSQAPK | 1270 |
| Z14895 | VDAKYAKEEYDAWNEIHTLPNLTIHALPNLTVDQVAAFISKLFDDPSQSSELLSEAKKLNDSQAPK | 1271 |
| Z14896 | VDAKYAKEERVAWNEIHKLPNLTISQMAAFITKLFDDPSQSSELLSEAKKLNDSQAPK | 1272 |
| Z14897 | VDAKYAKEEAHAWTEIHALPNLTIEQMAAFITKLFDDPSQSSELLSEAKKLNDSQAPK | 1273 |
| Z14898 | VDAKYAKEEYDAWVEIHLLPNLTINQMAAFITKLFDDPSQSSELLSEAKKLNDSQAPK | 1274 |
| Z14899 | VDAKYAKEEYRAWMEIHLLPNLTIEQMAAFITKLFDDPSQSSELLSEAKKLNDSQAPK | 1275 |
| Z14900 | VDAKYAKEESAAWTEIHLLPNLTIEQMAAFITKLFDDPSQSSELLSEAKKLNDSQAPK | 1276 |
| Z14901 | VDAKYAKEEYFAWTEIHVLPNLTVKQIAAFITKLFDDPSQSSELLSEAKKLNDSQAPK | 1277 |
| Z14902 | VDAKYAKEEFHAWSEIHLLPNLTVSQMAAFISKLFDDPSQSSELLSEAKKLNDSQAPK | 1278 |
| Z14903 | VDAKYAKEEYDAWTEIHALPNLTVDQMAAFITKLFDDPSQSSELLSEAKKLNDSQAPK | 1279 |
| Z14904 | VDAKYAKEEKAAWFEIHNLPNLTISQMAAFITKLFDDPSQSSELLSEAKKLNDSQAPK | 1280 |
| Z14905 | VDAKYAKEEYQAWIEIHALPNLTIEQMAAFITKLFDDPSQSSELLSEAKKLNDSQAPK | 1281 |
| Z14906 | VDAKYAKEEYDAWVEIHLLPNLTINQMAAFITKLFDDPSQSSELLSEAKKLNDSQAPK | 1282 |
| Z14907 | VDAKYAKEEQSAWMEIHILPNLTVSQIAAFISKLFDDPSQSSELLSEAKKLNDSQAPK | 1283 |
| Z14908 | VDAKYAKEERAAWNEIHSLPNLTVEQMAAFITKLFDDPSQSSELLSEAKKLNDSQAPK | 1284 |
| Z14909 | VDAKYAKEEHEAWNEIHKLPNLTIDQMAAFITKLFDDPSQSSELLSEAKKLNDSQAPK | 1285 |
| Z14910 | VDAKYAKEERFAWWEIHRLPNLTVRQVAAFITKLFDDPSQSSELLSEAKKLNDSQAPK | 1286 |
| Z14911 | VDAKYAKEEKDAWNEIHRLPNLTVDQVAAFITKLFDDPSQSSELLSEAKKLNDSQAPK | 1287 |

FIG. 1NN

| Designation | Sequence | SEQ ID NO |
|---|---|---|
| Z14912 | VDAKYAKEEARAWYEIHVLPNLTVHQIAAFITKLFDDPSQSSELLSEAKKLNDSQAPK | 1288 |
| Z14913 | VDAKYAKEERRAWNEIHKLPNLTVEQMAAFITKLFDDPSQSSELLSEAKKLNDSQAPK | 1289 |
| Z14914 | VDAKYAKEEYMAWDEIHRLPNLTVEQMAAFITKLFDDPSQSSELLSEAKKLNDSQAPK | 1290 |
| Z14915 | VDAKYAKEERNAWFEIHALPNLTIDQMAAFITKLFDDPSQSSELLSEAKKLNDSQAPK | 1291 |
| Z14916 | VDAKYAKEEAEAWQEIHLLPNLTVGQMAAFISKLFDDPSQSSELLSEAKKLNDSQAPK | 1292 |
| Z14917 | VDAKYAKEEKNAWYEIHLLPNLTIQQMAAFISKLFDDPSQSSELLSEAKKLNDSQAPK | 1293 |
| Z14918 | VDAKYAKEEAIAWHEIHLLPNLTITQMAAFITKLFDDPSQSSELLSEAKKLNDSQAPK | 1294 |
| Z14919 | VDAKYAKEEKDAWEEIHRLPNLTVTQMAAFISKLFDDPSQSSELLSEAKKLNDSQAPK | 1295 |
| Z14920 | VDAKYAKEEYDAWFEIHLLPNLTVQIAAFITKLFDDPSQSSELLSEAKKLNDSQAPK | 1296 |
| Z14921 | VDAKYAKEEAAAWMEIHLLPNLTVEQMAAFITKLFDDPSQSSELLSEAKKLNDSQAPK | 1297 |
| Z14922 | VDAKYAKEERKAWNEIHQLPNLTIQQVAAFITKLFDDPSQSSELLSEAKKLNDSQAPK | 1298 |
| Z14923 | VDAKYAKEEYAAWWEIHALPNLTVEQVAAFITKLFDDPSQSSELLSEAKKLNDSQAPK | 1299 |
| Z14924 | VDAKYAKEEKEAWMEIHILPNLTIDQMAAFITKLFDDPSQSSELLSEAKKLNDSQAPK | 1300 |
| Z14925 | VDAKYAKEEKIAWKEIHLLPNLTISQMAAFITKLFDDPSQSSELLSEAKKLNDSQAPK | 1301 |
| Z14926 | VDAKYAKEEHAAWMEIHLLPNLTVDQMAAFITKLFDDPSQSSELLSEAKKLNDSQAPK | 1302 |
| Z14927 | VDAKYAKEEKDAWYEIHIIPNLTVDQMAAFITKLFDDPSQSSELLSEAKKLNDSQAPK | 1303 |
| Z14928 | VDAKYAKEERAAWNEIHKLPNLTIEQMAAFITKLFDDPSQSSELLSEAKKLNDSQAPK | 1304 |
| Z14930 | VDAKYAKEEAAAWFEIHILLPNLTVGQIAAFITKLFDDPSQSSELLSEAKKLNDSQAPK | 1305 |
| Z14931 | VDAKYAKEEKFAWTEIHNLPNLTVDQMAAFITKLFDDPSQSSELLSEAKKLNDSQAPK | 1306 |
| Z14932 | VDAKYAKEEWLAWNEIHLLPNLTVDQMAAFITKLFDDPSQSSELLSEAKKLNDSQAPK | 1307 |
| Z14933 | VDAKYAKEEQRAWREIHILPNLTIDQMAAFITKLFDDPSQSSELLSEAKKLNDSQAPK | 1308 |
| Z14934 | VDAKYAKEEFQAWREIHLLPNLTIEQMAAFITKLFDDPSQSSELLSEAKKLNDSQAPK | 1309 |
| Z14935 | VDAKYAKEERMAWHEIHILPNLTVSQVAAFITKLFDDPSQSSELLSEAKKLNDSQAPK | 1310 |
| Z14936 | VDAKYAKEEKKAWYEIHILPNLTVNQIAAFITKLFDDPSQSSELLSEAKKLNDSQAPK | 1311 |
| Z14937 | VDAKYAKEEYYAWNEIHKLPNLTIVIQVAAFITKLFDDPSQSSELLSEAKKLNDSQAPK | 1312 |
| Z14938 | VDAKYAKEEADAWREIHLLPNLTLEQMAAFITKLFDDPSQSSELLSEAKKLNDSQAPK | 1313 |
| Z14939 | VDAKYAKEEYEAWNEIHRLPNLTIDQMAAFITKLFDDPSQSSELLSEAKKLNDSQAPK | 1314 |
| Z14940 | VDAKYAKEEKKAWWEIHALPNLTVNQVAAFITKLFDDPSQSSELLSEAKKLNDSQAPK | 1315 |
| Z14941 | VDAKYAKEEKTAWREIHLLPNLTIEQMAAFITKLFDDPSQSSELLSEAKKLNDSQAPK | 1316 |
| Z14942 | VDAKYAKEEKDAWYEIHLLPNLTVDQIAAFITKLFDDPSQSSELLSEAKKLNDSQAPK | 1317 |
| Z14943 | VDAKYAKEEYTAWYEIHILPNLTIKQMAAFISKLFDDPSQSSELLSEAKKLNDSQAPK | 1318 |
| Z14945 | VDAKYAKEEYHAWYEIHLLPNLTIEQIAAFITKLFDDPSQSSELLSEAKKLNDSQAPK | 1319 |
| Z14946 | VDAKYAKEEAHAWREIHLLPNLTVLQMAAFITKLFDDPSQSSELLSEAKKLNDSQAPK | 1320 |

FIG. 100

| Designation | Sequence | SEQ ID NO |
|---|---|---|
| Z14947 | VDAKYAKEEYEAWNEIHKLPNLTIDQMAAFITKLFDDPSQSSELLSEAKKLNDSQAPK | 1321 |
| Z14948 | VDAKYAKEERAAWNEIHALPNLTIDQMAAFITKLFDDPSQSSELLSEAKKLNDSQAPK | 1322 |
| Z14949 | VDAKYAKEEFDAWVEIHLLPNLTIDQMAAFITKLFDDPSQSSELLSEAKKLNDSQAPK | 1323 |
| Z14950 | VDAKYAKEEKAAWKEIHILPNLTVDQMAAFITKLFDDPSQSSELLSEAKKLNDSQAPK | 1324 |
| Z14951 | VDAKYAKEEWDAWLEIHALPNLTVDQVAAFISKLFDDPSQSSELLSEAKKLNDSQAPK | 1325 |
| Z14953 | VDAKYAKEEYNAWYEIHSLPNLTVEQMAAFITKLFDDPSQSSELLSEAKKLNDSQAPK | 1326 |
| Z14954 | VDAKYAKEEWNAWNEIHKLPNLTVEQMAAFITKLFDDPSQSSELLSEAKKLNDSQAPK | 1327 |
| Z14955 | VDAKYAKEEKEAWFEIHILPNLTVEQIAAFISKLFDDPSQSSELLSEAKKLNDSQAPK | 1328 |
| Z14956 | VDAKYAKEEATAWWEIHKLPNLTVQQVAAFISKLFDDPSQSSELLSEAKKLNDSQAPK | 1329 |
| Z14957 | VDAKYAKEEYEAWYEIHILPNLTVGQIAAFITKLFDDPSQSSELLSEAKKLNDSQAPK | 1330 |
| Z14958 | VDAKYAKEEANAWKEIHLLPNLTVGQVAAFITKLFDDPSQSSELLSEAKKLNDSQAPK | 1331 |
| Z14959 | VDAKYAKEEKRAWHEIHVLPNLTVEQIAAFITKLFDDPSQSSELLSEAKKLNDSQAPK | 1332 |
| Z14960 | VDAKYAKEEYDAWVEIHLLPNLTIDQIAAFITKLFDDPSQSSELLSEAKKLNDSQAPK | 1333 |
| Z14961 | VDAKYAKEEAEAWFEIHILPNLTINQIAAFITKLFDDPSQSSELLSEAKKLNDSQAPK | 1334 |
| Z14962 | VDAKYAKEEWHAWNEIHKLPNLTIDQMAAFITKLFDDPSQSSELLSEAKKLNDSQAPK | 1335 |
| Z14963 | VDAKYAKEEYEAWFEIHILPNLTVDQIAAFITKLFDDPSQSSELLSEAKKLNDSQAPK | 1336 |
| Z14964 | VDAKYAKEEYAWVEIHKLPNLTVEQVAAFITKLFDDPSQSSELLSEAKKLNDSQAPK | 1337 |
| Z14965 | VDAKYAKEERAAWFEIHILPNLTVSQMAAFITKLFDDPSQSSELLSEAKKLNDSQAPK | 1338 |
| Z14966 | VDAKYAKEEAQAWKEIHLLPNLTIEQMAAFISKLFDDPSQSSELLSEAKKLNDSQAPK | 1339 |
| Z14967 | VDAKYAKEEKAAWFEIHILPNLTIEQHMAAFITKLFDDPSQSSELLSEAKKLNDSQAPK | 1340 |
| Z14968 | VDAKYAKEEYAWIEIHNLPNLTIEQVAAFITKLFDDPSQSSELLSEAKKLNDSQAPK | 1341 |
| Z14969 | VDAKYAKEEKYAWVEIHKLPNLTVEQVAAFITKLFDDPSQSSELLSEAKKLNDSQAPK | 1342 |
| Z14970 | VDAKYAKEEYHAWWEIHLLPNLTIDQIAAFITKLFDDPSQSSELLSEAKKLNDSQAPK | 1343 |
| Z14971 | VDAKYAKEEKAAWNEIHLLPNLTIDQMAAFITKLFDDPSQSSELLSEAKKLNDSQAPK | 1344 |
| Z14972 | VDAKYAKEERAWIEIHILPNLTVEQMAAFISKLFDDPSQSSELLSEAKKLNDSQAPK | 1345 |
| Z14973 | VDAKYAKEEHDAWFEIHILPNLTVEQIAAFITKLFDDPSQSSELLSEAKKLNDSQAPK | 1346 |
| Z14974 | VDAKYAKEERNAWMEIHLLPNLTVDQMAAFITKLFDDPSQSSELLSEAKKLNDSQAPK | 1347 |
| Z14975 | VDAKYAKEEKHAWYEIHVLPNLTVGQMAAFITKLFDDPSQSSELLSEAKKLNDSQAPK | 1348 |
| Z14977 | VDAKYAKEEHDAWYEIHILPNLTVDQMAAFITKLFDDPSQSSELLSEAKKLNDSQAPK | 1349 |
| Z14978 | VDAKYAKEEAYAWREIHLLPNLTIHQMAAFITKLFDDPSQSSELLSEAKKLNDSQAPK | 1350 |
| Z14979 | VDAKYAKEEAAAWMEIHLLPNLTVNQMAAFITKLFDDPSQSSELLSEAKKLNDSQAPK | 1351 |
| Z14980 | VDAKYAKEEKEAWYEIHLLPNLTVDQMAAFITKLFDDPSQSSELLSEAKKLNDSQAPK | 1352 |
| Z14981 | VDAKYAKEEYQAWTEIHTLPNLTVDQMAAFITKLFDDPSQSSELLSEAKKLNDSQAPK | 1353 |

FIG. 1PP

| Designation | Sequence | SEQ ID NO |
|---|---|---|
| Z14982 | VDAKYAKEEKDAWYEIHLLPNLTVDQMAAFITKLFDDPSQSSELLSEAKKLNDSQAPK | 1354 |
| Z14983 | VDAKYAKEEANAWWEIHLLPNLTVEQMAAFITKLFDDPSQSSELLSEAKKLNDSQAPK | 1355 |
| Z14985 | VDAKYAKEEAKAWHEIHILPNLTITQMAAFITKLFDDPSQSSELLSEAKKLNDSQAPK | 1356 |
| Z14986 | VDAKYAKEEMSAWVEIHSLPNLTVSQIAAFITKLFDDPSQSSELLSEAKKLNDSQAPK | 1357 |
| Z14987 | VDAKYAKEERRAWYEIHILPNLTVEQMAAFITKLFDDPSQSSELLSEAKKLNDSQAPK | 1358 |
| Z14988 | VDAKYAKEEKDAWFEIHVLPNLTVDQMAAFITKLFDDPSQSSELLSEAKKLNDSQAPK | 1359 |
| Z14989 | VDAKYAKEEKRAWLEIHNLPNLTIDQMAAFISKLFDDPSQSSELLSEAKKLNDSQAPK | 1360 |
| Z14991 | VDAKYAKEEHGAWTEIHLLPNLTIEQVAAFITKLFDDPSQSSELLSEAKKLNDSQAPK | 1361 |
| Z14993 | VDAKYAKEERKAWIEIHLLPNLTIEQMAAFITKLFDDPSQSSELLSEAKKLNDSQAPK | 1362 |
| Z14994 | VDAKYAKEERSAWTEIHLLPNLTIDQMAAFITKLFDDPSQSSELLSEAKKLNDSQAPK | 1363 |
| Z14995 | VDAKYAKEELKAWTEIHNLPNLTIDQMAAFITKLFDDPSQSSELLSEAKKLNDSQAPK | 1364 |
| Z14996 | VDAKYAKEEANAWYEIHILPNLTVDQVAAFITKLFDDPSQSSELLSEAKKLNDSQAPK | 1365 |
| Z14997 | VDAKYAKEEWQAWWEIHALPNLTVEQVAAFITKLFDDPSQSSELLSEAKKLNDSQAPK | 1366 |
| Z14998 | VDAKYAKEEYNAWLEIHSLPNLTPNLTVTQMAAFITKLFDDPSQSSELLSEAKKLNDSQAPK | 1367 |
| Z14999 | VDAKYAKEEKKAWTEIHTLPNLTLPNLTVEQMAAFITKLFDDPSQSSELLSEAKKLNDSQAPK | 1368 |
| Z15000 | VDAKYAKEEKAAWYEIHLLPNLTPNLTVVQMAAFITKLFDDPSQSSELLSEAKKLNDSQAPK | 1369 |
| Z15001 | VDAKYAKEEKAAWREIHLLPNLTLPNLTINQMAAFITKLFDDPSQSSELLSEAKKLNDSQAPK | 1370 |
| Z15002 | VDAKYAKEEFEAWVEIHLLPNLTIEQIAAFITKLFDDPSQSSELLSEAKKLNDSQAPK | 1371 |
| Z15004 | VDAKYAKEEYAAWVEIHNLPNLTVEQMAAFITKLFDDPSQSSELLSEAKKLNDSQAPK | 1372 |
| Z15005 | VDAKYAKEESDAWYEIHTLPNLTINQMAAFISKLFDDPSQSSELLSEAKKLNDSQAPK | 1373 |
| Z15006 | VDAKYAKEEKFAWTEIHILPNLTVDQMAAFITKLFDDPSQSSELLSEAKKLNDSQAPK | 1374 |
| Z15007 | VDAKYAKEEAEAWWEIHILPNLTVSQIAAFISKLFDDPSQSSELLSEAKKLNDSQAPK | 1375 |
| Z15008 | VDAKYAKEEYQAWFEIHLLPNLTIDQMAAFITKLFDDPSQSSELLSEAKKLNDSQAPK | 1376 |
| Z15009 | VDAKYAKEEWEAWVEIHNLPNLTVHNLPNLTVDQMAAFITKLFDDPSQSSELLSEAKKLNDSQAPK | 1377 |
| Z15010 | VDAKYAKEEAKAWTEIHTLPNLTVDQMAAFITKLFDDPSQSSELLSEAKKLNDSQAPK | 1378 |
| Z15011 | VDAKYAKEEQLAWTEIHKLPNLTIDQMAAFITKLFDDPSQSSELLSEAKKLNDSQAPK | 1379 |
| Z15012 | VDAKYAKEEYDAWTEIHLLPNLTIEQMAAFITKLFDDPSQSSELLSEAKKLNDSQAPK | 1380 |
| Z15013 | VDAKYAKEEWDAWVEIHTLPNLTVDQMAAFITKLFDDPSQSSELLSEAKKLNDSQAPK | 1381 |
| Z15014 | VDAKYAKEEFEAWHEIHILPNLTVQQMAAFITKLFDDPSQSSELLSEAKKLNDSQAPK | 1382 |
| Z15016 | VDAKYAKEEWEAWVEIHNLPNLTIDQMAAFITKLFDDPSQSSELLSEAKKLNDSQAPK | 1383 |
| Z15017 | VDAKYAKEERAAWWEIHGLPNLTVDQMAAFITKLFDDPSQSSELLSEAKKLNDSQAPK | 1384 |
| Z15018 | VDAKYAKEERDAWHEIHRLPNLTIEQMAAFISKLFDDPSQSSELLSEAKKLNDSQAPK | 1385 |
| Z15019 | VDAKYAKEEKTAWTEIHILPNLTIHQMAAFISKLFDDPSQSSELLSEAKKLNDSQAPK | 1386 |
| | VDAKYAKEEFDAWMEIHLLPNLTINQMAAFITKLFDDPSQSSELLSEAKKLNDSQAPK | |

FIG. 1QQ

| Designation | Sequence | SEQ ID NO |
|---|---|---|
| Z15020 | VDAKYAKEEHLAWVEIHNLPNLTVEQMAAFITKLFDDPSQSSELLSEAKKLNDSQAPK | 1387 |
| Z15021 | VDAKYAKEERHAWWEIHKLPNLTIEQMAAFITKLFDDPSQSSELLSEAKKLNDSQAPK | 1388 |
| Z15022 | VDAKYAKEEYDAWFEIHLLPNLTVEQMAAFITKLFDDPSQSSELLSEAKKLNDSQAPK | 1389 |
| Z15023 | VDAKYAKEEKWAWTEIHLLPNLTIEQMAAFISKLFDDPSQSSELLSEAKKLNDSQAPK | 1390 |
| Z15026 | VDAKYAKEEAKAWFEIHILPNLTIEQIAAFITKLFDDPSQSSELLSEAKKLNDSQAPK | 1391 |
| Z15027 | VDAKYAKEEYRAWTEIHLLPNLTIHQMAAFITKLFDDPSQSSELLSEAKKLNDSQAPK | 1392 |
| Z15028 | VDAKYAKEEKHAWTEIHILPNLTVEQMAAFITKLFDDPSQSSELLSEAKKLNDSQAPK | 1393 |
| Z15029 | VDAKYAKEEARAWTEIHTLPNLTIDQIAAFITKLFDDPSQSSELLSEAKKLNDSQAPK | 1394 |
| Z15030 | VDAKYAKEEYAAWVEIHSLPNLTVDQMAAFITKLFDDPSQSSELLSEAKKLNDSQAPK | 1395 |
| Z15032 | VDAKYAKEEYDAWYEIHLLPNLTINQMAAFITKLFDDPSQSSELLSEAKKLNDSQAPK | 1396 |
| Z15033 | VDAKYAKEEFNAWNEIHLLPNLTVTQMAAFITKLFDDPSQSSELLSEAKKLNDSQAPK | 1397 |
| Z15034 | VDAKYAKEEKAAWNEIHLLPNLTIDQMAAFISKLFDDPSQSSELLSEAKKLNDSQAPK | 1398 |
| Z15035 | VDAKYAKEERIAWFEIHILPNLTIKQMAAFISKLFDDPSQSSELLSEAKKLNDSQAPK | 1399 |
| Z15037 | VDAKYAKEEYKAWYEIHILPNLTVQQMAAFITKLFDDPSQSSELLSEAKKLNDSQAPK | 1400 |
| Z15038 | VDAKYAKEEQHAWYEIHILPNLTIDQMAAFITKLFDDPSQSSELLSEAKKLNDSQAPK | 1401 |
| Z15039 | VDAKYAKEERYAWFEIHALPNLTVSQMAAFITKLFDDPSQSSELLSEAKKLNDSQAPK | 1402 |
| Z15040 | VDAKYAKEEYKAWIEIHILPNLTIDQIAAFISKLFDDPSQSSELLSEAKKLNDSQAPK | 1403 |
| Z15041 | VDAKYAKEERTAWFEIHILPNLTVDQIAAFITKLFDDPSQSSELLSEAKKLNDSQAPK | 1404 |
| Z15043 | VDAKYAKEEKHAWWEIHILPNLTINQMAAFITKLFDDPSQSSELLSEAKKLNDSQAPK | 1405 |
| Z15044 | VDAKYAKEEKMAWFEIHVLPNLTISQIAAFITKLFDDPSQSSELLSEAKKLNDSQAPK | 1406 |
| Z15045 | VDAKYAKEEFDAWTEIHLLPNLTVDQMAAFITKLFDDPSQSSELLSEAKKLNDSQAPK | 1407 |
| Z15046 | VDAKYAKEERDAWFEIHRLPNLTVSQMAAFITKLFDDPSQSSELLSEAKKLNDSQAPK | 1408 |
| Z15047 | VDAKYAKEEAVAWTEIHILPNLTVEQVAAFITKLFDDPSQSSELLSEAKKLNDSQAPK | 1409 |
| Z15048 | VDAKYAKEEWYAWREIHILPNLTVEQMAAFITKLFDDPSQSSELLSEAKKLNDSQAPK | 1410 |
| Z15049 | VDAKYAKEEFHAWYEIHILPNLTIDQMAAFITKLFDDPSQSSELLSEAKKLNDSQAPK | 1411 |
| Z15050 | VDAKYAKEEYEAWTEIHLLPNLTINQMAAFITKLFDDPSQSSELLSEAKKLNDSQAPK | 1412 |
| Z15051 | VDAKYAKEEWDAWTEIHALPNLTIDQMAAFITKLFDDPSQSSELLSEAKKLNDSQAPK | 1413 |
| Z15052 | VDAKYAKEESEAWTEIHLLPNLTIDQMAAFITKLFDDPSQSSELLSEAKKLNDSQAPK | 1414 |
| Z15054 | VDAKYAKEEFTAWSEIHNLPNLTVEQMAAFITKLFDDPSQSSELLSEAKKLNDSQAPK | 1415 |
| Z15055 | VDAKYAKEEADAWHEIHILPNLTVEQMAAFITKLFDDPSQSSELLSEAKKLNDSQAPK | 1416 |
| Z15056 | VDAKYAKEEKAAWFEIHILPNLTVDQMAAFITKLFDDPSQSSELLSEAKKLNDSQAPK | 1417 |
| Z15058 | VDAKYAKEERRAWHEIHILPNLTVEQMAAFISKLFDDPSQSSELLSEAKKLNDSQAPK | 1418 |
| Z15059 | VDAKYAKEERDAWWEIHKLPNLTVDQMAAFITKLFDDPSQSSELLSEAKKLNDSQAPK | 1419 |

FIG. 1RR

| Designation | Sequence | SEQ ID NO |
|---|---|---|
| Z15060 | VDAKYAKEEAYAWKEIHILPNLTIDQMAAFISKLFDDPSQSSELLSEAKKLNDSQAPK | 1420 |
| Z15061 | VDAKYAKEERAAWTEIHNLPNLTIDQMAAFITKLFDDPSQSSELLSEAKKLNDSQAPK | 1421 |
| Z15062 | VDAKYAKEEYAAWTEIHKLPNLTIDQMAAFITKLFDDPSQSSELLSEAKKLNDSQAPK | 1422 |
| Z15063 | VDAKYAKEERTAWMEIHGLPNLTIEQMAAFISKLFDDPSQSSELLSEAKKLNDSQAPK | 1423 |
| Z15064 | VDAKYAKEEWTAWMEIHLLPNLTIEQMAAFITKLFDDPSQSSELLSEAKKLNDSQAPK | 1424 |
| Z15065 | VDAKYAKEEKDAWFEIHILPNLTVHQIAAFISKLFDDPSQSSELLSEAKKLNDSQAPK | 1425 |
| Z15066 | VDAKYAKEEKSAWREIHLLPNLTIEQMAAFISKLFDDPSQSSELLSEAKKLNDSQAPK | 1426 |
| Z15068 | VDAKYAKEEYTAWLEIHALPNLTITQMAAFITKLFDDPSQSSELLSEAKKLNDSQAPK | 1427 |
| Z15069 | VDAKYAKEEKMAWMEIHKLPNLTIDQMAAFITKLFDDPSQSSELLSEAKKLNDSQAPK | 1428 |
| Z15070 | VDAKYAKEEYHAWYEIHLLPNLTVEQIAAFITKLFDDPSQSSELLSEAKKLNDSQAPK | 1429 |
| Z15071 | VDAKYAKEEKDAWFEIHALPNLTVDQMAAFITKLFDDPSQSSELLSEAKKLNDSQAPK | 1430 |
| Z15072 | VDAKYAKEEIRAAWFEIHLLPNLTVEQMAAFITKLFDDPSQSSELLSEAKKLNDSQAPK | 1431 |
| Z15073 | VDAKYAKEEYMAWLEIHNLPNLTVEQMAAFITKLFDDPSQSSELLSEAKKLNDSQAPK | 1432 |
| Z15074 | VDAKYAKEEYTAWREIHLLPNLTIDQMAAFISKLFDDPSQSSELLSEAKKLNDSQAPK | 1433 |
| Z15075 | VDAKYAKEEKAAWHEIHVLPNLTISQMAAFITKLFDDPSQSSELLSEAKKLNDSQAPK | 1434 |
| Z15076 | VDAKYAKEEWQAWNEIHLLPNLTIEQMAAFITKLFDDPSQSSELLSEAKKLNDSQAPK | 1435 |
| Z15078 | VDAKYAKEEWEAWFEIHLLPNLTISQMAAFISKLFDDPSQSSELLSEAKKLNDSQAPK | 1436 |
| Z15080 | VDAKYAKEEYHAWWEIHKLPNLTIEQMAAFITKLFDDPSQSSELLSEAKKLNDSQAPK | 1437 |
| Z15081 | VDAKYAKEEYAAWVEIHALPNLTVEQMAAFITKLFDDPSQSSELLSEAKKLNDSQAPK | 1438 |
| Z15083 | VDAKYAKEERMAWHEIHILPNLTVQQMAAFISKLFDDPSQSSELLSEAKKLNDSQAPK | 1439 |
| Z15084 | VDAKYAKEERDAWYEIHNLPNLTIDQMAAFITKLFDDPSQSSELLSEAKKLNDSQAPK | 1440 |
| Z15085 | VDAKYAKEESYAWWEIHKLPNLTIVEQMAAFITKLFDDPSQSSELLSEAKKLNDSQAPK | 1441 |
| Z15086 | VDAKYAKEEKRAWKEIHILPNLTIHALPNLTVEQIAAFITKLFDDPSQSSELLSEAKKLNDSQAPK | 1442 |
| Z15087 | VDAKYAKEEKEAWFEIHALPNLTVEQIAAFITKLFDDPSQSSELLSEAKKLNDSQAPK | 1443 |
| Z15088 | VDAKYAKEEYEAWNEIHLLPNLTVSQMAAFISKLFDDPSQSSELLSEAKKLNDSQAPK | 1444 |
| Z15089 | VDAKYAKEEAAAWMEIHLLPNLTIDQMAAFITKLFDDPSQSSELLSEAKKLNDSQAPK | 1445 |
| Z15090 | VDAKYAKEERNAWEEIHLLPNLTINQIAAFITKLFDDPSQSSELLSEAKKLNDSQAPK | 1446 |
| Z15091 | VDAKYAKEEYAWHEIHILPNLTVDQMAAFITKLFDDPSQSSELLSEAKKLNDSQAPK | 1447 |
| Z15092 | VDAKYAKEEANAWFEIHVLPNLTVEQMAAFISKLFDDPSQSSELLSEAKKLNDSQAPK | 1448 |
| Z15093 | VDAKYAKEEKNAWTEIHKLPNLTVDQMAAFITKLFDDPSQSSELLSEAKKLNDSQAPK | 1449 |
| Z15094 | VDAKYAKEEYDAWYEIHLLPNLTISQMAAFISKLFDDPSQSSELLSEAKKLNDSQAPK | 1450 |
| Z15095 | VDAKYAKEERLAWAEIHKLPNLTIEQVAAFISKLFDDPSQSSELLSEAKKLNDSQAPK | 1451 |
| Z15096 | VDAKYAKEERAAWNEIHILPNLTVQQMAAFITKLFDDPSQSSELLSEAKKLNDSQAPK | 1452 |

FIG. 1SS

| Designation | Sequence | SEQ ID NO |
|---|---|---|
| Z15098 | VDAKYAKEEAAAWDEIHRLPNLTVDQIAAFITKLFDDPSQSSELLSEAKKLNDSQAPK | 1453 |
| Z15099 | VDAKYAKEEKEAWWEIHGLPNLTVNQMAAFITKLFDDPSQSSELLSEAKKLNDSQAPK | 1454 |
| Z15100 | VDAKYAKEERKAWYEIHTLPNLTINQMAAFITKLFDDPSQSSELLSEAKKLNDSQAPK | 1455 |
| Z15101 | VDAKYAKEERRNAWYEIHILPNLTIEQMAAFITKLFDDPSQSSELLSEAKKLNDSQAPK | 1456 |
| Z15103 | VDAKYAKEEKLAWMEIHLLPNLTIEQMAAFITKLFDDPSQSSELLSEAKKLNDSQAPK | 1457 |
| Z15104 | VDAKYAKEEYMAWLEIHNLPNLTVDQMAAFITKLFDDPSQSSELLSEAKKLNDSQAPK | 1458 |
| Z15105 | VDAKYAKEESDAWREIHLLPNLTIEQMAAFISKLFDDPSQSSELLSEAKKLNDSQAPK | 1459 |
| Z15106 | VDAKYAKEEKEAWYEIHQLPNLTVNQMAAFISKLFDDPSQSSELLSEAKKLNDSQAPK | 1460 |
| Z15107 | VDAKYAKEEKQAWYEIHNLPNLTINQMAAFITKLFDDPSQSSELLSEAKKLNDSQAPK | 1461 |
| Z15108 | VDAKYAKEEYEAWTEIHRLPNLTIDQMAAFITKLFDDPSQSSELLSEAKKLNDSQAPK | 1462 |
| Z15109 | VDAKYAKEEKDAWYEIHVLPNLTISQMAAFITKLFDDPSQSSELLSEAKKLNDSQAPK | 1463 |
| Z15112 | VDAKYAKEERIAWYEIHILPNLTISQMAAFITKLFDDPSQSSELLSEAKKLNDSQAPK | 1464 |
| Z15113 | VDAKYAKEEQYAWTEIHLLPNLTIDQMAAFITKLFDDPSQSSELLSEAKKLNDSQAPK | 1465 |
| Z15114 | VDAKYAKEESDAWWEIHKLPNLTIDQMAAFITKLFDDPSQSSELLSEAKKLNDSQAPK | 1466 |
| Z15115 | VDAKYAKEEKFAWNEIHLLPNLTIEQMAAFITKLFDDPSQSSELLSEAKKLNDSQAPK | 1467 |
| Z15116 | VDAKYAKEERAAWYEIHILPNLTVNQIAAFITKLFDDPSQSSELLSEAKKLNDSQAPK | 1468 |
| Z15118 | VDAKYAKEEFHAWWEIHLLPNLTVEQVAAFITKLFDDPSQSSELLSEAKKLNDSQAPK | 1469 |
| Z15119 | VDAKYAKEEKQAWLEIHILPNLTVDQIAAFITKLFDDPSQSSELLSEAKKLNDSQAPK | 1470 |
| Z15120 | VDAKYAKEEHLAWTEIHLLPNLTINQMAAFITKLFDDPSQSSELLSEAKKLNDSQAPK | 1471 |
| Z15121 | VDAKYAKEEATAWREIHLLPNLTINQMAAFITKLFDDPSQSSELLSEAKKLNDSQAPK | 1472 |
| Z15123 | VDAKYAKEEKRAWYEIHILPNLTVEQVAAFITKLFDDPSQSSELLSEAKKLNDSQAPK | 1473 |
| Z15124 | VDAKYAKEEYEAWTEIHLLPNLTVSQMAAFITKLFDDPSQSSELLSEAKKLNDSQAPK | 1474 |
| Z15125 | VDAKYAKEESNAWWEIHKLPNLTVNQVAAFITKLFDDPSQSSELLSEAKKLNDSQAPK | 1475 |
| Z15127 | VDAKYAKEEKRAWMEIHLLPNLTVDQIAAFITKLFDDPSQSSELLSEAKKLNDSQAPK | 1476 |
| Z15128 | VDAKYAKEEKFAWKEIHILPNLTVDQIAAFITKLFDDPSQSSELLSEAKKLNDSQAPK | 1477 |
| Z15130 | VDAKYAKEERDAWFEIHVLPNLTILQMAAFITKLFDDPSQSSELLSEAKKLNDSQAPK | 1478 |
| Z15131 | VDAKYAKEEHYAWTEIHILPNLTVNQMAAFITKLFDDPSQSSELLSEAKKLNDSQAPK | 1479 |
| Z15132 | VDAKYAKEEKRAWMEIHLLPNLTVHQMAAFITKLFDDPSQSSELLSEAKKLNDSQAPK | 1480 |
| Z15133 | VDAKYAKEEYDAWVEIHLLPNLTVEQIAAFITKLFDDPSQSSELLSEAKKLNDSQAPK | 1481 |
| Z15134 | VDAKYAKEEHTAWFEIHILPNLTISQIAAFITKLFDDPSQSSELLSEAKKLNDSQAPK | 1482 |
| Z15135 | VDAKYAKEELQAWKEIHILPNLTVDQIAAFITKLFDDPSQSSELLSEAKKLNDSQAPK | 1483 |
| Z15136 | VDAKYAKEEYDAWLEIHLLPNLTISQMAAFITKLFDDPSQSSELLSEAKKLNDSQAPK | 1484 |
| Z15137 | VDAKYAKEEARAWREIHILPNLTVEQMAAFITKLFDDPSQSSELLSEAKKLNDSQAPK | 1485 |

FIG. 1TT

| Designation | Sequence | SEQ ID NO |
|---|---|---|
| Z15138 | VDAKYAKEERNAWFEIHILPNLTIDQMAAFITKLFDDPSQSSELLSEAKKLNDSQAPK | 1486 |
| Z15139 | VDAKYAKEEAYAWHEIHVLPNLTIDQMAAFITKLFDDPSQSSELLSEAKKLNDSQAPK | 1487 |
| Z15143 | VDAKYAKEEYFAWTEIHKLPNLTINQMAAFITKLFDDPSQSSELLSEAKKLNDSQAPK | 1488 |
| Z15144 | VDAKYAKEEAGAWYEIHLLPNLTVEQMAAFITKLFDDPSQSSELLSEAKKLNDSQAPK | 1489 |
| Z15146 | VDAKYAKEEKKAWYEIHILPNLTIEQMAAFISKLFDDPSQSSELLSEAKKLNDSQAPK | 1490 |
| Z15147 | VDAKYAKEEKQAWFEIHLLPNLTIEQMAAFISKLFDDPSQSSELLSEAKKLNDSQAPK | 1491 |
| Z15148 | VDAKYAKEEWHAWLEIHNLPNLTIEQMAAFITKLFDDPSQSSELLSEAKKLNDSQAPK | 1492 |
| Z15149 | VDAKYAKEEKSAWIEIHNLPNLTINQMAAFITKLFDDPSQSSELLSEAKKLNDSQAPK | 1493 |
| Z15150 | VDAKYAKEEYQAWNEIHILPNLTINQIAAFITKLFDDPSQSSELLSEAKKLNDSQAPK | 1494 |
| Z15152 | VDAKYAKEEAYAWVEIHKLPNLTVTQVAAFISKLFDDPSQSSELLSEAKKLNDSQAPK | 1495 |
| Z15153 | VDAKYAKEEYDAWMEIHNLPNLTIEQMAAFITKLFDDPSQSSELLSEAKKLNDSQAPK | 1496 |
| Z15154 | VDAKYAKEEYEAWVEIHNLPNLTIEQIAAFITKLFDDPSQSSELLSEAKKLNDSQAPK | 1497 |
| Z15155 | VDAKYAKEEREAWNEIHLLPNLTIEQIAAFITKLFDDPSQSSELLSEAKKLNDSQAPK | 1498 |
| Z15156 | VDAKYAKEEKRAWYEIHILPNLTVDQMAAFITKLFDDPSQSSELLSEAKKLNDSQAPK | 1499 |
| Z15157 | VDAKYAKEEKEAWTEIHILPNLTIHQVAAFITKLFDDPSQSSELLSEAKKLNDSQAPK | 1500 |
| Z15161 | VDAKYAKEEFEAWFEIHKLPNLTIQILPNLTITQMAAFISKLFDDPSQSSELLSEAKKLNDSQAPK | 1501 |
| Z15163 | VDAKYAKEESQAWTEIHVLPNLTVQQMAAFITKLFDDPSQSSELLSEAKKLNDSQAPK | 1502 |
| Z06777 | VDAKYAKEERKAWFEIHLLPNLTIEQMAAFITKLFDDPSQSSELLSEAKKLNDSQAPK | 1503 |
| Z06779 | VDAKYAKEERSAWFEIHTLPNLTVQQIAAFIWKLYDDPSQSSELLSEAKKLNDSQAPK | 1504 |
| Z06789 | VDAKYAKEERQAWWEIHSLPNLTVDQMAAFIVKLMDDPSQSSELLSEAKKLNDSQAPK | 1505 |
| Z06791 | VDAKYAKEQAKAWWEIHVLPNLTVHQVAAFITKLFDDPSQSSELLSEAKKLNDSQAPK | 1506 |
| Z06792 | VDAKYAKEERDAWHEIQILPNLTITQMAAFISKLFDDPSQSSELLSEAKKLNDSQAPK | 1507 |
| Z06799 | VDAKYAKEEQRAWTEIHVLPNLTVQQMAAFITKLFDDPSQSSELLSEAKKLNDSQAPK | 1508 |
| Z06802 | VDAKYAKETQHAWWEIHKLPNLTVSQMAAFITKLFDDPSQSSELLSEAKKLNDSQAPK | 1509 |
| Z06805 | VDAKYAKEEDRTAWWEIHKLPNLTIAEQMAAFIVDQLVAFITKLFDDPSQSSELLSEAKKLNDSQAPK | 1510 |
| Z06809 | VDAKYAKEERDAWREIHALPNLTVDQLVAFITKLFDDPSQSSELLSEAKKLNDSQAPK | 1511 |
| Z06814 | VDAKYAKEEQRAWREIHLLPNLTIEQMAAFIWKLLDDPSQSSELLSEAKKLNDSQAPK | 1512 |
| Z06829 | VDAKYAKEEQRAWTEIHVLPNLTVSQMSAFITKLFDDPSQSSELLSEAKKLNDSQAPK | 1513 |
| Z06834 | VDAKYAKEEQHQAWNEIHLLPNLTVNQMAAFIVKLFDDPSQSSELLSEAKKLNDSQAPK | 1514 |
| Z06844 | VDAKYAKEEHAAWLEIHLLPNLTVKQMAAFIGKLMDDPSQSSELLSEAKKLNDSQAPK | 1515 |
| Z06776 | VDAKYAKEEQMAWFEIHLLPNLTVGQMAAFIQKLFDDPSQSSELLSEAKKLNDSQAPK | 1516 |
| Z06778 | VDAKYAKEERSAWFEIHILPNLTISQKSAFIVKLFDDPSQSSELLSEAKKLNDSQAPK | 1517 |
| Z06780 | VDAKYAKEERSAWYEIHLLPNLTADQMAAFIAKLFDDPSQSSELLSEAKKLNDSQAPK | 1518 |

FIG. 1UU

| Designation | Sequence | SEQ ID NO |
|---|---|---|
| Z06787 | VDAKYAKEEQRAWYEIHLLPNLTIEQLTAFIMKLMDDPSQSSELLSEAKKLNDSQAPK | 1519 |
| Z06788 | VDAKYAKEERQAWWEITILPNLTIEQVAAFITKLFDDPSQSSELLSEAKKLNDSQAPK | 1520 |
| Z06793 | VDAKYAKEDYEAWVEIHVLPNLTVEQKAAFIVKLFDDPSQSSELLSEAKKLNDSQAPK | 1521 |
| Z06794 | VDAKYAKEVYNAWHEIHVLPNLTTLQISAFISKLFDDPSQSSELLSEAKKLNDSQAPK | 1522 |
| Z06796 | VDAKYAKEERKAWWEIHLLPNLTIEQRTAAFIWKLLDDPSQSSELLSEAKKLNDSQAPK | 1523 |
| Z06797 | VDAKYAKEEQAAWWEIHMLPNLTIEQRTAFIIKLFDDPSQSSELLSEAKKLNDSQAPK | 1524 |
| Z06806 | VDAKYAKEEQTAWFEIHILPNLTVNQRVAFITKLFDDPSQSSELLSEAKKLNDSQAPK | 1525 |
| Z06808 | VDAKYAKEEALAWREIHLLPNLTTVQISAFIAKLLDDPSQSSELLSEAKKLNDSQAPK | 1526 |
| Z06810 | VDAKYAKEEKFAWTEIHLLPNLTIGQQAAFIWKLFDDPSQSSELLSEAKKLNDSQAPK | 1527 |
| Z06811 | VDAKYAKEERAAWWEIHVLPNLTVSQMYAFITKLFDDPSQSSELLSEAKKLNDSQAPK | 1528 |
| Z06812 | VDAKYAKEEQRAWYEIHLLPNLTVRQRGAFITKLFDDPSQSSELLSEAKKLNDSQAPK | 1529 |
| Z06815 | VDAKYAKEHRQAWWEIHLLPNLTIRQIAAFIAKLFDDPSQSSELLSEAKKLNDSQAPK | 1530 |
| Z06823 | VDAKYAKEEKVAWREIHVLPNLTVSQISAFITKLFDDPSQSSELLSEAKKLNDSQAPK | 1531 |
| Z06824 | VDAKYAKEEKHAWYEIHLLPNLTISQLSAFIMKLFDDPSQSSELLSEAKKLNDSQAPK | 1532 |
| Z06830 | VDAKYAKESAFAWWEIHLLPNLTVEQIAAFIWKLLDDPSQSSELLSEAKKLNDSQAPK | 1533 |
| Z06836 | VDAKYAKEEQVAWREIHVLPNLTVEQVKAFINKLFDDPSQSSELLSEAKKLNDSQAPK | 1534 |
| Z06838 | VDAKYAKEEMDAWTEIHILPNLTVEQMEAFIVKLFDDPSQSSELLSEAKKLNDSQAPK | 1535 |
| Z06839 | VDAKYAKEEGRAWYEIHALPNLTVEQMSAFINKLFDDPSQSSELLSEAKKLNDSQAPK | 1536 |
| Z06841 | VDAKYAKEERNAWFEIHTIPNLTFLSQITAFIWKLLDDPSQSSELLSEAKKLNDSQAPK | 1537 |
| Z06842 | VDAKYAKEEHNAWTEIHRLPNLTVKQTSAFIEKLFDDPSQSSELLSEAKKLNDSQAPK | 1538 |
| Z06845 | VDAKYAKEEFKAWWEIHVLPNLTADQVAAFIVKLFDDPSQSSELLSEAKKLNDSQAPK | 1539 |
| Z06846 | VDAKYAKEQHMAWTEIHLLPNLTVAQMAAFIVKLFDDPSQSSELLSEAKKLNDSQAPK | 1540 |
| Z06854 | VDAKYAKEEQRAWWEIHLLPNLTARQTAAFIWKLMDDPSQSSELLSEAKKLNDSQAPK | 1541 |
| Z06855 | VDAKYAKEEQKSAWTEIHLLPNLTVHQISAFIAKLLDDPSQSSELLSEAKKLNDSQAPK | 1542 |
| Z06856 | VDAKYAKEEHLAWKEIHKLPNLTVIQMAAFIAKLFDDPSQSSELLSEAKKLNDSQAPK | 1543 |
| Z06857 | VDAKYAKEERAAWWEIHMLPNLTADQMAAFIAKLFDDPSQSSELLSEAKKLNDSQAPK | 1544 |
| Z06859 | VDAKYAKEQRTAWWEIHILPNLTVKQLVAFINKLFDDPSQSSELLSEAKKLNDSQAPK | 1545 |
| Z06861 | VDAKYAKEQIAWFEIHLLPNLTVGQRTAFIVKLFDDPSQSSELLSEAKKLNDSQAPK | 1546 |
| Z06862 | VDAKYAKEERRAWFEISVLPNLTIVDPNLTVDQTAAFIMKLFDDPSQSSELLSEAKKLNDSQAPK | 1547 |
| Z06864 | VDAKYAKEEADAWMEIHILPNLTVLQRSAFIIKLFDDPSQSSELLSEAKKLNDSQAPK | 1548 |
| Z06865 | VDAKYAKEEREAWFEIHVLPNLTIKQISAFIHKLFDDPSQSSELLSEAKKLNDSQAPK | 1549 |
| Z06866 | VDAKYAKEERRAWFEIHTLPNLTVEQIEAFINKLFDDPSQSSELLSEAKKLNDSQAPK | 1550 |
| Z06871 | VDAKYAKEERAAWWEIHGLPNLTVWQTAAFIVKLFDDPSQSSELLSEAKKLNDSQAPK | 1551 |

FIG. 1VV

| Designation | Sequence | SEQ ID NO |
|---|---|---|
| Z03638 | AEAKYAKELGWATWEIFNLPNLTGVQVKAFIDKLRDDPSQSSELLSEAKKLNDSQAPK | 1552 |
| Z04726 | VDAKYAKELGWATWEIFNLPNLTGVQVKAFIDKLRDDPSQSSELLSEAKKLNDSQAPK | 1553 |
| PP013 | LAEAKEAANAELDSYGVSDFYKRLIDKAKTVEGVEALKDAILAALP | 1554 |
| hIL-6 | PVPPGEDSKDVAAPHRQPLTSSERIDKQIRYILDGISALRKETCNKSNMCESSKEALAENNLNLPKMAEKDGCFQSGF NEETCLVKIITGLLEFEVYLEYLQNRFESSEEQARAVQMSTKVLIQFLQKKAKNLDAITTPDPTTNASLLTKLQAQNQ WLQDMTTHLILRSFKEFLQSSLRALRQM | 1555 |
| mIL-6 | MFPTSQVRRGDFTEDTTPNRPVYTTSQVGGLITHVLWEIVEMRKELCNGNSDCMNNDDALAENNLKLPEIQRNDGCYQ TGYNQEICLLKISSGLLEYHSYLEYMKNNLKDNKKDKARVLQRDTETLIHIFNQEVKDLHKIVLPTPISNALLTDKLE SQKEWLRTKTIQFILKSLEEFLKVTLRSTRQT | 1556 |

POLYPEPTIDE

CROSS REFERENCE TO RELATED APPLICATIONS

This application is a National Stage application of PCT/EP2015/063362, filed Jun. 15, 2015, which claims priority to EP Application No. 14172331.2, filed Jun. 13, 2014, both of which are incorporated by reference in their entirety herein.

JOINT RESEARCH AGREEMENT

The presently claimed invention was made by or on behalf of the below listed parties to a joint research agreement. The joint research agreement was in effect on or before the date the claimed invention was made and the claimed invention was made as a result of activities undertaken within the scope of the joint research agreement. The parties to the joint research agreement are Affibody AB, Solna, SE and AbClon Inc., Seoul, KR.

FIELD OF THE INVENTION

The present disclosure relates to a class of engineered polypeptides having a binding affinity for interleukin-6 (in the following referred to as IL-6). The present disclosure also relates to the use of such an IL-6 binding polypeptide as a therapeutic, prognostic and/or diagnostic agent.

BACKGROUND

Inflammation is a cytokine-driven response by the innate immune system to destroy for example pathogens and damaged cells. In some disease conditions, such as rheumatoid arthritis (RA) and Crohn's disease, the regulation of the inflammatory system is impaired leading to tissue damages. Among the most studied inducers of inflammation are the cytokines interleukin-6 (IL-6) and tumor necrosis factor (TNF). IL-6 is also known as B cell Stimulatory Factor 2 (BSF2), Hepatocyte Stimulating Factor (HSF), Hybridoma Growth Factor (HGF) and interferon-beta 2 (IFNB2).

Human IL-6 consists of a single polypeptide chain of 184 amino acids with a molecular weight of 21 kDa, however a variable glycosylation pattern accounts for sizes varying between 21-26 kDa. IL-6 is secreted by a wide variety of cell types including T cells, B cells, monocytes, fibroblasts, hepatocytes, endothelial cells and keratinocytes. Downstream signaling induces the transition from acute inflammation to either acquired immunity or chronic inflammatory disease. IL-6 signaling and its regulation is complex and involves a number of factors and mechanisms. IL-6 signaling may occur via the classical IL-6 singling pathway, also known as the cis-signaling pathway, or via the trans-signaling pathway. In the classical IL-6 signaling pathway, circulating IL-6 binds to a membrane bound IL-6 receptor a (IL-6Rα) followed by recruitment of the membrane anchored gp130 co-receptor, which results in the formation of a ternary complex. This complex subsequently dimerizes with a second adjacent ternary complex leading to signal transduction via the gp130 moities (Boulanger et al., 2003, Science 300(5628): 2101-2104). In circulation, IL-6 can also exist as bound to soluble ectodomains of IL-6Rα. Such complexes are responsible for the trans-signaling mechanism, involving IL-6 dependent activation of any cells that express the co-receptor gp130 but lack IL-6Rα (Chalaris et al., 2011, Eur J Cell Biol 90(6-7): 484-494; Assier et al., 2010, Joint Bone Spine 77(6):532-6). The trans-signaling, or pro-inflammatory, pathway has been suggested to be the pathway most related to disease conditions, and thus the most preferable to block. In contrast, the classical signaling pathway is regarded as being responsible for important anti-inflammatory and regenerative processes (Scheller et al., 2011, Biochim Biophys Acta 1813(5): 878-888).

The anti-IL-6Rα antibody tocilizumab (Actemra®), has been approved for clinical use for IL-6 related disorders. Other drug candidates are also being developed in order to address different IL-6 triggered pathways. These include the antibodies CNTO136 (sirukumab) (Xu et al., 2011, Br J Clin Pharmacol 72(2): 270-281; Zhuang et al., 2013, Int J Clin Pharmacol Ther 51(3): 187-199) and MED15117 (Finch et al., 2011, J Mol Biol 411(4): 791-807), which bind to the IL-6 cytokine itself. Additionally the gp130-Fc fusion CR5/18, aimed at selectively blocking the trans-signaling pathway, is under development (Kopf et al., 2010, Nat Rev Drug Discov 9(9): 703-718; Chalaris et al., 2012, Dig Dis 30(5): 492-499).

The unpredictable and chronic nature of inflammatory diseases, as well as a high unmet medical need, warrants the development of new modes of treatment. Since tissue penetration rate is negatively associated with the size of the molecule, a relatively large antibody molecule inherently has poor tissue distribution and penetration capacity.

Thus, the use of monoclonal antibodies is not always optimal for therapy and there is continued need for provision of agents with a high affinity for IL-6. Of great interest is also the provision of uses of such molecules in the treatment, diagnosis and prognosis of IL-6 related disorders.

SUMMARY OF THE INVENTION

It is an object of the present disclosure to provide new IL-6 binding agents, which could for example be used for therapeutic, prognostic and diagnostic applications.

It is an object of the present disclosure to provide a molecule allowing for efficient therapy targeting various forms of inflammatory and autoimmune diseases while alleviating the abovementioned and other drawbacks of current therapies.

It is furthermore an object of the present disclosure to provide a molecule suitable for prognostic and diagnostic applications.

These and other objects, which are evident to the skilled person from the present disclosure, are met by different aspects of the invention as claimed in the appended claims and as generally disclosed herein.

Thus, in the first aspect of the disclosure, there is provided an IL-6 binding polypeptide, comprising an IL-6 binding motif BM, which motif consists of an amino acid sequence selected from:

(SEQ ID NO: 1562)
i) $EEX_3X_4AWX_7EIHX_{11}LPNLX_{16}X_{17}X_{18}QX_{20}X_{21}AFIX_{25}X_{26}LX_{28}X_{29}$ wherein, independently from each other,
$X_3$ is selected from A, F, H, K, Q, R, S, W and Y;
$X_4$ is selected from A, D, E, F, H, I, K, L, M, N, Q, R, S, T, V and Y;
$X_7$ is selected from F, H, I, K, L, M, N, R, S, T, V, W and Y;
$X_{11}$ is selected from A, I, K, L, M, N, R, S, T and V;
$X_{16}$ is selected from N and T;
$X_{17}$ is selected from A, I, T and V;

$X_{18}$ is selected from D, E, G, H, K, N, Q, R, S and T;
$X_{20}$ is selected from I, L, M, R, T and V;
$X_{21}$ is selected from A, S, T and V;
$X_{25}$ is selected from I, M, Q, S, T, V and W;
$X_{26}$ is selected from K and S;
$X_{28}$ is selected from F, L, M and Y; and
$X_{29}$ is selected from D and R;
and
ii) an amino acid sequence which has at least 93% identity to the sequence defined in i).

The above definition of a class of sequence related, IL-6 binding polypeptides is based on a statistical analysis of a number of random polypeptide variants of a parent scaffold, that were selected for their interaction with IL-6 in several different selection experiments. The identified IL-6 binding motif, or "BM", corresponds to the target binding region of the parent scaffold, which region constitutes two alpha helices within a three-helical bundle protein domain. In the parent scaffold, the varied amino acid residues of the two BM helices constitute a binding surface for interaction with the constant Fc part of antibodies. In the present disclosure, the random variation of binding surface residues and subsequent selection of variants have replaced the Fc interaction capacity with a capacity for interaction with IL-6.

As the skilled person will realize, the function of any polypeptide, such as the IL-6 binding capacity of the polypeptide of the present disclosure, is dependent on the tertiary structure of the polypeptide. It is therefore possible to make minor changes to the sequence of amino acids in a polypeptide without affecting the function thereof. Thus, the disclosure encompasses modified variants of the IL-6 binding polypeptide, which are such that the IL-6 binding characteristics are retained.

In this way, also encompassed by the present disclosure is an IL-6 binding polypeptide comprising an amino acid sequence with 93% or greater identity to a polypeptide as defined in i). In some embodiments, the polypeptide may comprise a sequence which is at least 96% identical to a polypeptide as defined in i). For example, it is possible that an amino acid residue belonging to a certain functional grouping of amino acid residues (e.g. hydrophobic, hydrophilic, polar etc) could be exchanged for another amino acid residue from the same functional group.

In some embodiments, such changes may be made in any position of the sequence of the IL-6 binding polypeptide as disclosed herein. In other embodiments, such changes may be made only in the non-variable positions, also denoted scaffold amino acid residues. In such cases, changes are not allowed in the variable positions, i.e. positions denoted with an "X" in sequence i).

The term "% identity", as used throughout the specification, may for example be calculated as follows. The query sequence is aligned to the target sequence using the CLUSTAL W algorithm (Thompson et al, Nucleic Acids Research, 22: 4673-4680 (1994)). A comparison is made over the window corresponding to the shortest of the aligned sequences. The shortest of the aligned sequences may in some instances be the target sequence. In other instances, the query sequence may constitute the shortest of the aligned sequences. The amino acid residues at each position are compared and the percentage of positions in the query sequence that have identical correspondences in the target sequence is reported as % identity.

As used herein "$X_n$" and "$X_m$" are used to indicate amino acids in positions n and m in the sequence i) as defined above, wherein n and m are integers which indicate the position of an amino acid within said sequence as counted from the N-terminal end of said sequence. For example, $X_3$ and $X_7$ indicate the amino acid in position three and seven, respectively, from the N-terminal end of sequence i).

In embodiments according to the first aspect, there are provided polypeptides wherein $X_n$ in sequence i) is independently selected from a group of possible residues according to Table 1. The skilled person will appreciate that $X_n$ may be selected from any one of the listed groups of possible residues and that this selection is independent from the selection of amino acids in $X_m$, wherein n≠m. Thus, any of the listed possible residues in position $X_n$ in Table 1 may be independently combined with any of the listed possible residues any other variable position in Table 1.

The skilled person will appreciate that Table 1 is to be read as follows: In one embodiment according to the first aspect, there is provided a polypeptide wherein amino acid residue "$X_n$" in sequence i) is selected from "Possible residues". Thus, Table 1 discloses several specific and individualized embodiments of the first aspect of the present disclosure. For example, in one embodiment according to the first aspect, there is provided a polypeptide wherein $X_3$ in sequence i) is selected from A, H, K, Q, R and Y, and in another embodiment according to the first aspect, there is provided a polypeptide wherein $X_3$ in sequence i) is selected from A, K, Q, R and Y. For avoidance of doubt, the listed embodiments may be freely combined in yet other embodiments. For example, one such combined embodiment is a polypeptide in which $X_3$ is selected from A, K, R and Y, while $X_4$ is selected from H and K, and $X_{11}$ is selected from A, I, L and T.

TABLE 1

Embodiments of the first aspect of the present disclosure

| $X_n$ | Possible residues |
|---|---|
| $X_3$ | A, F, H, K, Q, R, W, Y |
| $X_3$ | A, H, K, Q, R, S, W, Y |
| $X_3$ | A, H, K, Q, R, W, Y |
| $X_3$ | A, H, K, Q, R, Y |
| $X_3$ | A, K, Q, R, Y |
| $X_3$ | A, K, R, Y |
| $X_3$ | A, K, R |
| $X_3$ | A, R, Y |
| $X_3$ | K, R |
| $X_3$ | A, R |
| $X_3$ | R, Y |
| $X_3$ | R |
| $X_3$ | K |
| $X_3$ | A |
| $X_3$ | Y |
| $X_4$ | A, D, E, F, H, K, L, M, N, Q, R, S, T, V, Y |
| $X_4$ | A, D, E, F, H, I, K, M, N, Q, R, S, T, V, Y |
| $X_4$ | A, D, E, F, H, K, L, M, N, Q, R |
| $X_4$ | A, D, E, F, H, K, M, N, Q, R, S, T, V, Y |
| $X_4$ | A, D, E, F, H, K, N, Q, R, S, T, Y |
| $X_4$ | A, D, E, H, K, N, Q, R, S, T, Y |
| $X_4$ | A, D, E, H, K, Q, R, T |
| $X_4$ | A, D, E, F, H, K, M, Q, R, S, T, V, Y |
| $X_4$ | A, D, E, F, H, K, Q, R, S, T, V |
| $X_4$ | A, D, E, H, K, Q, R |
| $X_4$ | A, D, E, H, K, R |
| $X_4$ | D, E, H, K, R |
| $X_4$ | A, D, E, K, R |
| $X_4$ | A, D, E, H, K |
| $X_4$ | D, E, K, R |
| $X_4$ | A, D, E, K |
| $X_4$ | D, E, H, K |
| $X_4$ | D, H, K, Q |
| $X_4$ | E, H, K, R |
| $X_4$ | D, E, R |
| $X_4$ | D, E, K |
| $X_4$ | H, K, Q |

TABLE 1-continued Embodiments of the first aspect of the present disclosure

| $X_n$ | Possible residues |
|---|---|
| $X_4$ | D, K, Q |
| $X_4$ | D, H, Q |
| $X_4$ | D, H, K |
| $X_4$ | E, H, K |
| $X_4$ | E, H, R |
| $X_4$ | H, K, R |
| $X_4$ | K, E, R |
| $X_4$ | D, E |
| $X_4$ | R, E |
| $X_4$ | K, E |
| $X_4$ | E, H |
| $X_4$ | D, K |
| $X_4$ | H, K |
| $X_4$ | K, Q |
| $X_4$ | K, D |
| $X_4$ | D, Q |
| $X_4$ | H, Q |
| $X_4$ | K |
| $X_4$ | H |
| $X_4$ | D |
| $X_4$ | Q |
| $X_4$ | E |
| $X_4$ | R |
| $X_7$ | F, H, I, K, L, M, N, R, T, V, W, Y |
| $X_7$ | F, H, I, K, L, M, N, R, T, W, Y |
| $X_7$ | F, H, I, L, M, N, R, T, W, Y |
| $X_7$ | F, H, K, L, M, N, R, S, T, V, W, Y |
| $X_7$ | F, H, K, L, M, N, R, T, V, W, Y |
| $X_7$ | F, H, K, L, M, N, R, T, W, Y |
| $X_7$ | F, H, L, M, N, R, T, W, Y |
| $X_7$ | F, H, R, T, W, Y |
| $X_7$ | F, I, N, R, T, W, Y |
| $X_7$ | F, I, R, W, Y |
| $X_7$ | F, N, R, W, Y |
| $X_7$ | F, R, T, W, Y |
| $X_7$ | F, H, T, W, Y |
| $X_7$ | F, H, W, Y |
| $X_7$ | F, T, W, Y |
| $X_7$ | F, R, W, Y |
| $X_7$ | F, H, L, M, R, T, V, W, Y |
| $X_7$ | F, H, R, T, W, Y |
| $X_7$ | I, R, W, Y |
| $X_7$ | F, W, Y |
| $X_7$ | F, R, Y |
| $X_7$ | R, W, Y |
| $X_7$ | I, R, Y |
| $X_7$ | I, W, Y |
| $X_7$ | F, Y |
| $X_7$ | W, Y |
| $X_7$ | I, Y |
| $X_7$ | R, Y |
| $X_7$ | F |
| $X_7$ | W |
| $X_7$ | Y |
| $X_7$ | I |
| $X_7$ | R |
| $X_{11}$ | A, I, K, L, N, R, S, T, V |
| $X_{11}$ | A, I, K, L, M, N, S, T, V |
| $X_{11}$ | A, I, K, L, N, S, T, V |
| $X_{11}$ | A, I, K, L, S, T, V |
| $X_{11}$ | A, I, K, L, N, T, V |
| $X_{11}$ | A, I, K, L, T, V |
| $X_{11}$ | A, I, K, L, T |
| $X_{11}$ | I, K, L, T |
| $X_{11}$ | A I, L, T |
| $X_{11}$ | A I, K, L |
| $X_{11}$ | A, K, L, N, S, T |
| $X_{11}$ | A, K, L, N, S |
| $X_{11}$ | A, K, L, S, T |
| $X_{11}$ | A, K, L, S |
| $X_{11}$ | K, L, S |
| $X_{11}$ | A, K, L |
| $X_{11}$ | A, I, L |
| $X_{11}$ | I, L |
| $X_{11}$ | A, L, N |
| $X_{11}$ | A, L |
| $X_{11}$ | L, N |
| $X_{11}$ | L |
| $X_{11}$ | A |
| $X_{11}$ | N |
| $X_{11}$ | S |
| $X_{11}$ | I |
| $X_{11}$ | K |
| $X_{11}$ | T |
| $X_{16}$ | N |
| $X_{16}$ | T |
| $X_{17}$ | I, T, V |
| $X_{17}$ | A, I, V |
| $X_{17}$ | I, V |
| $X_{17}$ | I |
| $X_{17}$ | V |
| $X_{18}$ | D, E, H, K, N, Q, R, S, T |
| $X_{18}$ | D, E, G, H, N, Q, R, S, T |
| $X_{18}$ | D, E, H, N, Q, R, S, T |
| $X_{18}$ | D, E, H, N, Q, S, T |
| $X_{18}$ | D, E, N, Q, S, T |
| $X_{18}$ | D, E, N, S, T |
| $X_{18}$ | D, E, Q, S, T |
| $X_{18}$ | D, E, S, T |
| $X_{18}$ | D, E, Q, S |
| $X_{18}$ | D, E, N, S |
| $X_{18}$ | D, E, S |
| $X_{18}$ | D, E, N |
| $X_{18}$ | D, E |
| $X_{18}$ | E |
| $X_{18}$ | D |
| $X_{20}$ | I, L, M, R, V |
| $X_{20}$ | I, M, R, T, V |
| $X_{20}$ | I, M, R, V |
| $X_{20}$ | I, L, M, V |
| $X_{20}$ | I, M, V |
| $X_{20}$ | I, M |
| $X_{20}$ | M, V |
| $X_{20}$ | M |
| $X_{21}$ | A, S, T |
| $X_{21}$ | A, S, V |
| $X_{21}$ | A, S |
| $X_{21}$ | A, V |
| $X_{21}$ | A, T |
| $X_{21}$ | A |
| $X_{25}$ | I, Q, S, T, V, W |
| $X_{25}$ | I, Q, S, T, V |
| $X_{25}$ | I, Q, S, T, W |
| $X_{25}$ | I, Q, S, T |
| $X_{25}$ | I, S, T |
| $X_{25}$ | Q, S, T |
| $X_{25}$ | S, T, W |
| $X_{25}$ | S, T |
| $X_{25}$ | S |
| $X_{25}$ | T |
| $X_{26}$ | K |
| $X_{26}$ | S |
| $X_{28}$ | F, L, Y |
| $X_{28}$ | F, M, Y |
| $X_{28}$ | F, L, M |
| $X_{28}$ | F, L |
| $X_{28}$ | F, Y |
| $X_{28}$ | F |
| $X_{29}$ | D |
| $X_{29}$ | R |

In one particular embodiment according to the first aspect, there is provided polypeptide wherein, in sequence i), $X_3$ is selected from A, H, K, Q, R and Y;

$X_4$ is selected from A, D, E, F, H, I, K, L, M, N, Q, R, S, T, V and Y;

$X_7$ is selected from F, H, I, K, L, M, N, R, T, V, W and Y;

$X_{11}$ is selected from A, I, K, L, N, S, T and V;

$X_{16}$ is T;

$X_{17}$ is selected from A, I, T and V;

$X_{18}$ is selected from D, E, H, K, N, Q, R, S and T;
$X_{20}$ is selected from I, L, M, R and V;
$X_{21}$ is selected from A, S and V;
$X_{25}$ is selected from I, Q, S, T, V and W;
$X_{26}$ is K;
$X_{28}$ is selected from F, L, M and Y; and
$X_{29}$ is D.

In a more specific embodiment defining a sub-class of IL-6 binding polypeptides, sequence i) fulfills at least six of the eleven conditions I-XI:
I. $X_3$ is selected from K and R;
II. $X_{11}$ is selected from A and L;
III. $X_{16}$ is T;
IV. $X_{17}$ is selected from I and V;
V. $X_{18}$ is selected from D and E;
VI. $X_{20}$ is M;
VII. $X_{21}$ is A;
VIII. $X_{25}$ is selected from S and T;
IX. $X_{26}$ is K;
X. $X_{28}$ is F; and
XI. $X_{29}$ is D.

In some examples of an IL-6 binding polypeptide according to the first aspect, sequence i) fulfils at least seven of the eleven conditions I-XI. More specifically, sequence i) may fulfill at least eight of the eleven conditions I-XI, such as at least nine of the eleven conditions I-XI, such as at least ten of the eleven conditions I-XI, such as all of the eleven conditions I-XI.

In some embodiments of an IL-6 binding polypeptide according to the first aspect, there is provided an IL-6 binding polypeptide, wherein $X_{17}X_{20}X_{21}$ is selected from VMA and IMA. In some embodiments, $X_{20}X_{21}X_{28}$ is MAF. In some embodiments, $X_{17}X_{20}X_{28}$ is selected from VMF and IMF. In some embodiments, $X_{17}X_{21}X_{28}$ is selected from VAF and IAF.

As described in detail in the experimental section to follow, the selection of IL-6 binding polypeptide variants has led to the identification of a number of individual IL-6 binding motif (BM) sequences. These sequences constitute individual embodiments of sequence i) according to this aspect. The sequences of individual IL-6 binding motifs correspond to amino acid positions 8-36 in SEQ ID NO:1-1551 presented in FIG. 1A-VV. Hence, in one embodiment of the IL-6 binding polypeptide according to this aspect, sequence i) corresponds to the sequence from position 8 to position 36 in a sequence selected from the group consisting of SEQ ID NO:1-1551. In one embodiment, sequence i) corresponds to the sequence from position 8 to position 36 in a sequence selected from the group consisting of SEQ ID NO:1-1502. In one embodiment, sequence i) corresponds to the sequence from position 8 to position 36 in a sequence selected from the group consisting of SEQ ID NO:7, SEQ ID NO:15-89 and SEQ ID NO:151-871. In one embodiment, sequence i) corresponds to the sequence from position 8 to position 36 in a sequence selected from the group consisting of SEQ ID NO:1-6, SEQ ID NO:8-14, SEQ ID NO:90-150 and SEQ ID NO:872-1502. In one embodiment, sequence i) corresponds to the sequence from position 8 to position 36 in a sequence selected from the group consisting of SEQ ID NO:1-152 and SEQ ID NO:1503-1515. In one embodiment, sequence i) corresponds to the sequence from position 8 to position 36 in a sequence selected from the group consisting of SEQ ID NO:1-150 and SEQ ID NO:1503-1515. In one embodiment, sequence i) corresponds to the sequence from position 8 to position 36 in a sequence selected from the group consisting of SEQ ID NO:1-152. In another embodiment, sequence i) corresponds to the sequence from position 8 to position 36 in a sequence selected from the group consisting of SEQ ID NO:1-150. In yet another embodiment, sequence i) corresponds to the sequence from position 8 to position 36 in a sequence selected from the group consisting of SEQ ID NO:7, SEQ ID NO:15-89 and SEQ ID NO:151-152. In one embodiment, sequence i) corresponds to the sequence from position 8 to position 36 in a sequence selected from the group consisting of SEQ ID NO:1-6, SEQ ID NO:8-14 and SEQ ID NO:90-150. In one embodiment, sequence i) corresponds to the sequence from position 8 to position 36 in a sequence selected from the group consisting of SEQ ID NO:1-14 and SEQ ID NO:1503-1515. In one embodiment, sequence i) corresponds to the sequence from position 8 to position 36 in a sequence selected from the group consisting of SEQ ID NO:1-14 and SEQ ID NO:1512. In one embodiment, sequence i) corresponds to the sequence from position 8 to position 36 in a sequence selected from the group consisting of SEQ ID NO:1-14. In one embodiment, sequence i) corresponds to the sequence from position 8 to position 36 in a sequence selected from the group consisting of SEQ ID NO:1-5. In one embodiment, sequence i) corresponds to the sequence from position 8 to position 36 in SEQ ID NO:1512. In specific individual embodiments, sequence i) corresponds to the sequence from position 8 to position 36 in any one of SEQ ID NO:1-14 individually.

In some embodiments of the present disclosure, the BM as defined above "forms part of" a three-helix bundle protein domain. This is understood to mean that the sequence of the BM is "inserted" into or "grafted" onto the sequence of the original three-helix bundle domain, such that the BM replaces a similar structural motif in the original domain. For example, without wishing to be bound by theory, the BM is thought to constitute two of the three helices of a three-helix bundle, and can therefore replace such a two-helix motif within any three-helix bundle. As the skilled person will realize, the replacement of two helices of the three-helix bundle domain by the two BM helices has to be performed so as not to affect the basic structure of the polypeptide. That is, the overall folding of the Cα backbone of the polypeptide according to this embodiment of the invention is substantially the same as that of the three-helix bundle protein domain of which it forms a part, e.g. having the same elements of secondary structure in the same order etc. Thus, a BM according to the disclosure "forms part" of a three-helix bundle domain if the polypeptide according to this embodiment of the aspect has the same fold as the original domain, implying that the basic structural properties are shared, those properties e.g. resulting in similar CD spectra. The skilled person is aware of other parameters that are relevant.

In particular embodiments, the IL-6 binding motif (BM) thus forms part of a three-helix bundle protein domain. For example, the BM may essentially constitute two alpha helices with an interconnecting loop, within said three-helix bundle protein domain. In particular embodiments, said three-helix bundle protein domain is selected from domains of bacterial receptor proteins. Non-limiting examples of such domains are the five different three-helical domains of Protein A from *Staphylococcus aureus*, such as domain B, and derivatives thereof. In some embodiments, the three-helical bundle protein domain is a variant of protein Z, which is derived from domain B of staphylococcal Protein A.

In some embodiments where the IL-6 binding polypeptide as disclosed herein forms part of a three-helix bundle protein domain, the IL-6 binding polypeptide may comprise a binding module (BMod), the amino acid sequence of which is selected from:

(SEQ ID NO: 1563)
iii) K-[BM]-DPSQSX$_a$X$_b$LLX$_c$EAKKLX$_d$X$_e$X$_f$Q;

wherein
[BM] is an IL-6 binding motif as defined herein, provided that X$_{29}$ is ID,
X$_a$ is selected from A and S;
X$_b$ is selected from N and E;
X$_c$ is selected from A, S and C;
X$_d$ is selected from E, N and S;
X$_e$ is selected from D, E and S;
X$_f$ is selected from A and S; and
iv) an amino acid sequence which has at least 91% identity to a sequence defined by iii).

It may be beneficial in some embodiments that said polypeptides exhibit high structural stability, such as resistance to isomerization, to chemical modifications, to changes in physical conditions and to proteolysis, during production and storage, as well as in vivo. Thus, in other embodiments where the IL-6 binding polypeptide as disclosed herein forms part of a three-helix bundle protein domain, the IL-6 binding polypeptide may comprise a binding module (BMod), the amino acid sequence of which is selected from:

(SEQ ID NO: 1564)
v) K-[BM]-QPEQSX$_a$X$_b$LLX$_c$EAKKLX$_d$X$_e$X$_f$Q, wherein
[BM] is an IL-6 binding motif as defined herein, provided that X$_{29}$ is R;
X$_a$ is selected from A and S;
X$_b$ is selected from N and E;
X$_c$ is selected from A, S and C;
X$_d$ is selected from E, N and S;
X$_e$ is selected from D, E and S;
X$_f$ is selected from A and S; and
vi) an amino acid sequence which has at least 91% identity to a sequence defined by v).

As discussed above, polypeptides comprising minor changes as compared to the above amino acid sequences, which do not largely affect the tertiary structure and the function of the polypeptide are also within the scope of the present disclosure. Thus, in some embodiments, sequence iv) and vi) have at least 93%, such as at least 95%, such as at least 97% identity to a sequence defined by iii) and v), respectively.

In one embodiment, X$_a$ in sequence iii) or v) is A.
In one embodiment, X$_a$ in sequence iii) or v) is S.
In one embodiment, X$_b$ in sequence iii) or v) is N.
In one embodiment, X$_b$ in sequence iii) or v) is E.
In one embodiment, X$_c$ in sequence iii) or v) is A.
In one embodiment, X$_c$ in sequence iii) or v) is S.
In one embodiment, X$_c$ in sequence iii) or v) is C.
In one embodiment, X$_d$ in sequence iii) or v) is E.
In one embodiment, X$_d$ in sequence iii) or v) is N.
In one embodiment, X$_d$ in sequence iii) or v) is S.
In one embodiment, X$_e$ in sequence iii) or v) is D.
In one embodiment, X$_e$ in sequence iii) or v) is E.
In one embodiment, X$_e$ in sequence iii) or v) is S.
In one embodiment, X$_d$X$_e$ in sequence iii) or v) is selected from EE, ES, SE, SD and SS.

In one embodiment, X$_d$X$_e$ in sequence iii) or v) is ES.
In one embodiment, X$_d$X$_e$ in sequence iii) or v) is SE.
In one embodiment, X$_d$X$_e$ in sequence iii) or v) is SD.
In one embodiment, X$_f$ in sequence iii) or v) is A.
In one embodiment, X$_f$ in sequence iii) or v) is S.
In one embodiment, in sequence iii) or v), X$_a$ is A; X$_b$ is N; X$_c$ is A and X$_f$ is A.
In one embodiment, in sequence iii) or v), X$_a$ is A; X$_b$ is N; X$_c$ is C and X$_f$ is A.
In one embodiment, in sequence iii) or v), X$_a$ is S; X$_b$ is E; X$_c$ is S and X$_f$ is S.
In one embodiment, in sequence iii) or v), X$_a$ is S; X$_b$ is E; X$_c$ is C and X$_f$ is S.
In one embodiment, in sequence iii) or v), X$_a$ is A; X$_b$ is N; X$_c$ is A; X$_d$X$_e$ is ND and X$_f$ is A.
In one embodiment, in sequence iii) or v), X$_a$ is A; X$_b$ is N; X$_c$ is C; X$_d$X$_e$ is ND and X$_f$ is A.
In one embodiment, in sequence iii) or v), X$_a$ is S; X$_b$ is E; X$_c$ is S; X$_d$X$_e$ is ND and X$_f$ is S.
In one embodiment, in sequence iii) or v), X$_a$ is S; X$_b$ is E; X$_c$ is C; X$_d$X$_e$ is ND and X$_f$ is S.
In one embodiment, in sequence iii) or v), X$_a$ is A; X$_b$ is N; X$_c$ is A; X$_d$X$_e$ is SE and X$_f$ is A.
In one embodiment, in sequence iii) or v), X$_a$ is A; X$_b$ is N; X$_c$ is C; X$_d$X$_e$ is SE and X$_f$ is A.
In one embodiment, in sequence iii) or v), X$_a$ is S; X$_b$ is E; X$_c$ is S; X$_d$X$_e$ is SE and X$_f$ is S.
In one embodiment, in sequence iii) or v), X$_a$ is S; X$_b$ is E; X$_c$ is C; X$_d$X$_e$ is SE and X$_f$ is S.
In one embodiment, in sequence iii) or v), X$_a$ is A; X$_b$ is N; X$_c$ is A; X$_d$X$_e$ is SD and X$_f$ is A.
In one embodiment, in sequence iii) or v), X$_a$ is A; X$_b$ is N; X$_c$ is C; X$_d$X$_e$ is SD and X$_f$ is A.
In one embodiment, in sequence iii) or v), X$_a$ is S; X$_b$ is E; X$_c$ is S; X$_d$X$_e$ is SD and X$_f$ is S.
In one embodiment, in sequence iii) or v), X$_a$ is S; X$_b$ is E; X$_c$ is C; X$_d$X$_e$ is SD and X$_f$ is S.
In one embodiment, in sequence iii) or v), X$_a$ is A; X$_b$ is N; X$_c$ is A; X$_d$X$_e$ is ES and X$_f$ is A.
In one embodiment, in sequence iii) or v), X$_a$ is A; X$_b$ is N; X$_c$ is C; X$_d$X$_e$ is ES and X$_f$ is A.
In one embodiment, in sequence iii) or v), X$_a$ is S; X$_b$ is E; X$_c$ is S; X$_d$X$_e$ is ES and X$_f$ is S.
In one embodiment, in sequence iii) or v), X$_a$ is S; X$_b$ is E; X$_c$ is C; X$_d$X$_e$ is ES and X$_f$ is S.

In yet a further embodiment, sequence iii) corresponds to the sequence from position 7 to position 55 in a sequence selected from the group consisting of SEQ ID NO:1-1551 presented in FIG. 1A-VV. In another embodiment, sequence iii) corresponds to the sequence from position 7 to position 55 in a sequence selected from the group consisting of SEQ ID NO:1-1502. In one embodiment, sequence iii) corresponds to the sequence from position 7 to position 55 in a sequence selected from the group consisting of SEQ ID NO:7, SEQ ID NO:15-89 and SEQ ID NO:151-871. In one embodiment, sequence iii) corresponds to the sequence from position 7 to position 55 in a sequence selected from the group consisting of SEQ ID NO:1-6, SEQ ID NO:8-14, SEQ ID NO:90-150 and SEQ ID NO:872-1502. In one embodiment, sequence iii) corresponds to the sequence from position 7 to position 55 in a sequence selected from the group consisting of SEQ ID NO:1-152 and SEQ ID NO:1503-1515. In one embodiment, sequence iii) corresponds to the sequence from position 7 to position 55 in a sequence selected from the group consisting of SEQ ID NO:1-150 and SEQ ID NO:1503-1515. In one embodiment, sequence iii) corresponds to the sequence from position 7 to position 55 in a sequence selected from the group consisting of SEQ ID NO:1-152. In another embodiment, sequence iii) corresponds to the sequence from position 7 to position 55 in a sequence selected from the group consisting of SEQ ID NO:1-150. In yet another embodiment, sequence iii) corresponds to the sequence from position 7 to position 55 in a sequence selected from the group consisting of SEQ ID NO:7, SEQ ID NO:15-89 and SEQ ID NO:151-152. In one embodiment, sequence iii) corresponds to the sequence from position 7 to position 55 in a sequence selected from the group consisting of SEQ ID NO:1-6, SEQ ID NO:8-14 and SEQ ID NO:90-150. In one embodiment, sequence iii) corresponds to the sequence from position 7 to position 55 in a sequence selected from the group consisting of SEQ ID NO:1-14 and SEQ ID NO:1503-1515. In one embodiment, sequence iii) corresponds to the sequence from position 7 to position 55 in a sequence selected from the group consisting of SEQ ID NO:1-14 and SEQ ID NO:1512. In one embodiment, sequence iii) corresponds to the sequence from position 7 to position 55 in a sequence selected from the group consisting of SEQ ID NO:1-14. In one embodiment, sequence iii) corresponds to the sequence from position 7 to position 55 in a sequence selected from the group consisting of SEQ ID NO:1-5. In one embodiment, sequence iii) corresponds to the sequence from position 7 to position 55 in sequence SEQ ID NO:1512. In specific individual embodiments, sequence iii) corresponds to the sequence from position 7 to position 55 in any one of SEQ ID NO:1-14 individually.

Also, in a further embodiment, there is provided an IL-6 binding polypeptide, which comprises an amino acid sequence selected from:
vii) YA-[BMod]-AP;
wherein [BMod] is an IL-6 binding module as defined above; and
viii) an amino acid sequence which has at least 90% identity to a sequence defined by vii).

Alternatively, there is provided an IL-6 binding polypeptide, which comprises an amino acid sequence selected from:
ix) FN-[BMod]-AP;
wherein [BMod] is an IL-6 binding module as defined above; and
x) an amino acid sequence which has at least 90% identity to a sequence defined by ix).

As discussed above, polypeptides comprising minor changes as compared to the above amino acid sequences, which do not largely affect the tertiary structure and the function of the polypeptide, also fall within the scope of the present disclosure. Thus, in some embodiments, sequence viii) and x) may for example be least 92%, such as at least 94%, such as at least 96%, such as at least 98% identical to a sequence defined by vii) and ix), respectively.

In some embodiments, the IL-6 binding motif may form part of a polypeptide comprising an amino acid sequence selected from

```
                                    (SEQ ID NO: 1565)
ADNNFNK-[BM]-DPSQSANLLSEAKKLNESQAPK;

(SEQ ID NO: 1566)
ADNKFNK-[BM]-DPSQSANLLAEAKKLNDAQAPK;

(SEQ ID NO: 1567)
ADNKFNK-[BM]-DPSVSKEILAEAKKLNDAQAPK;
```

```
                                    (SEQ ID NO: 1568)
ADAQQNNFNK-[BM]-DPSQSTNVLGEAKKLNESQAPK;

(SEQ ID NO: 1569)
AQHDE-[BM]-DPSQSANVLGEAQKLNDSQAPK;

(SEQ ID NO: 1570)
VDNKFNK-[BM]-DPSQSANLLAEAKKLNDAQAPK;

(SEQ ID NO: 1571)
AEAKYAK-[BM]-DPSESSELLSEAKKLNKSQAPK;

(SEQ ID NO: 1572)
VDAKYAK-[BM]-DPSQSSELLAEAKKLNDAQAPK;

(SEQ ID NO: 1573)
VDAKYAK-[BM]-DPSQSSELLAEAKKLNDSQAPK;

(SEQ ID NO: 1574)
AEAKYAK-[BM]-DPSQSSELLSEAKKLNDSQAPK;

(SEQ ID NO: 1575)
AEAKYAK-[BM]-DPSQSSELLSEAKKLSESQAPK;

(SEQ ID NO: 1576)
AEAKYAK-[BM]-QPEQSSELLSEAKKLSESQAPK;

(SEQ ID NO: 1577)
AEAKYAK-[BM]-DPSQSSELLSEAKKLESSQAPK;

(SEQ ID NO: 1578)
AEAKYAK-[BM]-QPEQSSELLSEAKKLESSQAPK;

(SEQ ID NO: 1579)
VDAKYAK-[BM]-DPSQSSELLSEAKKLNDSQAPK;

(SEQ ID NO: 1580)
VDAKYAK-[BM]-DPSQSSELLSEAKKLSESQAPK;

(SEQ ID NO: 1581)
VDAKYAK-[BM]-QPEQSSELLSEAKKLSESQAPK;

(SEQ ID NO: 1582)
VDAKYAK-[BM]-DPSQSSELLSEAKKLESSQAPK;

(SEQ ID NO: 1583)
VDAKYAK-[BM]-QPEQSSELLSEAKKLESSQAPK;

(SEQ ID NO: 1584)
VDAKYAK-[BM]-DPSQSSELLAEAKKLNKAQAPK;
and (SEQ ID NO: 1585)
AEAKYAK-[BM]-DPSQSSELLAEAKKLNKAQAPK;
``` wherein [BM] is an IL-6 binding motif as defined above.

In one embodiment, the IL-6 binding polypeptide comprises an amino acid sequence selected from:

```
                                    (SEQ ID NO: 1586)
xi)  VDAKYAK-[BM]-DPSQSSELLSEAKKLNDSQAPK;
``` wherein [BM] is an IL-6 binding motif as defined above; and
xii) an amino acid sequence which has at least 89% identity to the sequence defined in xi).

In another embodiment, the IL-6 binding polypeptide comprises an amino acid sequence selected from:

```
                                    (SEQ ID NO: 1587)
xiii)  AEAKYAK-[BM]-DPSQSSELLSEAKKLNDSQAPK;
``` wherein [BM] is an IL-6 binding motif as defined above; and
xiv) an amino acid sequence which has at least 89% identity to the sequence defined in xiii).

Again, polypeptides comprising minor changes as compared to the above amino acid sequences, which do not largely affect the tertiary structure and the function of the polypeptide, also fall within the scope of the present disclosure. Thus, in some embodiments, sequence xii) and xiv) may for example be at least 91%, such as at least 93%, such as at least 94%, such as at least 96%, such as at least 98% identical to the sequence defined by xi) and xiii), respectively.

Sequence xi) in such a polypeptide may be selected from the group consisting of SEQ ID NO:1-1551. In another embodiment, sequence xi) is selected from the group consisting of SEQ ID NO:1-1502. In one embodiment, sequence xi) is selected from the group consisting of SEQ ID NO:7, SEQ ID NO:15-89 and SEQ ID NO:151-871. In one embodiment, sequence xi) is selected from the group consisting of SEQ ID NO:1-6, SEQ ID NO:8-14, SEQ ID NO:90-150 and SEQ ID NO:872-1502. In one embodiment, sequence xi) is selected from the group consisting of SEQ ID NO:1-152 and SEQ ID NO:1503-1515. In one embodiment, sequence xi) is selected from the group consisting of SEQ ID NO:1-150 and SEQ ID NO:1503-1515. In one embodiment, sequence xi) is selected from the group consisting of SEQ ID NO:1-152. In another embodiment, sequence xi) is selected from the group consisting of SEQ ID NO:1-150. In yet another embodiment, sequence xi) is selected from the group consisting of SEQ ID NO:7, SEQ ID NO:15-89 and SEQ ID NO:151-152. In one embodiment, sequence xi) is selected from the group consisting of SEQ ID NO:1-6, SEQ ID NO:8-14 and SEQ ID NO:90-150. In one embodiment, sequence xi) is selected from the group consisting of SEQ ID NO:1-14 and SEQ ID NO:1503-1515. In one embodiment, sequence xi) is selected from the group consisting of SEQ ID NO:1-14 and SEQ ID NO:1512. In one embodiment, sequence xi) is selected from the group consisting of SEQ ID NO:1-14. In one embodiment, sequence xi) is selected from the group consisting of SEQ ID NO:1-5. In one embodiment, sequence xi) is SEQ ID NO:1512. In specific individual embodiments, sequence xi) is any one of SEQ ID NO:1-14 individually.

Binding of a polypeptide as defined herein to IL-6 may interfere with canonical cis- and/or with trans-signaling via IL-6 in vivo or in vitro. Thus, in one embodiment, there is provided an IL-6 binding polypeptide as defined herein which is capable of blocking IL-6 dependent signaling via the cis-signaling pathway. In another embodiment, the IL-6 binding polypeptide as defined herein is capable of blocking IL-6 dependent signaling via the trans-signaling pathway. In another embodiment, the IL-6 binding polypeptide as defined herein is capable of blocking IL-6 dependent signaling via both the cis-signaling pathway and the trans-signaling pathway.

The half maximal inhibitory concentration (IC50) is a measure of the effectiveness of a substance in inhibiting a specific biological or biochemical function. This quantitative measure indicates how much of a particular substance is needed to inhibit a given biological process by half, and is commonly used in the art. In one particular embodiment, there is provided an IL-6 binding polypeptide as defined herein capable of blocking IL-6 signaling such that the half maximal inhibitory concentration (IC50) of the blocking is at most $1\times10^{-6}$ M, such as at most $1\times10^{-7}$ M, such as at most $1\times10^{-8}$ M, such as at most $1\times10^{-9}$ M, such as at most $1\times10^{-10}$ M. This blocking may be blocking of either the cis- or the trans-signaling pathway. In one embodiment, the IL-6 binding polypeptide is capable of blocking the interaction of IL-6/IL-6Rα with gp130.

The terms "IL-6 binding" and "binding affinity for IL-6" as used in this specification refer to a property of a polypeptide which may be tested for example by ELISA or the use of surface plasmon resonance (SPR) technology. For example as described in the examples below, IL-6 binding affinity may be tested in an experiment in which samples of the polypeptide are captured on antibody-coated ELISA plates and biotinylated IL-6 is added followed by streptavidin-conjugated HRP. TMB substrate is added and the absorbance at 450 nm is measured using a multi-well plate reader, such as Victor³ (Perkin Elmer). The skilled person may then interpret the results obtained by such experiments to establish at least a qualitative measure of the binding affinity of the polypeptide for IL-6. If a quantitative measure is desired, for example to determine the EC50 value (the half maximal effective concentration) for the interaction, ELISA may also be used. The response of the polypeptide against a dilution series of biotinylated IL-6 is measured using ELISA as described above. The skilled person may then interpret the results obtained by such experiments, and EC50 values may be calculated from the results using for example Graph Pad Prism 5 and non-linear regression.

IL-6 binding affinity may also be tested in an experiment in which IL-6, or a fragment thereof, is immobilized on a sensor chip of a surface plasmon resonance (SPR) instrument, and the sample containing the polypeptide to be tested is passed over the chip. Alternatively, the polypeptide to be tested is immobilized on a sensor chip of the instrument, and a sample containing IL-6, or a fragment thereof, is passed over the chip. The skilled person may then interpret the results obtained by such experiments to establish at least a qualitative measure of the binding affinity of the polypeptide for IL-6. If a quantitative measure is desired, for example to determine a $K_D$ value for the interaction, surface plasmon resonance methods may also be used. Binding values may for example be defined in a Biacore (GE Healthcare) or ProteOn XPR 36 (Bio-Rad) instrument. IL-6 is suitably immobilized on a sensor chip of the instrument, and samples of the polypeptide whose affinity is to be determined are prepared by serial dilution and injected in random order. $K_D$ values may then be calculated from the results using for example the 1:1 Langmuir binding model of the BIAevaluation 4.1 software, or other suitable software, provided by the instrument manufacturer.

Thus, in one embodiment, there is provided an IL-6 binding polypeptide as defined herein, which is capable of binding to IL-6 such that the EC50 value of the interaction is at most $1\times10^{-7}$ M, such as at most $1\times10^{-8}$ M, such as at most $1\times10^{-9}$ M, such as at most $1\times10^{-10}$ M.

In one embodiment, the IL-6 binding polypeptide is capable of binding to IL-6 such that the $K_D$ value of the interaction is at most $1\times10^{-8}$ M, such as at most $1\times10^{-9}$ M, such as at most $1\times10^{-10}$ M.

The skilled person will understand that various modifications and/or additions can be made to an IL-6 binding polypeptide according to any aspect disclosed herein in order to tailor the polypeptide to a specific application without departing from the scope of the present disclosure.

For example, in one embodiment there is provided an IL-6 binding polypeptide as described herein, which polypeptide has been extended by and/or comprises additional amino acids at the C terminus and/or N terminus. Such a polypeptide should be understood as a polypeptide having one or more additional amino acid residues at the very first and/or the very last position in the polypeptide chain. Thus, an IL-6 binding polypeptide may comprise any suitable number of additional amino acid residues, for example at least one additional amino acid residue. Each additional amino acid residue may individually or collectively be added in order to, for example, improve production, purification, stabilization in vivo or in vitro, coupling or detection of the polypeptide. Such additional amino acid residues may comprise one or more amino acid residues added for the purpose of chemical coupling. One example of this is the addition of a cysteine residue. Additional amino acid residues may also provide a "tag" for purification or detection of the polypeptide, such as a $His_6$ tag, a $(HisGlu)_3$ tag ("HEHEHE" tag) (SEQ ID NO:1588) or a "myc" (c-myc) tag or a "FLAG" tag for interaction with antibodies specific to the tag or immobilized metal affinity chromatography (IMAC) in the case of a $His_6$-tag.

The further amino acids as discussed above may be coupled to the IL-6 binding polypeptide by means of chemical conjugation (using known organic chemistry methods) or by any other means, such as expression of the IL-6 binding polypeptide as a fusion protein or joined in any other fashion, either directly or via a linker, for example an amino acid linker.

The further amino acids as discussed above may for example comprise one or more polypeptide domain(s). A further polypeptide domain may provide the IL-6 binding polypeptide with another function, such as for example yet another binding function, an enzymatic function, a toxic function, a fluorescent signaling function or combinations thereof.

A further polypeptide domain may moreover provide another IL-6 binding moiety with the same IL-6 binding function. Thus, in a further embodiment, there is provided an IL-6 binding polypeptide in a multimeric form. Said multimer is understood to comprise at least two IL-6 binding polypeptides as disclosed herein as monomer units, the amino acid sequences of which may be the same or different. Multimeric forms of the polypeptides may comprise a suitable number of domains, each having an IL-6 binding motif, and each forming a monomer within the multimer. These domains may have the same amino acid sequence, but alternatively, they may have different amino acid sequences. In other words, the IL-6 binding polypeptide of the invention may form homo- or heteromultimers, for example homo- or heterodimers. In one embodiment, there is provided an IL-6 binding polypeptide, wherein said monomeric units are covalently coupled together. In another embodiment, said IL-6 binding polypeptide monomer units are expressed as a fusion protein. In one embodiment, there is provided an IL-6 binding polypeptide in dimeric form.

Additionally, "heterogenic" fusion polypeptides or proteins, or conjugates, in which an IL-6 binding polypeptide described herein, or multimer thereof, constitutes a first domain, or first moiety, and the second and further moieties have other functions than binding IL-6, are also contemplated and fall within the ambit of the present disclosure. The second and further moiety/moieties of the fusion polypeptide or conjugate in such a protein suitably also have a desired biological activity.

Thus, in a second aspect of the present disclosure, there is provided a fusion protein or a conjugate, comprising a first moiety consisting of an IL-6 binding polypeptide according to the first aspect, and a second moiety consisting of a polypeptide having a desired biological activity. In another embodiment, said fusion protein or conjugate may additionally comprise further moieties, comprising desired biological activities that can be either the same or different from the biological activity of the second moiety.

Non-limiting examples of a desired biological activity comprise a therapeutic activity, a binding activity and an enzymatic activity. In one embodiment, the second moiety having a desired biological activity is a therapeutically active polypeptide.

Non-limiting examples of therapeutically active polypeptides are biomolecules, such as molecules selected from the group consisting of human endogenous enzymes, hormones, growth factors, chemokines, cytokines and lymphokines.

Non-limiting examples of binding activities are binding activities which increase the in vivo half-life of the fusion protein or conjugate, and binding activities which act to block a biological activity. In one particular embodiment, the binding activity is an albumin binding activity which increases the in vivo half-life of the fusion protein or conjugate. In one embodiment, said albumin binding activity is provided by the albumin binding domain of streptococcal protein G or a derivative thereof.

In one embodiment of this aspect of the present disclosure, there is provided an IL-6 binding polypeptide, fusion protein or conjugate which comprises an additional immune response modifying agent. Non-limiting examples of additional immune response modifying agents include immunosuppressive or immunomodulating agents or other anti-inflammatory agents. For example, an IL-6 binding polypeptide, fusion protein or conjugate as described herein may be used in combination with disease-modifying anti-rheumatic drugs (DMARDs), such as gold salts, azathioprine, methotrexate and leflunomide; calcineurin inhibitors, such as cyclosporin A or FK 506; modulators of lymphocyte recirculation; mTOR inhibitors, such as rapamycin; an ascomycin having immuno-suppressive properties; glucocorticoids; corticosteroids; cyclophosphamide; immunosuppressive monoclonal antibodies; adhesion molecule inhibitors, such as LFA-1 antagonists, ICAM-1 or -3 antagonists, VCAM-4 antagonists or VLA-4 antagonists; anti-TNF agents, such as etanercept or monoclonal antibodies to TNF, for example infliximab, adalimumab, golimumab and certolizumab pegol; blockers of proinflammatory cytokines; IL-1 blockers such as anakinra or IL-1 trap; IL-17 blockers; chemokine blockers; non steroidal anti-inflammatory drugs (NSAIDs) such as aspirin; and anti-infectious agents and other immune response modulating agents. Thus, in one embodiment, said immune response modifying agent is selected from the group consisting of disease-modifying antirheumatic drugs (DMARDs), calcineurin inhibitors, modulators of lymphocyte recirculation, mTOR inhibitors, ascomycin having immuno-suppressive properties, glucocorticoids, corticosteroids, cyclophosphamide, immunosuppressive monoclonal antibodies, adhesion molecule inhibitors, anti-TNF agents, blockers of proinflammatory cytokines, IL-1 blockers, IL-17 blockers, chemokine blockers, non steroidal anti-inflammatory drugs (NSAIDs) and combinations thereof.

As the skilled person understands, the IL-6 binding polypeptide according to the first aspect may be useful in a fusion protein or as a conjugate partner to any other moiety. Therefore, the above lists of therapeutically active polypeptides and immune response modifying agents should not be construed as limiting in any way.

The skilled person is aware that the construction of a fusion protein often involves the use of linkers between the functional moieties to be fused, and there are different kinds of linkers with different properties, such as flexible amino acid linkers, rigid amino acid linkers and cleavable amino acid linkers. Linkers have been used to for example increase stability or improve folding of fusion proteins, to increase expression, improve biological activity, enable targeting and alter pharmacokinetics of fusion proteins. Thus, in one embodiment, a fusion protein as disclosed herein further comprises at least one linker, such as at least one linker selected from flexible amino acid linkers, rigid amino acid linkers and cleavable amino acid linkers.

Flexible linkers are often used in the art when the joined domains require a certain degree of movement or interaction, and may be particularly useful in some embodiments. Such linkers are generally composed of small, non-polar (for example G) or polar (for example S or T) amino acids. Some flexible linkers primarily consist of stretches of G and S residues, for example $(GGGGS)_p$. Adjusting the copy number "p" allows for optimization of linker in order to achieve appropriate separation between the functional moieties or to maintain necessary inter-moiety interaction. Apart from G and S linkers, other flexible linkers are known in the art, such as G and S linkers containing additional amino acid residues, such as T and A, to maintain flexibility, as well as polar amino acid residues to improve solubility. Examples of flexible linkers that are contemplated for use herein also include KESGSVSSEQLAQFRSLD (SEQ ID NO:1590), EGKSSGSGSEKST (SEQ ID NO:1591) and GSAG-SAAGSGEF (SEQ ID NO:1592).

Thus in one embodiment, said linker is a flexible linker comprising glycine (G), serine (S) and/or threonine (T) residues. In one embodiment, said linker has a general formula selected from $(G_nS_m)_p$ and $(S_mG_n)_p$, wherein, independently, n=1-7, m=0-7, n+m 8 and p=1-7. In one embodiment, n=1-5. In one embodiment, m=0-5. In one embodiment, p=1-5. In a more specific embodiment, n=4, m=1 and p=1-4. In an even more specific embodiment, said linker is (GGGGS) (SEQ ID NO:1589)$_3$. In another specific embodiment, said linker is GGGGS (SEQ ID NO:1589). In another specific embodiment, said linker is VDGS (SEQ ID NO:1593). In another specific embodiment, said linker is ASGS (SEQ ID NO:1594).

The above aspects furthermore encompass polypeptides in which the IL-6 binding polypeptide according to the first aspect, or the IL-6 binding polypeptide as comprised in a fusion protein or conjugate according to the second aspect, further comprises a label, such as a label selected from the group consisting of fluorescent dyes and metals, chromophoric dyes, chemiluminescent compounds and bioluminescent proteins, enzymes, radionuclides and radioactive particles. Such labels may for example be used for detection of the polypeptide.

For example, in embodiments where the labeled IL-6 binding polypeptide comprises an IL-6 binding polypeptide according to the first aspect of the disclosure and a label, the labeled polypeptide may for example be used for indirect labeling of IL-6 expressing cells, such as cells of inflammation associated cancers.

In other embodiments, the labeled IL-6 binding polypeptide is present as a moiety in a fusion protein or conjugate also comprising a second moiety having a desired biological activity. The label may in some instances be coupled only to the IL-6 binding polypeptide, and in some instances both to the IL-6 binding polypeptide and to the second or further moiety of the conjugate or fusion protein. Furthermore, it is also possible that the label may be coupled to a second or further moiety only and not the IL-6 binding moiety. Hence, in yet another embodiment there is provided an IL-6 binding polypeptide comprising a second and optionally a further moiety, wherein said label is coupled to said second or further moiety only.

In embodiments where the IL-6 binding polypeptide, fusion protein or conjugate is radiolabeled, such a radiolabeled polypeptide may comprise a radionuclide. A majority of radionuclides have a metallic nature and metals are typically incapable of forming stable covalent bonds with elements presented in proteins and peptides. For this reason, labeling of proteins and peptides with radioactive metals is performed with the use of chelators, i.e. multidentate ligands, which form non-covalent compounds, called chelates, with the metal ions. In an embodiment of the IL-6 binding polypeptide, fusion protein or conjugate, the incorporation of a radionuclide is enabled through the provision of a chelating environment, through which the radionuclide may be coordinated, chelated or complexed to the polypeptide.

One example of a chelator is the polyaminopolycarboxylate type of chelator. Two classes of such polyaminopolycarboxylate chelators can be distinguished: macrocyclic and acyclic chelators.

In one embodiment, the IL-6 binding polypeptide, fusion protein or conjugate comprises a chelating environment provided by a polyaminopolycarboxylate chelator conjugated to the IL-6 binding polypeptide via a thiol group of a cysteine residue or an epsilon amine group of a lysine residue.

The most commonly used macrocyclic chelators for radioisotopes of indium, gallium, yttrium, bismuth, radioactinides and radiolanthanides are different derivatives of DOTA (1,4,7,10-tetraazacyclododecane-1,4,7,10-tetraacetic acid). In one embodiment, a chelating environment of the IL-6 binding polypeptide, fusion protein or conjugate is provided by DOTA or a derivative thereof. More specifically, in one embodiment, the chelating polypeptides encompassed by the present disclosure are obtained by reacting the DOTA derivative 1,4,7,10-tetraazacyclododecane-1,4,7-trisacetic acid-10-maleimidoethylacetamide (maleimidomonoamide-DOTA) with said polypeptide.

Additionally, 1,4,7-triazacyclononane-1,4,7-triacetic acid (NOTA) and derivatives thereof may be used as chelators. Hence, in one embodiment, there is provided a IL-6 binding polypeptide, fusion protein or conjugate, wherein the polyaminopolycarboxylate chelator is 1,4,7-triazacyclononane-1,4,7-triacetic acid or a derivative thereof.

The most commonly used acyclic polyaminopolycarboxylate chelators are different derivatives of DTPA (diethylenetriamine-pentaacetic acid).

Hence, polypeptides having a chelating environment provided by diethylenetriaminepentaacetic acid or derivatives thereof are also encompassed by the present disclosure.

In further aspects of the present disclosure, there is provided a polynucleotide encoding an IL-6 binding polypeptide or a fusion protein as described herein; an expression vector comprising said polynucleotide; and a host cell comprising said expression vector.

Also encompassed by this disclosure is a method of producing a polypeptide or fusion protein as described above, comprising culturing said host cell under conditions permissive of expression of said polypeptide from its expression vector, and isolating the polypeptide.

The IL-6 binding polypeptide of the present disclosure may alternatively be produced by non-biological peptide synthesis using amino acids and/or amino acid derivatives having protected reactive side-chains, the non-biological peptide synthesis comprising step-wise coupling of the amino acids and/or the amino acid derivatives to form a polypeptide according to the first aspect having protected reactive side-chains, removal of the protecting groups from the reactive sidechains of the polypeptide, and folding of the polypeptide in aqueous solution.

It should be understood that the IL-6 binding polypeptide according to the present disclosure may be useful as a therapeutic, diagnostic or prognostic agent in its own right or as a means for targeting other therapeutic or diagnostic agents, with e.g. direct or indirect effects on IL-6. A direct therapeutic effect may for example be accomplished by inhibiting IL-6 signaling.

The small size and robustness of the molecules of the present disclosure confer several advantages over conventional monoclonal antibody based therapies. Such advantages include modes of administration, such as alternative routes of administration, administration at higher doses than antibodies and absence of Fc-mediated side effects. The small size combined with the potential for very high solubility and stability of the polypeptides disclosed herein allows for extreme molar amounts of drug in a small volume, for example for subcutaneous injections. For systemic administration, this suggests outpatient "home use" treatment using convenient, small prefilled syringes or auto-injectors, with low volume and well tolerated administration of doses. In addition, the capacity for high molar concentrations in drug preparations in combination with the ability to retain functional stability in diverse formulations opens up for topical (for example skin or lung) or oral administration routes. Non-limiting examples of indications where alternative administration routes could be especially relevant in IL-6 mediated disease include asthma and psoriasis.

In another aspect, there is provided a composition comprising an IL-6 binding polypeptide, fusion protein or conjugate as described herein and at least one pharmaceutically acceptable excipient or carrier. In one embodiment, said composition further comprises at least one additional active agent, such as at least two additional active agents, such as at least three additional active agents. Non-limiting examples of additional active agents that may prove useful in such combination are immune response modifying agents and anti-cancer agents as described herein.

Non-limiting examples of anti-cancer agents include agents selected from the group consisting of auristatin, anthracycline, calicheamycin, combretastatin, doxorubicin, duocarmycin, the CC-1065 anti-tumor antibiotic, ecteinsascidin, geldanamycin, maytansinoid, methotrexate, mycotoxin, taxol, ricin, bouganin, gelonin, pseudomonas exotoxin 38 (PE38), diphtheria toxin (DT), and their analogues, and derivates thereof and combinations thereof. A skilled person would appreciate that the non-limiting examples of cytotoxic agents include all possible variant of said agents, for example the agent auristatin includes for example auristatin E, auristatin F, auristatin PE, and derivates thereof.

The skilled person will appreciate that said IL-6 binding polypeptide, fusion protein or conjugate or a composition comprising an anti-IL-6 binding polypeptide, fusion protein or conjugate as described herein may be administered to a subject using standard administration techniques, including oral, topical, intravenous, intraperitoneal, subcutaneous, pulmonary, transdermal, intramuscular, intranasal, buccal, sublingual or suppository administration. Thus, in one embodiment, there is provided an IL-6 binding polypeptide, fusion protein or conjugate or a composition as described herein for oral, topical, intravenous, intraperitoneal, subcutaneous, pulmonary, transdermal, intramuscular, intranasal, buccal, sublingual or suppository administration.

IL-6 may also serve as a valuable marker for diagnosis and prognosis of certain cancers, such as inflammation associated-cancers, for example lung cancer, breast cancer and colon cancer. For example, IL-6 has been linked to the prognosis and poor survival in patients suffering from colorectal cancer (Ky et al., Jpn J Clin Oncol. 2010 June, 40(6):580-7).

Hence, in another aspect of the present disclosure, there is provided an IL-6 binding polypeptide, fusion protein, conjugate or composition as described herein for use as a medicament, a prognostic agent or a diagnostic agent. In one embodiment, said IL-6 binding polypeptide is provided for use as a medicament.

In one embodiment, there is provided an IL-6 binding polypeptide, fusion protein or conjugate or composition as described herein, for use as a medicament to modulate IL-6 function in vivo. As used herein, the term "modulate" refers to changing the activity, such as rendering IL-6 function hypomorph, partially inhibiting or fully inhibiting IL-6 function.

Non-limiting examples of IL-6 related disorders, wherein the IL-6 binding polypeptides may be useful for treatment, prognosis and/or diagnosis, include inflammatory disease, autoimmune disease, infectious disease, cancer, diabetes, neurological disease and depression, such as rheumatoid arthritis (RA), juvenile RA, juvenile idiopathic arthritis or systemic juvenile idiopathic arthritis, vasculitis, psoriatic arthritis, psoriasis, ankylosing spondylitis, chronic inflammatory bowel disease such as Crohn's disease and ulcerative colitis; Grave's disease, Behcet's disease, uveitis, giant cell arteritis, multiple sclerosis (MS), systemic sclerosis, systemic lupus erythematosus (SLE), polymyositis, polymyalgia rheumatic, asthma, chronic obstructive pulmonary disease (COPD), relapsing polychondritis, pancreatitis, peritonitis, nephritis, Kawasaki's disease, Sjögren's syndrome, adult Still's disease, colitis associated cancer, renal cancer, kidney cancer, prostate cancer, malignant lymphoma, multiple myeloma, Castleman's disease, breast cancer, lung cancer, Alzheimer's disease, HIV, diabetes, sepsis, cachexia, myelodysplastic syndrome (MDS), liver cirrhosis, graft versus host disease, myocardial infarction, endometriosis and osteoporosis. Non-limiting examples of IL-6 related cancers include lung cancer, breast cancer and colon cancer (Schafer and Brugge, J Clin Invest. (2007) 117(12): 3660-3663; Nagasaki et al., British Journal of Cancer (2014) 110, 469-478).

Thus, in one embodiment, there is provided an IL-6 binding polypeptide, fusion protein, conjugate or composition for use in the treatment, prognosis or diagnosis of an IL-6 related disorder, such as a disorder selected from the group consisting of inflammatory disease, autoimmune disease, infectious disease, cancer, diabetes, neurological disease and depression. In one embodiment, said IL-6 related disorder is selected from the group consisting of inflammatory diseases and autoimmune diseases. In one embodiment, said IL-6 related disorder is selected from the group consisting of rheumatoid arthritis (RA), juvenile RA, juvenile idiopathic arthritis or systemic juvenile idiopathic arthritis, vasculitis, psoriatic arthritis, psoriasis, ankylosing spondylitis, chronic inflammatory bowel disease such as Crohn's disease and ulcerative colitis; Grave's disease, Behcet's disease, uveitis, giant cell arteritis, multiple sclerosis (MS), systemic sclerosis, systemic lupus erythematosus (SLE), polymyositis, polymyalgia rheumatic, asthma, chronic obstructive pulmonary disease (COPD), relapsing polychondritis, pancreatitis, peritonitis, nephritis, Kawasaki's disease, Sjögren's syndrome and adult Still's disease. In another embodiment, said IL-6 related disorder is cancer, such as a cancer selected from the group consisting of colitis associated cancer, renal cancer, kidney cancer, prostate cancer, malignant lymphoma, multiple myeloma, Castleman's disease, breast cancer and lung cancer. In another embodiment, said IL-6 related disorder is selected from Alzheimer's disease, HIV, diabetes, sepsis, cachexia, myelodysplastic syndrome (MDS), liver cirrhosis, graft versus host disease, myocardial infarction, endometriosis and osteoporosis.

In a related aspect, there is provided a method of treatment of an IL-6 related disorder, comprising administering to a subject in need thereof an effective amount of an IL-6 binding polypeptide, fusion protein, conjugate or composition as described herein. In a more specific embodiment of said method, the IL-6 binding polypeptide, fusion protein, conjugate or composition as described herein modulates IL-6 function in vivo.

In one embodiment, said IL-6 related disorder is selected from the group consisting of inflammatory diseases, autoimmune diseases, infectious disease, cancer, diabetes, neurological disease and depression, such as the group consisting of inflammatory diseases and autoimmune diseases. In one particular embodiment of said aspect, the IL-6 related disorder is selected from the group consisting of rheumatoid arthritis (RA), juvenile RA, juvenile idiopathic arthritis or systemic juvenile idiopathic arthritis, vasculitis, psoriatic arthritis, psoriasis, ankylosing spondylitis, chronic inflammatory bowel disease such as Crohn's disease and ulcerative colitis; Grave's disease, Behcet's disease, uveitis, giant cell arteritis, multiple sclerosis (MS), systemic sclerosis, systemic lupus erythematosus (SLE), polymyositis, polymyalgia rheumatic, asthma, chronic obstructive pulmonary disease (COPD), relapsing polychondritis, pancreatitis, peritonitis, nephritis, Kawasaki's disease, Sjögren's syndrome and adult Still's disease. In another embodiment, said IL-6 related disorder is cancer, such as a cancer selected from the group consisting of colitis associated cancer, renal cancer, kidney cancer, prostate cancer, malignant lymphoma, multiple myeloma, Castleman's disease, breast cancer and lung cancer. In another embodiment, said IL-6 related disorder is selected from the group consisting of Alzheimer's disease, HIV, diabetes, sepsis, cachexia, myelodysplastic syndrome (MDS), liver cirrhosis, graft versus host disease, myocardial infarction, endometriosis and osteoporosis.

It may be beneficial to administer a therapeutically effective amount of an IL-6 binding polypeptide, fusion protein or conjugate or composition as described herein and at least one second drug substance, such as an immune response modulating agent as described above or an anti-cancer agent.

As used herein, the term "co-administration" encompasses both concomitant and sequential administration. Thus, in one embodiment there is provided a method as defined above further comprising co-administration of an immune response modulating agent as described above. In another embodiment there is provided a method as defined above further comprising co-administration of an anti-cancer agent as described above.

In another aspect of the present disclosure, there is provided a method of detecting IL-6, comprising providing a sample suspected to contain IL-6, contacting said sample with an IL-6 binding polypeptide, fusion protein, conjugate or a composition as described herein, and detecting the binding of the IL-6 binding polypeptide, fusion protein, conjugate or composition to indicate the presence of IL-6 in the sample. In one embodiment, said method further comprises an intermediate washing step for removing non-bound polypeptide, fusion protein, conjugate or composition, after contacting the sample.

In one embodiment, said method is a diagnostic or prognostic method for determining the presence of IL-6 in a subject, the method comprising the steps:
  contacting the subject, or a sample isolated from the subject, with an IL-6 binding polypeptide, fusion protein, conjugate or a composition as described herein, and
  obtaining a value corresponding to the amount of the IL-6 binding polypeptide, fusion protein, conjugate or composition that has bound in said subject or to said sample.

In one embodiment, said method further comprises an intermediate washing step for removing non-bound polypeptide, fusion protein, conjugate or composition, after contacting the subject or sample and before obtaining a value.

In one embodiment, said method further comprises a step of comparing said value to a reference. Said reference may be by a numerical value, a threshold or a visual indicator, for example based on a color reaction. The skilled person will appreciate that different ways of comparison to a reference are known in the art and may be suitable for use.

In one embodiment of such a method, said subject is a mammalian subject, such as a human subject.

In one embodiment, said method is performed in vivo. In another embodiment, said method is performed in vitro.

While the invention has been described with reference to various exemplary aspects and embodiments, it will be understood by those skilled in the art that various changes may be made and equivalents may be substituted for elements thereof without departing from the scope of the invention. In addition, many modifications may be made to adapt a particular situation or molecule to the teachings of the invention without departing from the essential scope thereof. Therefore, it is intended that the invention not be limited to any particular embodiment contemplated, but that the invention will include all embodiments falling within the scope of the appended claims.

BRIEF DESCRIPTION OF THE FIGURES

FIG. 1A-VV is a listing of amino acid sequences of examples of IL-6 binding polypeptides of the present disclosure (SEQ ID NO:1-1551), control polypeptides (SEQ ID NO:1552-1553), the albumin binding domain (ABD) variant PP013 (SEQ ID NO:1554) as well as the amino acid sequences of human IL-6 (SEQ ID NO:1555) and murine IL-6 (SEQ ID NO:1556) used for selection, screening and/or characterization for illustration of the invention. In the IL-6 binding polypeptides of the present disclosure, the deduced IL-6 binding motifs (BM) extend from position 8 to position 36 in each sequence. The amino acid sequences of the 49 amino acid residues long polypeptides predicted to constitute the complete three-helix bundle within each of these Z variants extend from position 7 to position 55 (referred herein to as BMod).

EXAMPLES

Summary

Figure 2:
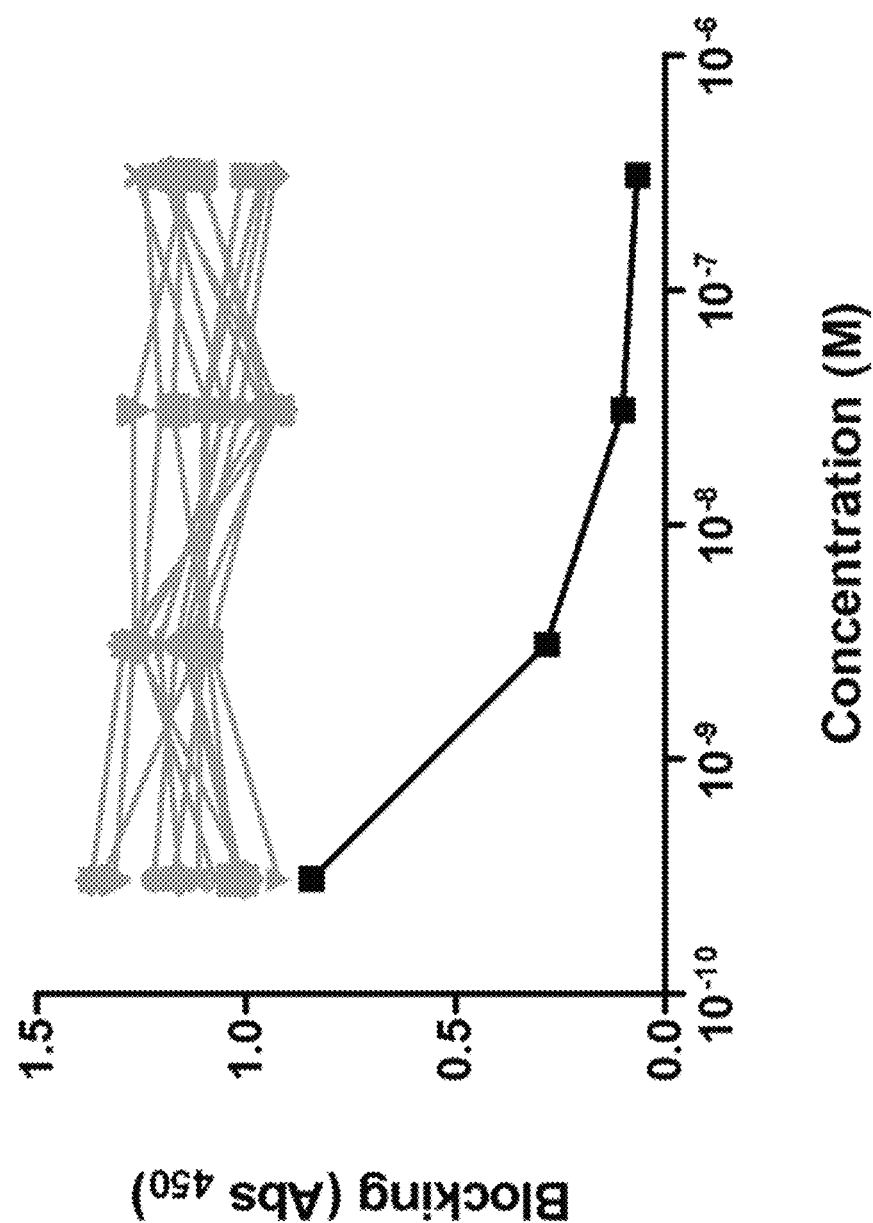
FIG. 2 shows the result of blocking of the interaction between hIL-6 and hIL-6Rα, assayed as described in Example 2. In contrast to the hIL-6Rα binding antibody tocilizumab (black), which was included for comparison, the tested IL-6 binding Z variants (gray) did not interfere with the binding of hIL-6 to its receptor hIL-6Rα.

The following Examples disclose the development of novel Z variant molecules targeting interleukin 6 (IL-6). The Z variants were obtained using phage display technology. The genes encoding IL-6 binding polypeptides described herein were sequenced, and the corresponding amino acid sequences are listed in FIG. 1A-VV and denoted by the identifiers SEQ ID NO:1-1551.

Example 1

Selection and ELISA Screening of IL-6 Binding Z Variants

In this Example, human (hIL-6) and murine IL-6 (mIL-6) were used as target proteins in phage display selections using a phage library of Z variants. The DNA of selected clones was sequenced and the clones were produced in *E. coli* periplasmic fractions and assayed against IL-6 in ELISA (enzyme-linked immunosorbent assay).

Materials and Methods

Biotinylation of the Target Proteins Human and Murine IL-6:

hIL-6 and mIL-6 (Peprotech, cat. no. 200-06 and 216-16, respectively) were biotinylated using No-Weigh EZ-Link Sulfo-NHS-LC-Biotin (Thermo Scientific, cat. no. 21327) at a 12× molar excess according to the manufacturer's recommendations. The reactions were performed at room temperature (RT) for 30 min. Next, buffer exchange to phosphate buffered saline (PBS, 10 mM phosphate, 137 mM NaCl, 2.68 mM KCl, pH 7.4) was performed using Slide-a-lyzer dialysis cassettes (Thermo Scientific, cat. no. 66333, 3,500 MWCO) according to the manufacturer's instructions.

Phage Display Selection of IL-6 Binding Z Variants:

A library of random variants of protein Z displayed on bacteriophage, constructed in phagemid pAY02592 essentially as described in Grönwall et al. (2007) J Biotechnol, 128:162-183, was used to select IL-6 binding Z variants. In this library, an albumin binding domain (abbreviated ABD and corresponding to GA3 of protein G from *Streptococcus* strain G148) was used as fusion partner to the Z variants. The library is denoted Zlib006Naive.II and has a size of 1.5×10^10 library members (Z variants). *E. coli* RRIΔM15 cells (Ruther et al., (1982) Nucleic Acids Res 10:5765-5772) from a glycerol stock containing the phagemid library Zlib006Naive.II were inoculated in 20 l of a defined proline free medium [7 g/l dipotassium hydrogenphosphate, 1 g/l trisodium citrate dihydrate, 0.02 g/l uracil, 6.7 g/l YNB (Difco™ Yeast Nitrogen Base w/o amino acids, Becton Dickinson), 5.5 g/l glucose monohydrate, 0.3 g/l L-alanine, 0.24 g/l L-arginine monohydrochloride, 0.11 g/l L-asparagine monohydrate, 0.1 g/l L-cysteine, 0.3 g/l L-glutamic acid, 0.1 g/l L-glutamine, 0.2 g/l glycine, 0.05 g/l L-histidine, 0.1 g/l L-isoleucine, 0.1 g/l L-leucine, 0.25 g/l L-lysine monohydrochloride, 0.1 g/l L-methionine, 0.2 g/l L-phenylalanine, 0.3 g/l L-serine, 0.2 g/l L-threonine, 0.1 g/l L-tryptophane, 0.05 g/l L-tyrosine, 0.1 g/l L-valine], supplemented with 100 µg/ml ampicillin. The cultivations were grown at 37° C. in a fermenter (Belach Bioteknik, BR20). When the cells reached an optical density at 600 nm ($OD_{600}$) of 0.75, approximately 2.6 l of the cultivation was infected using a 10× molar excess of M13K07 helper phage (New England Biolabs, cat. no. N0315S). The cells were incubated for 30 min, whereupon the fermenter was filled up to 20 l with TSB-YE (Tryptic Soy Broth-Yeast Extract; 30 g/l TSB, 5 g/l yeast extract) supplemented with 100 µM isopropyl-β-D-1-thiogalactopyranoside (IPTG) for induction of expression and with 25 µg/ml kanamycin and 12.5 µg/ml carbenicillin. Cells were grown at 30° C. for 22 h and the cells in the cultivation were pelleted by centrifugation at 15,900 g. Phage particles were precipitated from the supernatant twice in PEG/NaCl (polyethylene glycol/sodium chloride), filtered and dissolved in PBS and glycerol as described in Grönwall et al., supra. Phage stocks were stored at −80° C. before use.

Selection procedure and phage stock preparation were performed essentially as described for selection against another biotinylated target in WO2009/077175. In order to reduce the amount of background binders, pre-selection was performed by incubation of phage stock with SA-beads for 30 min at RT. All tubes and beads used in the selection were pre-blocked with PBS supplemented with 5% BSA. Selection was performed in PBS supplemented with 3% BSA and 0.1% Tween20 during 2 h at RT, followed by capture of target-phage complexes on Dynabeads® M-280 Streptavidin (SA-beads, Invitrogen, cat. no. 11206D) using 1 mg beads per 1.6 µg biotinylated hIL-6 or mIL-6. E. coli strain XL1-Blue (Agilent technologies, cat. no. 200268) was used for phage amplification.

Selections against biotinylated hIL-6 and mIL-6 were performed in four cycles divided in four different final tracks: track (1) in cycle 1 was divided either in the second cycle or the fourth cycle, resulting in totally three tracks (1-1 to 1-3) in cycle 2, three tracks (1-1-1 to 1-3-1) in cycle 3 and four tracks (1-1-1-1 to 1-3-1-2) in cycle 4. After washes, bound phage were eluted from the selection tracks using 500 µl 0.1 M glycine-HCl, pH 2.2, followed by immediate neutralization with 50 µl 1 M Tris-HCl, pH 8.0, and 450 µl PBS. An overview of the selection strategy and parameters used, describing the differences in the selection tracks in terms of lowered target concentration and increased number of washes, is shown in Table 2.

TABLE 2

Overview of the strategy for primary selection

| Cycle | Selection track | Phage stock from library or selection track | Target | Target concentration (nM) | Number of washes |
|---|---|---|---|---|---|
| 1 | 1 | Zlib006Naive.II | hIL-6 | 100 | 2 |
| 2 | 1-1 | 1 | hIL-6 | 50 | 5 |
| 2 | 1-2 | 1 | hIL-6 | 10 | 5 |
| 2 | 1-3 | 1 | mIL-6 | 100 | 4 |
| 3 | 1-1-1 | 1-1 | hIL-6 | 25 | 6 |
| 3 | 1-2-1 | 1-2 | hIL-6 | 2 | 8 |
| 3 | 1-3-1 | 1-3 | hIL-6 | 25 | 6 |
| 4 | 1-1-1-1 | 1-1-1 | hIL-6 | 10 | 8 |
| 4 | 1-2-1-1 | 1-2-1 | hIL-6 | 0.5 | 12 |
| 4 | 1-3-1-1 | 1-3-1 | mIL-6 | 10 | 8 |
| 4 | 1-3-1-2 | 1-3-1 | hIL-6 | 0.5 | 12 |

Sequencing:

PCR fragments were amplified from single colonies using a standard PCR program and the primers AFFI-21 (5'-tgcttccggctcgtatgttgtgtg; SEQ ID NO:1557) and AFFI-22 (5'-cggaaccagagccaccaccgg; SEQ ID NO:1558). Sequencing of amplified fragments was performed using the biotinylated oligonucleotide AFFI-72 (5'-biotin-cggaaccagagccaccac-cgg; SEQ ID NO:1559) and a BigDye® Terminator v3.1 Cycle Sequencing Kit (Applied Biosystems), used in accordance with the manufacturer's recommendations. The sequencing reactions were purified by binding to magnetic streptavidin coated beads (Detach Streptavidin Beads, Nordiag, cat. no. 2012-01) using a Magnatrix 8000 (Magnetic Biosolution) instrument and analyzed on an ABI PRISM® 3130xl Genetic Analyzer (PE Applied Biosystems).

Production of Z Variants for ELISA:

Sequenced Z variants were produced by inoculating single colonies from the selections in 1 ml TSB-YE medium supplemented with 100 µg/ml ampicillin and 0.1 mM IPTG in deep-well plates (Nunc, cat. no. 278752). The plates were incubated for 24 h at 37° C. Cells were pelleted by centrifugation, re-suspended in 200 µl PBST 0.05% (PBS supplemented with 0.05% Tween-20), frozen at −80° C. and thawed in a water bath to release the periplasmic fraction of the cells. The freeze-thawing procedure was repeated five times. The samples were diluted with PBST 0.05% to a total of 800 µl and cells were pelleted by centrifugation. The supernatant of the periplasmic extract contained the Z variants as fusions to ABD, expressed as AQHDEALE-[Z #####]-VDYV4ABDFYVPG (Grönwall et al., supra). Z ##### refers to individual, 58 amino acid residue Z variants.

ELISA Analysis of Z Variants:

The binding of Z variants to IL-6 was analyzed in an ELISA assay. Half-area 96-well ELISA plates (Costar, cat. no. 3690) were coated at 4° C. overnight with 2 µg/ml of an anti-ABD goat antibody (produced in-house) diluted in coating buffer (50 mM sodium carbonate, pH 9.6; Sigma, cat. no. C3041). The antibody solution was poured off and the wells were blocked with 100 µl of PBSC (PBS supplemented with 0.5% casein; Sigma, cat. no. C8654) for 1.5 h at RT. The blocking solution was discarded and 50 µl periplasmic solution was added to the wells and incubated for 1.5 h at RT under slow shaking. The supernatants were poured off and the wells were washed 4 times with PBST 0.05%. Next, 50 µl of biotinylated hIL-6 at a concentration of 7.7 nM in PBSC was added to each well. The plates were incubated for 1.5 h at RT followed by washes as described above. Streptavidin conjugated HRP (Thermo Scientific, cat. no. N100) was diluted 1:30 000 in PBSC and added to the wells followed by 45 min incubation. After washing as described above, 50 µl ImmunoPure TMB substrate (Thermo Scientific, cat. no. 34021) was added to the wells and the plates were treated according to the manufacturer's recommendations. A Z variant binding a specific irrelevant protein was used as a positive control by assaying against that specific irrelevant protein, and as a negative control by assaying against hIL-6. As blank control, PBST 0.05% was added instead of the periplasmic sample. Absorbance was measured at 450 nm using a multi-well plate reader (Victor$^3$, Perkin Elmer).

Results

Phage Display Selection of IL-6 Binding Z Variants:

Individual clones were prepared after four cycles of phage display selections against biotinylated hIL-6 and mIL-6.

Sequencing:

Sequencing was performed for clones picked at random from selection round four. Each Z variant was given a unique identification number #####, and individual variants are referred to as Z #####. The amino acid sequences of 58 residues long Z variants are listed in FIG. 1A-VV and in the sequence listing as SEQ ID NO:1503-1551. The deduced IL-6 binding motifs (BM) extend from position 8 to position 36 in each sequence. The amino acid sequences of the 49 amino acid residues long polypeptides predicted to constitute the complete three-helix bundle within each of these Z variants (BMod) extend from position 7 to position 55.

ELISA Analysis of Z Variants:

The clones obtained after four cycles of selection were produced in 96-well plates and screened for hIL-6 binding activity in ELISA. All clones giving a response with signals corresponding to at least 3× the negative control were considered as positive IL-6 binders. The control molecule specific for an irrelevant protein gave a positive signal for the specific protein, whereas no signal was obtained against hIL-6.

Example 2

Production and In Vitro Characterization of IL-6 Binding Z Variants

In this Example, a subset of Z variants were subcloned, produced and functionally assessed in competition ELISAs and cell assays. Two different ELISA assays were applied to investigate if the IL-6 binding Z variants were able to block the specific interaction between IL-6 and IL-6Rα or between IL-6 and the gp130 receptor, respectively. The potency of the Z variant polypeptides was assessed using two different cell assays, mimicking the classical cis-signaling pathway and trans-signaling pathway, respectively. Finally, circular dichroism (CD) spectroscopy was performed for a subset of the Z variants in order to investigate their secondary structure and determine their melting temperatures, Tm.

Materials and Methods

Subcloning of Z Variants:

The DNA of 13 IL-6 binding Z variants, Z06777 (SEQ ID NO:1503), Z06779 (SEQ ID NO:1504), Z06789 (SEQ ID NO:1505), Z06791 (SEQ ID NO:1506), Z06792 (SEQ ID NO:1507), Z06799 (SEQ ID NO:1508), Z06802 (SEQ ID NO:1509), Z06805 (SEQ ID NO:1510), Z06809 (SEQ ID NO:1511), Z06814 (SEQ ID NO:1512), Z06829 (SEQ ID NO:1513), Z06834 (SEQ ID NO:1514), Z06844 (SEQ ID NO:1515) was amplified from the library vector pAY02592. A subcloning strategy for construction of monomeric Z variant molecules with an N-terminal $His_6$ tag was applied using standard molecular biology techniques (essentially as described in WO2009/077175 for Z variants binding another target). The Z gene fragments were subcloned into the expression vector pAY01448 resulting in the encoded sequence MGSSHHHHHHLQ-[Z #####]-VD.

A subset of five IL-6 binding Z variants, Z06789, Z06799, Z06809, Z06814 and Z06829, and two control Z variants binding an irrelevant target, Z03638 (SEQ ID NO:1552) and Z04726 (SEQ ID NO:1553), were subcloned in fusion with the ABD variant PP013 (SEQ ID NO:1554). The constructs encoded by the expression vectors were MGSSLQ-[Z #####]-VDGS-PP013.

Cultivation and Purification:

*E. coli* BL21(DE3) cells (Novagen) were transformed with plasmids containing the gene fragment of each respective IL-6 binding Z variant and cultivated at 37° C. in 800 or 1000 ml of TSB-YE medium supplemented with 50 µg/ml kanamycin. In order to induce protein expression, IPTG was added to a final concentration of 0.2 mM at $OD_{600}$=2 and the cultivation was incubated at 37° C. for another 5 h. The cells were harvested by centrifugation.

Purification of IL-6 Binding Z Variants with a $His_6$-Tag:

Protein purification was performed under either native or denatured conditions.

The purification under native conditions was performed as follows:

Approximately 2-5 g of each cell pellet was resuspended in 10 ml PBS. After cell disruption by sonication, cell debris was removed by centrifugation and each supernatant was applied on 2 ml Talon cobolt columns (Clontech, cat. no. 635504) equilibrated with 20 ml wash buffer (46.6 mM $Na_2HPO_4$, 3.4 mM $NaH_2PO_4$, and 300 mM NaCl, pH 7.0). Contaminants were removed by washing with wash buffer, and the IL-6 binding Z variants were subsequently eluted with elution buffer (50 mM $NaH_2PO_4$, 100 mM NaCl, 30 mM HAc and 70 mM NaAc, pH 5.0).

The purification under denatured conditions was performed as follows: Approximately 2-5 g of each cell pellet was resuspended in 10 ml lysis buffer (7 M guanidinium hydrochloride, 47 mM $Na_2HPO_4$, 2.65 mM $NaH_2PO_4$, 10 mM Tris-HCl, 104 mM NaCl, pH 8.0) followed by incubation at 37° C., 150 rpm for 2 h. The washing and elution steps were performed as for the native purification but using different buffers (wash buffer: 6 M guanidinium hydrochloride, 47 mM $Na_2HPO_4$, 3.4 mM $NaH_2PO_4$, 300 mM NaCl, pH 8.0; elution buffer: 6 M urea, 0.1 M NaCl, 29.6 mM HAc, 70.4 mM NaAc and 50 mM $NaH_2PO_4$, pH 5.0). Purified Z variants were buffer exchanged to PBS using PD-10 columns (GE Healthcare) according to the manufacturer's protocol.

Protein concentrations were determined by measuring the absorbance at 280 nm using the extinction coefficient of the respective protein. The purity of the IL-6 binding Z variants was analyzed by SDS-PAGE stained with Coomassie Blue.

Purification of IL-6 Binding Z Variants in Fusion with ABD:

Approximately 2.5 g of each cell pellet was re-suspended in 20 ml TST-buffer (25 mM Tris-HCl, 1 mM EDTA, 200 mM NaCl, 0.05% Tween20, pH 8.0) supplemented with Benzonase® (Merck). After cell disruption by sonication and clarification by centrifugation, each supernatant was applied on a gravity flow column with 1 ml anti-ABD agarose (WO2014/064237). After washing with TST-buffer and 5 mM $NH_4Ac$ pH 5.5 buffer, the ABD fused Z variants were eluted with 0.1 M HAc. Buffer exchange to PBS (2.68 mM KCl, 137 mM NaCl, 1.47 mM $KH_2PO_4$, 8.1 mM $Na_2HPO_4$, pH 7.4) was performed using PD-10 columns (GE Healthcare). Next, the ABD fused Z variants were purified on 1 ml Detoxi-Gel Endotoxin Removing Columns (Pierce, cat. no. 20344) to ensure low endotoxin content. Protein concentrations were determined by measuring the absorbance at 280 nm, using the extinction coefficient of the respective protein. The purity was analyzed by SDS-PAGE stained with Coomassie Blue and the identity of each purified Z-ABD variant was confirmed using LC/MS analysis.

Analysis of Binding Site:

A first assay was employed to evaluate the interference of the IL-6 binding Z variants with the interaction between hIL-6 and the human IL-6Rα (hIL-6Rα). In this experiment, half area 96-well ELISA plates were coated with anti-IL-6R capture antibody (R&D Systems) at a concentration of 2 µg/ml. Plates were incubated overnight at 4° C. and then washed twice in tap water. Next, the plates were blocked for 1 h in PBSC, and hIL-6Rα (R&D Systems) was added at a concentration of 250 ng/ml. Plates were incubated for 1.5 h at RT and then washed 4 times with 200 µl 0.05% Tween/PBS. In separate plates, serial dilutions (concentration range 500-0.5 nM) of the 13 $His_6$-tagged Z variant polypeptides were titrated with 2.5 nM of biotinylated hIL-6. The IL-6Rα antibody tocilizumab (Roche) was prepared in the same way and included for comparison. Each pre-mixed complex of Z variant and biotinylated hIL-6 was then transferred to wells containing hIL-6Rα. Plates were incubated for another 1.5 h and then washed four times. A 1:8000 dilution of streptavidin-HRP (Thermo Scientific) was added and the plates were incubated for 1 h. Plates were washed a final four times with 0.05% Tween/PBS and TMB substrate (Thermo Scientific) was added for 15 min before the reaction was stopped with 2 M $H_2SO_4$. The absorbance was measured at 450 nm using a microplate reader (Victor$^3$, Perkin Elmer).

A second assay was employed to evaluate the interference of the IL-6 binding Z variants on the interaction between human gp130 (hgp130) and the hIL-6/hIL-6Rα complex. In this experiment, half area 96-well ELISA plates were coated with Fc-fused hgp130 (hgp130-Fc) at a concentration of 4 µg/ml. Plates were incubated overnight at 4° C. and then washed twice in tap water. Next, the plates were blocked for 1 h in PBSC. Plates were incubated for 1.5 h at RT and then washed 4 times with 200 µl 0.05% Tween/PBS. In separate plates, serial dilutions (concentration range 500-0.5 nM) of the 13 $His_6$-tagged Z variant polypeptides were titrated with fixed concentration of hIL-6/hIL-6Rα (0.5 nM and 5 nM, respectively).

The IL-6Rα binding antibody tocilizumab (Roche) was prepared in the same way and included for comparison. The pre-mixed complex of each Z variant polypeptide and hIL- 6/hIL-6Rα was then transferred to wells containing hgp130. Plates were incubated for 1.5 h and then washed 4 times. A biotinylated anti-IL-6Rα antibody (R&D Systems) was added and the plates were incubated for another 1.5 h followed by washing. A 1:8000 dilution of streptavidin-HRP (Thermo Scientific) was added and the plates were incubated for 1 h. Next, plates were washed four times and TMB substrate (Thermo Scientific) was added for 15 min before the reaction was stopped with 2 M $H_2SO_4$. The absorbance was measured at 450 nm using a microplate reader (Victor$^3$, Perkin Elmer).

In Vitro Neutralization Assays:

A first assay, evaluating the classical signaling pathway, used the TF-1 cell line that proliferates in response to human IL-6, TNF and GM-CSF. TF-1 cells were cultured in RPMI1640 with L-glut (Lonza) supplemented with 10% FCS (Gibco), Pen-Strep (Lonza) and 2 ng/ml rhGM-CSF (R&D Systems). Prior to use, cells were washed twice in RPMI1640 in the absence of rhGM-CSF. Cells were then counted and dispensed into 96 well flat bottomed plates at a density of 4×10$^4$ cells per well. In separate plates, serial dilutions of the inhibitory compounds (IL-6 binding Z variants, with a His$_6$-tag (concentration range 1000-0.1 nM) or in fusion with the ABD variant PP013 (SEQ ID NO:1554, concentration range 200-0.007 nM)), and the IL-6Rα binding antibody tocilizumab (Roche; concentration range 200-0.007 nM) were incubated in the presence of 0.099 nM rhIL-6 (R&D Systems, UK). In addition, the ABD-fused variants were incubated with or without 9 µM rhHSA (Novozymes). The pre-mixed complexes of the Z variant polypeptides and hIL-6 were then transferred to wells containing TF-1 cells which were incubated for 72 h at 37° C. in a humidified 5% CO$_2$ atmosphere. During the last four hours of incubation 10 µl of CCK-8 (Fluke, Sigma Aldrich) was added per well to determine the number of proliferating cells. The absorbance was measured at 450 nm (Abs450) using a microplate reader (Victor$^3$, Perkin Elmer). The data on cell growth was assessed by non-linear regression to a four-parameter dose-response curve, and the half maximal inhibitory concentration (IC50) was determined using GraphPadPrism program. The inhibition of IL-6-dependent proliferation of TF-1 cells by the inhibitory molecules was as Abs450 minus control wells that contained cells but no hIL-6.

To address the trans-signaling pathway, a second assay was used. Herein, human umbilical vein endothelial cells (HUVECs) were stimulated with hIL-6 and soluble hIL-6Rα and the readout was the production of monocyte chemoattractant protein-1 (MCP-1). HUVECs (Lonza) were grown in EGM-2 bullet kit media (Lonza) and passaged in culture no more than eight times. Cells were grown until 75% confluence before use. Cells were detached using trypsin/EDTA (Lonza), resuspended and washed once in fresh medium. Next, cells were counted and dispensed into 96 well flat bottom plates at a density of 2×10$^4$ cells per well. Cells were cultured overnight at 37° C. in a humidified 5% CO$_2$ atmosphere. In separate plates, serial dilutions (100-0.0015 nM) of the IL-6 binding Z variants Z06789, Z06799, Z06809, Z06814 and Z06829 in fusion with the ABD variant PP013 (SEQ ID NO:1554), PP013-fused negative control Z03638 (SEQ ID NO:1552) binding a different target, and serial dilutions (200-0.003 nM) of tocilizumab (Roche) were incubated in the presence of recombinant hIL-6 (10 ng/ml; 0.5 nM) and soluble hIL-6Rα at a fixed concentration of 200 ng/ml (5.6 nM) with or without 9 µM rhHSA (Novozymes). The pre-mixed solutions with the test molecules and hIL-6/hIL-6Rα were then transferred to wells containing HUVECs, which were incubated for 24 h at 37° C. in a humidified 5% CO$_2$ atmosphere. Cell free supernatant was collected after the incubation period and human MCP-1 levels were determined by sandwich ELISA using the MCP-1 Duoset ELISA development system (R&D Systems).

MCP-1 ELISA:

Half area 96-well ELISA plates were coated with anti-MCP-1 capture antibody (R&D Systems) at a concentration of 1 µg/ml. Plates were incubated overnight at 4° C., washed twice in tap water and blocked for 1 h in PBSC. Plates were then washed four times with 4×200 µl 0.05% Tween/PBS before standards and samples were added. Plates were incubated for 2 h at RT and washed before addition of 0.1 µg/ml biotinylated anti-MCP-1 antibody (R&D Systems). Plates were then incubated for another 1.5 h, then washed four times. Next, a 1:8000 dilution of streptavidin-HRP (Thermo Scientific) was added and the plates were incubated for 1 h. The plates were washed a final four times and TMB substrate (Thermo Scientific) was added for 20 min before the reaction was stopped with 2 M $H_2SO_4$. The absorbance was measured at 450 nm using a microplate reader (Victor$^3$, Perkin Elmer).

CD Analysis:

A subset of the purified His$_6$-tagged Z variants was diluted to 0.5 mg/ml in PBS. For each diluted Z variant, a CD spectrum at 250-195 nm was obtained at 20° C. In addition, a variable temperature measurement (VTM) was performed to determine the melting temperature (Tm). In the VTM, the absorbance was measured at 221 nm while the temperature was raised from 20 to 90° C., with a temperature slope of 5° C./min. The CD measurements were performed on a Jasco J-810 spectropolarimeter (Jasco Scandinavia AB) using a cell with an optical path-length of 1 mm.

Results

Cultivation and Purification:

The 13 IL-6 binding Z variants (SEQ ID NO:1503-1515), constructed with an N-terminal His$_6$ tag, were produced in *E. coli*. The amount of IMAC-purified protein from approximately 2-5 g bacterial pellets, determined spectrophotometrically by measuring the absorbance at 280 nm, ranged from approximately 10 mg to 20 mg for the different IL-6 binding Z variants. 2 mg to 12 mg were obtained from approximately 2.5 g bacterial pellet of the five Z variants fused to the ABD variant PP013 (SEQ ID NO:1554). SDS-PAGE analysis of each final protein preparation showed that these predominantly contained the IL-6 binding Z variant. The correct identity and molecular weight of each IL-6 binding Z variant was confirmed by HPLC-MS analysis.

Figure 3:
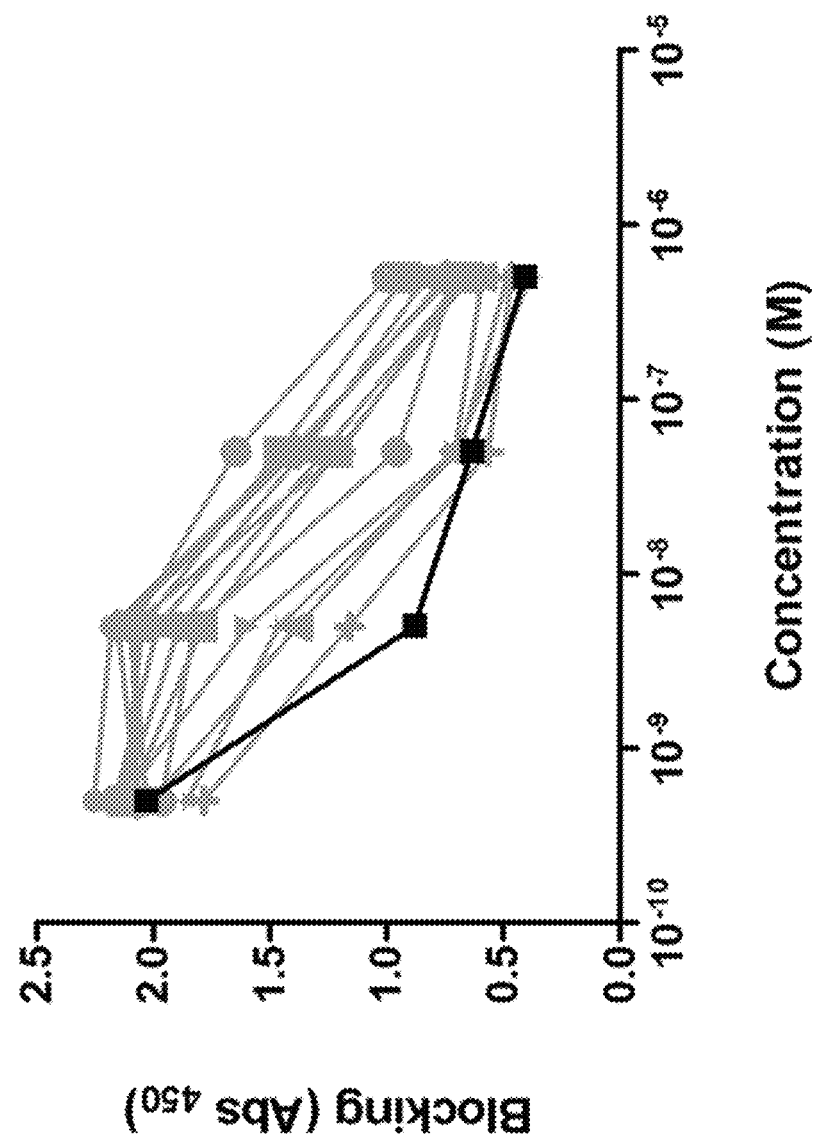
FIG. 3 shows the result of blocking of the binding of the hIL-6/hIL-6Rα complex to hgp130, assayed as described in Example 2. Concentration dependent blocking was seen for all tested primary IL-6 binding Z variants (gray) as well as for tocilizumab (black), which was included for comparison. The calculated IC50 value of each variant is shown in Table 3.

Analysis of Binding Site:

The ability of the 13 tested IL-6 binding His$_6$-tagged Z variants to block the interactions between either (i) hIL-6 and hIL-6Rα or (ii) hgp130 and preformed hIL-6/hIL-6Rα complex was investigated in two separate competitive ELISA experiments. None of the 13 Z variants showed any significant effect when tested for blocking of the hIL-6/hIL-6Rα interaction (FIG. 2). However, all Z variants showed a clear concentration-dependent blocking of the interaction between pre-formed hIL-6/hIL-6Rα and hgp130, i.e. the trans-signaling-resembling interaction (FIG. 3). The calculated IC50 value for each Z variant is shown in Table 3. The antibody tocilizumab, included for comparison, showed a blocking effect in both experiments.

TABLE 3

IC50 values for primary Z variants blocking
the hIL-6/hIL-6Rα interaction with hgp130

| Z variant | SEQ ID NO of Z variant: | IC50 (M) |
|---|---|---|
| His$_6$-Z06777 | 1503 | $4.6 \times 10^{-8}$ |
| His$_6$-Z06779 | 1504 | $3.6 \times 10^{-8}$ |
| His$_6$-Z06789 | 1505 | $6.2 \times 10^{-9}$ |
| His$_6$-Z06791 | 1506 | $2.3 \times 10^{-8}$ |
| His$_6$-Z06792 | 1507 | $1.7 \times 10^{-8}$ |
| His$_6$-Z06799 | 1508 | $3.7 \times 10^{-9}$ |
| His$_6$-Z06802 | 1509 | $2.7 \times 10^{-8}$ |
| His$_6$-Z06805 | 1510 | $4.2 \times 10^{-8}$ |
| His$_6$-Z06809 | 1511 | $3.3 \times 10^{-9}$ |
| His$_6$-Z06814 | 1512 | $1.6 \times 10^{-9}$ |
| His$_6$-Z06829 | 1513 | $1.1 \times 10^{-8}$ |
| His$_6$-Z06834 | 1514 | $5.3 \times 10^{-8}$ |
| His$_6$-Z06844 | 1515 | $8.7 \times 10^{-8}$ |

In Vitro Neutralization Assays:

Two different cell assays were used for investigating the ability of the IL-6 binding Z variants to block IL-6 dependent signaling in the classical signaling pathway and the trans-signaling pathway, respectively. The first assay, evaluating the classical signaling pathway, employed the TF-1 cell line that proliferates in response to human IL-6, TNF and GM-CSF. The direct signaling of IL-6 to cell surface IL-6 receptor, in conjunction with a signaling receptor sub-unit called gp130, is termed cis-signaling. This assay showed that all 13 variants were capable of blocking IL-6 dependent growth of the TF-1 cells. The calculated 1050 values for His$_6$-tagged Z variants and Z variants recombinantly fused to the ABD variant PP013 (SEQ ID NO:1554), as well as for the hIL-6Rα binding antibody tocilizumab included for comparison, are shown in Table 4.

TABLE 4

IC50 values for primary Z variants blocking
the IL-6 dependent growth of TF-1 cells

| Z variant | SEQ ID NO of Z variant: | IC50 (M) |
|---|---|---|
| His$_6$-Z06777 | 1503 | $7.2 \times 10^{-8}$ |
| His$_6$-Z06779 | 1504 | $3.0 \times 10^{-8}$ |
| His$_6$-Z06789 | 1505 | $8.6 \times 10^{-9}$ |
| His$_6$-Z06791 | 1506 | $5.2 \times 10^{-9}$ |
| His$_6$-Z06792 | 1507 | $5.3 \times 10^{-8}$ |
| His$_6$-Z06799 | 1508 | $3.9 \times 10^{-9}$ |
| His$_6$-Z06802 | 1509 | $4.3 \times 10^{-8}$ |
| His$_6$-Z06805 | 1510 | $7.7 \times 10^{-8}$ |
| His$_6$-Z06809 | 1511 | $2.0 \times 10^{-8}$ |
| His$_6$-Z06814 | 1512 | $1.6 \times 10^{-9}$ |
| His$_6$-Z06829 | 1513 | $2.8 \times 10^{-8}$ |
| His$_6$-Z06834 | 1514 | $6.1 \times 10^{-8}$ |
| His$_6$-Z06844 | 1515 | $1.1 \times 10^{-7}$ |
| Z06789-ABD | 1505 | $\sim 1 \times 10^{-7}$ |
| Z06799-ABD | 1508 | $2.4 \times 10^{-8}$ |
| Z06809-ABD | 1511 | $1.0 \times 10^{-8}$ |
| Z06814-ABD | 1512 | $8.0 \times 10^{-10}$ |
| Z06829-ABD | 1513 | $1.5 \times 10^{-8}$ |
| tocilizumab | | $3.0 \times 10^{-10}$ |

Figure 4:
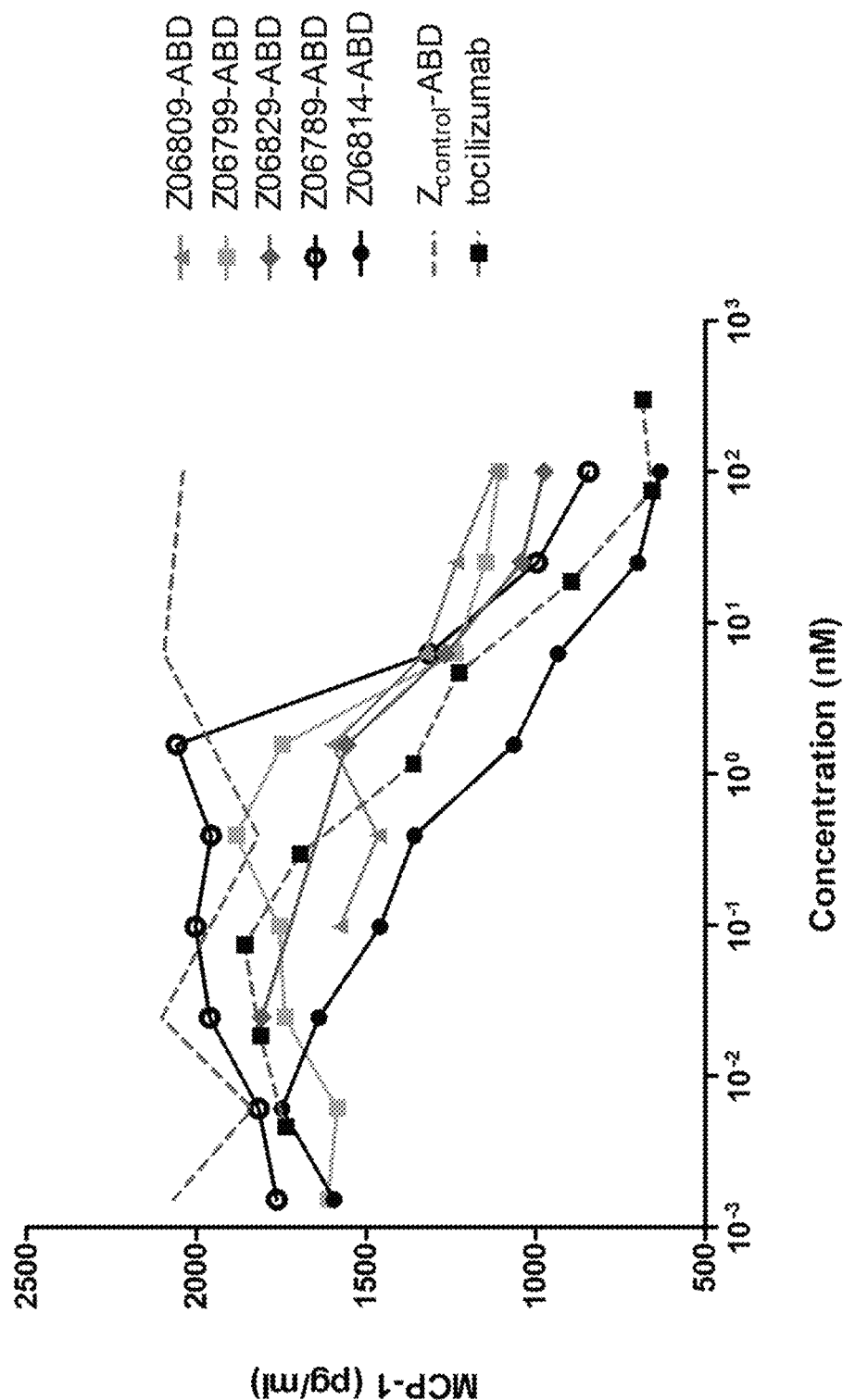
FIG. 4 shows concentration dependent inhibition of IL-6 mediated trans-signaling in a gp130 expressing human umbilical vein endothelial cell (HUVEC) based system, assayed as described in Example 2. IL-6 binding Z variants C-terminally fused to the ABD variant PP013 (SEQ ID NO:1554) inhibited the trans-signaling, whereas the control Z variant Z03638 (SEQ ID NO:1552) in fusion with PP013 did not. Tocilizumab was included for comparison.

To investigate if also the trans-signaling pathway could be blocked in a cell based system, a second assay using gp130 expressing human umbilical vein endothelial cells (HUVECs) was performed. Incubation of HUVECs with pre-formed hIL-6/hIL-6Rα complexes results in IL-6 trans-signaling dependent secretion of Monocyte Chemoattractant Protein-1 (MCP-1), allowing for analysis of any trans-signaling blocking capabilities of IL-6 binding Z variants. In this assay, five Z variants recombinantly fused to the ABD variant PP013 (SEQ ID NO:1554) were analyzed in the presence of HSA. The hIL-6Rα binding antibody tocilizumab was included for comparison. All five investigated Z variants were shown to inhibit trans-signaling (FIG. 4). One variant, Z06814-ABD, was shown to be more potent than tocilizumab and exhibited an approximate IC50 value of 1 nM compared to 5 nM for tocilizumab.

CD Analysis:

The CD spectra determined for seven Z variants showed that each had an α-helical structure at 20° C. The melting temperatures (Tm) determined through variable temperature measurements are shown in Table 5.

TABLE 5

Melting temperatures for a selection of Z variants

| Z variant | SEQ ID NO: | Tm (° C.) |
|---|---|---|
| His$_6$-Z06779 | 1504 | 51 |
| His$_6$-Z06789 | 1505 | 52 |
| His$_6$-Z06792 | 1507 | 48 |
| His$_6$-Z06799 | 1508 | 44 |
| His$_6$-Z06809 | 1511 | 51 |
| His$_6$-Z06814 | 1512 | 49 |
| His$_6$-Z06829 | 1513 | 40 |

Example 3

Design and Construction of a First Maturated Library of IL-6 Binding Z Variants

In this Example, a maturated library was constructed. The library was used for selections of new IL-6 binding Z variants. Selections from maturated libraries are usually expected to result in binders with increased affinity (Orlova et al., (2006) Cancer Res 66(8):4339-48). In this study randomized single stranded linkers were generated, using split-pool synthesis, enabling incorporation of defined codons in desired positions in the synthesis.

Materials and Methods

Library Design:

The library was based on a selection of sequences of the IL-6 binding Z variants described in Example 1 and 2. In the new library, 12 variable positions in the Z molecule scaffold were biased towards certain amino acid residues and one position was kept constant, according to a strategy based on the Z variant sequences defined in SEQ ID NO:1503-1551. Using split-pool synthesis, a DNA linker of 147 bp was generated, encoding a partially randomized helix 1 and 2 of the Z variant amino acid sequence. Thus, 5'-AA ATA AAT CTC GAG GTA GAT GCC AAA TAC GCC AAA GAA NNN NNN NNN GCG TGG NNN GAG ATC NNN NNN CTG CCT AAC CTC ACC NNN NNN CAA NNN NNN GCC TTC ATC NNN AAA TTA NNN GAT GAC CCA AGC CAG AGC TCA TTA TTT A-3' (SEQ ID NO:1560, randomized codons denoted NNN) flanked by restriction sites XhoI and SacI, was ordered from DNA 2.0 (Menlo Park, Calif., USA). The theoretical distributions of amino acid residues in the new library including 12 variable positions (9, 10, 11, 14, 17, 18, 24, 25, 27, 28, 32 and 35) in the Z molecule scaffold are given in Table 6. The resulting theoretical library size is $3.6 \times 10^9$ variants.

TABLE 6

Library design, first maturation

| Amino acid position in Z | Randomization (amino acid abbreviations) | No of amino acids | Proportion |
|---|---|---|---|
| 9 | E (70%), H, Q, T, | 4 | 1/10, 7/10 (E) |
| 10 | A, H, Q, R, | 4 | 1/4 |
| 11 | A, D, E, H, K, Q, R, S, T, V | 10 | 1/10 |
| 13 | W | 1 | 1/1 |
| 14 | A, F, H, L, R, S, T, W, Y | 9 | 1/9 |
| 17 | H (70%), Q, S, T | 4 | 1/10, 7/10 (H) |
| 18 | A, H, I, K, L, M, S, T, V | 9 | 1/9 |
| 24 | A, H, I, T, V | 5 | 1/5 |
| 25 | D, E, H, N, Q, R, S, T | 8 | 1/8 |
| 27 | A, H, I, L, M, R, T, V | 8 | 1/8 |
| 28 | A, E, H, S, T, V | 6 | 1/6 |
| 32 | A, H, I, M, Q, S, T, V, W | 9 | 1/9 |
| 35 | F, L, M, Y | 4 | 1/4 |

Library Construction:

The library was amplified using AmpliTaq Gold polymerase (Applied Biosystems, cat. no. 4311816) during 12 cycles of PCR and pooled products were purified with QIAquick PCR Purification Kit (QIAGEN, cat. no. 28106) according to the supplier's recommendations. The purified pool of randomized library fragments was digested with restriction enzymes XhoI and SacI-HF (New England Biolabs, cat. no. R0146L, and cat. no. R3156M) and concentrated using a PCR Purification Kit (Qiagen, cat. no. 28106). Subsequently, the product was run on a preparative 2.5% agarose gel (Nuisieve GTC agarose, Cambrex, Invitrogen) and purified using a QIAGEN gel extraction Kit (QIAGEN, cat. no. 28706) according to the supplier's recommendations.

The phagemid vector pAY02592 (essentially as pAffi1 described in Grönwall et al, supra) was restricted with the same enzymes and purified using phenol/chloroform extraction and ethanol precipitation. The restricted fragments and vector were ligated in a molar ratio of 5:1 with T4 DNA ligase (Fermentas, cat. no. EL0011) for 2 h at RT, followed by overnight incubation at 4° C. The ligated DNA was recovered by phenol/chloroform extraction and ethanol precipitation, followed by dissolution in 10 mM Tris-HCl, pH 8.5. Thus, the resulting library in vector pAY02592 encoded Z variants, each fused to an albumin binding domain (ABD) derived from streptococcal protein G.

The ligation reactions (approximately 160 ng DNA/transformation) were electroporated into electrocompetent *E. coli* ER2738 cells (50 μl, Lucigen, Middleton, Wis., USA). Immediately after electroporation, approximately 1 ml of recovery medium (supplied with the ER2738 cells) was added. The transformed cells were incubated at 37° C. for 60 min. Samples were taken for titration and for determination of the number of transformants. Next, the cells were pooled and cultivated overnight at 37° C. in 1 l of TSB-YE medium, supplemented with 2% glucose, 10 μg/ml tetracycline and 100 μg/ml ampicillin. The cells were pelleted for 7 min at 4,000 g and resuspended in a PBS/glycerol solution (approximately 40% glycerol), aliquoted and stored at −80° C. Clones from the library of Z variants were sequenced in order to verify the content and to evaluate the outcome of the constructed library vis-à-vis the library design. Sequencing was performed as described in Example 1 and the amino acid distribution was verified.

Preparation of Phage Stock:

Phage stock containing the phagemid library was prepared in a 20 l fermenter (Belach Bioteknik). Cells from a glycerol stock containing the phagemid library were inoculated in 10 l of TSB-YE (Tryptic Soy Broth-Yeast Extract; 30 g/l TSB, 5 g/l yeast extract) supplemented with 1 g/l glucose, 100 mg/l ampicillin and 10 mg/l tetracycline. When the cells reached an optical density at 600 nm ($OD_{600}$) of 0.64, approximately 1.1 l of the cultivation was infected using a 5× molar excess of M13K07 helper phage. The cells were incubated for 30 min, whereupon the fermenter was filled up to 10 l with complex fermentation medium [2.5 g/l $(NH_4)_2SO_4$, 5.0 g/l yeast extract; 30 g/l tryptone, 2 g/l $K_2HPO_4$; 3 g/l $KH_2PO_4$, 1.25 g/l, $Na_3C_6H_5O_7.2H_2O$; Breox FMT30 antifoaming agent 0.1 ml/l]. The following components were added: 10 ml carbenicillin 25 mg/ml, 5 ml kanamycin 50 mg/ml, 1 ml 1 M isopropyl-8-D-1-thiogalactopyranoside (IPTG); 17.5 ml/l of 300 g/l $MgSO_4$ and 5 ml of a trace element solution [35 g/l $FeCl_3.6H_2O$; 10.56 g/l $ZnSO_4.7H_2O$; 2.64 g/l $CuSO_4.5H_2O$; 13.2 g/l $MnSO_4.H_2O$; 13.84 g/l $CaCl_2.2H_2O$, dissolved in 1.2 M HCl]. A glucose limited fed-batch cultivation was started where a 600 g/l glucose solution was fed to the reactor (3.5 g/h in the start, 37.5 g/h after 20 h and until the end of the cultivation). The pH was controlled at pH 7 through the automatic addition of 25% $NH_4OH$. Air was supplemented (5 l/min) and the stirrer was set at 500 rpm. After 24 h of fed-batch cultivation the $OD_{600}$ was 22. The cells in the cultivation were pelleted by centrifugation at 15,900 g. The phage particles were precipitated twice from the supernatant in PEG/NaCl, filtered and dissolved in PBS and glycerol as described in Example 1. Phage stocks were stored at −80° C. until use in selection.

Results

Library Construction:

The new library was designed based on a set of IL-6 binding Z variants with verified binding properties (Example 1 and 2). The theoretical size of the designed library was 3.6×10⁹ Z variants. The actual size of the library, determined by titration after transformation to *E. coli* ER2738 cells, was 3.5×10⁹ transformants.

The library quality was tested by sequencing of 192 transformants and by comparing their actual sequences with the theoretical design. The contents of the actual library compared to the designed library were shown to be satisfactory. A maturated library of potential binders to IL-6 was thus successfully constructed.

Example 4

Selection, Screening and Characterization of Z Variants from the First Maturated Library Materials and Methods Phage Display Selection of Matured IL-6 Binding Z Variants:

The target proteins hIL-6 (R&D Systems, cat. no. 206-IL/CF) and mIL-6 (Abnova, cat. no. P4346 I16) were biotinylated as described in Example 1. Phage display selections, using the new library of Z variant molecules described in Example 3, were performed in four cycles against hIL-6 and mIL-6 essentially as described in Example 1 with the following exceptions. At selection, fetal calf serum (FCS, Gibco, cat. no. 10108-165) and human serum albumin (HSA, Albucult, Novozymes, cat. no. 230-005) were added to the selection buffer to a final concentration of 10% and 1.5 μM, respectively. All tubes and beads used in the selection were pre-blocked with PBST 0.1% supplemented with 3% BSA. In cycle 1A, a pre-selection step was performed by incubation of phage stock with SA-beads. The selection volume was 2 ml in cycle 1 for all tracks. For capture of phage-target complexes, 1 mg beads per 4 µg biotinylated hIL-6 or mIL-6 was used.

The six tracks (1-6) in cycle 1 were divided either in the second cycle or the third cycle, resulting in totally seven tracks (1-1 to 6-2) in cycle 2, twelve tracks (1-1-1 to 6-2-1) in cycle 3 and twelve tracks (1-1-1-1 to 6-2-1-1) in cycle 4.

The bound phage particles were eluted using two different procedures; 1) 500 µl 0.1 M glycine-HCl, pH 2.2, followed by immediate neutralization with 50 µl 1 M Tris-HCl, pH 8.0, and 450 µl PBS, or 2) 500 µl of 100 mM sodium phosphate and 150 mM sodium chloride, pH 5.5 and neutralization with 500 µl PBS.

An overview of the selection strategy, describing an increased stringency in subsequent cycles obtained by using a lowered target concentration and an increased number of washes, is shown in Table 7.

TABLE 7

Overview of the selection strategy for the first maturation

| Cycle | Selection track | Phage stock from library or selection track | Target | Target concentration (nM) | Number of washes | Elution at |
|---|---|---|---|---|---|---|
| 1 | 1 | Zlib006IL-6.I | hIL-6 | 50 | 2 | pH 2.2 |
| 1 | 2 | Zlib006IL-6.I | hIL-6 | 25 | 2 | pH 2.2 |
| 1 | 3 | Zlib006IL-6.I | hIL-6 | 10 | 3 | pH 2.2 |
| 1 | 4 | Zlib006IL-6.I | hIL-6 | 50 | 2 | pH 5.45 |
| 1 | 5 | Zlib006IL-6.I | hIL-6 | 25 | 2 | pH 5.45 |
| 1 | 6 | Zlib006IL-6.I | mIL-6 | 100 | 2 | pH 2.2 |
| 2 | 1-1 | 1 | hIL-6 | 25 | 8 | pH 2.2 |
| 2 | 2-1 | 2 | hIL-6 | 10 | 8 | pH 2.2 |
| 2 | 3-1 | 3 | hIL-6 | 2.5 | 12 | pH 2.2 |
| 2 | 4-1 | 4 | hIL-6 | 25 | 8 | pH 5.45 |
| 2 | 5-1 | 5 | hIL-6 | 10 | 8 | pH 5.45 |
| 2 | 6-1 | 6 | mIL-6 | 100 | 4 | pH 2.2 |
| 2 | 6-2 | 6 | mIL-6 | 50 | 6 | pH 2.2 |
| 3 | 1-1-1 | 1-1 | hIL-6 | 5 | 12 | pH 2.2 |
| 3 | 1-1-2 | 1-1 | hIL-6 | 1.25 | 15 | pH 2.2 |
| 3 | 2-1-1 | 2-1 | hIL-6 | 1.25 | 12 | pH 2.2 |
| 3 | 2-1-2 | 2-1 | hIL-6 | 0.5 | 15 | pH 2.2 |
| 3 | 3-1-1 | 3-1 | hIL-6 | 0.5 | 20 | pH 2.2 |
| 3 | 3-1-2 | 3-1 | hIL-6 | 0.05 | 20 | pH 2.2 |
| 3 | 4-1-1 | 4-1 | hIL-6 | 5 | 12 | pH 5.45 |
| 3 | 4-1-2 | 4-1 | hIL-6 | 1.25 | 15 | pH 5.45 |
| 3 | 5-1-1 | 5-1 | hIL-6 | 2.5 | 12 | pH 5.45 |
| 3 | 5-1-2 | 5-1 | hIL-6 | 1 | 15 | pH 5.45 |
| 3 | 6-1-1 | 6-1 | mIL-6 | 50 | 11 | pH 2.2 |
| 3 | 6-2-1 | 6-2 | mIL-6 | 25 | 11 | pH 2.2 |
| 4 | 1-1-1-1 | 1-1-1 | hIL-6 | 0.5 | 16 | pH 2.2 |
| 4 | 1-1-2-1 | 1-1-2 | hIL-6 | 0.05 | 20 | pH 2.2 |
| 4 | 2-1-1-1 | 2-1-1 | hIL-6 | 0.1 | 16 | pH 2.2 |
| 4 | 2-1-2-1 | 2-1-2 | hIL-6 | 0.025 | 20 | pH 2.2 |
| 4 | 3-1-1-1 | 3-1-1 | hIL-6 | 0.025 | 30 | pH 2.2 |
| 4 | 3-1-2-1 | 3-1-2 | hIL-6 | 0.0025 | 30 | pH 2.2 |
| 4 | 4-1-1-1 | 4-1-1 | hIL-6 | 1 | 16 | pH 5.45 |
| 4 | 4-1-2-1 | 4-1-2 | hIL-6 | 0.1 | 20 | pH 5.45 |
| 4 | 5-1-1-1 | 5-1-1 | hIL-6 | 0.2 | 16 | pH 5.45 |
| 4 | 5-1-2-1 | 5-1-2 | hIL-6 | 0.05 | 20 | pH 5.45 |
| 4 | 6-1-1-1 | 6-1-1 | mIL-6 | 10 | 12 | pH 2.2 |
| 4 | 6-2-1-1 | 6-2-1 | mIL-6 | 1 | 16 | pH 2.2 |

Amplification of Phage Particles:

Amplification of phage particles between selection cycle 1 and 2 was performed essentially as described in Example 1, with the following exceptions. E. coli ER2738 was used for phage amplification and M13K07 helper phage was used in 5× excess. The amplification of phage particles between the selection cycles 2 and 4 was done by infection of bacteria in solution according to the following. After infection of log phase E. coli ER2738 with phage particles, TSB supplemented with 2% glucose, 10 µg/ml tetracycline and 100 µg/ml ampicillin was added, followed by incubation with rotation for 30 min at 37° C. Thereafter, the bacteria were infected with M13K07 helper phage. The infected bacteria were pelleted by centrifugation, re-suspended in TSB-YE medium supplemented with 100 µM IPTG, 25 µg/ml kanamycin and 100 µg/ml ampicillin, and grown overnight at 30° C. The overnight cultures were centrifuged and phage particles in the supernatant were precipitated twice with PEG/NaCl buffer. Finally, the phage particles were re-suspended in selection buffer before entering the next selection cycle. In the last selection cycle, log phase bacteria were infected with eluate and diluted before spreading onto TBAB plates (30 g/l tryptose blood agar base, Oxoid cat. no. CMO233B) supplemented with 0.2 g/l ampicillin in order to form single colonies for use in ELISA screening.

Sequencing of Potential Binders:

Individual clones from the different selection tracks were picked for sequencing. All clones run in the ELISA screening were sequenced. Amplification of gene fragments and sequence analysis of gene fragments were performed essentially as described in Example 1.

ELISA Screening of Z Variants:

Single colonies containing Z variants (expressed as Z variant ABD fusion proteins) were randomly picked from the selected clones of the IL-6 maturated library and cultivated as described in Example 1. Preparation of the periplasmic supernatants was performed as in Example 1 but with six freeze thawing cycles. ELISA screenings were performed essentially as described in Example 1 using biotinylated hIL-6 at a concentration of 0.58 nM. The periplasmic fraction of the primary IL-6 binder Z06814 was used as a positive control. A negative control was created by using periplasm containing ABD only.

ELISA EC50 Analysis of Human IL-6 Binders:

A selection of IL-6 binders was subjected to an analysis of the response against a dilution series of biotinylated hIL-6 using ELISA as described above. Biotinylated protein was added at a concentration of 25 nM and diluted stepwise 1:3 down to 11 pM. All Z variants were also assayed without added target protein as a background control. Periplasm samples containing the primary IL-6 binder Z06814 (SEQ ID. NO:1512) were included and analyzed as a positive control. As a negative control, periplasm containing ABD only was assayed against biotinylated hIL-6. Two binders originating from the selection against mIL-6, Z11612 (SEQ ID NO:151) and Z11616 (SEQ ID NO:152) were subjected to an analysis of the response against a dilution series of biotinylated mIL-6 using ELISA as described above. Biotinylated protein was added at a concentration of 227 nM and diluted stepwise 1:3 down to 104 pM. Obtained values were analyzed using GraphPad Prism 5 and non-linear regression.

Results

Phage Display Selection of Maturated IL-6 Binding Z Variants:

Selection was performed in totally 12 parallel tracks containing four cycles each. The different selection tracks differed in target concentration, target type (hIL-6 or mIL-6), selection time, wash conditions and the pH of the elution buffer.

Sequencing:

Randomly picked clones were sequenced. Each individual Z variant was given an identification number, Z #####, as described in Example 1. In total, 809 new unique Z variant molecules were identified.

The amino acid sequences of 58 residues long Z variants are listed in FIG. 1A-VV and in the sequence listing as SEQ ID NO:7, SEQ ID NO:15-89 and SEQ ID NO:151-871. The deduced IL-6 binding motifs (BM) extend from position 8 to position 36 in each sequence. The amino acid sequences of the 49 amino acid residues long polypeptides predicted to constitute the complete three-helix bundle within each of these Z variants (BMod) extend from position 7 to position 55.

ELISA Screening of Z Variants:

Clones obtained after four selection cycles were produced in 96-well plates and screened for hIL-6 binding activity using ELISA. All randomly picked clones were analyzed. 796 of the 809 unique Z variants were found to give a response of 3× the negative control or higher (0.3-2.1 AU) against hIL-6 at a concentration of 0.58 nM. Clones from all selection tracks using hIL-6 as selection target showed positive signals. The negative controls had absorbencies of 0.078-0.102 AU. The average response of the blank controls of a representative set of plates was 0.087 AU.

ELISA EC50 Analysis of IL-6 Binders:

A subset of Z variants was selected based on the result in the ELISA experiment described above (highest ELISA value normalized against the positive control on each plate, respectively) and subjected to a target titration in ELISA format. Periplasm samples were incubated with a serial dilution of biotinylated hIL-6 or mIL-6. A periplasm sample with the primary binder Z06814 (SEQ ID NO:1512) was also assayed against hIL-6 as a positive control. Obtained values were analyzed and their respective EC50 values were calculated (Tables 8 and 9).

TABLE 8

Calculated EC50 values against hIL-6

| Z variant | SEQ ID NO | EC50 ELISA (M) |
|---|---|---|
| Z11213 | 15 | $1.5 \times 10^{-10}$ |
| Z11214 | 16 | $1.3 \times 10^{-10}$ |
| Z11215 | 17 | $1.4 \times 10^{-10}$ |
| Z11217 | 18 | $1.3 \times 10^{-10}$ |
| Z11222 | 19 | $1.4 \times 10^{-10}$ |
| Z11251 | 20 | $1.4 \times 10^{-10}$ |
| Z11277 | 21 | $1.2 \times 10^{-10}$ |
| Z11278 | 22 | $1.5 \times 10^{-10}$ |
| Z11283 | 23 | $1.8 \times 10^{-10}$ |
| Z11300 | 24 | $1.9 \times 10^{-10}$ |
| Z11321 | 25 | $1.4 \times 10^{-10}$ |
| Z11329 | 26 | $1.4 \times 10^{-10}$ |
| Z11351 | 27 | $1.7 \times 10^{-10}$ |
| Z11380 | 28 | $1.7 \times 10^{-10}$ |
| Z11384 | 29 | $1.5 \times 10^{-10}$ |
| Z11433 | 30 | $2.1 \times 10^{-10}$ |
| Z11472 | 31 | $1.8 \times 10^{-10}$ |
| Z11552 | 32 | $1.2 \times 10^{-9}$ |
| Z11632 | 7 | $1.9 \times 10^{-10}$ |
| Z11642 | 33 | $2.3 \times 10^{-10}$ |
| Z11644 | 34 | $2.4 \times 10^{-10}$ |
| Z11674 | 35 | $2.6 \times 10^{-10}$ |
| Z11698 | 36 | $2.0 \times 10^{-10}$ |
| Z11711 | 37 | $3.5 \times 10^{-10}$ |
| Z11723 | 38 | $2.5 \times 10^{-10}$ |
| Z11781 | 39 | $2.9 \times 10^{-10}$ |
| Z11784 | 40 | $2.7 \times 10^{-10}$ |
| Z11788 | 41 | $2.5 \times 10^{-10}$ |
| Z11789 | 42 | $2.4 \times 10^{-10}$ |
| Z11791 | 43 | $3.4 \times 10^{-10}$ |

TABLE 8-continued

Calculated EC50 values against hIL-6

| Z variant | SEQ ID NO | EC50 ELISA (M) |
|---|---|---|
| Z11794 | 44 | $2.2 \times 10^{-10}$ |
| Z11802 | 45 | $2.6 \times 10^{-10}$ |
| Z11803 | 46 | $2.8 \times 10^{-10}$ |
| Z11805 | 47 | $3.4 \times 10^{-10}$ |
| Z11814 | 48 | $2.5 \times 10^{-10}$ |
| Z11815 | 49 | $2.8 \times 10^{-10}$ |
| Z11817 | 50 | $2.5 \times 10^{-10}$ |
| Z11818 | 51 | $2.4 \times 10^{-10}$ |
| Z11819 | 52 | $2.5 \times 10^{-10}$ |
| Z11823 | 53 | $2.1 \times 10^{-10}$ |
| Z11824 | 54 | $2.3 \times 10^{-10}$ |
| Z11833 | 55 | $2.9 \times 10^{-10}$ |
| Z11835 | 56 | $2.9 \times 10^{-10}$ |
| Z11836 | 57 | $3.6 \times 10^{-10}$ |
| Z11860 | 58 | $1.8 \times 10^{-10}$ |
| Z11861 | 59 | $2.2 \times 10^{-10}$ |
| Z11862 | 60 | $1.9 \times 10^{-10}$ |
| Z11865 | 61 | $2.3 \times 10^{-10}$ |
| Z11866 | 62 | $2.5 \times 10^{-10}$ |
| Z11871 | 63 | $1.7 \times 10^{-10}$ |
| Z11872 | 64 | $2.8 \times 10^{-10}$ |
| Z11874 | 65 | $3.1 \times 10^{-10}$ |
| Z11875 | 66 | $2.1 \times 10^{-10}$ |
| Z11881 | 67 | $1.7 \times 10^{-10}$ |
| Z11882 | 68 | $1.4 \times 10^{-10}$ |
| Z11883 | 69 | $2.1 \times 10^{-10}$ |
| Z11890 | 70 | $1.9 \times 10^{-10}$ |
| Z11892 | 71 | $2.3 \times 10^{-10}$ |
| Z11893 | 72 | $2.0 \times 10^{-10}$ |
| Z11895 | 73 | $2.8 \times 10^{-10}$ |
| Z11896 | 74 | $2.9 \times 10^{-10}$ |
| Z11897 | 75 | $3.0 \times 10^{-10}$ |
| Z11901 | 76 | $1.7 \times 10^{-10}$ |
| Z11903 | 77 | $2.3 \times 10^{-10}$ |
| Z11904 | 78 | $2.4 \times 10^{-10}$ |
| Z11905 | 79 | $3.1 \times 10^{-10}$ |
| Z11906 | 80 | $2.5 \times 10^{-10}$ |
| Z11907 | 81 | $3.6 \times 10^{-10}$ |
| Z11912 | 82 | $1.8 \times 10^{-10}$ |
| Z11918 | 83 | $3.2 \times 10^{-10}$ |
| Z11922 | 84 | $2.7 \times 10^{-10}$ |
| Z11923 | 85 | $2.1 \times 10^{-10}$ |
| Z11929 | 86 | $2.6 \times 10^{-10}$ |
| Z11933 | 87 | $1.6 \times 10^{-10}$ |
| Z11937 | 88 | $3.0 \times 10^{-10}$ |
| Z11939 | 89 | $2.1 \times 10^{-10}$ |
| Z06814 | 1512 | $2.9 \times 10^{-10}$ |

TABLE 9

Calculated EC50 values against mIL-6

| Z variant | SEQ ID NO | EC50 ELISA (M) |
|---|---|---|
| Z11612 | 151 | $9.3 \times 10^{-9}$ |
| Z11616 | 152 | $7.7 \times 10^{-9}$ |

Example 5

Design and Construction of a Second Maturated Library of IL-6 Binding Z Variants In this Example, a second maturated library was constructed essentially as described in Example 4. The library was used for selections of IL-6 binding Z variants.

Materials and Methods

Library Design:

The library was primarily based on a selection of sequences of the human IL-6 binding Z variants described in Example 4. In the new library, 13 variable positions in the Z molecule scaffold were biased towards certain amino acid residues, according to a strategy mainly based on the Z variants from the first maturation, i.e. sequences defined in SEQ ID NO:7, SEQ ID NO:15-89 and SEQ ID NO:151-871. Randomized double stranded linkers were generated by the Colibra™ technology, which enables incorporation of randomized sets of trinucleotide building blocks using ligations and restrictions of the subsequently built up double stranded DNA. A library of double-stranded DNA, 5'-AA ATA AAT CTC GAG GTA GAT GCC AAA TAC GCC AAA GAA NNN NNN NNN GCT NNN NNN GAG ATC NNN NNN CTG CCG AAC CTG ACC NNN NNN CAG NNN NNN GCC TTC ATC NNN AAA TTA NNN GAT GAC CCA AGC CAG AGC TCA TTA TTT A-3' (SEQ ID NO:1561, randomized codons are denoted NNN) encoding a partially randomized helix 1 and 2 of the Z variant amino acid sequence, flanked by restriction sites XhoI and SacI, was ordered from Isogenica (Essex, UK). The theoretical distributions of amino acid residues in the new library, including eight variable amino acid positions (10, 11, 14, 18, 24, 25, 27 and 32) and five constant amino acid positions (9, 13, 17, 28, and 35) in the Z molecule scaffold are given in Table 10. The resulting theoretical library size was $2.6 \times 10^7$ variants.

Library Construction and Phage Stock Preparation:

The library was constructed essentially as described in Example 3. Phage stock of the library was prepared as described in Example 3.

TABLE 10

Library design, second maturation

| Amino acid position in Z | Allowed amino acids | No of amino acids | Proportion |
|---|---|---|---|
| 9 | E | 1 | 1/1 |
| 10 | A, D, E, F, H, I, K, L, N, Q, R, S, T, V, W, Y | 1 | 1/16 |
| 11 | A, D, E, F, G, H, I, K, L, M, N, Q, R, S, T, V, W, Y | 17 | 1/18 |
| 13 | W | 1 | 1/1 |
| 14 | A, D, E, F, H, I, K, L, M, N, Q, R, S, T, V, W, Y | 7 | 1/17 |
| 17 | H | 1 | 1/1 |
| 18 | A, D, E, F, G, H, I, K, L, N, Q, R, S, T, V, W, Y | 17 | 1/17 |
| 24 | I, L, V | 1 | 1/3 |
| 25 | A, D, E, F, G, H, I, K, L, N, Q, R, S, T, V, W, Y | 10 | 1/17 |
| 27 | I, M, V | 1 | 1/3 |
| 28 | A | 12 | 1/1 |
| 32 | S, T | 16 | 1/2 |
| 35 | F | 1 | 1/1 |

Results

Library Construction and Phage Stock Preparation:

The new library was designed based on a set of IL-6 binding Z variants with verified binding properties (Example 4). The theoretical size of the designed library was $2.6 \times 10^7$ Z variants. The actual size of the library, determined by titration after transformation to E. coli ER2738 cells, was $1.8 \times 10^9$ transformants.

The library quality was tested by sequencing of 192 transformants and by comparing their actual sequences with the theoretical design. The contents of the actual library compared to the theoretical library were shown to be satisfying. A maturated library of potential binders to IL-6 was thus successfully constructed.

Example 6

Selection, Screening and Characterization of Z Variants from the Second Maturated Library Materials and Methods Second Phage Display Selection of Maturated IL-6 Binding Z Variants:

The target protein hIL-6 was biotinylated as described in Example 4. Phage display selections, using the second maturated library of Z variant molecules described in Example 5 were performed against hIL-6 essentially as described in Example 4, with the following exceptions. The selection volume was 4 ml in cycle 1 for all tracks. In cycle 2, selection tracks 1-2 and 1-3 were handled in one common tube and not separated until after the last 1 min wash, whereupon they were treated separately. Also in cycle 4, each set of the selection tracks 1-1-1-1 to 1-1-1-3, 1-1-1-4 to 1-1-1-6, 1-1-2-1 to 1-1-2-3 and 1-1-2-4 to 1-1-2-6, respectively, were handled in a common tube and split into three separate tubes after the last 1 min wash and thereafter treated separately using the different washing strategies outlined in Table 11. The bound phage particles were eluted using glycine-HCl, pH 2.2, as described in Example 1. The amplification of phage particles between the selection cycles was performed essentially as described in Example 1.

An overview of the selection strategy and parameters used, describing the differences in the selection tracks in terms of lowered target concentration and an increased number of washes, is shown in Table 11.

Sequencing of Potential Binders:

Individual clones from the different selection tracks were picked for sequencing. All clones subjected to the ELISA screening were sequenced. Amplification of gene fragments and sequence analysis of gene fragments were performed essentially as described in Example 1.

ELISA Screening of Z Variants:

Single colonies containing Z variants (expressed as Z variant ABD fusion proteins as described in Example 1) were randomly picked from the selected clones of the IL-6 second maturated library and cultivated as described in Example 1. Preparation of the periplasmic supernatants and ELISA screenings were performed essentially as described in Example 1 and freeze thawing was performed in 150 µl PBST 0.05% and repeated 8 times. Biotinylated hIL-6 was used at a concentration of 0.25 nM. The periplasmic fraction of the IL-6 binder Z06814 (SEQ ID NO:1512) was used in duplicate as positive control on each ELISA plate. As a negative control, periplasm containing ABD only was assayed against biotinylated hIL-6.

TABLE 11

Overview of the selection strategy for the second maturation

| Cycle | Selection track | Phage stock from library or selection track | Target concentration (nM) | Number of 1 min washes | Number of 4 h washes | Number of 4 h washes with unlabeled Z06814 | Number of overnight washes | Number of over weekend washes |
|---|---|---|---|---|---|---|---|---|
| 1 | 1 | Zlib006IL-6A.II | 50 | 5 | — | — | — | — |
| 1 | 2 | Zlib006IL-6A.II | 10 | 5 | — | — | — | — |
| 2 | 1-1 | 1 | 10 | 15 | — | — | — | — |
| 2 | 1-2 | 1 | 5 | 15 | — | — | — | — |
| 2 | 1-3 | 1 | 5 | 15 | 1 | — | — | — |
| 2 | 2-1 | 2 | 2.5 | 12 | — | — | — | — |
| 3 | 1-1-1 | 1-1 | 1 | 5 | — | 1 | — | — |
| 3 | 1-1-2 | 1-1 | 1 | 5 | — | 1 | — | — |
| 3 | 1-2-1 | 1-2 | 0.5 | 15 | — | — | — | — |
| 3 | 1-3-1 | 1-3 | 0.5 | 15 | — | — | — | — |
| 3 | 2-1-1 | 2-1 | 0.5 | 12 | — | — | — | — |
| 3 | 2-1-2 | 2-1 | 0.1 | 12 | — | — | — | — |
| 4 | 1-1-1-1 | 1-1-1 | 1 | 5 | — | 1 | — | — |
| 4 | 1-1-1-2 | 1-1-1 | 1 | 5 | — | — | 1 | — |
| 4 | 1-1-1-3 | 1-1-1 | 1 | 5 | — | — | — | 1 |
| 4 | 1-1-1-4 | 1-1-1 | 1 | 5 | — | 1 | — | — |
| 4 | 1-1-1-5 | 1-1-1 | 1 | 5 | — | — | 1 | — |
| 4 | 1-1-1-6 | 1-1-1 | 1 | 5 | — | — | — | 1 |
| 4 | 1-1-2-1 | 1-1-2 | 1 | 5 | — | 1 | — | — |
| 4 | 1-1-2-2 | 1-1-2 | 1 | 5 | — | — | 1 | — |
| 4 | 1-1-2-3 | 1-1-2 | 1 | 5 | — | — | — | 1 |
| 4 | 1-1-2-4 | 1-1-2 | 1 | 5 | — | 1 | — | — |
| 4 | 1-1-2-5 | 1-1-2 | 1 | 5 | — | — | 1 | — |
| 4 | 1-1-2-6 | 1-1-2 | 1 | 5 | — | — | — | 1 |
| 4 | 1-2-1-1 | 1-2-1 | 0.5 | 15 | — | — | — | — |
| 4 | 1-2-1-2 | 1-2-1 | 0.5 | 15 | 1 | — | — | — |
| 4 | 1-3-1-1 | 1-3-1 | 0.5 | 15 | — | — | — | — |
| 4 | 2-1-1-1 | 2-1-1 | 0.5 | 12 | — | — | — | — |
| 4 | 2-1-2-1 | 2-1-2 | 0.1 | 12 | — | — | — | — |

ELISA EC50 Analysis of IL-6 Binders:

A selection of IL-6 binders was subjected to an analysis of the response against a dilution series of biontinylated hIL-6 using ELISA as described in Example 2. Biotinylated protein was added at a concentration of 5 nM and diluted stepwise 1:3 down to 83 fM. As a background control, all Z variants were also assayed without added target protein. Periplasm samples containing the primary IL-6 binder Z06814 (SEQ ID NO:1512) as well as maturated binder Z11632 (SEQ ID NO:7) were included as positive controls. As a negative control, periplasm containing ABD only was assayed against biotinylated hIL-6. Obtained values were analyzed using Graph Pad Prism 5 and non-linear regression.

Results

Second Phage Display Selection of Maturated IL-6 Binding Z Variants:

Selection was performed in 17 parallel tracks in total, each track containing four cycles. The selection tracks differed in target concentration, selection time and wash conditions as outlined in Table 11.

Sequencing of Potential Binders:

Randomly picked clones were sequenced. Each individual Z variant was given an identification number, Z #####, as described in Example 1. In total, 707 new unique Z variant molecules were identified. The amino acid sequences of 58 residues long Z variants are listed in FIG. 1A-VV and in the sequence listing as SEQ ID NO:1-6, SEQ ID NO:8-14, SEQ ID NO:90-150 and SEQ ID NO:872-1502. The deduced IL-6 binding motifs (BM) extend from position 8 to position 36 in each sequence. The amino acid sequences of the 49 amino acid residues long polypeptides predicted to constitute the complete three-helix bundle within each of these Z variants (BMod) extend from position 7 to position 55.

ELISA Screening of Z Variants:

Clones obtained after four selection cycles were produced in 96-well plates and screened for human IL-6 binding activity using ELISA. All randomly picked clones were analyzed. 705 of the 707 unique Z variants were found to give a response of 3× the negative controls or higher (0.3-2.3 AU) against hIL-6 at a concentration of 0.25 nM. Positive signals were shown for clones originating from all selection tracks. The average response of the negative controls on the plates was 0.085 AU.

ELISA EC50 Analysis of IL-6 Binders:

A subset of Z variants was selected based on the result in the ELISA experiment described above. All Z variants exhibiting an absorbance of over 1.6 AU or a response over 1.7 after normalizing the response against the average response of the duplicate positive control Z06814 (SEQ ID NO:1512) on each plate were subjected to a target titration in ELISA format as described in Example 4. Periplasm samples with the maturated binder Z11632 (SEQ ID NO:7) as well as the primary binder Z06814 (SEQ ID NO:1512) were also assayed as positive controls. Obtained values were analyzed and their respective EC50 values were calculated (Table 12).

TABLE 12

Calculated EC50 values from ELISA titration analysis of Z variants from the second maturation as well as positive controls Z06814 and Z11632

| Z variant | SEQ ID NO | EC50 ELISA (M) |
|---|---|---|
| Z14521 | 90 | $2.3 \times 10^{-10}$ |
| Z14524 | 91 | $2.7 \times 10^{-10}$ |
| Z14525 | 92 | $2.5 \times 10^{-10}$ |
| Z14538 | 93 | $3.2 \times 10^{-10}$ |
| Z14547 | 94 | $2.5 \times 10^{-10}$ |
| Z14550 | 95 | $2.7 \times 10^{-10}$ |
| Z14551 | 96 | $2.6 \times 10^{-10}$ |
| Z14556 | 97 | $2.8 \times 10^{-10}$ |
| Z14559 | 98 | $2.3 \times 10^{-10}$ |
| Z14596 | 99 | $2.4 \times 10^{-10}$ |
| Z14609 | 100 | $3.0 \times 10^{-10}$ |
| Z14614 | 101 | $3.8 \times 10^{-10}$ |
| Z14620 | 102 | $3.1 \times 10^{-10}$ |
| Z14630 | 6 | $2.5 \times 10^{-10}$ |
| Z14634 | 103 | $2.3 \times 10^{-10}$ |
| Z14645 | 104 | $2.5 \times 10^{-10}$ |
| Z14651 | 105 | $2.4 \times 10^{-10}$ |
| Z14662 | 106 | $2.7 \times 10^{-10}$ |
| Z14673 | 107 | $2.3 \times 10^{-10}$ |
| Z14700 | 8 | $2.4 \times 10^{-10}$ |
| Z14706 | 108 | $2.3 \times 10^{-10}$ |
| Z14710 | 109 | $2.6 \times 10^{-10}$ |
| Z14712 | 9 | $2.6 \times 10^{-10}$ |
| Z14720 | 110 | $2.2 \times 10^{-10}$ |
| Z14722 | 111 | $3.2 \times 10^{-10}$ |
| Z14731 | 112 | $2.1 \times 10^{-10}$ |
| Z14746 | 113 | $2.8 \times 10^{-10}$ |
| Z14765 | 114 | $2.7 \times 10^{-10}$ |
| Z14767 | 115 | $2.4 \times 10^{-10}$ |
| Z14782 | 116 | $2.4 \times 10^{-10}$ |
| Z14783 | 117 | $2.4 \times 10^{-10}$ |
| Z14784 | 118 | $2.5 \times 10^{-10}$ |
| Z14788 | 119 | $3.0 \times 10^{-10}$ |
| Z14829 | 120 | $2.7 \times 10^{-10}$ |
| Z14861 | 4 | $2.3 \times 10^{-10}$ |
| Z14862 | 10 | $2.2 \times 10^{-10}$ |
| Z14867 | 121 | $2.6 \times 10^{-10}$ |
| Z14868 | 122 | $2.8 \times 10^{-10}$ |
| Z14878 | 123 | $2.9 \times 10^{-10}$ |
| Z14888 | 124 | $2.2 \times 10^{-10}$ |
| Z14929 | 125 | $2.1 \times 10^{-10}$ |
| Z14944 | 126 | $1.9 \times 10^{-10}$ |
| Z14976 | 1 | $1.6 \times 10^{-10}$ |
| Z14984 | 5 | $1.6 \times 10^{-10}$ |
| Z14990 | 127 | $2.5 \times 10^{-10}$ |
| Z14992 | 128 | $2.8 \times 10^{-10}$ |
| Z15003 | 129 | $3.0 \times 10^{-10}$ |
| Z15015 | 2 | $1.8 \times 10^{-10}$ |
| Z15024 | 130 | $3.1 \times 10^{-10}$ |
| Z15025 | 131 | $2.1 \times 10^{-10}$ |
| Z15031 | 132 | $2.1 \times 10^{-10}$ |
| Z15036 | 11 | $2.4 \times 10^{-10}$ |
| Z15042 | 133 | $2.2 \times 10^{-10}$ |
| Z15053 | 134 | $2.4 \times 10^{-10}$ |
| Z15057 | 135 | $2.3 \times 10^{-10}$ |
| Z15067 | 136 | $2.2 \times 10^{-10}$ |
| Z15079 | 137 | $2.1 \times 10^{-10}$ |
| Z15082 | 138 | $2.2 \times 10^{-10}$ |
| Z15097 | 139 | $2.2 \times 10^{-10}$ |
| Z15102 | 140 | $2.1 \times 10^{-10}$ |
| Z15110 | 12 | $2.0 \times 10^{-10}$ |
| Z15111 | 141 | $2.3 \times 10^{-10}$ |
| Z15117 | 142 | $2.1 \times 10^{-10}$ |
| Z15122 | 3 | $1.7 \times 10^{-10}$ |
| Z15126 | 13 | $1.5 \times 10^{-10}$ |
| Z15129 | 143 | $2.1 \times 10^{-10}$ |
| Z15140 | 144 | $2.1 \times 10^{-10}$ |
| Z15141 | 145 | $2.3 \times 10^{-10}$ |
| Z15142 | 14 | $1.6 \times 10^{-10}$ |
| Z15145 | 146 | $2.3 \times 10^{-10}$ |
| Z15151 | 147 | $1.9 \times 10^{-10}$ |
| Z15159 | 148 | $1.8 \times 10^{-10}$ |
| Z15162 | 149 | $1.8 \times 10^{-10}$ |
| Z15164 | 150 | $2.0 \times 10^{-10}$ |
| Z06814 | 1512 | $3.2 \times 10^{-10}$ |
| Z11632 | 7 | $2.5 \times 10^{-10}$ |

Example 7

Subcloning, Production and Characterization of a Subset of IL-6 Binding Z Variants In this Example, a subset of affinity-matured IL-6 binding Z variants were produced and functionally assessed by SPR, ELISA, cell-based assays and CD. SPR was used for measuring the kinetic parameters of Z variants interacting with IL-6. Competition ELISA was applied to investigate the binding mode of Z variants to human IL-6 protein. A TF-1 cell-based assay was applied to assess the ability of Z variants to block IL-6 dependent signaling. CD was used to investigate the secondary structure of the Z variants and determine their melting temperatures.

Materials and Methods

Subcloning of Z Variants into Expression Vectors:

The DNA of 14 IL-6 binding Z variants, Z11632 (SEQ ID NO:7), Z14630 (SEQ ID NO:6), Z14700 (SEQ ID NO:8), Z14712 (SEQ ID NO:9), Z14861 (SEQ ID NO:4), Z14862 (SEQ ID NO:10), Z14976 (SEQ ID NO:1), Z14984 (SEQ ID NO:5), Z15015 (SEQ ID NO:2), Z15036 (SEQ ID NO:11), Z15110 (SEQ ID NO:12), Z15122 (SEQ ID NO:3), Z15126 (SEQ ID NO:13) and Z15142 (SEQ ID NO:14), was amplified from the library vector pAY02592. The subcloning was performed as described in Example 2. The Z gene fragments were subcloned into the expression vector pAY01448 resulting in the encoded sequence MGSSHHHHHHLQ-[Z #####]-VD (SEQ ID NO: 1595).

Protein Expression and Purification Under Denatured Conditions:

*E. coli* Rosetta cells (Novagen) were transformed with plasmids containing the gene fragment of each respective IL-6 binding Z variant and cultivated at 37° C. in 100 ml of TSB-YE medium supplemented with 50 µg/ml kanamycin. Expression was induced at $OD_{600}$=0.8 by addition of IPTG at a final concentration of 1 mM and the cultures were incubated at 25° C. for another 16-20 h. The cells were harvested by centrifugation.

Protein purification was performed under denatured conditions essentially as described in Example 2. Protein concentrations were determined by measuring the absorbance at 280 nm, using the extinction coefficient of the respective protein. The purity of the IL-6 binding Z variants was analyzed by SDS-PAGE stained with Coomassie Blue.

Protein Expression and Purification Under Native Conditions:

*E. coli* BL21 (DE3) cells (NEB, cat. no. C25271) were transformed with plasmids containing gene fragments of matured variants Z11632 (SEQ ID NO:7), Z14630 (SEQ ID NO:6), Z14700 (SEQ ID NO:8), Z14712 (SEQ ID NO:9), Z14861 (SEQ ID NO:4), Z14862 (SEQ ID NO:10), Z14976 (SEQ ID NO:1), Z14984 (SEQ ID NO:5), Z15015 (SEQ ID NO:2), Z15036 (SEQ ID NO:11), Z15110 (SEQ ID NO:12), Z15122 (SEQ ID NO:3), Z15142 (SEQ ID NO:14), of the primary Z variant Z06814 (SEQ ID NO:1512), as well as of the control Z variant Z04726 (SEQ ID NO:1553). Transformed bacterial cells were cultivated at 37° C. in 1000 ml of LB medium supplemented with 50 µg/ml kanamycin. In order to induce protein expression, IPTG was added to a final concentration of 0.1 mM at $OD_{600}=0.8$ and the cultures were incubated at 25° C. for 17 h. The cells were harvested by centrifugation at 4° C. and 8000 rpm for 30 min. Supernatants were discarded and cell pellets re-suspended in 10 ml PBS. After cell disruption by sonication, cell debris was removed by centrifugation and each supernatant was applied on 2 ml Ni-NTA columns (QIAGEN, cat. no. 30410) equilibrated with 20 ml wash buffer (20 mM $NaH_2PO_4$, 10 mM NaCl, 20 mM imidazole, pH 6.0). Contaminants were removed by washing with wash buffer, and Z variants were eluted with elution buffer (20 mM $NaH_2PO_4$, 10 mM NaCl, 250 mM imidazole, pH 6.0). The eluents were subjected to purification on an ion exchange column (Life Technologies, cat. no. 4481317), and Z variants were eluted by an increasing salt concentration. Buffer solutions of eluents were then changed to PBS (10 mM $Na_2HPO_4$, 1.8 mM $KH_2PO_4$, 137 mM NaCl, 2.7 mM KCl) using a VIVASPIN 6 column (Sartorius, cat. no. VS0691). The purity of Z variants was analyzed by SDS-PAGE stained with Coomassie Blue.

ProteOn Kinetic Analysis:

Kinetic constants ($k_{on}$ and $k_{off}$) and affinities ($K_D$) for human IL-6 were determined for 6 $His_6$-tagged Z variants purified under denatured conditions. The IL-6 binding variants Z06814 (SEQ ID NO:1512), Z14861 (SEQ ID NO:4), Z014976 (SEQ ID NO:1), Z14984 (SEQ ID NO:5), Z15015 (SEQ ID NO:2), and Z15122 (SEQ ID NO:3) were diluted to 5 µg/ml in 10 mM NaAc buffer, pH 4.5, and immobilized separately on GLC chip (Bio-Rad, cat. no. 176-5011). The immobilization was performed using amine coupling chemistry according to the manufacturer's recommendations and PBST 0.05% was used as running buffer. PBST 0.05% was also used as running buffer in the kinetic experiment using a flow rate was 60 µl/min. The analyte hIL-6 was diluted in the PBST 0.05% running buffer to final concentrations of 50 nM, 12.5 nM, 3.1 nM, 0.78 nM, 0.19 nM and 0 nM and injected in triplicate for 3 min, followed by dissociation in running buffer for 90 min. After dissociation, the surfaces were regenerated with HCl supplemented with 0.05% Tween 20. Kinetic constants were calculated from the sensorgrams using a 1:1 model in Bio-Rad manager Software (Bio-Rad).

Analysis of Binding Site:

The interference of 14 maturated IL-6 binding Z variants (purified under denatured conditions) with the interaction between human gp130 (hgp130) and the hIL-6/hIL-6Rα complex was assessed as described in Example 2. The primary binder Z06814 and the hIL-6Rα binding antibody tocilizumab were included for comparison.

TF-1 Cell-Based Assay:

TF-1 cells were cultured in RPMI1640 with L-glutamine (HyClone, cat. no. SH30027) supplemented with 10% FBS (HyClone, cat. no. SH30919.03), Pen-Strep (HyClone, cat. no. 15140-163) and 2 ng/ml rhGM-CSF (R&D Systems, cat. no. 215-GM-010). Prior to use, cells were washed twice in RPMI-1640 in absence of rhGM-CSF. Cells were then counted and dispensed into a 96-well plate (Corning, cat. no. 3596) at a density of $4\times10^4$ cells per well. In separate plates, serial dilutions (concentration range 10-0.00061 nM) of Z variants (purified under native conditions), tocilizumab (Roche) and control IgG (Jackson Immunoresearch, cat. no. Jac-009-000-003) were incubated in the presence of 0.099 nM rhIL-6 (R&D Systems, cat. no. 206-IL/CF). These pre-mixtures were then transferred to wells containing TF-1 cells, which were incubated for 72 h at 37° C. in a humidified 5% $CO_2$ atmosphere. During the last four hours of incubation, 10 µl of WST (DoGen, cat. no. EZ3000) were included per well. The absorbance was measured at 450 nM using a Victor X3 plate reader (Perkin Elmer). Relative cell viability was calculated by dividing the absorbance of each well by the mean absorbance of IL-6-treated wells in each plate. The data was assessed by non-linear regression to a four-parameter dose-response curve, and the half-maximal inhibitory concentration (IC50) was determined using Graphpad Prism software.

CD Analysis:

CD analysis was performed as described in Example 2 using Z variants purified under native conditions.

Results

ProteOn Kinetic Analysis:

The interactions of 6 $His_6$-tagged IL-6-binding Z variants with human IL-6 were analyzed in a ProteOn instrument by injecting various concentrations of the hIL-6 over surfaces containing different immobilized Z variants. The ligand immobilization levels of the surfaces were between 100-220 RU each. A summary of the kinetic parameters ($K_D$, $k_a$ ($k_{on}$) and $k_d$ ($k_{off}$)) for binding of hIL-6 to the Z variants using a 1:1 interaction model is given in Table 13.

TABLE 13

Kinetic parameters for binding of hIL-6 to Z variants

| Z variant | SEQ ID NO: | $k_{on}$ ($M^{-1}s^{-1}$) | $k_{off}$ ($s^{-1}$) | $K_D$ (M) |
|---|---|---|---|---|
| $His_6$-Z06814 | 1512 | $4.3 \times 10^5$ | $8.8 \times 10^{-5}$ | $2.0 \times 10^{-10}$ |
| $His_6$-Z14861 | 4 | $3.6 \times 10^5$ | $6.3 \times 10^{-5}$ | $1.7 \times 10^{-10}$ |
| $His_6$-Z14976 | 1 | $3.1 \times 10^5$ | $2.7 \times 10^{-5}$ | $8.8 \times 10^{-11}$ |
| $His_6$-Z14984 | 5 | $3.0 \times 10^5$ | $7.4 \times 10^{-5}$ | $2.5 \times 10^{-10}$ |
| $His_6$-Z15015 | 2 | $4.3 \times 10^5$ | $7.2 \times 10^{-5}$ | $1.7 \times 10^{-10}$ |
| $His_6$-Z15122 | 3 | $3.1 \times 10^5$ | $3.9 \times 10^{-5}$ | $1.2 \times 10^{-10}$ |

Figure 5:
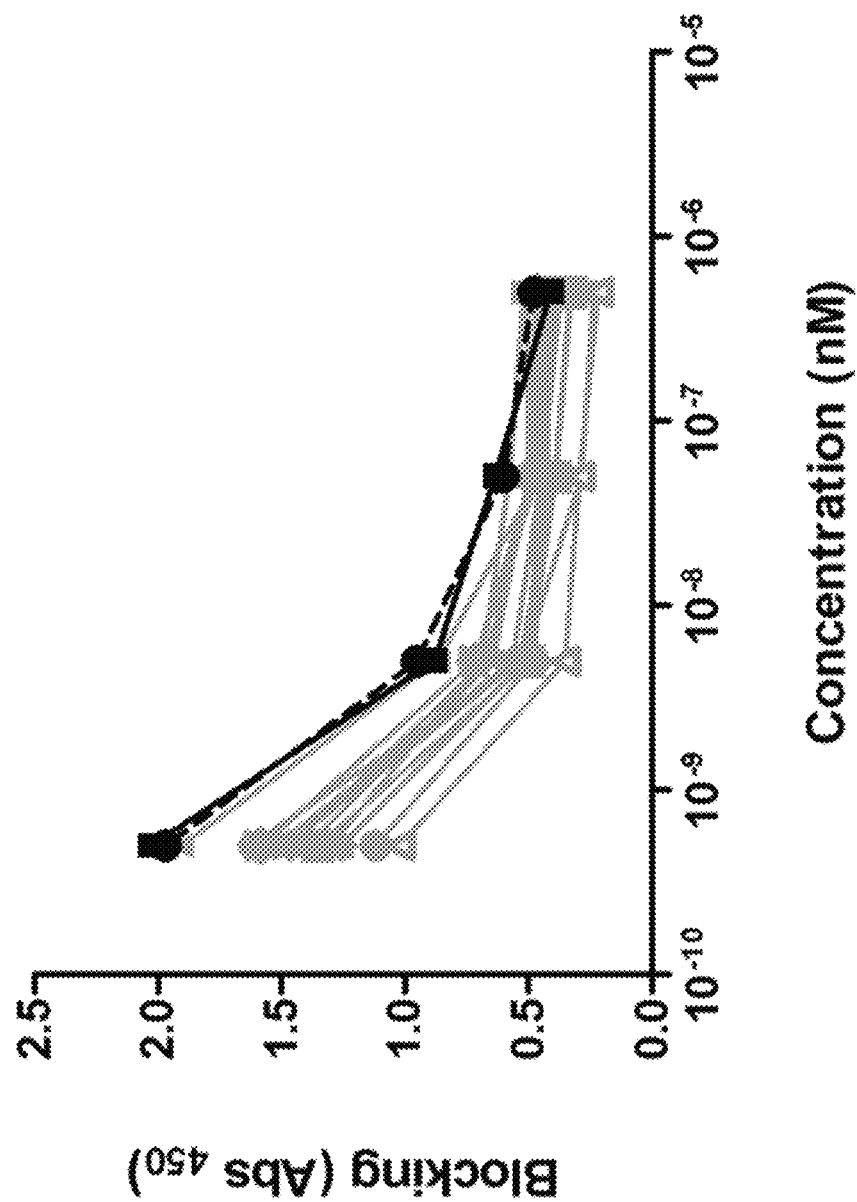
FIG. 5 shows the result of blocking of the binding of the hIL-6/hIL-6Rα complex to hgp130, assayed as described in Example 7. Concentration dependent blocking was seen for all tested maturated IL-6 binding Z variants (gray) as well as for tocilizumab (black) and the primary binder Z06814 (SEQ ID NO:1512, broken line), which were both included for comparison. All maturated IL-6 binding Z variants showed more efficient blocking than the primary binders assayed in Example 2 (compare FIG. 3).

Analysis of Binding Site:

All maturated IL-6 binding Z variants showed a clear concentration-dependent blocking of the trans-signaling resembling interaction between preformed hIL-6/hIL-6Rα complexes and hgp130 (FIG. 5). Each maturated Z variant showed a higher blocking capacity than both the primary binder Z06814 and tocilizumab, i.e. which would correspond to IC50 values less than 1.6 nM.

Figure 6:
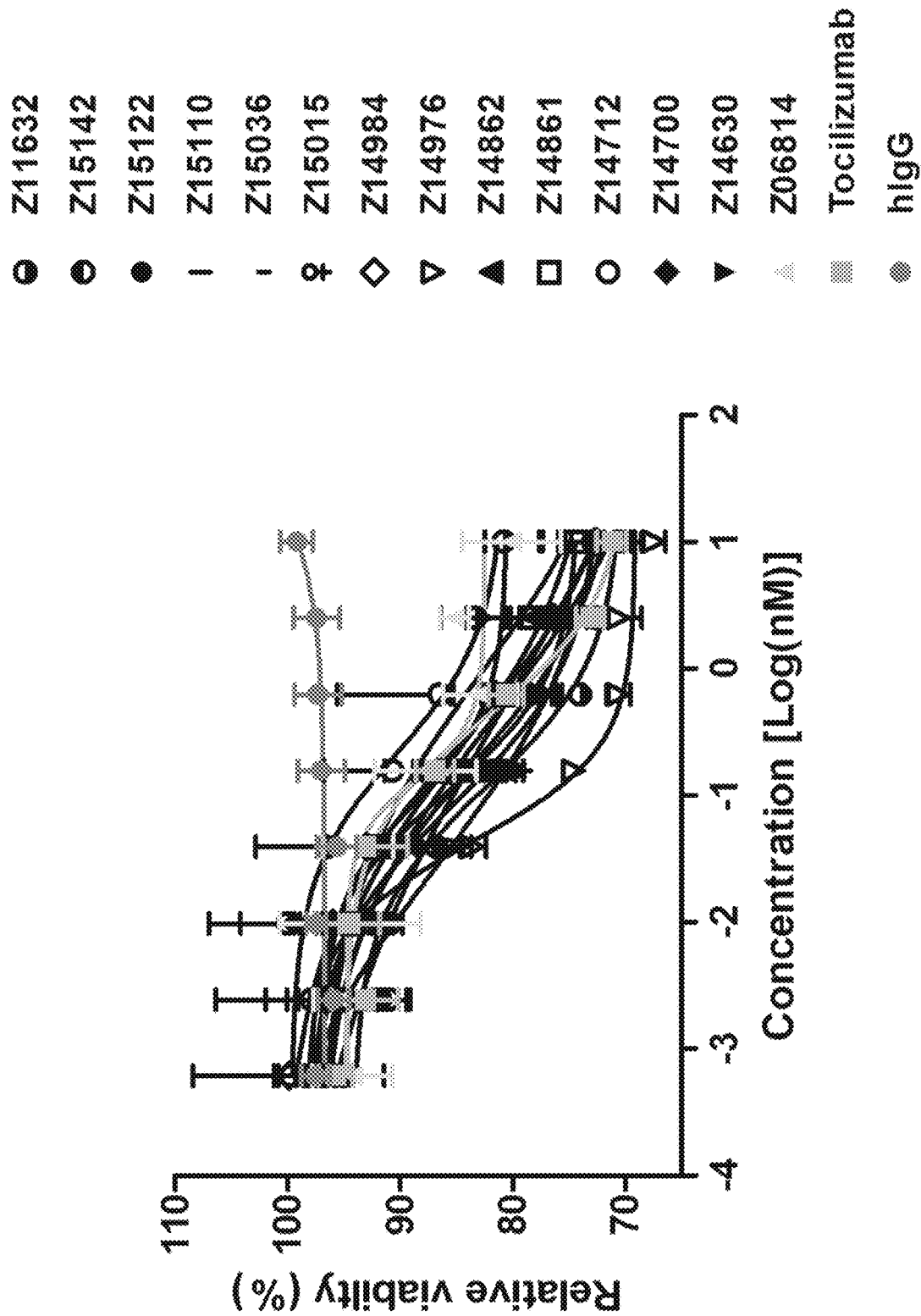
FIG. 6 shows the result of the TF-1 cell neutralizing assay described in Example 7. Concentration dependent inhibition of IL-6 induced TF-1 cell proliferation was seen for all tested IL-6 binding Z variants (matured Z variants shown in black; primary binder Z06814 (SEQ ID NO:1512) shown as grey filled triangles) and for tocilizumab (grey filled squares), but not for the negative control antibody hIgG (grey filled circles).

TF-1 Cell-Based Assay:

A TF-1 cell-based assay was conducted to evaluate the efficacy and potency of IL-6 binding Z variants in the classical signaling pathway. This assay showed that all affinity-matured IL-6 binding Z variants were capable of blocking IL-6 dependent growth of the TF-1 cells (FIG. 6). The calculated IC50 values for Z variants and for the hIL-6Rα binding antibody tocilizumab are shown in Table 14.

TABLE 14

IC50 values for matured Z variants blocking the IL-6 dependent growth of TF-1 cells

| Z variant | SEQ ID NO: | IC50 (M) |
|---|---|---|
| $His_6$-Z11632 | 7 | $1.2 \times 10^{-10}$ |
| $His_6$-Z14630 | 6 | $8.7 \times 10^{-11}$ |
| $His_6$-Z14700 | 8 | $1.0 \times 10^{-10}$ |
| $His_6$-Z14712 | 9 | $2.2 \times 10^{-10}$ |
| $His_6$-Z14861 | 4 | $1.9 \times 10^{-10}$ |
| $His_6$-Z14862 | 10 | $4.3 \times 10^{-10}$ |
| $His_6$-Z14976 | 1 | $4.2 \times 10^{-11}$ |

TABLE 14-continued

IC50 values for matured Z variants blocking
the IL-6 dependent growth of TF-1 cells

| Z variant | SEQ ID NO: | IC50 (M) |
|---|---|---|
| His$_6$-Z14984 | 5 | $2.7 \times 10^{-10}$ |
| His$_6$-Z15015 | 2 | $2.7 \times 10^{-11}$ |
| His$_6$-Z15036 | 11 | $1.8 \times 10^{-10}$ |
| His$_6$-Z15110 | 12 | $9.3 \times 10^{-10}$ |
| His$_6$-Z15122 | 3 | $8.5 \times 10^{-11}$ |
| His$_6$-Z15142 | 14 | $5.1 \times 10^{-10}$ |
| His$_6$-Z06814 | 1512 | $1.3 \times 10^{-10}$ |
| tocilizumab | N/A | $4.1 \times 10^{-10}$ |

CD Analysis:

The CD spectra determined for 10 matured Z variants showed that each one had an α-helical structure at 20° C. The melting temperatures (Tm) determined by variable temperature measurement are shown in Table 15.

TABLE 15

Melting temperatures for a subset of matured Z variants

| Z variant | SEQ ID NO: | Tm (° C.) |
|---|---|---|
| His$_6$-Z11632 | 7 | 51 |
| His$_6$-Z14630 | 6 | 57 |
| His$_6$-Z14700 | 8 | 53 |
| His$_6$-Z14712 | 9 | 55 |
| His$_6$-Z14861 | 4 | 48 |
| His$_6$-Z14862 | 10 | 53 |
| His$_6$-Z15015 | 2 | 56 |
| His$_6$-Z15036 | 11 | 59 |
| His$_6$-Z15110 | 12 | 50 |
| His$_6$-Z15142 | 14 | 53 |

Example 8

In Vivo Activity of IL-6 Binding Z Variants in Fusion with ABD

A Serum Amyloid A (SAA) mouse model was used in order to explore the in vivo blocking effect of the IL-6 binding Z variants in fusion with ABD. The acute phase protein SAA is secreted from liver cells and can be induced by the proinflammatory cytokines IL-1, IL-6 and TNF. Due to the sequence homology of the human and mouse cytokines, the human variants are able to act on their corresponding mouse receptors and induce a murine SAA response. Note, that the human TNF protein is only able to interact with murine TNFRII (not murine TNFRI).

Materials and Methods

The IL-6 targeting Z variant Z06814 (SEQ ID NO:1512) and a control Z variant Z04726 (SEQ ID NO:1535) binding an irrelevant target, were cloned and produced in fusion with the ABD variant PP013 (SEQ ID NO:1554) as described in Example 2. Four groups of Balb/c mice (n=8) were injected subcutaneously (s.c.) with various doses (0, 0.025, 2.5 or 25 mg/kg body weight) of Z06814-ABD 9 h prior to intraperitoneal (i.p.) administration of hIL-6 at 5 μg/kg (R&D Systems). A fifth group of mice (n=8) received 25 mg/kg of Z04726-ABD. Two additional control groups of mice received PBS (n=4) and 25 mg/kg of Z06814-ABD (n=8), respectively, but no subsequent IL-6 injection. After 20 h, the blood was taken by cardiac puncture and serum was collected.

Serum was assessed for the content of murine SAA by ELISA (Tridelta) according to the manufacturer's instructions. In brief, diluted serum samples were added to SAA-precoated plates together with anti-SAA-HRP. The plates were incubated for 1 h and then washed four times. TMB substrate was added for 20 min and the reaction was stopped with stop solution. The absorbance was measured at 450 nm using a microplate reader (Victor³, Perkin Elmer).

Results

Figure 7:
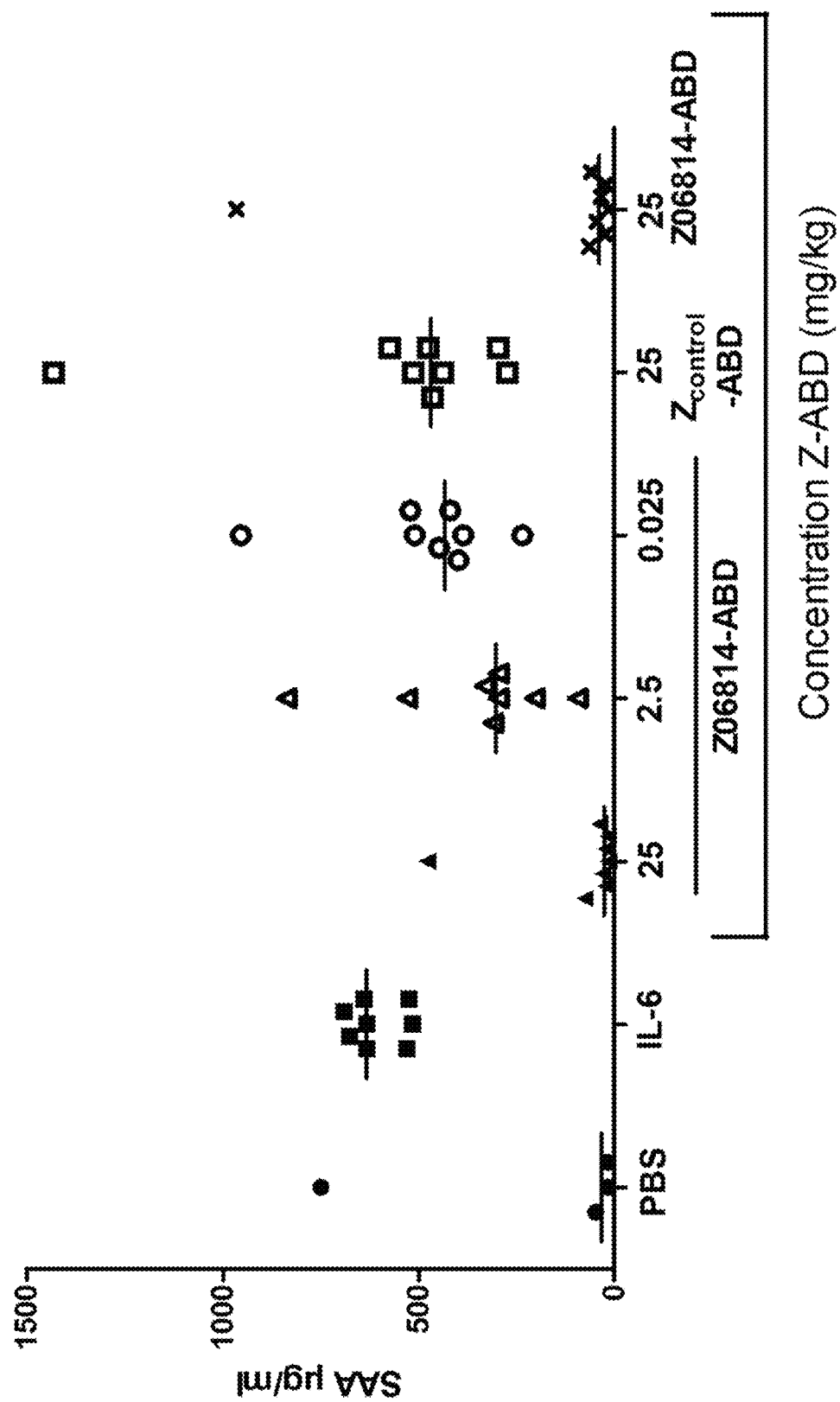
FIG. 7 shows the in vivo efficacy of the Z variant Z06814 (SEQ ID NO:1512) in fusion with the ABD variant PP013 (SEQ ID NO:1554) as scored by assaying IL-6 triggered serum amyloid-A (SAA) protein release in an anti-arthritic mouse model as described in Example 8. Four groups of mice were given 0 (filled squares), 0.025 (open dots), 2.5 (open triangles) or 25 (closed triangles) mg/kg body weight of the IL-6 binding Z06814-ABD fusion protein. As a control, mice were given 25 mg/kg of a control Z variant (Z04726; SEQ ID NO:1553) in fusion with ABD (referred to as $Z_{control}$-ABD) (open squares). Mice were injected with hIL-6 and subsequently the levels of SAA protein were measured. Two additional control groups of mice received PBS (filled circles) and 25 mg/kg Z06814-ABD (crosses), respectively, but no subsequent IL-6 injection.

The anti-arthritic efficacy of the Z variant Z06814 (SEQ ID NO:1512) was assessed in vivo using a mouse model for IL-6 triggered serum amyloid-A (SAA) protein release. Four groups of mice were given 0, 0.025, 2.5 or 25 mg/kg body weight of the IL-6 binding Z06814-ABD fusion protein or 25 mg/kg of a control Z04726-ABD fusion protein 9 h before an injection of 5 μg/kg body weight of hIL-6. After an additional 22 h, the levels of SAA protein were measured and compared between the different groups. In animals receiving either no Z06814-ABD or 25 mg/kg of the control Z04726-ABD fusion, SAA protein levels in serum increased to levels of approximately 500-600 μg/ml. Control animals given PBS only (and no hIL-6) exhibited levels in the range of 16-64 μg/ml. In animals given Z06814-ABD, significantly lower SAA protein levels were measured in a dose-dependent manner (FIG. 7). For the group given the highest dose of Z06814-ABD (25 mg/kg body weight), SAA protein levels were as low as for animals given no hIL-6 injection.

ITEMIZED LISTING OF EMBODIMENTS

1. IL-6 binding polypeptide, comprising an IL-6 binding motif BM, which motif consists of an amino acid sequence selected from:

(SEQ ID NO: 1562)
i) EEX$_3$X$_4$AWX$_7$EIHX$_{11}$LPNLX$_{16}$X$_{17}$X$_{18}$QX$_{20}$X$_{21}$AFIX$_{25}$X$_{26}$LX$_{28}$X$_{29}$ wherein, independently from each other, X$_3$ is selected from A, F, H, K, Q, R, S, W and Y;
X$_4$ is selected from A, D, E, F, H, I, K, L, M, N, Q, R, S, T, V and Y;
X$_7$ is selected from F, H, I, K, L, M, N, R, S, T, V, W and Y;
X$_{11}$ is selected from A, I, K, L, M, N, R, S, T and V;
X$_{16}$ is selected from N and T;
X$_{17}$ is selected from A, I, T and V;
X$_{18}$ is selected from D, E, G, H, K, N, Q, R, S and T;
X$_{20}$ is selected from I, L, M, R, T and V;
X$_{21}$ is selected from A, S, T and V;
X$_{25}$ is selected from I, M, Q, S, T, V and W;
X$_{26}$ is selected from K and S;
X$_{28}$ is selected from F, L, M and Y; and
X$_{29}$ is selected from D and R;

and ii) an amino acid sequence which has at least 93% identity to the sequence defined in i).

2. IL-6 binding polypeptide according to item 1, wherein in sequence i):

X$_3$ is selected from A, H, K, Q, R and Y;
X$_4$ is selected from A, D, E, F, H, I, K, L, M, N, Q, R, S, T, V and Y;
X$_7$ is selected from F, H, I, K, L, M, N, R, T, V, W and Y;
X$_{11}$ is selected from A, I, K, L, N, S, T and V;
X$_{16}$ is T;
X$_{17}$ is selected from A, I, T and V;
X$_{18}$ is selected from D, E, H, K, N, Q, R, S and T;
X$_{20}$ is selected from I, L, M, R and V;
X$_{21}$ is selected from A, S and V;

$X_{25}$ is selected from I, Q, S, T, V and W;
$X_{26}$ is K;
$X_{28}$ is selected from F, L, M and Y; and
$X_{29}$ is D.

3. IL-6 binding polypeptide according to item 1 or 2, wherein sequence i) fulfills at least six of the eleven conditions I-XI:
I. $X_3$ is selected from K and R;
II. $X_{11}$ is selected from A and L;
III. $X_{16}$ is T;
IV. $X_{17}$ is selected from I and V;
V. $X_{18}$ is selected from D and E;
VI. $X_{20}$ is M;
VII. $X_{21}$ is A;
VIII. $X_{25}$ is selected from S and T;
IX. $X_{26}$ is K;
X. $X_{28}$ is F; and
XI. $X_{29}$ is D.

4. IL-6 binding polypeptide according to item 3, wherein sequence i) fulfills at least seven of the eleven conditions I-XI.

5. IL-6 binding polypeptide according to item 4, wherein sequence i) fulfills at least eight of the eleven conditions I-XI.

6. IL-6 binding polypeptide according to item 5, wherein sequence i) fulfills at least nine of the eleven conditions I-XI.

7. IL-6 binding polypeptide according to item 6, wherein sequence i) fulfills at least ten of the eleven conditions I-XI.

8. IL-6 binding polypeptide according to item 7, wherein sequence i) fulfills all of the eleven conditions I-XI.

9. IL-6 binding polypeptide according to any preceding item, wherein $X_{17}X_{20}X_{21}$ is selected from VMA and IMA.

10. IL-6 binding polypeptide according to any one of items 1-8, wherein $X_{20}X_{21}X_{28}$ is MAF.

11. IL-6 binding polypeptide according to any one of items 1-8, wherein $X_{17}X_{20}X_{28}$ is selected from VMF and IMF.

12. IL-6 binding polypeptide according to any one of items 1-8, wherein $X_{17}X_{21}X_{28}$ is selected from VAF and IAF.

13. IL-6 binding polypeptide according to any preceding item, wherein sequence i) corresponds to the sequence from position 8 to position 36 in a sequence selected from the group consisting of SEQ ID NO:1-1551.

14. IL-6 binding polypeptide according to item 13, wherein sequence i) corresponds to the sequence from position 8 to position 36 in a sequence selected from the group consisting of SEQ ID NO:1-1502.

15. IL-6 binding polypeptide according to item 14, wherein sequence i) corresponds to the sequence from position 8 to position 36 in a sequence selected from the group consisting of SEQ ID NO:7, SEQ ID NO:15-89 and SEQ ID NO:151-871.

16. IL-6 binding polypeptide according to item 14, wherein sequence i) corresponds to the sequence from position 8 to position 36 in a sequence selected from the group consisting of SEQ ID NO:1-6, SEQ ID NO:8-14, SEQ ID NO:90-150 and SEQ ID NO:872-1502.

17. IL-6 binding polypeptide according to item 13, wherein sequence i) corresponds to the sequence from position 8 to position 36 in a sequence selected from the group consisting of SEQ ID NO:1-152 and SEQ ID NO:1503-1515.

18. IL-6 binding polypeptide according to item 17, wherein sequence i) corresponds to the sequence from position 8 to position 36 in a sequence selected from the group consisting of SEQ ID NO:1-150 and SEQ ID NO:1503-1515.

19. IL-6 binding polypeptide according to item 17, wherein sequence i) corresponds to the sequence from position 8 to position 36 in a sequence selected from the group consisting of SEQ ID NO:1-152.

20. IL-6 binding polypeptide according to item 18 or 19, wherein sequence i) corresponds to the sequence from position 8 to position 36 in a sequence selected from the group consisting of SEQ ID NO:1-150.

21. IL-6 binding polypeptide according to item 19, wherein sequence i) corresponds to the sequence from position 8 to position 36 in a sequence selected from the group consisting of SEQ ID NO:7, SEQ ID NO:15-89 and SEQ ID NO:151-152.

22. IL-6 binding polypeptide according to item 20, wherein sequence i) corresponds to the sequence from position 8 to position 36 in a sequence selected from the group consisting of SEQ ID NO:1-6, SEQ ID NO:8-14 and SEQ ID NO:90-150.

23. IL-6 binding polypeptide according to item 18, wherein sequence i) corresponds to the sequence from position 8 to position 36 in a sequence selected from the group consisting of SEQ ID NO:1-14 and SEQ ID NO:1503-1515.

24. IL-6 binding polypeptide according to item 23, wherein sequence i) corresponds to the sequence from position 8 to position 36 in a sequence selected from the group consisting of SEQ ID NO:1-14 and SEQ ID NO:1512.

25. IL-6 binding polypeptide according to item 24, wherein sequence i) corresponds to the sequence from position 8 to position 36 in a sequence selected from the group consisting of SEQ ID NO:1-14.

26. IL-6 binding polypeptide according to any one of items 16, 22 and 25, wherein sequence i corresponds to the sequence from position 8 to position 36 in a sequence selected from the group consisting of SEQ ID NO:1-5.

27. IL-6 binding polypeptide according to item 24, wherein sequence i) corresponds to the sequence from position 8 to position 36 in SEQ ID NO:1512.

28. IL-6 binding polypeptide according to any preceding item, wherein said IL-6 binding motif forms part of a three-helix bundle protein domain.

29. IL-6 binding polypeptide according to item 28, wherein said IL-6 binding motif essentially forms part of two helices with an interconnecting loop, within said three-helix bundle protein domain.

30. IL-6 binding polypeptide according to item 29, wherein said three-helix bundle protein domain is selected from bacterial receptor domains.

31. IL-6 binding polypeptide according to item 30, wherein said three-helix bundle protein domain is selected from domains of protein A from *Staphylococcus aureus* or derivatives thereof.

32. IL-6 binding polypeptide according to any preceding item, which comprises a binding module BMod, the amino acid sequence of which is selected from:

(SEQ ID NO: 1563)
iii) K-[BM]-DPSQSX$_a$X$_b$LLX$_c$EAKKLX$_d$X$_e$X$_f$Q;

wherein
[BM] is an IL-6 binding motif as defined in any one of items 1-27
provided that $X_{29}$ is D;

$X_a$ is selected from A and S;
$X_b$ is selected from N and E;
$X_c$ is selected from A, S and C;
$X_d$ is selected from E, N and S;
$X_e$ is selected from D, E and S;
$X_f$ is selected from A and S; and
iv) an amino acid sequence which has at least 91% identity to a sequence defined by iii).

33. IL-6 binding polypeptide according to any one of items 1-31, which comprises a binding module BMod, the amino acid sequence of which is selected from:

(SEQ ID NO: 1564)
v) K-[BM]-QPEQSX$_a$X$_b$LLX$_c$EAKKLX$_d$X$_e$X$_f$Q, wherein
[BM] is an IL-6 binding motif as defined in any one of items 1-27
provided that $X_{29}$ is R;
$X_a$ is selected from A and S;
$X_b$ is selected from N and E;
$X_c$ is selected from A, S and C;
$X_d$ is selected from E, N and S;
$X_e$ is selected from D, E and S;
$X_f$ is selected from A and S; and
vi) an amino acid sequence which has at least 91% identity to a sequence defined by v).

34. IL-6 binding polypeptide according to any one of items 1-32, wherein sequence iii) corresponds to the sequence from position 7 to position 55 in a sequence selected from the group consisting of SEQ ID NO:1-1551.

35. IL-6 binding polypeptide according to item 34, wherein sequence iii) corresponds to the sequence from position 7 to position 55 in a sequence selected from the group consisting of SEQ ID NO:1-1502.

36. IL-6 binding polypeptide according to item 35, wherein sequence iii) corresponds to the sequence from position 7 to position 55 in a sequence selected from the group consisting of SEQ ID NO:7, SEQ ID NO:15-89 and SEQ ID NO:151-871.

37. IL-6 binding polypeptide according to item 35, wherein sequence iii) corresponds to the sequence from position 7 to position 55 in a sequence selected from the group consisting of SEQ ID NO:1-6, SEQ ID NO:8-14, SEQ ID NO:90-150 and SEQ ID NO:872-1502.

38. IL-6 binding polypeptide according to item 34, wherein sequence iii) corresponds to the sequence from position 7 to position 55 in a sequence selected from the group consisting of SEQ ID NO:1-152 and SEQ ID NO:1503-1515.

39. IL-6 binding polypeptide according to item 38, wherein sequence iii) corresponds to the sequence from position 7 to position 55 in a sequence selected from the group consisting of SEQ ID NO:1-150 and SEQ ID NO:1503-1515.

40. IL-6 binding polypeptide according to item 35 or 38, wherein sequence iii) corresponds to the sequence from position 7 to position 55 in a sequence selected from the group consisting of SEQ ID NO:1-152.

41. IL-6 binding polypeptide according to item 39 or 40, wherein sequence iii) corresponds to the sequence from position 7 to position 55 in a sequence selected from the group consisting of SEQ ID NO:1-150.

42. IL-6 binding polypeptide according to item 40, wherein sequence iii) corresponds to the sequence from position 7 to position 55 in a sequence selected from the group consisting of SEQ ID NO:7, SEQ ID NO:15-89 and SEQ ID NO:151-152.

43. IL-6 binding polypeptide according to item 41, wherein sequence iii) corresponds to the sequence from position 7 to position 55 in a sequence selected from the group consisting of SEQ ID NO:1-6, SEQ ID NO:8-14 and SEQ ID NO:90-150.

44. IL-6 binding polypeptide according to item 39, wherein sequence iii) corresponds to the sequence from position 7 to position 55 in a sequence selected from the group consisting of SEQ ID NO:1-14 and SEQ ID NO:1503-1515.

45. IL-6 binding polypeptide according to item 44, wherein sequence iii) corresponds to the sequence from position 7 to position 55 in a sequence selected from the group consisting of SEQ ID NO:1-14 and SEQ ID NO:1512.

46. IL-6 binding polypeptide according to item 45, wherein sequence iii) corresponds to the sequence from position 7 to position 55 in a sequence selected from the group consisting of SEQ ID NO:1-14.

47. IL-6 binding polypeptide according to any one of items 37, 43 and 46, wherein sequence iii) corresponds to the sequence from position 7 to position 55 in a sequence selected from the group consisting of SEQ ID NO:1-5.

48. IL-6 binding polypeptide according to item 45, wherein sequence iii) corresponds to the sequence from position 7 to position 55 in SEQ ID NO:1512.

49. IL-6 binding polypeptide according to any preceding item, which comprises an amino acid sequence selected from:
vii) YA-[BMod]-AP,
wherein [BMod] is an IL-6 binding module as defined in any one of items 32-48; and
viii) an amino acid sequence which has at least 90% identity to a sequence defined by vii).

50. IL-6 binding polypeptide according to any one of items 1-48, which comprises an amino acid sequence selected from:
ix) FN-[BMod]-AP;
wherein [BMod] is an IL-6 binding module as defined in any one of items 32-48; and
x) an amino acid sequence which has at least 90% identity to a sequence defined by ix).

51. IL-6 binding polypeptide according to any preceding item, which comprises an amino acid sequence selected from:

ADNNFNK-[BM]-DPSQSANLLSEAKKLNESQAPK;

ADNKFNK-[BM]-DPSQSANLLAEAKKLNDAQAPK;

ADNKFNK-[BM]-DPSVSKEILAEAKKLNDAQAPK;

ADAQQNNFNK-[BM]-DPSQSTNVLGEAKKLNESQAPK;

AQHDE-[BM]-DPSQSANVLGEAQKLNDSQAPK;

VDNKFNK-[BM]-DPSQSANLLAEAKKLNDAQAPK;

AEAKYAK-[BM]-DPSESSELLSEAKKLNKSQAPK;

VDAKYAK-[BM]-DPSQSSELLAEAKKLNDAQAPK;

VDAKYAK-[BM]-DPSQSSELLAEAKKLNDSQAPK;

AEAKYAK-[BM]-DPSQSSELLSEAKKLNDSQAPK;

AEAKYAK-[BM]-DPSQSSELLSEAKKLSESQAPK;

AEAKYAK-[BM]-QPEQSSELLSEAKKLSESQAPK;

AEAKYAK-[BM]-DPSQSSELLSEAKKLESSQAPK;

AEAKYAK-[BM]-QPEQSSELLSEAKKLESSQAPK;

VDAKYAK-[BM]-DPSQSSELLSEAKKLNDSQAPK;

VDAKYAK-[BM]-DPSQSSELLSEAKKLSESQAPK;

VDAKYAK-[BM]-QPEQSSELLSEAKKLSESQAPK;

VDAKYAK-[BM]-DPSQSSELLSEAKKLESSQAPK;

VDAKYAK-[BM]-QPEQSSELLSEAKKLESSQAPK;

VDAKYAK-[BM]-DPSQSSELLAEAKKLNKAQAPK;
and

AEAKYAK-[BM]-DPSQSSELLAEAKKLNKAQAPK;

wherein [BM] is an IL-6 binding motif as defined in any one of items 1-27.

52. IL-6 binding polypeptide according to any one of items 1-49, which comprises an amino acid sequence selected from:

xi) VDAKYAK-[BM]-DPSQSSELLSEAKKLNDSQAPK;

wherein [BM] is an IL-6 binding motif as defined in any one of items 1-27; and xii) an amino acid sequence which has at least 89% identity to the sequence defined in xi).

53. IL-6 binding polypeptide according to any one of items 1-49, which comprises an amino acid sequence selected from:

xiii) AEAKYAK-[BM]-DPSQSSELLSEAKKLNDSQAPK;

wherein [BM] is an IL-6 binding motif as defined in any one of items 1-27; and xiv) an amino acid sequence which has at least 89% identity to the sequence defined in xiii).

54. IL-6 binding polypeptide according to item 52, wherein sequence xi) is selected from the group consisting of SEQ ID NO:1-1551.

55. IL-6 binding polypeptide according to item 54, wherein sequence xi) is selected from the group consisting of SEQ ID NO:1-1502.

56. IL-6 binding polypeptide according to item 55, wherein sequence xi) is selected from the group consisting of SEQ ID NO:7, SEQ ID NO:15-89 and SEQ ID NO:151-871.

57. IL-6 binding polypeptide according to item 55, wherein sequence xi) is selected from the group consisting of SEQ ID NO:1-6, SEQ ID NO:8-14, SEQ ID NO:90-150 and SEQ ID NO:872-1502.

58. IL-6 binding polypeptide according to item 54, wherein sequence xi) is selected from the group consisting of SEQ ID NO:1-152 and SEQ ID NO:1503-1515.

59. IL-6 binding polypeptide according to item 58, wherein sequence xi) is selected from the group consisting of SEQ ID NO:1-150 and SEQ ID NO:1503-1515.

60. IL-6 binding polypeptide according to item 55 or 58, wherein sequence xi) is selected from the group consisting of SEQ ID NO:1-152.

61. IL-6 binding polypeptide according to item 59 or 60, wherein sequence xi) is selected from the group consisting of SEQ ID NO:1-150.

62. IL-6 binding polypeptide according to item 60, wherein sequence xi) is selected from the group consisting of SEQ ID NO:7, SEQ ID NO:15-89 and SEQ ID NO:151-152.

63. IL-6 binding polypeptide according to item 61, wherein sequence xi) is selected from the group consisting of SEQ ID NO:1-6, SEQ ID NO:8-14 and SEQ ID NO:90-150.

64. IL-6 binding polypeptide according to item 59, wherein sequence xi) is selected from the group consisting of SEQ ID NO:1-14 and SEQ ID NO:1503-1515.

65. IL-6 binding polypeptide according to item 64, wherein sequence xi) is selected from the group consisting of SEQ ID NO:1-14 and SEQ ID NO:1512.

66. IL-6 binding polypeptide according to item 65, wherein sequence xi) is selected from the group consisting of SEQ ID NO:1-14.

67. IL-6 binding polypeptide according to any one of items 57, 63 and 66, wherein sequence xi) is selected from the group consisting of SEQ ID NO:1-5.

68. IL-6 binding polypeptide according to item 65, wherein sequence xi) is SEQ ID NO:1512.

69. IL-6 binding polypeptide according to any preceding item, which is capable of blocking the IL-6 dependent signaling via the cis-signaling pathway and/or the trans-signaling pathway.

70. IL-6 binding polypeptide according to item 69, wherein the half maximal inhibitory concentration (IC50) of the blocking is at most $1\times10^{-6}$ M, such as at most $1\times10^{-7}$ M, such as at most $1\times10^{-8}$ M, such as at most $1\times10^{-9}$ M, such as at most $1\times10^{-10}$ M.

71. IL-6 binding polypeptide according to item 69 or 70, which is capable of blocking the interaction of IL-6/IL-6Rα with gp130.

72. IL-6 binding polypeptide according to any preceding item, which is capable of binding to IL-6 such that the EC50 value of the interaction is at most $1\times10^{-7}$ M, such as at most $1\times10^{-8}$ M, such as at most $1\times10^{-9}$ M, such as at most $1\times10^{-10}$ M.

73. IL-6 binding polypeptide according to any preceding item, which is capable of binding to IL-6 such that the $K_D$ value of the interaction is at most $1\times10^{-8}$ M, such as at most $1\times10^{-9}$ M, such as at most $1\times10^{-10}$ M.

74. IL-6 binding polypeptide according to any preceding item which comprises additional amino acids at the C-terminal and/or N-terminal end.

75. IL-6 binding polypeptide according to item 74, wherein said additional amino acid(s) improve(s) production, purification, stabilization in vivo or in vitro, coupling or detection of the polypeptide.

76. IL-6 binding polypeptide according to any preceding item in multimeric form, comprising at least two IL-6 binding polypeptide monomer units, whose amino acid sequences may be the same or different.

77. IL-6 binding polypeptide according to item 76, wherein said IL-6 binding polypeptide monomer units are covalently coupled together.

78. IL-6 binding polypeptide according to item 77, wherein the IL-6 binding polypeptide monomer units are expressed as a fusion protein.

79. IL-6 binding polypeptide according to item 78, in dimeric form.

80. Fusion protein or conjugate comprising
a first moiety consisting of an IL-6 binding polypeptide according to any preceding item; and
a second moiety consisting of a polypeptide having a desired biological activity.

81. Fusion protein or conjugate according to item 80, wherein said desired biological activity is a therapeutic activity.

82. Fusion protein or conjugate according to item 80, wherein said desired biological activity is a binding activity.

83. Fusion protein or conjugate according to item 82, wherein said binding activity is albumin binding activity which increases in vivo half-life of the fusion protein or conjugate.

84. Fusion protein or conjugate according to item 83, wherein said second moiety comprises the albumin binding domain of streptococcal protein G or a derivative thereof.

85. Fusion protein or conjugate according to item 82, wherein said binding activity acts to block a biological activity.

86. Fusion protein or conjugate according to item 80, wherein said desired biological activity is an enzymatic activity.

87. Fusion protein or conjugate according to item 81, wherein the second moiety is a therapeutically active polypeptide.

88. Fusion protein or conjugate according to item 87, wherein the second moiety is an immune response modifying agent.

89. Fusion protein or conjugate according to item 87, wherein the second moiety is an anti-cancer agent.

90. Fusion protein or conjugate according to any one of items 80, 81, 86, 88 and 89, wherein the second moiety is selected from the group consisting of human endogenous enzymes, hormones, growth factors, chemokines, cytokines and lymphokines.

91. IL-6 binding polypeptide, fusion protein or conjugate according to any preceding item, further comprising a label.

92. IL-6 binding polypeptide, fusion protein or conjugate according to item 91, wherein said label is selected from the group consisting of fluorescent dyes and metals, chromophoric dyes, chemiluminescent compounds and bioluminescent proteins, enzymes, radionuclides and radioactive particles.

93. IL-6 binding polypeptide, fusion protein or conjugate according to any preceding item, comprising a chelating environment provided by a polyaminopolycarboxylate chelator conjugated to the IL-6 binding polypeptide via a thiol group of a cysteine residue or an amine group of a lysine residue.

94. A polynucleotide encoding a polypeptide according to any one of items 1-79.

95. Expression vector comprising a polynucleotide according to item 94.

96. Host cell comprising an expression vector according to item 95.

97. Method of producing a polypeptide according to any one of items 1-79, comprising
culturing a host cell according to item 96 under conditions permissive of expression of said polypeptide from said expression vector, and
isolating said polypeptide.

98. Composition comprising an IL-6 binding polypeptide, fusion protein or conjugate according to any one of items 1-93 and at least one pharmaceutically acceptable excipient or carrier.

99. Composition according to item 98, further comprising at least one additional active agent, such as an agent selected from an immune response modifying agent and an anti-cancer agent.

100. IL-6 binding polypeptide, fusion protein or conjugate according to any one of items 1-93 or a composition according to any one of items 98-99 for oral, topical, intravenous, intraperitoneal, subcutaneous, pulmonary, transdermal, intramuscular, intranasal, buccal, sublingual or suppository administration, such as for topical administration.

101. IL-6 binding polypeptide, fusion protein or conjugate according to any one of items 1-93 or a composition according to any one of items 98-99 for use as a medicament, a diagnostic agent or a prognostic agent.

102. IL-6 binding polypeptide, fusion protein or conjugate according to any one of items 1-93 or a composition according to any one of items 98-99 for use as a medicament.

103. IL-6 binding polypeptide, fusion protein, conjugate or composition for use according to item 102, wherein said polypeptide, fusion protein, conjugate or composition modulates IL-6 function in vivo.

104. IL-6 binding polypeptide, fusion protein, conjugate or composition for use according to any one of items 101-103, in the treatment, prognosis or diagnosis of an IL-6 related disorder.

105. IL-6 binding polypeptide, fusion protein, conjugate or composition for use according to any one of items 101-103, in the treatment of an IL-6 related disorder.

106. IL-6 binding polypeptide, fusion protein, conjugate or composition for use according to item 105, wherein said IL-6 related disorder is selected from the group consisting of inflammatory diseases, autoimmune diseases, infectious disease, cancer, diabetes, neurological disease and depression.

107. IL-6 binding polypeptide, fusion protein, conjugate or composition for use according to item 106, wherein said IL-6 related disorder is selected from the group consisting of inflammatory diseases and autoimmune diseases.

108. IL-6 binding polypeptide, fusion protein, conjugate or composition for use according to item 107, wherein said IL-6 related disorder is selected from the group consisting of rheumatoid arthritis (RA), juvenile RA, juvenile idiopathic arthritis or systemic juvenile idiopathic arthritis, vasculitis, psoriatic arthritis, psoriasis, ankylosing spondylitis, chronic inflammatory bowel disease such as Crohn's disease and ulcerative colitis; Grave's disease, Behcet's disease, uveitis, giant cell arteritis, multiple sclerosis (MS), systemic sclerosis, systemic lupus erythematosus (SLE), polymyositis, polymyalgia rheumatic, asthma, chronic obstructive pulmonary disease (COPD), relapsing polychondritis, pancreatitis, peritonitis, nephritis, Kawasaki's disease, Sjögren's syndrome and adult Still's disease.

109. IL-6 binding polypeptide, fusion protein, conjugate or composition for use according to item 106, wherein said IL-6 related disorder is cancer, such as a cancer selected from the group consisting of colitis associated cancer, renal cancer, kidney cancer, prostate cancer, malignant lymphoma, multiple myeloma, Castleman's disease, breast cancer and lung cancer.

110. IL-6 binding polypeptide, fusion protein, conjugate or composition for use according to item 106, wherein said IL-6 related disorder is selected from Alzheimer's disease, HIV, diabetes, sepsis, cachexia, myelodysplastic syndrome (MDS), liver cirrhosis, graft versus host disease, myocardial infarction, endometriosis and osteoporosis.

111. Method of treatment of an IL-6 related disorder, comprising administering to a subject in need thereof an effective amount of an IL-6 binding polypeptide, fusion protein or conjugate according to any one of items 1-93 or a composition according to any one of items 98-99.

112. Method according to item 111, wherein said IL-6 related disorder is selected from the group consisting of inflammatory diseases, autoimmune diseases, infectious disease, cancer, diabetes, neurological disease and depression.

113. Method according to item 112, wherein said IL-6 related disorder is selected from the group consisting of inflammatory diseases and autoimmune diseases.

114. Method according to item 113, wherein said IL-6 related disorder is selected from the group consisting of rheumatoid arthritis (RA), juvenile RA, juvenile idiopathic arthritis or systemic juvenile idiopathic arthritis, vasculitis, psoriatic arthritis, psoriasis, ankylosing spondylitis, chronic inflammatory bowel disease such as Crohn's disease and ulcerative colitis; Grave's disease, Behcet's disease, uveitis, giant cell arteritis, multiple sclerosis (MS), systemic sclerosis, systemic lupus erythematosus (SLE), polymyositis, polymyalgia rheumatic, asthma, chronic obstructive pulmonary disease (COPD), relapsing polychondritis, pancreatitis, peritonitis, nephritis, Kawasaki's disease, Sjögren's syndrome and adult Still's disease.

115. Method according to item 112, wherein said IL-6 related disorder is cancer, such as a cancer selected from the group consisting of selected from the group consisting of colitis associated cancer, renal cancer, kidney cancer, prostate cancer, malignant lymphoma, multiple myeloma, Castleman's disease, breast cancer and lung cancer.

116. Method according to item 112, wherein said IL-6 related disorder is selected from Alzheimer's disease, HIV, diabetes, sepsis, cachexia, myelodysplastic syndrome (MDS), liver cirrhosis, graft versus host disease, myocardial infarction, endometriosis and osteoporosis.

117. Method of detecting IL-6, comprising providing a sample suspected to contain IL-6, contacting said sample with an IL-6 binding polypeptide, fusion protein or conjugate according to any one of items 1-90 or a composition according to any one of items 98-99, and detecting the binding of the IL-6 binding polypeptide, fusion protein, conjugate or composition to indicate the presence of IL-6 in the sample.

118. Method for determining the presence of IL-6 in a subject, the method comprising the steps:
contacting the subject, or a sample isolated from the subject, with an IL-6 binding polypeptide, fusion protein or conjugate according to any one of items 1-93 or a composition according to any one of items 98-99, and
obtaining a value corresponding to the amount of the IL-6 binding polypeptide, fusion protein, conjugate or composition that has bound in said subject or to said sample.

119. Method according to item 118, further comprising a step of comparing said value to a reference.

120. Method according to item 118 or 119, wherein said subject is a mammalian subject, such as a human subject.

121. Method according to any one of items 118-120, wherein the method is performed in vivo.

122. Method according to any one of items 118-120, wherein the method is performed in vitro.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10669314B2). An electronic copy of the "Sequence Listing" will also be available from the USPTO upon request and payment of the fee set forth in 37 CFR 1.19(b)(3).

The invention claimed is:

1. An interleukin-6 (IL-6) binding polypeptide, comprising an IL-6 binding motif (BM), which motif consists of the amino acid sequence selected from:

$$\text{i) } EEX_3X_4AWX_7EIHX_{11}LPNLX_{16}X_{17}X_{18}QX_{20}X_{21}AFIX_{25}X_{26}LX_{28}X_{29} \quad \text{(SEQ ID NO: 1562)}$$

wherein, independently from each other,
$X_3$ is selected from A, F, H, K, Q, R, S, W and Y;
$X_4$ is selected from A, D, E, F, H, I, K, L, M, N, Q, R, S, T, V and Y;
$X_7$ is selected from F, H, I, K, L, M, N, R, S, T, V, W and Y;
$X_{11}$ is selected from A, I, K, L, M, N, R, S, T and V;
$X_{16}$ is selected from N and T;
$X_{17}$ is selected from A, I, T and V;
$X_{18}$ is selected from D, E, G, H, K, N, Q, R, S and T;
$X_{20}$ is selected from I, L, M, R, T and V;
$X_{21}$ is selected from A, S, T and V;
$X_{25}$ is selected from I, M, Q, S, T, V and W;
$X_{26}$ is selected from K and S;
$X_{28}$ is selected from F, L, M and Y; and
$X_{29}$ is selected from D and R;

and
ii) an amino acid sequence which has at least 93% identity to the full-length sequence defined in i).

2. The IL-6 binding polypeptide according to claim 1, wherein sequence i) is the sequence from position 8 to position 36 in a sequence selected from the group consisting of SEQ ID NO:1-1551.

3. The IL-6 binding polypeptide according to claim 1, wherein said IL-6 binding motif forms part of a three-helix bundle protein domain.

4. The IL-6 binding polypeptide according to claim 1, which comprises a binding module BMod, the amino acid sequence of which is selected from:

$$\text{iii) } K\text{-}[BM]\text{-}DPSQSX_aX_bLLX_cEAKKLX_dX_eX_fQ; \quad \text{(SEQ ID NO: 1563)}$$

wherein
[BM] is an IL-6 binding motif as defined in claim 1 provided that $X_{29}$ is D;
$X_a$ is selected from A and S;
$X_b$ is selected from N and E;
$X_c$ is selected from A, S and C;
$X_d$ is selected from E, N and S;
$X_e$ is selected from D, E and S;

$X_f$ is selected from A and S; and iv) an amino acid sequence which has at least 95% identity to the full length sequence defined by iii).

5. The IL-6 binding polypeptide according to claim 1, which comprises the amino acid sequence selected from:

```
                                    (SEQ ID NO: 1586)
xi) VDAKYAK-[BM]-DPSQSSELLSEAKKLNDSQAPK;
``` wherein [BM] is an IL-6 binding motif as defined in claim 1; and xii) an amino acid sequence which has at least 96% identity to the full length sequence defined in xi).

6. The IL-6 binding polypeptide according to claim 5, wherein sequence xi) is selected from the group consisting of SEQ ID NO:1-1551.

7. The IL-6 binding polypeptide according to claim 1, which is capable of blocking the IL-6 dependent signaling via the cis-signaling pathway and/or the trans-signaling pathway.

8. The IL-6 binding polypeptide according to claim 7, wherein the half maximal inhibitory concentration of the blocking is at most $1 \times 10^{-6}$ M.

9. The IL-6 binding polypeptide according to claim 7, which is capable of blocking the interaction of IL-6/IL-6Rα with gp130.

10. The IL-6 binding polypeptide according to claim 1, which is capable of binding to IL-6 such that the EC50 value of the interaction is at most $1 \times 10^{-7}$ M or such that the $K_D$ value of the interaction is at most $1 \times 10^{-8}$ M.

11. A composition comprising the IL-6 binding polypeptide according to claim 1 and at least one pharmaceutically acceptable excipient or carrier.

12. The IL-6 binding polypeptide according to claim 1, wherein said IL-6 binding polypeptide modulates IL-6 function in vivo.

13. The IL-6 binding polypeptide according to claim 2, wherein sequence i) is the sequence from position 8 to position 36 in a sequence selected from the group consisting of SEQ ID NO:1-14 and SEQ ID NO:1512.

14. The IL-6 binding polypeptide according to claim 13, wherein sequence i) is the sequence from position 8 to position 36 in SEQ ID NO:1512.

15. A fusion protein or conjugate comprising
a first moiety consisting of the IL-6 binding polypeptide according to claim 1; and
a second moiety consisting of a polypeptide having a desired biological activity.

16. A polynucleotide encoding the IL-6 binding polypeptide according to claim 1.

17. A method of detecting IL-6, comprising
contacting a sample suspected to contain IL-6 with the IL-6 binding polypeptide according to claim 1, and
detecting the binding of the IL-6 binding polypeptide to IL-6 to indicate the presence of IL-6 in the sample.

18. A method of treatment of an IL-6 related disorder, comprising administering the IL-6 binding polypeptide according to claim 1 to a subject in need of treatment of an IL-6 related disorder that receives benefit from at least partial blocking of IL-6 signaling, wherein the IL-6 related disorder is rheumatoid arthritis, juvenile rheumatoid arthritis, juvenile idiopathic arthritis, systemic juvenile idiopathic arthritis, vasculitis, psoriatic arthritis, psoriasis, a chronic inflammatory bowel disease, Crohn's disease, ulcerative colitis, Grave's disease, Behçet's disease, uveitis, giant cell arteritis, multiple sclerosis, systemic sclerosis, systemic lupus erythematosus, polymyositis, polymyalgia rheumatic, relapsing polychondritis, pancreatitis, peritonitis, nephritis, Sjögren's syndrome, adult Still's disease, or Castleman's disease.

19. The method of claim 18, wherein the blocking is of the cis- or the trans-signaling pathway.

20. The method of claim 18, wherein the IL-6 binding polypeptide blocks the interaction of IL-6/IL-6Rα with gp130.

* * * * *